US008153410B2

(12) United States Patent
Jaffe

(10) Patent No.: US 8,153,410 B2
(45) Date of Patent: *Apr. 10, 2012

(54) ALTERNATE MORPHEEIN FORMS OF ALLOSTERIC PROTEINS AS A TARGET FOR THE DEVELOPMENT OF BIOACTIVE MOLECULES

(75) Inventor: Eileen K. Jaffe, Jenkintown, PA (US)

(73) Assignee: Fox Chase Cancer Center, Jenkintown, PA (US)

( * ) Notice: Subject to any disclaimer, the term of this patent is extended or adjusted under 35 U.S.C. 154(b) by 644 days.

This patent is subject to a terminal disclaimer.

(21) Appl. No.: 12/142,435

(22) Filed: Jun. 19, 2008

(65) Prior Publication Data

US 2009/0048324 A1 Feb. 19, 2009

Related U.S. Application Data

(63) Continuation-in-part of application No. 11/327,762, filed on Jan. 6, 2006, now abandoned, which is a continuation-in-part of application No. PCT/US2004/021722, filed on Jul. 7, 2004.

(60) Provisional application No. 60/485,253, filed on Jul. 7, 2003, provisional application No. 60/577,312, filed on Jun. 4, 2004, provisional application No. 60/690,649, filed on Jun. 15, 2005.

(51) Int. Cl.
C07K 14/00 (2006.01)
C12N 9/99 (2006.01)
C12N 9/10 (2006.01)

(52) U.S. Cl. ........ 435/184; 435/189; 435/193; 435/194; 435/196; 435/232; 530/402

(58) Field of Classification Search ............... 514/6, 569; 800/278; 435/193, 184, 189, 194, 196, 232; 530/402

See application file for complete search history.

(56) References Cited

U.S. PATENT DOCUMENTS

| | | | |
|---|---|---|---|
| 4,879,236 | A | 11/1989 | Smith et al. |
| 5,061,620 | A | 10/1991 | Tsukamoto et al. |
| 5,583,973 | A | 12/1996 | DeLisi et al. |
| 5,612,894 | A | 3/1997 | Wertz |
| 5,681,559 | A | 10/1997 | DiGiusto et al. |
| 5,871,986 | A | 2/1999 | Boyce |
| 6,140,363 | A | 10/2000 | Hur et al. |
| 6,335,195 | B1 | 1/2002 | Rodgers |
| 6,645,489 | B2 | 11/2003 | Pykett et al. |
| 6,667,064 | B2 | 12/2003 | Surette |
| 6,689,372 | B1 | 2/2004 | Holzl et al. |
| 6,740,311 | B2 | 5/2004 | White, Jr. |
| 7,863,029 | B2 * | 1/2011 | Jaffe ............... 435/184 |
| 2006/0162014 | A1 | 7/2006 | Jaffe | |

FOREIGN PATENT DOCUMENTS

| | | |
|---|---|---|
| WO | WO8402913 | 8/1984 |
| WO | WO9007861 | 7/1990 |
| WO | WO9110741 | 7/1991 |
| WO | WO9117271 | 11/1991 |
| WO | WO9118980 | 12/1991 |
| WO | WO9201047 | 1/1992 |
| WO | 9204449 A1 | 3/1992 |
| WO | 9206201 A1 | 4/1992 |
| WO | WO9306121 | 4/1993 |
| WO | WO9312227 | 6/1993 |
| WO | 9319189 A1 | 9/1993 |
| WO | WO9319189 | 9/1993 |
| WO | WO9408051 | 4/1994 |
| WO | WO9512608 | 5/1995 |
| WO | WO9530642 | 11/1995 |
| WO | WO9535503 | 12/1995 |
| WO | WO2005007817 | 1/2005 |

OTHER PUBLICATIONS

Pons et al., Eur. J. Biochem. 84, 257-266 (1978).*
Baker et al., Proteins: Structure, Function, and Genetics 12, 75-86 (1992)).*
Anfinsen, C.B. (1973) Principles that govern the folding of protein chains. Science 181 (96), 223-230.
Morgan, G.J. (2003) Historical review: viruses, crystals and geodesic domes. Trends Biochem Sci 28 (2), 86-90.
Koshland, D.E., Jr. et al. (1966) Comparison of experimental binding data and theoretical models in proteins containing subunits. Biochemistry 5 (1), 365-385.
Monod, J. et al. (1965) On the Nature of Allosteric Transitions: A Plausible Model. J Mol Biol 12, 88-118.
Jordan, P.M. (1994) Highlights in haem biosynthesis. Curr Opin Struct Biol 4 (6), 902-911.
Battersby, A.R. and Leeper, F.J. (1997) Biosynthesis of vitamin B12. Topics in Current Chemistry 195(Biosynthesis: Polyketides and Vitamins), 143-193.
Battersby, A.R. (2000) Tetrapyrroles: the pigments of life. Nat Prod Rep 17 (6), 507-526.
Jaffe, E.K. (2000) The porphobilinogen synthase family of metalloenzymes. Acta Crystallogr D Biol Crystallogr 56 ( Pt 2), 115-128.
Berman, H.M. et al. (2000) The Protein Data Bank. Nucleic Acids Res 28 (1), 235-242.
Jaffe, E.K. (2003) An unusual phylogenetic variation in the metal ion binding sites of porphobilinogen synthase. Chem Biol 10 (1), 25-34.
Jaffe, E.K. and Hanes, D. (1986) Dissection of the early steps in the porphobilinogen synthase catalyzed reaction. Requirements for Schiff's base formation. J Biol Chem 261 (20), 9348-9353.

(Continued)

Primary Examiner — Chih-Min Kam
(74) Attorney, Agent, or Firm — Caesar Rivise Bernstein Cohen & Pokotilow, Ltd.

(57) ABSTRACT

A composition having an agent adapted to affect a multimeric protein by binding to a binding site of the multimeric protein and thereby affecting an equilibrium of units, wherein the multimeric protein has an assembly having a plurality of said units, wherein each of the units has a first complementary surface and a second complementary surface and wherein the first complementary surface of one unit is associated with the second complementary surface of another unit, provided that the assembly is at least one of different quaternary isoforms on a condition that in the multimeric protein (1) a structure of each of the units determines a structure of the different quaternary isoforms, (2) the units are in the equilibrium and (3) the structure of the different quaternary isoforms influences a function of the multimeric protein.

9 Claims, 54 Drawing Sheets

OTHER PUBLICATIONS

Kervinen, J. et al. (2000) Porphobilinogen synthase from pea: expression from an artificial gene, kinetic characterization, and novel implications for subunit interactions. Biochemistry 39 (30), 9018-9029.

Petrovich, R.M. et al. (1996) Bradyrhizobium japonicum porphobilinogen synthase uses two Mg(II) and monovalent cations. J Biol Chem 271 (15), 8692-8699.

Bollivar, D.W. et al. (2004) Rhodobacter capsulatus porphobilinogen synthase, a high activity metal ion independent hexamer. BMC Biochem 5 (1), 17.

Kundrat, L. et al. (2003) A structural basis for half-of-the-sites metal binding revealed in Drosophila melanogaster porphobilinogen synthase. J. Biol. Chem. 278 (33), 31325-31330.

Bevan, D.R. et al. (1980) Mechanism of porphobilinogen synthase. Requirement of $Zn^{2+}$ for enzyme activity. J Biol Chem 255 (5), 2030-2035.

Snook, C.F. et al. (2003) Crystal structure of GDP-mannose dehydrogenase: a key enzyme of alginate biosynthesis in *P. aeruginosa*. Biochemistry 42 (16), 4658-4668.

Naught, L.E. et al. (2002) Allosterism and cooperativity in *Pseudomonas aeruginosa* GDP-mannose dehydrogenase. Biochemistry 41 (30), 9637-9645.

Poncet, S. et al. (2004) HPr kinase/phosphorylase, a Walker motif A-containing bifunctional sensor enzyme controlling catabolite repression in Gram-positive bacteria. Biochim Biophys Acta 1697 (1-2), 123-135.

Rochet, J.C. et al. (2000) Pig heart CoA transferase exists as two oligomeric forms separated by a large kinetic barrier. Biochemistry 39 (37), 11291-11302.

Bzowska, A. et al. (1995) Calf spleen purine nucleoside phosphorylase: purification, sequence and crystal structure of its complex with an N(7)-acycloguanosine inhibitor. FEBS Lett 367 (3), 214-218.

Koellner, G. et al. (1998) Crystal structure of the ternary complex of *E. coli* purine nucleoside phosphorylase with formycin B, a structural analogue of the substrate inosine, and phosphate (Sulphate) at 2.1 A resolution. J Mol Biol 280 (1), 153-166.

Poole, L.B. (2005) Bacterial defenses against oxidants: mechanistic features of cysteine-based peroxidases and their flavoprotein reductases. Arch Biochem Biophys 433 (1), 240-254.

Wood, Z.A. et al. (2002) Dimers to doughnuts: redox-sensitive oligomerization of 2-cysteine peroxiredoxins. Biochemistry 41 (17), 5493-5504.

Akagi, R. et al. (1999) A novel mutation of delta-aminolaevulinate dehydratase in a healthy child with 12% erythrocyte enzyme activity. Br J Haematol 106 (4), 931-937.

Maruno, M. et al. (2001) Highly heterogeneous nature of delta-aminolevulinate dehydratase (ALAD) deficiencies in ALAD porphyria. Blood 97 (10), 2972-2978.

Jaffe, E.K. (2004) The porphobilinogen synthase catalyzed reaction mechanism. Bioorg Chem 32 (5), 316-325.

Frankenberg, N. et al. (1999) High resolution crystal structure of a $Mg^{2+}$-dependent porphobilinogen synthase. J Mol Biol 289 (3), 591-602.

Kervinen, J. et al. (2001) Mechanistic basis for suicide inactivation of porphobilinogen synthase by 4,7-dioxosebacic acid, an inhibitor that shows dramatic species selectivity. Biochemistry 40 (28), 8227-8236.

Jaffe, E.K. et al. (1995) Characterization of the role of the stimulatory magnesium of *Escherichia coli* porphobilinogen synthase. Biochemistry 34 (1), 244-251.

Frankenberg, N. et al. (1999) Pseudomonas aeruginosa contains a novel type V porphobilinogen synthase with no required catalytic metal ions. Biochemistry 38 (42), 13976-13982.

Papenbrock, J. et al. (2000) Role of magnesium chelatase activity in the early steps of the tetrapyrrole biosynthetic pathway. Plant Physiol 122 (4), 1161-1169.

Papenbrock, J. and Grimm, B. (2001) Regulatory network of tetrapyrrole biosynthesis—studies of intracellular signalling involved in metabolic and developmental control of plastids. Planta 213 (5), 667-681.

Walker, D.A. (1976) Regulatory mechanisms in photosynthetic carbon metabolism. Curr Top Cell Regul 11, 203-241.

Stolz, M. and Dornemann, D. (1996) Purification, metal cofactor, N-terminal sequence and subunit composition of a 5-aminolevulinic acid dehydratase from the unicellular green alga Scenedesmus obliquus, mutant C-2A'. Eur J Biochem 236 (2), 600-608.

Tamai, H. et al. (1979) Plant Cell Physiol. 20, 435-444.

Breinig, S. et al. (2003) Control of tetrapyrrole biosynthesis by alternate quaternary forms of porphobilinogen synthase. Nat. Struct. Biol. 10, 757-763.

Frere, F. et al. (2002) Structure of porphobilinogen synthase from *Pseudomonas aeruginosa* in complex with 5-fluorolevulinic acid suggests a double Schiff base mechanism. J Mol Biol 320 (2), 237-247.

Friesner, R.A. et al. (2004) Glide: a new approach for rapid, accurate docking and scoring. 1. Method and assessment of docking accuracy. J Med Chem 47 (7), 1739-1749.

Halgren, T.A. et al. (2004) Glide: a new approach for rapid, accurate docking and scoring. 2. Enrichment factors in database screening. J Med Chem 47 (7), 1750-1759.

Cooperman, B.S. and Kashlan, O.B. (2003) A comprehensive model for the allosteric regulation of Class la ribonucleotide reductases. Adv Enzyme Regul 43, 167-182.

Dhanasekaran, S. et al. (2004) Delta-aminolevulinic acid dehydratase from Plasmodium falciparum: indigenous versus imported. J Biol Chem 279 (8), 6934-6942.

Irwin, J.J. and Shoichet, B.K. (2005) Zinc—a free database of commercially available compounds for virtual screening. J Chem Int Model 45 (1), 177-182.

Shimizu-Sato, S. et al. (2002) A light-switchable gene promoter system. Nat Biotechnol 20 (10), 1041-1044.

Daniell, H. et al. (1998) Containment of herbicide resistance through genetic engineering of the chloroplast genome. Nat. Biotechnol. 16 (4), 345-348.

Potrykus, I. et al. (1985) Molecular and general genetics of a hybrid foreign gene introduced into tobacco by direct gene transfer. Mol. Gen. Genet. 199 (2), 169-177.

Stalker, D.M. et al. (1988) Purification and properties of a nitrilase specific for the herbicide bromoxynil and corresponding nucleotide sequence analysis of the bxn gene. J. Biol. Chem. 263 (13), 6310-6314.

Thillet, J. et al. (1988) Site-directed mutagenesis of mouse dihydrofolate reductase. Mutants with increased resistance to methotrexate and trimethoprim. J. Biol. Chem. 263 (25), 12500-12508.

Fraley, R.T. et al. (1983) Expression of bacterial genes in plant cells. Proc. Natl. Acad. Sci. U S A 80 (15), 4803-4807.

Schmidhauser, T.J. and Helinski, D.R. (1985) Regions of broad-host-range plasmid RK2 involved in replication and stable maintenance in nine species of Gram-negative bacteria. J. Bacteriol. 164, 446-455.

Anderson, M.J. et al., Crystal Structure of a Hyperactive *Escherichia coli* Glycerol Kinase Mutant Gly230→Asp Obtained Using Microfluidic Crystallization Devices†‡, Biochemistry, 2007, vol. 46, pp. 5722-5731.

Avilan, L. et al., Hysteresis of cytosolic NADP-malic enzyme II from Trypanosoma cruzi, Molecular and Biochemical Parasitology, 1994, vol. 65, pp. 225-232.

Babady, N. et al., Cryptic proteolytic activity of dihydrolipoamide dehydrogenase, PNAS, Apr. 10, 2007, vol. 104, No. 15, pp. 6158-6163.

Barrientos, L.G. et al., The Domain-Swapped Dimer of Cyanovirin-N. Is in a Metastable Folded State: Reconciliation of X-Ray and NMR Structures, Structure, May 2002, vol. 10, pp. 673-686.

Barrientos, L. et al., The highly specific carbohydrate-binding protein C, Mini Rev Med Chem, Jan. 2005, 5 (1):21-31.

Besche, H. et al., Mutational analysis of conserved AAA+ residues in the archaeal Lon protease from Thermoplasma acidophilum, FEBS Letters, 2004, vol. 574, pp. 161-166.

Botos, I, et al., The Catalytic Domain of *Escherichia coli* Lon Protease Has a Unique Fold and a Ser-Lys Dyad in the Active Site*, The Journal of Biological Chemistry, vol. 279, No. 9, Feb. 27, 2004, pp. 8140-8148.

Cai, G. et al., Regulation and quaternary structural changes in rabbit muscle phosphofructokinase, Biophysical Chemistry, 1990, vol. 37, pp. 97-106.

Chang, G. et al., Reversible dissociation of the catalytically active subunits of pigeon liver malic enzyme, Biochem. J. 1988, vol. 254, pp. 123-130.

Chazarra, S., et al., Hysteresis and Positive Cooperativity of Iceberg Lettuce Polyphenol Oxidase, Biochemical and Biophysical Research Communications, 2001, vol. 289, pp. 769-775.

Chung, C.H., et al., The product of the lon (capR) gene in *Escherichia coli* is the ATP-dependent protease, protease La, Proc. Natl. Acad. Sci., Aug. 1981, vol. 78, No. 8, pp. 4931-4935.

de Riel, J.K., et al., Subunit Dissociation in the Allosteric Regulation of Glycerol Kinase from *Escherichia coli*, 2. Physical Evidence†, Subunit Dissociation of Glycerol Kinase 2, 1978, vol. 17, No. 24, pp. 5141-5146.

DeZoysa, L., et al., Evaluation of Types of Interactions in Subunit Association in *Bacillus subtilis Adenylosuccinate Lyase*†, Biochemistry, 2008, vol. 47, pp. 2923-2934.

Dey, S. et al., Crystal Structure of Mycobacterium tuberculosis D-3-Phosphoglycerate Dehydrogenase, The Journal of Biological Chemistry, Apr. 15, 2005, vol. 280, No. 15, pp. 14892-14899.

Edwards, G.E. et al., Review Article No. 66, NADP-Malic Enzyme From Plants, Phytochemistry, 1992, vol. 31, No. 6, pp. 1845-1857.

Felicetti, B. et al., Aristolochene Synthase: Mechanistic Analysis of Active Site Residues by Site-Directed Mutagenesis, J. Am. Chem. Soc., 2004, vol. 126, pp. 7212-7221.

Flatmark, T., Structural Insight into the Aromatic Amino Acid Hydroxylases and Their Disease-Related Mutant Forms, Chem. Rev. 1999, vol. 99, pp. 2137-2160.

Goda, S., et al., Intersubunit Interaction Induced by Subunit Rearrangement Is Essential for the Catalytic Activity of the Hyperthermophilic Glutamate Dehydrogenase from Pyrobaculum islandicum†, Biochemistry, 2005, vol. 44, 15304-15313.

Guranowski, A. et al., Adenosylhomocysteinase from Yellow Lupin Seeds, Purification and Properties, Eur. J. Biochem., 1977, vol. 80, pp. 517-523.

Hardman, M.J. et al., Kinetics of activation of L-lactate dehydrogenase from Streptococcus faecalis by fructose 1,6-bisphosphate and by metal ions, Biochimica et Biophysica Acta, 1987, vol. 912, pp. 185-190.

Harel, E., et al., Interconversion of Sub-units of catechol oxidase from Apple Chloroplasts, Phytochemistry, 1968, vol. 7, pp. 199-204.

Hartmann, H. et al., [5] Small-Angle Scattering Techniques for Analyzing Conformational Transitions in Hemocyanins, Methods in Enzymology, 2004, vol. 379, pp. 81-106.

Hoang, J.V. et al., Trapping Choline Oxidase in a Nonfunctional Conformation by Freezing at Low pH, Proteins: Structure, Function, and Bioinformatics, 2007, vol. 66, pp. 611-620.

Hohman, R.J., et al., Purification of S-Adenosyl-L-homocysteine Hydrolase from Dictyostelium discoideum: Reversible Inactivation by cAMP and 2-Deoxyadenosine, Archives of Biochemistry and Biophysics, Sep. 1984, vol. 233, No. 2, pp. 785-795.

Hohn, T.M., et al., Purification and Characterization of the Sesquiterpene Cyclase Aristolochene Synthase from *Penicillium roqueforti*, Archives of Biochemistry and Biophysics, Jul. 1989, vol. 272, No. 1, pp. 137-143.

Jensen, K.F. et al., Different oligomeric states are involved in the allosteric behavior of uracil phosphoribosyltransferase from *Escherichia coli*, Eur. J. Biochem. 1996, vol. 240, pp. 637-645.

Jerebzoff-Quintin, S., et al., L-Asparaginase activity in *Leptosphaeria michotii*. Isolation and properties of two forms of the enzyme, Physiol, Plant., Copenhagen 1985, vol. 64, pp. 74-80.

Jolley, R.L., et al., The Multiple Forms of Mushroom Tyrosinase, J.X. Khym, Mar. 1965, vol. 240, No. 3, pp. 1489-1491.

Jolley, R.L., et al., The Multiple Forms of Mushroom Tyrosinase, The Journal of Biological Chemistry, Jun. 25, 1969, vol. 244, No. 12, pp. 3251-3257.

Kajander, E.O. et al., Affinity-chromatographic purification of S-adenosyl-L-homocysteine hydrolase, Biochem. J., 1981, vol. 193, pp. 503-512.

Kotaka, M. et al., Structures of R- and T-state *Escherichia coli* Aspartokinase III, Mechanisms of the Allosteric Transition and Inhibition by Lysine*, Journal of Biological Chemistry, Oct. 20, 2006, vol. 281, No. 42, pp. 31544-31552.

Kwon, K. et al., Function of a conserved sequence motif in biotin holoenzyme synthetases, Protein Science, 2000, vol. 9, pp. 1530-1539.

Maurus, R., et al., Insights into the Evolution of Allosteric Properties. The NADH Binding Site of Hexameric Type II Citrate Synthasestt, Biochemistry, 2003, vol. 42, pp. 5555-5565.

Massey, V. et al., A Temperature-dependent Conformational Change in D-Amino Acid Oxidase and Its Effect on Catalysis, The Journal of Biological Chemistry, May 25, 1966, vol. 241, No. 10, pp. 2347-2357.

Mallette, M. et al., On the nature of highly purified mushroom tyrosina, Archives of biochemisstry, 1949, vol. 23, No. 1, pp. 29-44.

Meyer, C.R., et al., Regulation of Phosphoenolpyruvate Carboxylase from Crassula argentea: Effect of Incubation with Ligands and Dilution on Oligomeric State, Activity, and Allosteric Properties, Archives of Biochemistry and Biophysics, Aug. 1, 1991, vol. 288, No. 2, pp. 343-349.

Ngam-Ek, A., et al., Malate-Induced Hysteresis of Phosphoenolpyruvate Carboxylase from Crassula argentea, Plant Physiol., 1989, vol. 91, pp. 954-960.

Park, S., et al., Oligomeric Structure of the ATP-dependent Protease La (Lon) of *Escherichia coli*, Mol. Cells, 2006, vol. 21, No. 1, pp. 129-134.

Roudiak, S.G., et al., Functional Role of the N-Terminal Region of the Lon Protease from *Mycobacterium smegmatis*, Biochemistry, 1998, vol. 37, pp. 11255-11263.

Shatilov, V.R., et al., Coenzyme non-specific glutamate dehydrogenase from *Chlorella pyrenoidosa* 82T: electron microscopic studies, Biochimica et Biophysica Acta., 1989, vol. 995, pp. 17-20.

Shen, Y. et al., A Mechanism for the Potent Inhibition of Eukaryotic Acetyl-Coenzyme A Carboxylase by Soraphen A, a Macrocyclic Polyketide Natural Product, Molecular Cell, vol. 16, Dec. 22, 2004, vol. 16, pp. 881-891.

Simanshu, D.K. et al., Crystal Structures of *Salmonella typhimurium* Biodegradative Threonine Deaminase and Its Complex with CMP Provide Structural Insights into Ligand-induced Oligomerization and Enzyme Activation, Journal of Biological Chemistry, Dec. 22, 2006, vol. 281, No. 51, pp. 39630-39641.

Stahlberg, H. et al., Mitochondrial Lon of *Saccharamyces cerevisiae* is a ring-shaped protease with seven flexible subunits, Proc. Natl., Acad. Sci., Jun. 1999, vol. 96, pp. 6787-6790.

Stewart, L. et al., Kinetic parameters for dimeric and tetrameric forms of bovine dopamine β-monooxygenase and their relationship to non-Michaelis-Menten behavior, FEBS Letters, 1999, vol. 454, pp. 229-232.

Trompier, D. et al., Transition from Dimers to Higher Oligomeric Forms Occurs during the ATPase Cycle of the ABCA1 Transporter, Journal of Biological Chemistry, Jul. 21, 2006, vol. 281, No. 29, pp. 20283-20290.

Tsilibaris, V. et al., Biological roles of the Lon ATP-dependent protease, Research in Microbiology, 2006, vol. 157, pp. 701-713.

Wang, C. et al., Association-Dissociation and Abnormal Kinetics of Bovine α-Acetylgalactosaminidase, Biochemistry, 1971, vol. 10, No. 6, pp. 1067-1072.

Wohl, R.C., et al., Phosphoenolpyruvate Carboxylase of *Escherichia coli*, Journal of Biological Chemistry, Sep. 25, 1972, vol. 247, No. 18, pp. 5785-5792.

Xing, C. et al., Identification of GAPDH as a protein target of the saframycin antiproliferative agents, PNAS, Apr. 20, 2004, vol. 101, No. 16, pp. 5862-5866.

Yu, P. et al., Linkage between Fructose 1,6-Bisphosphate Binding and the Dimer-Tetramer Equilibrium of *Escherichia coli* Glycerol Kinase: Critical Behavior Arising from Change of Ligand Stoichiometry, Biochemistry, 2003, vol. 42, pp. 4243-4252.

Yun, M. et al., Crystal Structure and Allosteric Regulation of the Cytoplasmic *Escherichia coli* L-Asparaginase I, J. Mol. Biol. 2007, vol. 369, pp. 794-811.

Jaffe et al., "Morpheeins—a new structural paradigm for allosteric regulation", Trends in Biochemical Sciences, Elsevier, Haywards, GB, vol. 30, No. 9, Sep. 1, 2005, pp. 490-497.

Kimmel et al., "Inactivation of GDP-mannose dehydrogenase from *Pseudomonas aeruginosa* by penicllic acid identifies a critical active site loop", Archives of Biochemistry and Biophysics, NY, US, vol. 441, No. 2, Sep. 15, 2005, pp. 132-140.
Supplementary European Search Report for EP 06 77 3249, (Jun. 2008).

U.S. Appl. No. 11/327,762, filed Jan. 6, 2006.
U.S. Appl. No. 12/106,498, filed Apr. 21, 2008.

* cited by examiner (PRIOR ART)

Porphobilinogen Synthase sequences for Eubacteria available April 2002 - Metal binding site Information

| NCBI TAXONOMIC CLASSIFICATION | SPECIES NAME | ACTIVE SITE AMINO ACIDS, (numbered as for human PBGS) 120 | | | | | | | | | | | | | | 134 | 221 | | | | 225 |
|---|---|---|---|---|---|---|---|---|---|---|---|---|---|---|---|---|---|---|---|---|---|
| Firmicutes; Actinobacteria | *Streptomyces coelicolor A3(2)* | D | L | C | L | D | E | F | T | D | H | G | H | C | G | V | R | K | T | Y | Q |
| Firmicutes; Actinobacteria | *Propionibacterium freudenreichii subsp. shermanii* | D | V | C | L | D | E | F | T | D | H | G | H | C | G | V | R | R | A | Y | Q |
| Firmicutes; Actinobacteria | *Mycobacterium tuberculosis H37Rv* | D | T | C | L | D | E | F | T | D | H | G | H | C | G | V | R | R | T | Y | Q |
| Firmicutes; Actinobacteria | *Mycobacterium avium* | D | T | C | L | D | E | F | T | D | H | G | H | C | G | V | R | R | T | Y | Q |
| Firmicutes; Actinobacteria | *Mycobacterium leprae* | D | T | C | L | D | E | F | T | D | H | G | H | C | G | V | R | R | T | Y | Q |
| Firmicutes; Actinobacteria | *Mycobacterium bovis* | D | T | C | L | D | E | F | T | D | H | G | H | C | G | V | R | R | T | Y | Q |
| Firmicutes; Actinobacteria | *Mycobacterium smegmatis* | D | T | C | L | D | E | F | T | D | H | G | H | C | G | V | R | R | T | Y | Q |
| Firmicutes; Actinobacteria | *Corynebacterium diphtheriae* | D | T | C | L | D | E | F | T | D | H | G | H | C | G | I | R | R | A | Y | Q |
| Firmicutes; Bacillus/Clostridium group | *Staphylococcus epidermidis* | D | T | C | L | C | E | Y | T | D | H | G | H | C | G | V | R | K | T | Y | Q |
| Firmicutes; Bacillus/Clostridium group | *Staphylococcus aureus* | D | T | C | L | C | E | Y | T | D | H | G | H | C | G | V | R | K | T | Y | Q |
| Firmicutes; Bacillus/Clostridium group | *Bacillus subtilis* | D | T | C | L | C | E | Y | T | D | H | G | H | C | G | L | R | K | T | Y | Q |
| Firmicutes; Bacillus/Clostridium group | *Bacillus halodurans* | D | T | C | L | C | Q | F | T | D | H | G | H | C | G | V | R | K | T | Y | Q |
| Firmicutes; Bacillus/Clostridium group | *Bacillus anthracis* | D | T | C | L | C | Q | F | T | S | H | G | H | C | G | V | R | K | T | Y | Q |
| Firmicutes; Bacillus/Clostridium group | *Geobacillus stearothermophilus* | D | T | C | L | C | E | Y | T | S | H | G | H | C | G | V | R | K | T | Y | Q |
| Firmicutes; Bacillus/Clostridium group | *Listeria innocua* | D | T | C | L | C | E | F | T | D | H | G | H | C | G | V | R | K | S | Y | Q |
| Firmicutes; Bacillus/Clostridium group | *Listeria monocytogenes EGD-e* | D | T | C | L | C | E | F | T | D | H | G | H | C | G | V | R | K | S | Y | Q |
| Firmicutes; Bacillus/Clostridium group | *Desulfitobacterium hafniense* | D | V | C | L | C | E | Y | T | D | H | G | H | C | G | V | R | R | T | Y | Q |
| Firmicutes; Bacillus/Clostridium group | *Selenomonas ruminantium* | D | V | C | M | C | E | Y | T | D | H | G | H | C | G | H | R | R | Q | Y | Q |
| Firmicutes; Bacillus/Clostridium group | *Clostridium botulinum* | D | V | C | M | C | Q | Y | T | S | H | G | H | C | G | I | R | K | T | Y | Q |
| Firmicutes; Bacillus/Clostridium group | *Clostridium difficile* | D | V | C | M | C | Q | Y | T | S | H | G | H | C | G | I | R | K | T | Y | Q |
| Firmicutes; Bacillus/Clostridium group | *Clostridium josui* | D | I | C | M | C | E | Y | T | S | H | G | H | C | G | I | | | | | |
| Firmicutes; Bacillus/Clostridium group | *Clostridium acetobutylicum* | D | V | C | M | C | E | Y | T | S | H | G | H | C | G | I | R | K | S | Y | Q |
| Firmicutes; Bacillus/Clostridium group | *Clostridium perfringens* | D | V | C | M | C | E | Y | T | S | H | G | H | C | G | I | R | K | T | Y | Q |
| Aquificae | *Aquifex aeolicus* | D | V | C | F | C | E | Y | T | T | H | G | H | C | G | V | R | R | T | Y | Q |
| Thermus/Deinococcus group | *Deinococcus radiodurans* | D | T | C | L | C | E | Y | T | S | H | G | H | C | G | H | R | A | S | Y | Q |
| Fibrobacter/Acidobacteria group | *Fibrobacter succinogenes* | D | V | C | L | C | E | Y | M | S | H | G | H | C | G | I | R | K | S | Y | Q |
| Chloroflexi | *Chloroflexus aurantiacus* | | | | | | | | | | | | | | | | R | S | Q | Y | Q |
| Proteobacteria; delta subdivision; Desulfuromonas group | *Geobacter sulfurreducens* | D | V | C | M | C | E | Y | T | D | H | G | H | C | G | I | R | R | S | Y | Q |
| Proteobacteria; delta subdivision; Desulfovibrio | *Desulfovibrio vulgaris* | D | V | C | L | C | E | Y | T | D | H | G | H | C | G | L | R | K | T | Y | Q |
| Proteobacteria; epsilonsubdivision; Campylobacter group | *Campylobacter jejuni* | D | L | C | F | C | E | Y | T | D | H | G | H | C | G | I | R | K | S | Y | Q |
| Proteobacteria; epsilonsubdivision; Helicobacter group | *Helicobacter pylori 26695* | D | L | C | F | C | E | Y | T | D | H | G | H | C | G | I | R | K | S | Y | Q |
| Proteobacteria; epsilonsubdivision; Helicobacter group | *Helicobacter pylori J99* | D | L | C | F | C | E | Y | T | D | H | G | H | C | G | I | R | K | S | Y | Q |
| Proteobacteria; magnetotactic cocci | *Magnetococcus spMC-1* | D | V | C | M | C | E | Y | T | D | H | A | H | C | G | I | R | R | G | Y | Q |
| Proteobacteria; gamma subdivision; Pseudomonadaceae | *Pseudomonas fluorescens* | D | T | C | F | C | E | Y | T | D | H | G | H | C | G | V | R | K | S | Y | Q |
| Proteobacteria; gamma subdivision; Legionellaceae group | *Coxiella burnetii* | D | L | C | F | C | E | Y | T | D | H | G | H | C | G | V | R | K | T | Y | Q |
| Proteobacteria; gamma subdivision; Legionellaceae group | *Legionella pneumophila* | D | L | C | F | C | E | Y | T | D | H | G | H | C | G | V | R | K | A | Y | Q |
| Proteobacteria; gamma subdivision; Acidithiobacillus | *Thiobacillus ferrooxidans* | D | A | C | F | C | E | Y | T | A | H | G | H | C | G | V | R | K | G | Y | Q |
| Proteobacteria; gamma subdivision; Enterobacteriaceae | *Escherichia coli* | D | T | C | F | C | E | Y | T | S | H | G | H | C | G | V | R | K | S | Y | Q |
| Proteobacteria; gamma subdivision; Enterobacteriaceae | *Salmonella enterica subsp. enterica serovar Typhi]* | D | T | C | F | C | E | Y | T | S | H | G | H | C | G | V | R | K | T | Y | Q |
| Proteobacteria; gamma subdivision; Enterobacteriaceae | *Salmonella enteritidis* | D | T | C | F | C | E | Y | T | S | H | G | H | C | G | V | R | K | T | Y | Q |
| Proteobacteria; gamma subdivision; Enterobacteriaceae | *Salmonella typhimurium LT2* | D | T | C | F | C | E | Y | T | S | H | G | H | C | G | V | R | K | T | Y | Q |
| Proteobacteria; gamma subdivision; Enterobacteriaceae | *Yersinia enterocolitica* | D | V | A | L | D | P | Y | T | T | H | G | Q | D | G | V | K | K | T | Y | Q |
| Proteobacteria; gamma subdivision; Enterobacteriaceae | *Yersinia pestis* | D | V | A | L | D | P | Y | T | T | H | G | Q | D | G | V | K | K | T | Y | Q |
| Proteobacteria; gamma subdivision; Pseudomonadaceae | *Pseudomonas syringae* | D | V | A | L | D | P | F | T | T | H | G | Q | D | G | I | K | A | S | Y | Q |
| Proteobacteria; gamma subdivision; Pseudomonadaceae | *Pseudomonas aeruginosa* | D | V | A | L | D | P | F | T | T | H | G | Q | D | G | I | K | A | T | Y | Q |
| Proteobacteria; gamma subdivision; Pasteurellaceae | *Actinobacillus actinomycetemcomitans* | D | V | A | L | D | P | Y | T | V | H | G | Q | D | G | I | K | K | T | Y | Q |

Figure 15C

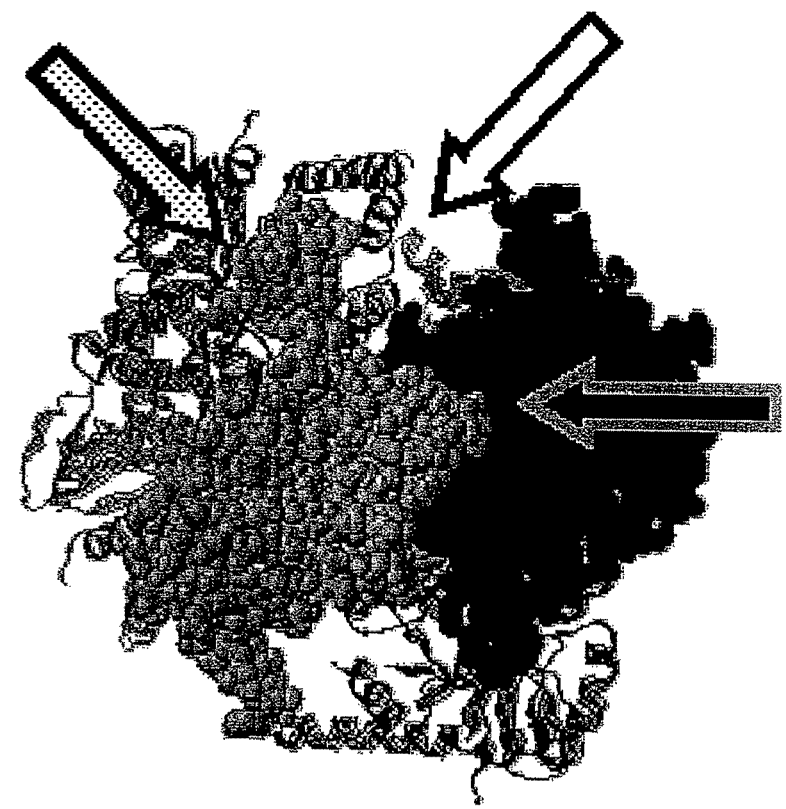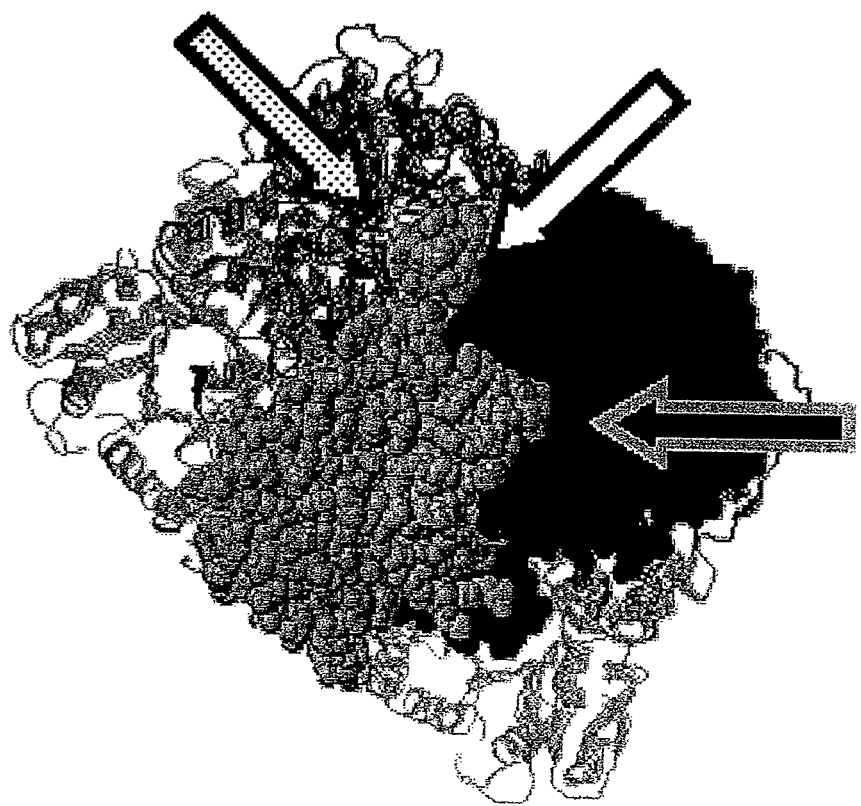
Figure 18B

Human hexamer
structure favored by
Leu-12 containing
chains

Human octamer
structure favored by
Phe-12 containing
chains

Spheres show water molecules that are within 4.0 Å of both subunits A and B.

Figure 30
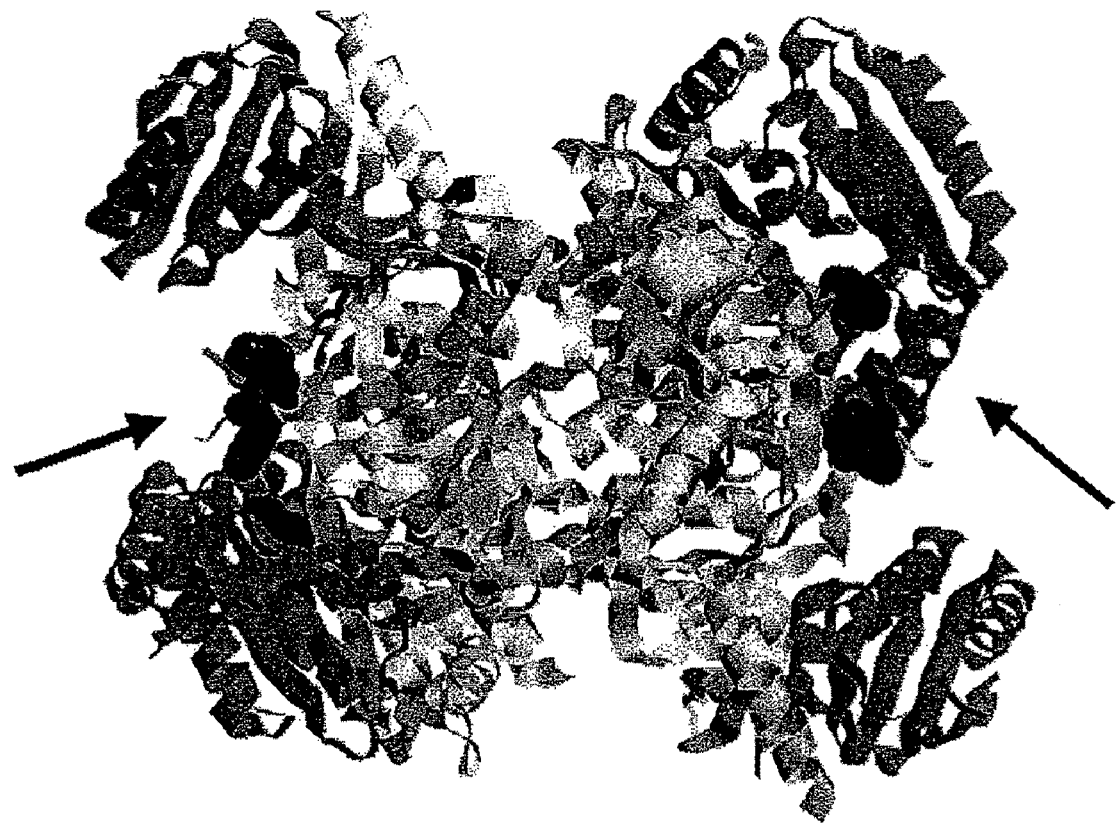

Figure 32
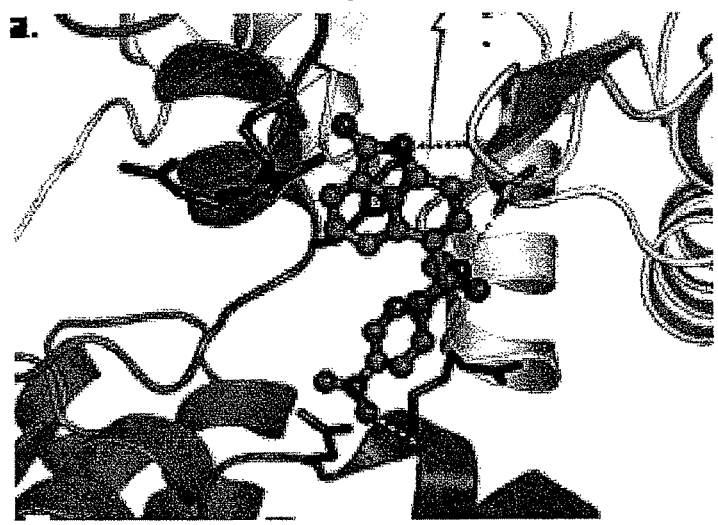
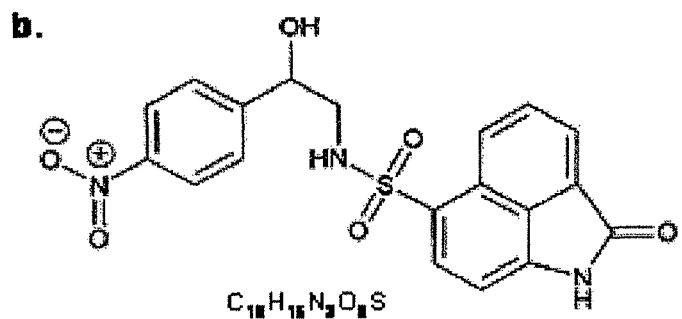
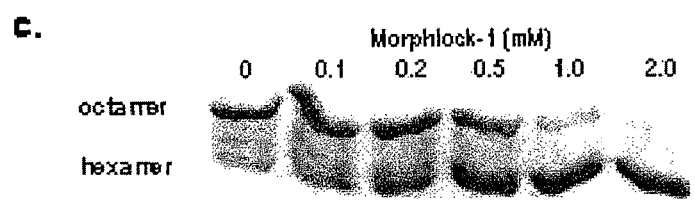
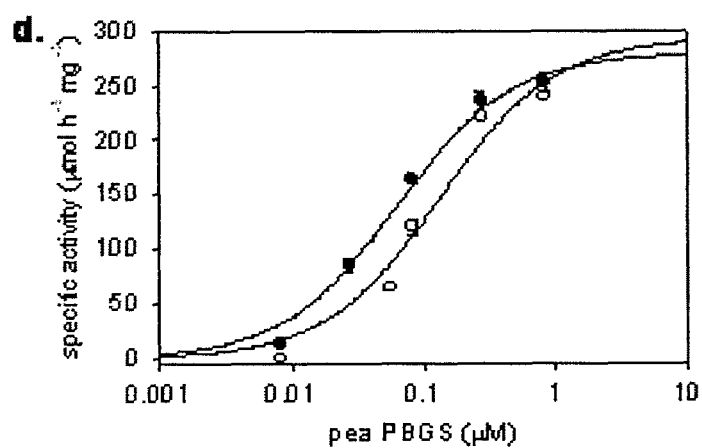

Figure 34
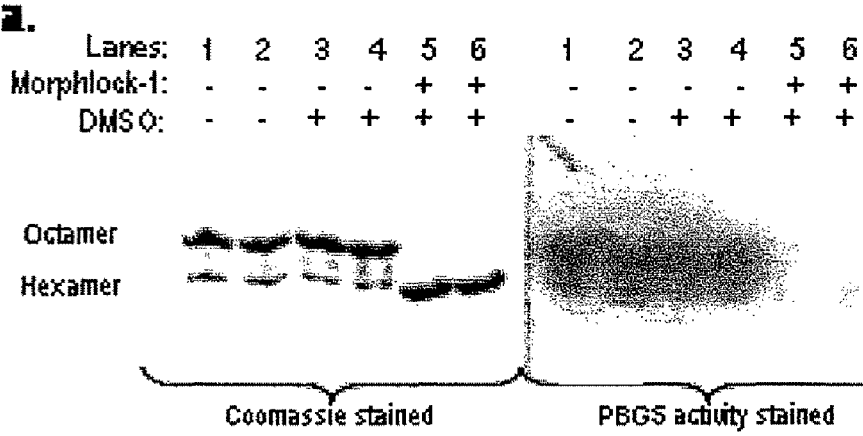
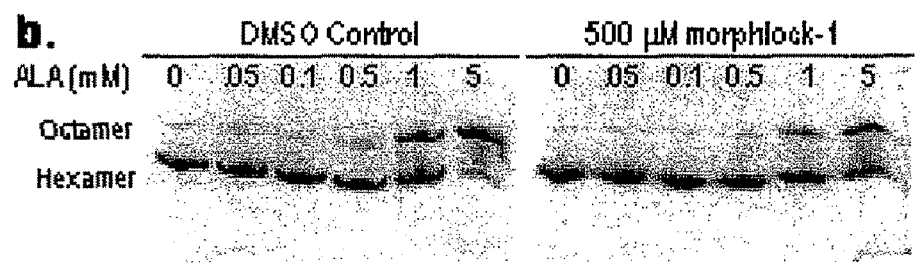
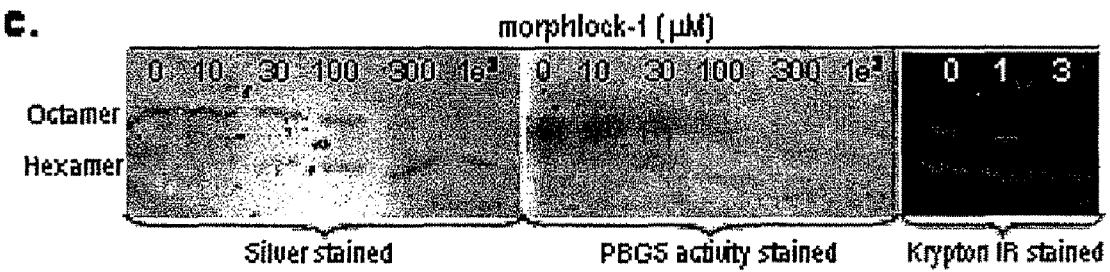

Figure 37
A
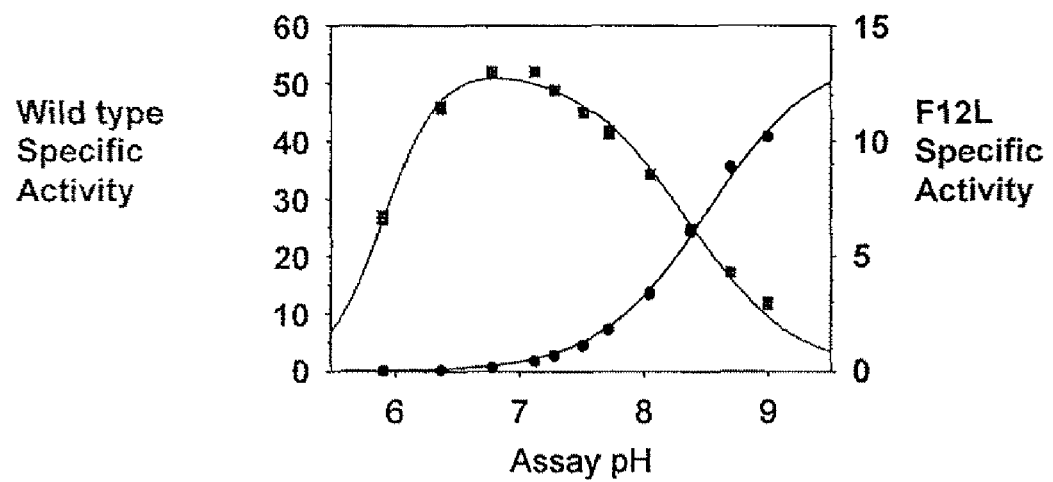
B
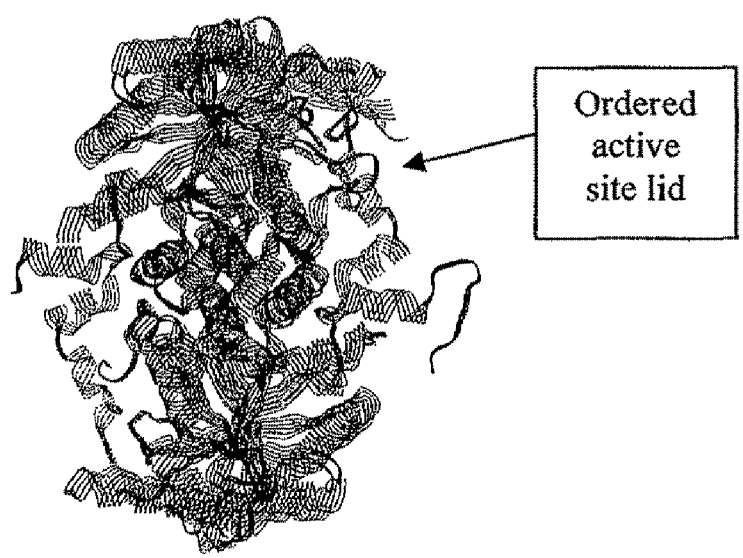
Ordered active site lid

SEQUENCE LISTING

```
<160> NUMBER OF SEQ ID NOS: 153

<210> SEQ ID NO 1
<211> LENGTH: 3142
<212> TYPE: DNA
<213> ORGANISM: Homo sapiens

<400> SEQUENCE: 1
cttacgcggt ctgtgggaga ccggagcggg agacagcggt gacaggagca gcggccggga      60
gcccttaggg aggcagacag agcctgcagc caatgcccca ggagccctcg gttccaacca     120
actgatgccc ctgtgcccac tggcccacgc catgcagccc cagtccgttc tgcacagcgg     180
ctacttccac ccactacttc gggcctggca gacagccacc accaccctca atgcctccaa     240
cctcatctac cccatctttg tcacggatgt tcctgatgac atacagccta tcaccagcct     300
cccaggagtg gccaggtatg gtgtgaagcg gctggaagag atgctgaggc ccttggtgga     360
agagggccta cgctgtgtct tgatctttgg cgtccccagc agagttccca aggacgagcg     420
gggttccgca gctgactccg aggagtcccc agctattgag gcaatccatc tgttgaggaa     480
gaccttcccc aacctcctgg tggcctgtga tgtctgcctg tgtcctaca cctcccatgg      540 tcactgcggg ctcctgagtg aaaacggagc attccgggct gaggagagcc gccagcggct     600
ggctgaggtg gcattggcgt atgccaaggc aggatgtcag gtggtagccc cgtcggacat     660
gatggatgga cgcgtggaag ccatcaaaga ggccctgatg gcacatggac ttggcaacag     720
ggtatcggtg atgagctaca gtgccaaatt tgcttcctgt ttctatggcc ctttccggga     780
tgcagctaag tcaagcccag cttttgggga ccgccgctgc taccagctgc ccctggagc     840 acgaggcctg gctctccgag ctgtggaccg ggatgtacgg gaaggagctg acatgctcat     900
ggtgaagccg ggaatgccct acctggacat cgtgcggag gtaaaggaca agcaccctga      960
cctccctctc gccgtgtacc acgtctctgg agagtttgcc atgctgtggc atggagccca    1020
ggccggggca tttgatctca aggctgccgt actggaggcc atgactgcct tccgcagagc    1080
aggtgctgac atcatcatca cctactacac accgcagctg ctgcagtggc tgaaggagga    1140
atgatggaga cagtgccagg cccaagaact agaactttaa aacgttcccg gggcctcaga    1200
caagtgaaaa ccaaagtaaa tgctgctttt agaactgtgc cctcatgccc tcttcctgct    1260
cacatgctag cggggcccag cagccctggg tggttttgcc agcatgctaa ctcttgtaac    1320
tcgcagctgc atcctatgag ctctcccaag cttccccgcc cctccctgg gtcagccgtg     1380 aggcccacct ttgccaccct cagctctttc ctctggtgtg gcttcagctt gaaagcaacc    1440
tggagtcggg ggcacagcct ttggggcctg gctgggagag ggtcttggag cattagggga    1500
agaagagagc agtgggatct tggggcctga gaagccttgg aacgcttctg gcagcagagc    1560
tgggtgtggg aatgaggcc agatcgatat ccctgggtta gagttgaaat tgccgcaat     1620
```

```
tccactggaa ggcatttccc acgaggccag aggttgccag gctgcctgag gtctcctatt    1680
ctactctgaa ccataaaccc agagaagaat tactcattaa ccagcataaa tactgcctga    1740
ggatcaaaac tcagaggcaa agagggagtt cctgactgct agaggtgcca ccaccacaaa    1800
cactttttat tcaggagata cttttttgaga atctctgctc tgttcctagg ttcagtgctg    1860
ggtcctggga atacagcagg acagacctca gcttatctct tcatagaaat tatacaaaga    1920
gaattgggga gacagctaag aagaaaacaa agaaataaag cagttacaaa ttgtgataag    1980
tgctttgaag gaaagaaggg gtctgagaca acaacaggga aggggcctct cttgaaacag    2040
tagttgggaa ggaggcagac atgcaccagt gatgtggtga caggtgctct gaaggaggtc    2100
accaggacct gacctctttg aaggatcaga aaatacttcc ctgaaggact gacatttgag    2160
cctagacctg aagggtgagc catcaagcta agacaattgg ggaagagcat tccagggaga    2220
gggaggagtt gtgcaaaggc cctggggctc cttctagctg gaggaatgca aggctagctt    2280
gtctggagca ctgagaggat ggcctgaact gagtggagag agacagacca ggaccaaacc    2340
atgcagaggt caagggccac attcaccttt tcagagtgac tcaatcaaat ttgtagtttg    2400
taaaagtatt ttaacagctc tgcggcaaag tgcaaatgaa aagtcttgat ggcatggact    2460
ggagcgggga cagtggggat ggagaaaggg gaatggattg tggatgtgtt tagaaggtag    2520
attcgatgtg aaggatgaat ctggcttgac cttctgggtg gctgatgggc catttactga    2580 gatgggcag cctggaagag gaacagaagc agggtcgggg tggagggaga atactaaact    2640
tagcttgaga cattttgcaa taaggaagct atatctagag tgcttatgtg actcacctaa    2700
ggccactcaa caagtttgtg gcagaactgg attagaactg cacagaaaac agccaagctg    2760
ggatttgaac ccatgtagtc caactccaag gcctctgccc ctaaccactg tgccatacca    2820
cctcccaata atcaacagca aaattatagg tctaacaatg ttttatagac acccctccat    2880
ttatgtgatg ggttttgcatc ctgataaacc catcataagt tgaaaatatg atcataagtt    2940
gaaaatatga tcataagtca aaaatgtatt taatatacct aacctaccaa acatcatagc    3000
ttagcctagc ctgccttaaa catgctcaga acacttacat tagcctacag tgggcaaaac    3060
tatccaacac aaaatctata ttgtaataaa gttgtaaaga attttgaata aaaattcaat    3120
atttgaaaaa aaaaaaaaa aa                                              3142

<210> SEQ ID NO 2
<211> LENGTH: 1154
<212> TYPE: DNA
<213> ORGANISM: Homo sapiens

<400> SEQUENCE: 2
gcagccaaag ccccaggagc cctaggttcc aaccaactga tgcccctgtg cccactggcc      60
cacgccatgc agccccagtc cgttctgcac agcggctact ccacccact acttcgggcc     120 tggcagacag ccaccaccac cctcaatgcc tccaacctca tctacccat cttttgtcacg     180 gatgttcctg atgacataca gcctatcacc agcctcccag gagtggccag gtatggtgtg     240
aagcggctgg aagagatgct gaggcccttg gtggaagagg gcctacgctg tgtcttgatc     300
tttggcgtcc ccagcagagt tcccaaggac gagcggggtt ccgcagctga ctccgaggag     360
tccccagcta ttgaggcaat ccatctgttg aggaagacct tccccaacct cctggtggcc     420
tgtgatgtct gcctgtgtcc ctacacctcc catggtcact gcgggctcct gagtgaaaac     480
ggagcattcc gggctgagga gagccgccag cggctggctg aggtggcatt ggcgtatgcc     540
aaggcaggat gtcaggtggt agccccgtcg gacatgatgg atggacgcgt ggaagccatc      600
```

-continued

```
aaagaggccc tgatggcaca tggacttggc aacagggtat cggtgatgag ctacagtgcc    660
aaatttgctt cctgtttcta tggccctttc cgggatgcag ctaagtcaag cccagctttt    720
ggggaccgcc gctgctacca gctgcccct ggagcacgag gcctggctct ccgagctgtg    780
gaccgggatg tacgggaagg agctgacatg ctcatggtga agccgggaat gccctacctg    840
gacatcgtgc gggaggtaaa ggacaagcac cctgacctcc ctctcgccgt gtaccacgtc    900
tctggagagt ttgccatgct gtggcatgga gcccaggccg gggcatttga tctcaaggct    960
gccgtactgg aggccatgac tgccttccgc agagcaggtg ctgacatcat catcacctac   1020
tacacaccgc agctgctgca gtggctgaag aggaatgat ggaggacagt gccaggccca   1080
agaactagaa ctttcaaacg ttcccggggc ctcagacaag tgacaaccaa agtaaatgct   1140
gcttttagaa ctgt                                                     1154
```

<210> SEQ ID NO 3
<211> LENGTH: 330
<212> TYPE: PRT
<213> ORGANISM: Homo sapiens

<400> SEQUENCE: 3

```
Met Gln Pro Gln Ser Val Leu His Ser Gly Tyr Phe His Pro Leu Leu
1               5                   10                  15

Arg Ala Trp Gln Thr Ala Thr Thr Thr Leu Asn Ala Ser Asn Leu Ile
            20                  25                  30

Tyr Pro Ile Phe Val Thr Asp Val Pro Asp Asp Ile Gln Pro Ile Thr
        35                  40                  45

Ser Leu Pro Gly Val Ala Arg Tyr Gly Val Lys Arg Leu Glu Glu Met
    50                  55                  60

Leu Arg Pro Leu Val Glu Glu Gly Leu Arg Cys Val Leu Ile Phe Gly
65                  70                  75                  80

Val Pro Ser Arg Val Pro Lys Asp Glu Arg Gly Ser Ala Ala Asp Ser
                85                  90                  95

Glu Glu Ser Pro Ala Ile Glu Ala Ile His Leu Leu Arg Lys Thr Phe
            100                 105                 110

Pro Asn Leu Leu Val Ala Cys Asp Val Cys Leu Cys Pro Tyr Thr Ser
        115                 120                 125

His Gly His Cys Gly Leu Leu Ser Glu Asn Gly Ala Phe Arg Ala Glu
    130                 135                 140

Glu Ser Arg Gln Arg Leu Ala Glu Val Ala Leu Ala Tyr Ala Lys Ala
145                 150                 155                 160

Gly Cys Gln Val Val Ala Pro Ser Asp Met Met Asp Gly Arg Val Glu
                165                 170                 175

Ala Ile Lys Glu Ala Leu Met Ala His Gly Leu Gly Asn Arg Val Ser
            180                 185                 190

Val Met Ser Tyr Ser Ala Lys Phe Ala Ser Cys Phe Tyr Gly Pro Phe
        195                 200                 205

Arg Asp Ala Ala Lys Ser Ser Pro Ala Phe Gly Asp Arg Arg Cys Tyr
    210                 215                 220

Gln Leu Pro Pro Gly Ala Arg Gly Leu Ala Leu Arg Ala Val Asp Arg
225                 230                 235                 240

Asp Val Arg Glu Gly Ala Asp Met Leu Met Val Lys Pro Gly Met Pro
                245                 250                 255

Tyr Leu Asp Ile Val Arg Glu Val Lys Asp Lys His Pro Asp Leu Pro
            260                 265                 270

Leu Ala Val Tyr His Val Ser Gly Glu Phe Ala Met Leu Trp His Gly
```

```
                  275                 280                 285
Ala Gln Ala Gly Ala Phe Asp Leu Lys Ala Ala Val Leu Glu Ala Met
            290                 295                 300

Thr Ala Phe Arg Arg Ala Gly Ala Asp Ile Ile Ile Thr Tyr Tyr Thr
305                 310                 315                 320

Pro Gln Leu Leu Gln Trp Leu Lys Glu Glu
                325                 330

<210> SEQ ID NO 4
<211> LENGTH: 27
<212> TYPE: DNA
<213> ORGANISM: Homo sapiens

<400> SEQUENCE: 4
ggctacctcc acccactgct tcgggcc                                         27

<210> SEQ ID NO 5
<211> LENGTH: 20
<212> TYPE: PRT
<213> ORGANISM: Spinacia oleracea

<400> SEQUENCE: 5

Asp Val Ala Leu Asp Pro Tyr Tyr Tyr Asp Gly His Asp Gly Ile Lys
1               5                   10                  15

Lys Thr Tyr Gln
            20

<210> SEQ ID NO 6
<211> LENGTH: 20
<212> TYPE: PRT
<213> ORGANISM: Arabidopsis thaliana

<400> SEQUENCE: 6

Asp Val Ala Leu Asp Pro Tyr Ser Ser Asp Gly His Asp Gly Ile Lys
1               5                   10                  15

Lys Thr Tyr Gln
            20

<210> SEQ ID NO 7
<211> LENGTH: 20
<212> TYPE: PRT
<213> ORGANISM: Raphanus sativus

<400> SEQUENCE: 7

Asp Val Ala Leu Asp Pro Tyr Ser Ser Asp Gly His Asp Gly Ile Lys
1               5                   10                  15

Lys Thr Tyr Gln
            20

<210> SEQ ID NO 8
<211> LENGTH: 20
<212> TYPE: PRT
<213> ORGANISM: Lycopersicon esculentum

<400> SEQUENCE: 8

Asp Val Ala Leu Asp Pro Tyr Ser Ser Asp Gly His Asp Gly Ile Lys
1               5                   10                  15

Lys Thr Tyr Gln
            20

<210> SEQ ID NO 9
<211> LENGTH: 20
```

```
<212> TYPE: PRT
<213> ORGANISM: Glycine max

<400> SEQUENCE: 9

Asp Val Ala Leu Asp Pro Tyr Ser Ser Asp Gly His Asp Gly Ile Lys
1               5                   10                  15

Lys Thr Tyr Gln
            20

<210> SEQ ID NO 10
<211> LENGTH: 20
<212> TYPE: PRT
<213> ORGANISM: Pisum sativum

<400> SEQUENCE: 10

Asp Val Ala Leu Asp Pro Tyr Ser Ser Asp Gly His Asp Gly Ile Lys
1               5                   10                  15

Lys Thr Tyr Gln
            20

<210> SEQ ID NO 11
<211> LENGTH: 20
<212> TYPE: PRT
<213> ORGANISM: Amaranthus tricolor

<400> SEQUENCE: 11

Asp Val Ala Leu Asp Pro Tyr Ser Ser Asp Gly His Asp Gly Ile Lys
1               5                   10                  15

Lys Thr Tyr Gln
            20

<210> SEQ ID NO 12
<211> LENGTH: 20
<212> TYPE: PRT
<213> ORGANISM: Hordeum vulgare

<400> SEQUENCE: 12

Asp Val Ala Leu Asp Pro Tyr Ser Ser Asp Gly His Asp Gly Ile Lys
1               5                   10                  15

Lys Thr Tyr Gln
            20

<210> SEQ ID NO 13
<211> LENGTH: 20
<212> TYPE: PRT
<213> ORGANISM: Selaginella martensii

<400> SEQUENCE: 13

Asp Val Ala Leu Asp Pro Tyr Ser Ser Asp Gly His Asp Gly Ile Lys
1               5                   10                  15

Lys Thr Tyr Gln
            20

<210> SEQ ID NO 14
<211> LENGTH: 20
<212> TYPE: PRT
<213> ORGANISM: Physcomitrella patens

<400> SEQUENCE: 14

Asp Val Ala Leu Asp Pro Tyr Ser Ser Asp Gly His Asp Gly Ile Lys
1               5                   10                  15

Lys Thr Tyr Gln
            20
```

<210> SEQ ID NO 15
<211> LENGTH: 20
<212> TYPE: PRT
<213> ORGANISM: Chlamydomonas reinhardtii

<400> SEQUENCE: 15

Asp Val Ala Leu Asp Pro Tyr Asn Ser Asp Gly His Asp Gly Ile Lys
1               5                   10                  15

Lys Thr Tyr Gln
            20

<210> SEQ ID NO 16
<211> LENGTH: 11
<212> TYPE: PRT
<213> ORGANISM: Volvox carteri

<400> SEQUENCE: 16

Asp Gly His Asp Gly Ile Lys Lys Thr Tyr Gln
1               5                   10

<210> SEQ ID NO 17
<211> LENGTH: 20
<212> TYPE: PRT
<213> ORGANISM: Cyanophora paradoxa

<400> SEQUENCE: 17

Asp Ile Ala Leu Asp Pro Tyr Asn Ser Asp Gly His Asp Gly Ile Lys
1               5                   10                  15

Thr Thr Tyr Gln
            20

<210> SEQ ID NO 18
<211> LENGTH: 5
<212> TYPE: PRT
<213> ORGANISM: Guillardia theta

<400> SEQUENCE: 18

Lys Arg Thr Tyr Gln
1               5

<210> SEQ ID NO 19
<211> LENGTH: 20
<212> TYPE: PRT
<213> ORGANISM: Fucus vesiculosus

<400> SEQUENCE: 19

Asp Val Ala Leu Asp Pro Tyr Ser Asp Gln Gly His Asp Gly Val Lys
1               5                   10                  15

Lys Thr Tyr Gln
            20

<210> SEQ ID NO 20
<211> LENGTH: 20
<212> TYPE: PRT
<213> ORGANISM: Laminaria saccharina

<400> SEQUENCE: 20

Asp Val Ala Leu Asp Pro Tyr Ser Asp Gln Gly His Asp Gly Val Lys
1               5                   10                  15

Lys Thr Tyr Gln
            20

-continued

```
<210> SEQ ID NO 21
<211> LENGTH: 20
<212> TYPE: PRT
<213> ORGANISM: Odontella sinensis

<400> SEQUENCE: 21

Asp Val Ala Leu Asp Pro Tyr Ser Asp Gln Gly His Asp Gly Val Lys
1               5                   10                  15

Lys Thr Tyr Gln
            20

<210> SEQ ID NO 22
<211> LENGTH: 20
<212> TYPE: PRT
<213> ORGANISM: Gracilaria sp.

<400> SEQUENCE: 22

Asp Val Ala Leu Asp Pro Tyr Ser Asp Gln Gly His Asp Gly Val Lys
1               5                   10                  15

Asn Thr Tyr Gln
            20

<210> SEQ ID NO 23
<211> LENGTH: 20
<212> TYPE: PRT
<213> ORGANISM: Gonyaulax polyedra

<400> SEQUENCE: 23

Asp Val Ala Leu Asp Pro Tyr Asn Ser Leu Gly His Asp Gly Ile Lys
1               5                   10                  15

Gln Thr Tyr Gln
            20

<210> SEQ ID NO 24
<211> LENGTH: 20
<212> TYPE: PRT
<213> ORGANISM: Plasmodium falciparum

<400> SEQUENCE: 24

Asp Val Ala Leu Asp Pro Tyr Asn Ile Tyr Gly His Asp Gly Ile Lys
1               5                   10                  15

Gln Ser Tyr Gln
            20

<210> SEQ ID NO 25
<211> LENGTH: 20
<212> TYPE: PRT
<213> ORGANISM: Mus musculus

<400> SEQUENCE: 25

Asp Val Cys Leu Cys Pro Tyr Thr Ser His Gly His Cys Gly Leu Arg
1               5                   10                  15

Arg Cys Tyr Gln
            20

<210> SEQ ID NO 26
<211> LENGTH: 20
<212> TYPE: PRT
<213> ORGANISM: Homo sapiens

<400> SEQUENCE: 26

Asp Val Cys Leu Cys Pro Tyr Thr Ser His Gly His Cys Gly Leu Arg
1               5                   10                  15
```

Arg Cys Tyr Gln
        20

<210> SEQ ID NO 27
<211> LENGTH: 20
<212> TYPE: PRT
<213> ORGANISM: Rattus norvegicus

<400> SEQUENCE: 27

Asp Val Cys Leu Cys Pro Tyr Thr Ser His Gly His Cys Gly Leu Arg
1               5                   10                  15

Arg Cys Tyr Gln
        20

<210> SEQ ID NO 28
<211> LENGTH: 20
<212> TYPE: PRT
<213> ORGANISM: Drosophila melanogaster

<400> SEQUENCE: 28

Asp Val Cys Ile Cys Pro Tyr Ser Ser His Gly His Cys Gly Leu Arg
1               5                   10                  15

Arg Cys Tyr Gln
        20

<210> SEQ ID NO 29
<211> LENGTH: 20
<212> TYPE: PRT
<213> ORGANISM: Saccharomyces cerevisiae

<400> SEQUENCE: 29

Asp Val Cys Leu Cys Glu Tyr Thr Ser His Gly His Cys Gly Val Arg
1               5                   10                  15

Lys Cys Tyr Gln
        20

<210> SEQ ID NO 30
<211> LENGTH: 20
<212> TYPE: PRT
<213> ORGANISM: Aspergillus fumigatus

<400> SEQUENCE: 30

Asp Val Cys Leu Cys Glu Tyr Thr Ser His Gly His Cys Gly Ile Arg
1               5                   10                  15

Arg Cys Tyr Gln
        20

<210> SEQ ID NO 31
<211> LENGTH: 20
<212> TYPE: PRT
<213> ORGANISM: Candida glabrata

<400> SEQUENCE: 31

Asp Val Cys Leu Cys Glu Tyr Thr Ser His Gly His Cys Gly Val Arg
1               5                   10                  15

Lys Cys Tyr Gln
        20

<210> SEQ ID NO 32
<211> LENGTH: 20
<212> TYPE: PRT
<213> ORGANISM: Schizosaccharomyces pombe

<400> SEQUENCE: 32

-continued

Asp Val Cys Leu Cys Glu Tyr Thr Asp His Gly His Cys Gly Leu Arg
1               5                   10                  15

Ser Cys Tyr Gln
            20

<210> SEQ ID NO 33
<211> LENGTH: 20
<212> TYPE: PRT
<213> ORGANISM: Candida albicans

<400> SEQUENCE: 33

Asp Val Cys Leu Cys Glu Tyr Thr Asp His Gly His Cys Gly Ile Arg
1               5                   10                  15

Lys Ala Tyr Gln
            20

<210> SEQ ID NO 34
<211> LENGTH: 20
<212> TYPE: PRT
<213> ORGANISM: Sulfolobus sp.

<400> SEQUENCE: 34

Asp Glu Cys Thr Asp Glu Tyr Thr Ser His Gly His Cys Gly Ile Arg
1               5                   10                  15

Arg Gly Tyr Gln
            20

<210> SEQ ID NO 35
<211> LENGTH: 20
<212> TYPE: PRT
<213> ORGANISM: Sulfolobus solfataricus

<400> SEQUENCE: 35

Asp Glu Cys Thr Asp Glu Tyr Met Ala Asn Gly His Cys Gly Leu Arg
1               5                   10                  15

Arg Gly Tyr Gln
            20

<210> SEQ ID NO 36
<211> LENGTH: 20
<212> TYPE: PRT
<213> ORGANISM: Pyrobaculum aerophilum

<400> SEQUENCE: 36

Asp Val Cys Leu Cys Glu Tyr Thr Glu His Gly His Cys Gly Val Arg
1               5                   10                  15

Arg Thr Tyr Gln
            20

<210> SEQ ID NO 37
<211> LENGTH: 20
<212> TYPE: PRT
<213> ORGANISM: Aeropyrum pernix

<400> SEQUENCE: 37

Asp Val Cys Leu Cys Gly Tyr Thr Asp His Gly His Cys Gly Tyr Arg
1               5                   10                  15

Arg Ser Tyr Gln
            20

<210> SEQ ID NO 38
<211> LENGTH: 20

```
<212> TYPE: PRT
<213> ORGANISM: Thermoplasma volcanium

<400> SEQUENCE: 38

Asp Leu Cys Leu Cys Glu Tyr Thr Asp Thr Gly Gln Cys Gly Leu Arg
1               5                   10                  15

Lys Ser Tyr Gln
            20

<210> SEQ ID NO 39
<211> LENGTH: 20
<212> TYPE: PRT
<213> ORGANISM: ferroplasma acidarmanus

<400> SEQUENCE: 39

Asp Leu Cys Leu Cys Glu Tyr Thr Asp Thr Gly His Cys Gly Val Arg
1               5                   10                  15

Lys Ser Tyr Gln
            20

<210> SEQ ID NO 40
<211> LENGTH: 20
<212> TYPE: PRT
<213> ORGANISM: Thermoplasma acidophilum

<400> SEQUENCE: 40

Asp Leu Cys Leu Cys Glu Tyr Thr Asp Thr Gly Gln Cys Gly Leu Arg
1               5                   10                  15

Lys Ser Tyr Gln
            20

<210> SEQ ID NO 41
<211> LENGTH: 20
<212> TYPE: PRT
<213> ORGANISM: Methanothermus sociabilis

<400> SEQUENCE: 41

Asp Val Cys Leu Cys Gln Tyr Thr Glu His Gly His Cys Gly Ile Arg
1               5                   10                  15

Ser Thr Tyr Gln
            20

<210> SEQ ID NO 42
<211> LENGTH: 20
<212> TYPE: PRT
<213> ORGANISM: methanothermobacter thermautotrophicus

<400> SEQUENCE: 42

Asp Val Cys Leu Cys Gln Tyr Thr Ser His Gly His Cys Gly Ile Arg
1               5                   10                  15

Arg Ser Tyr Gln
            20

<210> SEQ ID NO 43
<211> LENGTH: 20
<212> TYPE: PRT
<213> ORGANISM: Archaeoglobus fulgidus

<400> SEQUENCE: 43

Asp Val Cys Leu Cys Glu Tyr Thr Thr His Gly His Cys Gly Val Arg
1               5                   10                  15

Arg Gly Tyr Gln
            20
```

```
<210> SEQ ID NO 44
<211> LENGTH: 20
<212> TYPE: PRT
<213> ORGANISM: Halobacterium sp.

<400> SEQUENCE: 44

Asp Val Cys Leu Cys Glu Tyr Thr Ser His Gly His Cys Gly Val Arg
1               5                   10                  15

Arg His Tyr Gln
            20

<210> SEQ ID NO 45
<211> LENGTH: 20
<212> TYPE: PRT
<213> ORGANISM: Methanococcus jannaschii

<400> SEQUENCE: 45

Asp Cys Cys Leu Cys Glu Tyr Thr Ser His Gly His Cys Gly Ile Arg
1               5                   10                  15

Lys Ser Tyr Gln
            20

<210> SEQ ID NO 46
<211> LENGTH: 18
<212> TYPE: PRT
<213> ORGANISM: Methanosarcina barkeri

<400> SEQUENCE: 46

Asp Val Cys Met Cys Glu Tyr Thr Ser His Gly His Cys Gly Ile Arg
1               5                   10                  15

Ser Thr

<210> SEQ ID NO 47
<211> LENGTH: 20
<212> TYPE: PRT
<213> ORGANISM: Streptomyces coelicolor

<400> SEQUENCE: 47

Asp Ile Ala Leu Asp Pro Tyr Thr Thr His Gly Gln Asp Gly Ile Lys
1               5                   10                  15

Lys Thr Tyr Gln
            20

<210> SEQ ID NO 48
<211> LENGTH: 20
<212> TYPE: PRT
<213> ORGANISM: Mycobacterium tuberculosis

<400> SEQUENCE: 48

Asp Val Ala Leu Asp Pro Phe Thr Thr His Gly Gln Asp Gly Ile Lys
1               5                   10                  15

His Ser Tyr Gln
            20

<210> SEQ ID NO 49
<211> LENGTH: 20
<212> TYPE: PRT
<213> ORGANISM: Mycobacterium avium

<400> SEQUENCE: 49

Asp Val Ala Leu Asp Pro Phe Thr Ser His Gly Gln Asp Gly Leu Lys
1               5                   10                  15
```

Tyr Ser Tyr Gln
        20

<210> SEQ ID NO 50
<211> LENGTH: 20
<212> TYPE: PRT
<213> ORGANISM: Mycobacterium leprae

<400> SEQUENCE: 50

Asp Val Ala Leu Asp Pro Phe Thr Thr His Gly Gln Asp Gly Ile Lys
1               5                   10                  15

Lys Asn Tyr Gln
        20

<210> SEQ ID NO 51
<211> LENGTH: 20
<212> TYPE: PRT
<213> ORGANISM: Mycobacterium bovis

<400> SEQUENCE: 51

Asp Val Ala Leu Asp Pro Tyr Thr Thr His Gly Gln Asp Gly Ile Lys
1               5                   10                  15

Lys Thr Tyr Gln
        20

<210> SEQ ID NO 52
<211> LENGTH: 20
<212> TYPE: PRT
<213> ORGANISM: Mycobacterium smegmatis

<400> SEQUENCE: 52

Asp Val Ala Leu Asp Pro Tyr Thr Asp His Gly His Asp Gly Ile Lys
1               5                   10                  15

Ser Ser Tyr Gln
        20

<210> SEQ ID NO 53
<211> LENGTH: 20
<212> TYPE: PRT
<213> ORGANISM: Corynebacterium diphtheriae

<400> SEQUENCE: 53

Asp Val Ala Leu Asp Pro Phe Thr Asp His Gly His Asp Gly Val Lys
1               5                   10                  15

Lys Thr Tyr Gln
        20

<210> SEQ ID NO 54
<211> LENGTH: 20
<212> TYPE: PRT
<213> ORGANISM: Staphylococcus epidermidis

<400> SEQUENCE: 54

Asp Val Ala Leu Asp Pro Phe Thr Ser His Gly His Asp Gly Ile Lys
1               5                   10                  15

Asn Ser Tyr Tyr
        20

<210> SEQ ID NO 55
<211> LENGTH: 20
<212> TYPE: PRT
<213> ORGANISM: Staphylococcus aureus

```
<400> SEQUENCE: 55

Asp Val Ala Leu Asp Pro Phe Thr Ser His Gly His Asp Gly Ile Lys
1               5                   10                  15

Lys Thr Tyr Tyr
            20

<210> SEQ ID NO 56
<211> LENGTH: 20
<212> TYPE: PRT
<213> ORGANISM: Bacillus subtilis

<400> SEQUENCE: 56

Asp Ala Ala Leu Asp Pro Phe Thr Thr His Gly His Asp Gly Ile Lys
1               5                   10                  15

Lys Thr Tyr Tyr
            20

<210> SEQ ID NO 57
<211> LENGTH: 20
<212> TYPE: PRT
<213> ORGANISM: Bacillus halodenitrificans

<400> SEQUENCE: 57

Asp Val Ala Leu Asp Pro Tyr Thr Ser His Gly His Asp Gly Leu Lys
1               5                   10                  15

Arg Thr Tyr Gln
            20

<210> SEQ ID NO 58
<211> LENGTH: 20
<212> TYPE: PRT
<213> ORGANISM: Bacillus anthracis

<400> SEQUENCE: 58

Asp Ala Ala Leu Asp Pro Phe Thr Ser His Gly His Asp Gly Ile Lys
1               5                   10                  15

Lys Thr Tyr Tyr
            20

<210> SEQ ID NO 59
<211> LENGTH: 20
<212> TYPE: PRT
<213> ORGANISM: geobacillus staerothermophilus

<400> SEQUENCE: 59

Asp Val Ala Leu Asp Pro Phe Thr Ser His Gly His Asp Gly Leu Lys
1               5                   10                  15

Arg Thr Tyr Gln
            20

<210> SEQ ID NO 60
<211> LENGTH: 20
<212> TYPE: PRT
<213> ORGANISM: Listeria innocua

<400> SEQUENCE: 60

Asp Ala Ala Leu Asp Pro Phe Thr Thr His Gly His Asp Gly Ile Lys
1               5                   10                  15

Lys Thr Tyr Tyr
            20

<210> SEQ ID NO 61
```

```
<211> LENGTH: 20
<212> TYPE: PRT
<213> ORGANISM: Listeria monocytogenes

<400> SEQUENCE: 61

Asp Ile Ala Leu Asp Pro Tyr Asn Ala Asn Gly His Asp Gly Leu Lys
1               5                   10                  15

Lys Thr Tyr Gln
            20

<210> SEQ ID NO 62
<211> LENGTH: 20
<212> TYPE: PRT
<213> ORGANISM: Desulfitobacterium hafniense

<400> SEQUENCE: 62

Asp Val Ala Leu Asp Pro Tyr Asn Ala Asn Gly His Asp Gly Leu Lys
1               5                   10                  15

Lys Thr Tyr Gln
            20

<210> SEQ ID NO 63
<211> LENGTH: 20
<212> TYPE: PRT
<213> ORGANISM: Selenomonas ruminantium

<400> SEQUENCE: 63

Asp Val Ala Leu Asp Pro Tyr Asn Ser Asp Gly His Asp Gly Leu Lys
1               5                   10                  15

Lys Thr Tyr Gln
            20

<210> SEQ ID NO 64
<211> LENGTH: 20
<212> TYPE: PRT
<213> ORGANISM: Clostridium botulinum

<400> SEQUENCE: 64

Asp Val Ala Leu Asp Pro Tyr Thr Thr His Gly His Asp Gly Ile Lys
1               5                   10                  15

Ser Ser Tyr Gln
            20

<210> SEQ ID NO 65
<211> LENGTH: 20
<212> TYPE: PRT
<213> ORGANISM: Clostridium difficile

<400> SEQUENCE: 65

Asp Val Ala Leu Asp Pro Tyr Thr Ile Ser Gly His Asp Gly Ile Lys
1               5                   10                  15

Ser Ser Tyr Gln
            20

<210> SEQ ID NO 66
<211> LENGTH: 20
<212> TYPE: PRT
<213> ORGANISM: Clostridium josui

<400> SEQUENCE: 66

Asp Val Ala Leu Asp Pro Tyr Thr Ile His Gly His Asp Gly Ile Lys
1               5                   10                  15

Ser Gly Tyr Gln
```

<210> SEQ ID NO 67
<211> LENGTH: 20
<212> TYPE: PRT
<213> ORGANISM: Clostridium acetobutylicum

<400> SEQUENCE: 67

Asp Val Ala Leu Asp Pro Tyr Thr Ser His Gly Gln Asp Gly Leu Lys
1               5                   10                  15

Lys Thr Tyr Gln
            20

<210> SEQ ID NO 68
<211> LENGTH: 20
<212> TYPE: PRT
<213> ORGANISM: Clostridium perfringens

<400> SEQUENCE: 68

Asp Val Ala Leu Asp Pro Tyr Thr Ser His Gly Gln Asp Gly Val Lys
1               5                   10                  15

Met Ala Tyr Gln
            20

<210> SEQ ID NO 69
<211> LENGTH: 20
<212> TYPE: PRT
<213> ORGANISM: Aquifex pyrophilus

<400> SEQUENCE: 69

Asp Val Ala Leu Asp Pro Tyr Thr Ser His Gly Gln Asp Gly Val Lys
1               5                   10                  15

Met Ala Tyr Gln
            20

<210> SEQ ID NO 70
<211> LENGTH: 20
<212> TYPE: PRT
<213> ORGANISM: Deinococcus radiodurans

<400> SEQUENCE: 70

Asp Val Ala Leu Asp Pro Tyr Thr Ser His Gly Gln Asp Gly Leu Lys
1               5                   10                  15

Tyr Thr Tyr Gln
            20

<210> SEQ ID NO 71
<211> LENGTH: 20
<212> TYPE: PRT
<213> ORGANISM: Fibrobacter succinogenes

<400> SEQUENCE: 71

Asp Val Ala Leu Asp Pro Tyr Thr Ser His Gly Gln Asp Gly Val Lys
1               5                   10                  15

Met Thr Tyr Gln
            20

<210> SEQ ID NO 72
<211> LENGTH: 20
<212> TYPE: PRT
<213> ORGANISM: Chloroflexus aurantiacus

<400> SEQUENCE: 72

Asp Val Ala Leu Asp Pro Tyr Thr Ser His Gly Gln Asp Gly Val Lys
1               5                   10                  15

Met Thr Tyr Gln
            20

<210> SEQ ID NO 73
<211> LENGTH: 20
<212> TYPE: PRT
<213> ORGANISM: Geobacter sulfurreducens

<400> SEQUENCE: 73

Asp Val Ala Leu Asp Pro Tyr Thr Ser His Gly Gln Asp Gly Val Lys
1               5                   10                  15

Met Thr Tyr Gln
            20

<210> SEQ ID NO 74
<211> LENGTH: 20
<212> TYPE: PRT
<213> ORGANISM: Desulfacinum infernum

<400> SEQUENCE: 74

Asp Val Ala Leu Asp Pro Tyr Thr Val His Gly Gln Asp Gly Leu Lys
1               5                   10                  15

Lys Thr Tyr Gln
            20

<210> SEQ ID NO 75
<211> LENGTH: 20
<212> TYPE: PRT
<213> ORGANISM: Campylobacter jejuni

<400> SEQUENCE: 75

Asp Val Ala Leu Asp Pro Tyr Thr Val His Gly Gln Asp Gly Leu Lys
1               5                   10                  15

Lys Thr Tyr Gln
            20

<210> SEQ ID NO 76
<211> LENGTH: 20
<212> TYPE: PRT
<213> ORGANISM: Helicobacter pylori

<400> SEQUENCE: 76

Asp Val Ala Leu Asp Pro Tyr Thr Ser His Gly Gln Asp Gly Val Lys
1               5                   10                  15

Met Thr Tyr Gln
            20

<210> SEQ ID NO 77
<211> LENGTH: 20
<212> TYPE: PRT
<213> ORGANISM: magnetic coccus MP17

<400> SEQUENCE: 77

Asp Val Ala Leu Asp Pro Tyr Thr Ser His Gly Gln Asp Gly Val Lys
1               5                   10                  15

Met Thr Tyr Gln
            20

<210> SEQ ID NO 78
<211> LENGTH: 20
<212> TYPE: PRT

<213> ORGANISM: Pseudomonas fluorescens

<400> SEQUENCE: 78

Asp Ile Ala Leu Asp Pro Phe Thr Thr Ser Gly His Asp Gly Ile Lys
1               5                   10                  15

Arg Gln Tyr Gln
        20

<210> SEQ ID NO 79
<211> LENGTH: 20
<212> TYPE: PRT
<213> ORGANISM: Coxiella burnetii

<400> SEQUENCE: 79

Asp Ile Ala Leu Asp Pro Phe Thr Thr Ser Gly His Asp Gly Ile Lys
1               5                   10                  15

Arg Thr Tyr Gln
        20

<210> SEQ ID NO 80
<211> LENGTH: 20
<212> TYPE: PRT
<213> ORGANISM: Legionella pneumophila

<400> SEQUENCE: 80

Asp Ile Ala Leu Asp Pro Tyr Thr Thr His Gly His Asp Gly Ile Lys
1               5                   10                  15

Lys Gln Tyr Gln
        20

<210> SEQ ID NO 81
<211> LENGTH: 20
<212> TYPE: PRT
<213> ORGANISM: Thiobacillus ferrooxidans

<400> SEQUENCE: 81

Asp Ile Ala Leu Asp Pro Tyr Thr Thr His Gly His Asp Gly Ile Lys
1               5                   10                  15

Arg Asn Tyr Gln
        20

<210> SEQ ID NO 82
<211> LENGTH: 20
<212> TYPE: PRT
<213> ORGANISM: Escherichia coli

<400> SEQUENCE: 82

Asp Val Ala Leu Asp Pro Phe Thr Pro Phe Gly His Asp Gly Leu Lys
1               5                   10                  15

Ser Thr Tyr Gln
        20

<210> SEQ ID NO 83
<211> LENGTH: 20
<212> TYPE: PRT
<213> ORGANISM: Salmonella enterica

<400> SEQUENCE: 83

Asp Val Ala Leu Asp Pro Phe Thr Pro Phe Gly His Asp Gly Leu Lys
1               5                   10                  15

Ser Thr Tyr Gln
        20

```
<210> SEQ ID NO 84
<211> LENGTH: 20
<212> TYPE: PRT
<213> ORGANISM: Salmonella enteritidis

<400> SEQUENCE: 84

Asp Val Ala Leu Asp Pro Tyr Ser Ser Asp Gly His Asp Gly Ile Lys
1               5                   10                  15

Lys Thr Tyr Gln
        20

<210> SEQ ID NO 85
<211> LENGTH: 20
<212> TYPE: PRT
<213> ORGANISM: Salmonella typhimurium

<400> SEQUENCE: 85

Asp Val Ala Leu Asp Pro Tyr Ser Ser Asp Gly His Asp Gly Ile Lys
1               5                   10                  15

Lys Thr Tyr Gln
        20

<210> SEQ ID NO 86
<211> LENGTH: 20
<212> TYPE: PRT
<213> ORGANISM: Yersinia enterocolitica

<400> SEQUENCE: 86

Asp Val Ala Leu Asp Pro Tyr Ser Cys Asp Gly His Asp Gly Ile Lys
1               5                   10                  15

Ser Thr Tyr Gln
        20

<210> SEQ ID NO 87
<211> LENGTH: 20
<212> TYPE: PRT
<213> ORGANISM: Pseudomonas syringae

<400> SEQUENCE: 87

Asp Val Ala Leu Asp Pro Tyr Ser Cys Asp Gly His Asp Gly Leu Lys
1               5                   10                  15

Ser Thr Tyr Gln
        20

<210> SEQ ID NO 88
<211> LENGTH: 20
<212> TYPE: PRT
<213> ORGANISM: Pseudomonas aeruginosa

<400> SEQUENCE: 88

Asp Val Ala Leu Asp Pro Tyr Ser Cys Asp Gly His Asp Gly Ile Lys
1               5                   10                  15

Asp Thr Tyr Gln
        20

<210> SEQ ID NO 89
<211> LENGTH: 20
<212> TYPE: PRT
<213> ORGANISM: Actinobacillus sp.

<400> SEQUENCE: 89

Asp Val Ala Leu Asp Pro Phe Thr Thr His Gly His Asp Gly Leu Lys
1               5                   10                  15
```

Lys Thr Tyr Gln
        20

<210> SEQ ID NO 90
<211> LENGTH: 20
<212> TYPE: PRT
<213> ORGANISM: Pasteurella multocida

<400> SEQUENCE: 90

Asp Thr Cys Leu Cys Glu Tyr Thr Ser His Gly His Cys Gly Tyr Arg
1               5                   10                  15

Arg Thr Tyr Gln
        20

<210> SEQ ID NO 91
<211> LENGTH: 20
<212> TYPE: PRT
<213> ORGANISM: Shewanella putrefaciens

<400> SEQUENCE: 91

Asp Thr Cys Leu Cys Glu Tyr Thr Ser His Gly His Cys Gly Tyr Arg
1               5                   10                  15

Arg Thr Tyr Gln
        20

<210> SEQ ID NO 92
<211> LENGTH: 20
<212> TYPE: PRT
<213> ORGANISM: Methylococcus capsulatus

<400> SEQUENCE: 92

Asp Thr Cys Leu Cys Glu Tyr Thr Asn His Gly His Cys Gly Tyr Arg
1               5                   10                  15

Arg Thr Tyr Gln
        20

<210> SEQ ID NO 93
<211> LENGTH: 20
<212> TYPE: PRT
<213> ORGANISM: Vibrio cholerae

<400> SEQUENCE: 93

Asp Leu Cys Leu Asp Glu Phe Thr Asp His Gly His Cys Gly Val Arg
1               5                   10                  15

Lys Thr Tyr Gln
        20

<210> SEQ ID NO 94
<211> LENGTH: 20
<212> TYPE: PRT
<213> ORGANISM: Xylella fastidiosa

<400> SEQUENCE: 94

Asp Val Cys Leu Asp Glu Phe Thr Asp His Gly His Cys Gly Val Arg
1               5                   10                  15

Arg Ala Tyr Gln
        20

<210> SEQ ID NO 95
<211> LENGTH: 20
<212> TYPE: PRT
<213> ORGANISM: PROTEOBACTERIUM EBAC31A08

```
<400> SEQUENCE: 95

Asp Thr Cys Leu Asp Glu Phe Thr Asp His Gly His Cys Gly Val Arg
1               5                   10                  15

Arg Thr Tyr Gln
            20

<210> SEQ ID NO 96
<211> LENGTH: 20
<212> TYPE: PRT
<213> ORGANISM: Caulobacter crescentus

<400> SEQUENCE: 96

Asp Thr Cys Leu Asp Glu Phe Thr Asp His Gly His Cys Gly Val Arg
1               5                   10                  15

Arg Thr Tyr Gln
            20

<210> SEQ ID NO 97
<211> LENGTH: 20
<212> TYPE: PRT
<213> ORGANISM: Agrobacterium tumefaciens

<400> SEQUENCE: 97

Asp Thr Cys Leu Asp Glu Phe Thr Asp His Gly His Cys Gly Val Arg
1               5                   10                  15

Arg Thr Tyr Gln
            20

<210> SEQ ID NO 98
<211> LENGTH: 20
<212> TYPE: PRT
<213> ORGANISM: Sinorhizobium meliloti

<400> SEQUENCE: 98

Asp Thr Cys Leu Asp Glu Phe Thr Asp His Gly His Cys Gly Val Arg
1               5                   10                  15

Arg Thr Tyr Gln
            20

<210> SEQ ID NO 99
<211> LENGTH: 20
<212> TYPE: PRT
<213> ORGANISM: Brucella melitensis

<400> SEQUENCE: 99

Asp Thr Cys Leu Asp Glu Phe Thr Asp His Gly His Cys Gly Val Arg
1               5                   10                  15

Arg Thr Tyr Gln
            20

<210> SEQ ID NO 100
<211> LENGTH: 20
<212> TYPE: PRT
<213> ORGANISM: Rhodopseudomonas palustris

<400> SEQUENCE: 100

Asp Thr Cys Leu Asp Glu Phe Thr Asp His Gly His Cys Gly Ile Arg
1               5                   10                  15

Arg Ala Tyr Gln
            20

<210> SEQ ID NO 101
```

```
<211> LENGTH: 20
<212> TYPE: PRT
<213> ORGANISM: mesorhizobium loti

<400> SEQUENCE: 101

Asp Thr Cys Leu Cys Glu Tyr Thr Asp His Gly His Cys Gly Val Arg
1               5                   10                  15

Lys Thr Tyr Gln
            20

<210> SEQ ID NO 102
<211> LENGTH: 20
<212> TYPE: PRT
<213> ORGANISM: Bradyrhizobium japonicum

<400> SEQUENCE: 102

Asp Thr Cys Leu Cys Glu Tyr Thr Asp His Gly His Cys Gly Val Arg
1               5                   10                  15

Lys Thr Tyr Gln
            20

<210> SEQ ID NO 103
<211> LENGTH: 20
<212> TYPE: PRT
<213> ORGANISM: Brucella melitensis

<400> SEQUENCE: 103

Asp Thr Cys Leu Cys Glu Tyr Thr Asp His Gly His Cys Gly Leu Arg
1               5                   10                  15

Lys Thr Tyr Gln
            20

<210> SEQ ID NO 104
<211> LENGTH: 20
<212> TYPE: PRT
<213> ORGANISM: Rhodobacter capsulatus

<400> SEQUENCE: 104

Asp Thr Cys Leu Cys Gln Phe Thr Asp His Gly His Cys Gly Val Arg
1               5                   10                  15

Lys Thr Tyr Gln
            20

<210> SEQ ID NO 105
<211> LENGTH: 20
<212> TYPE: PRT
<213> ORGANISM: Rhodobacter sphaeroides

<400> SEQUENCE: 105

Asp Thr Cys Leu Cys Gln Phe Thr Ser His Gly His Cys Gly Val Arg
1               5                   10                  15

Lys Thr Tyr Gln
            20

<210> SEQ ID NO 106
<211> LENGTH: 20
<212> TYPE: PRT
<213> ORGANISM: Magnetospirillum magnetotacticum

<400> SEQUENCE: 106

Asp Thr Cys Leu Cys Glu Tyr Thr Ser His Gly His Cys Gly Val Arg
1               5                   10                  15

Lys Thr Tyr Gln
```

<210> SEQ ID NO 107
<211> LENGTH: 20
<212> TYPE: PRT
<213> ORGANISM: Rickettsia conorii

<400> SEQUENCE: 107

Asp Thr Cys Leu Cys Glu Phe Thr Asp His Gly His Cys Gly Val Arg
1               5                   10                  15

Lys Ser Tyr Gln
            20

<210> SEQ ID NO 108
<211> LENGTH: 20
<212> TYPE: PRT
<213> ORGANISM: Rickettsia prowazekii

<400> SEQUENCE: 108

Asp Thr Cys Leu Cys Glu Phe Thr Asp His Gly His Cys Gly Val Arg
1               5                   10                  15

Lys Ser Tyr Gln
            20

<210> SEQ ID NO 109
<211> LENGTH: 20
<212> TYPE: PRT
<213> ORGANISM: Wolbachia sp.

<400> SEQUENCE: 109

Asp Val Cys Leu Cys Glu Tyr Thr Asp His Gly His Cys Gly Val Arg
1               5                   10                  15

Arg Thr Tyr Gln
            20

<210> SEQ ID NO 110
<211> LENGTH: 20
<212> TYPE: PRT
<213> ORGANISM: novosphingobium aromaticivorans

<400> SEQUENCE: 110

Asp Val Cys Met Cys Glu Tyr Thr Asp His Gly His Cys Gly His Arg
1               5                   10                  15

Arg Gln Tyr Gln
            20

<210> SEQ ID NO 111
<211> LENGTH: 20
<212> TYPE: PRT
<213> ORGANISM: Bordetella bronchiseptica

<400> SEQUENCE: 111

Asp Val Cys Met Cys Gln Tyr Thr Ser His Gly His Cys Gly Ile Arg
1               5                   10                  15

Lys Thr Tyr Gln
            20

<210> SEQ ID NO 112
<211> LENGTH: 20
<212> TYPE: PRT
<213> ORGANISM: Bordetella pertussis

<400> SEQUENCE: 112

Asp Val Cys Met Cys Gln Tyr Thr Ser His Gly His Cys Gly Ile Arg
1               5                   10                  15

Lys Thr Tyr Gln
            20

<210> SEQ ID NO 113
<211> LENGTH: 15
<212> TYPE: PRT
<213> ORGANISM: Nitrosomonas europaea

<400> SEQUENCE: 113

Asp Ile Cys Met Cys Glu Tyr Thr Ser His Gly His Cys Gly Ile
1               5                   10                  15

<210> SEQ ID NO 114
<211> LENGTH: 20
<212> TYPE: PRT
<213> ORGANISM: Burkholderia mallei

<400> SEQUENCE: 114

Asp Val Cys Met Cys Glu Tyr Thr Ser His Gly His Cys Gly Ile Arg
1               5                   10                  15

Lys Ser Tyr Gln
            20

<210> SEQ ID NO 115
<211> LENGTH: 20
<212> TYPE: PRT
<213> ORGANISM: Burkholderia pseudomallei

<400> SEQUENCE: 115

Asp Val Cys Met Cys Glu Tyr Thr Ser His Gly His Cys Gly Ile Arg
1               5                   10                  15

Lys Thr Tyr Gln
            20

<210> SEQ ID NO 116
<211> LENGTH: 20
<212> TYPE: PRT
<213> ORGANISM: Burkholderia sp.

<400> SEQUENCE: 116

Asp Val Cys Phe Cys Glu Tyr Thr Thr His Gly His Cys Gly Val Arg
1               5                   10                  15

Arg Thr Tyr Gln
            20

<210> SEQ ID NO 117
<211> LENGTH: 20
<212> TYPE: PRT
<213> ORGANISM: Neisseria meningitidis

<400> SEQUENCE: 117

Asp Thr Cys Leu Cys Glu Tyr Thr Ser His Gly His Cys Gly His Arg
1               5                   10                  15

Ala Ser Tyr Gln
            20

<210> SEQ ID NO 118
<211> LENGTH: 20
<212> TYPE: PRT
<213> ORGANISM: Neisseria gonorrhoeae

<400> SEQUENCE: 118

```
Asp Val Cys Leu Cys Glu Tyr Met Ser His Gly His Cys Gly Ile Arg
1               5                   10                  15

Lys Ser Tyr Gln
            20

<210> SEQ ID NO 119
<211> LENGTH: 5
<212> TYPE: PRT
<213> ORGANISM: Ralstonia solanacearum

<400> SEQUENCE: 119

Arg Ser Gln Tyr Gln
1               5

<210> SEQ ID NO 120
<211> LENGTH: 20
<212> TYPE: PRT
<213> ORGANISM: Ralstonia sp.

<400> SEQUENCE: 120

Asp Val Cys Met Cys Glu Tyr Thr Asp His Gly His Cys Gly Ile Arg
1               5                   10                  15

Arg Ser Tyr Gln
            20

<210> SEQ ID NO 121
<211> LENGTH: 20
<212> TYPE: PRT
<213> ORGANISM: Chlamydia sp.

<400> SEQUENCE: 121

Asp Val Cys Leu Cys Glu Tyr Thr Asp His Gly His Cys Gly Leu Arg
1               5                   10                  15

Lys Thr Tyr Gln
            20

<210> SEQ ID NO 122
<211> LENGTH: 20
<212> TYPE: PRT
<213> ORGANISM: Chlamydia trachomatis

<400> SEQUENCE: 122

Asp Leu Cys Phe Cys Glu Tyr Thr Asp His Gly His Cys Gly Ile Arg
1               5                   10                  15

Lys Ser Tyr Gln
            20

<210> SEQ ID NO 123
<211> LENGTH: 20
<212> TYPE: PRT
<213> ORGANISM: Chlamydia pneumoniae

<400> SEQUENCE: 123

Asp Leu Cys Phe Cys Glu Tyr Thr Asp His Gly His Cys Gly Ile Arg
1               5                   10                  15

Lys Ser Tyr Gln
            20

<210> SEQ ID NO 124
<211> LENGTH: 20
<212> TYPE: PRT
<213> ORGANISM: Chlamydia psittaci
```

```
<400> SEQUENCE: 124

Asp Leu Cys Phe Cys Glu Tyr Thr Asp His Gly His Cys Gly Ile Arg
1               5                   10                  15

Lys Ser Tyr Gln
            20

<210> SEQ ID NO 125
<211> LENGTH: 20
<212> TYPE: PRT
<213> ORGANISM: Chlorobium vibrioforme

<400> SEQUENCE: 125

Asp Val Cys Met Cys Glu Tyr Thr Asp His Ala His Cys Gly Ile Arg
1               5                   10                  15

Arg Gly Tyr Gln
            20

<210> SEQ ID NO 126
<211> LENGTH: 20
<212> TYPE: PRT
<213> ORGANISM: Chlorobium tepidum

<400> SEQUENCE: 126

Asp Thr Cys Phe Cys Glu Tyr Thr Asp His Gly His Cys Gly Val Arg
1               5                   10                  15

Lys Ser Tyr Gln
            20

<210> SEQ ID NO 127
<211> LENGTH: 20
<212> TYPE: PRT
<213> ORGANISM: Rhodothermus marinus

<400> SEQUENCE: 127

Asp Leu Cys Phe Cys Glu Tyr Thr Asp His Gly His Cys Gly Val Arg
1               5                   10                  15

Lys Thr Tyr Gln
            20

<210> SEQ ID NO 128
<211> LENGTH: 20
<212> TYPE: PRT
<213> ORGANISM: Cytophaga sp.

<400> SEQUENCE: 128

Asp Leu Cys Phe Cys Glu Tyr Thr Asp His Gly His Cys Gly Val Arg
1               5                   10                  15

Lys Ala Tyr Gln
            20

<210> SEQ ID NO 129
<211> LENGTH: 20
<212> TYPE: PRT
<213> ORGANISM: Prochlorococcus marinus

<400> SEQUENCE: 129

Asp Ala Cys Phe Cys Glu Tyr Thr Ala His Gly His Cys Gly Val Arg
1               5                   10                  15

Lys Gly Tyr Gln
            20

<210> SEQ ID NO 130
```

```
<211> LENGTH: 20
<212> TYPE: PRT
<213> ORGANISM: Prochlorococcus marinus

<400> SEQUENCE: 130

Asp Thr Cys Phe Cys Glu Tyr Thr Ser His Gly His Cys Gly Val Arg
1               5                   10                  15

Lys Ser Tyr Gln
            20

<210> SEQ ID NO 131
<211> LENGTH: 20
<212> TYPE: PRT
<213> ORGANISM: Synechococcus sp.

<400> SEQUENCE: 131

Asp Thr Cys Phe Cys Glu Tyr Thr Ser His Gly His Cys Gly Val Arg
1               5                   10                  15

Lys Thr Tyr Gln
            20

<210> SEQ ID NO 132
<211> LENGTH: 20
<212> TYPE: PRT
<213> ORGANISM: Nostoc sp.

<400> SEQUENCE: 132

Asp Thr Cys Phe Cys Glu Tyr Thr Ser His Gly His Cys Gly Val Arg
1               5                   10                  15

Lys Thr Tyr Gln
            20

<210> SEQ ID NO 133
<211> LENGTH: 20
<212> TYPE: PRT
<213> ORGANISM: Nostoc sp.

<400> SEQUENCE: 133

Asp Thr Cys Phe Cys Glu Tyr Thr Ser His Gly His Cys Gly Val Arg
1               5                   10                  15

Lys Thr Tyr Gln
            20

<210> SEQ ID NO 134
<211> LENGTH: 20
<212> TYPE: PRT
<213> ORGANISM: Nostoc sp.

<400> SEQUENCE: 134

Asp Val Ala Leu Asp Pro Tyr Thr Thr His Gly Gln Asp Gly Val Lys
1               5                   10                  15

Lys Thr Tyr Gln
            20

<210> SEQ ID NO 135
<211> LENGTH: 20
<212> TYPE: PRT
<213> ORGANISM: Synechocystis PCC6803

<400> SEQUENCE: 135

Asp Val Ala Leu Asp Pro Tyr Thr Thr His Gly Gln Asp Gly Val Lys
1               5                   10                  15

Lys Thr Tyr Gln
```

<210> SEQ ID NO 136
<211> LENGTH: 91
<212> TYPE: PRT
<213> ORGANISM: Homo sapiens

<400> SEQUENCE: 136

Phe His Pro Leu Leu Arg Ala Trp Gln Thr Ala Thr Thr Leu Asn
1               5                   10                  15

Met Arg Gly Asn Arg Val Ser Val Ser Ser Ala Lys Phe Ala Asp Arg
            20                  25                  30

Arg Cys Tyr Gln Leu Pro Pro Gly Ala Arg Gly Leu Ala Leu Arg Ala
        35                  40                  45

Val Asp Arg Asp Val Arg Glu Gly Ala Asp Met Leu Pro Tyr Leu Asp
    50                  55                  60

Ile Val Arg Glu Val Lys Asp Lys His Pro Asp Leu Pro Leu Val Leu
65                  70                  75                  80

Glu Ala Met Thr Ala Phe Arg Arg Ala Gly Ala
                85                  90

<210> SEQ ID NO 137
<211> LENGTH: 90
<212> TYPE: PRT
<213> ORGANISM: Drosophila melanogaster

<400> SEQUENCE: 137

His His Ala Thr Leu Arg Gln Leu Gln Glu Ser Gly Cys Glu Ile Asn
1               5                   10                  15

Met Val Asn Ser Val Ser Leu Ala Ser Ala Lys Phe Thr Asp Arg Arg
            20                  25                  30

Cys Tyr Gln Leu Pro Ser Gly Ser Arg Ser Leu Ala Met Arg Ala Ile
        35                  40                  45

Gln Arg Asp Val Ala Glu Gly Ala Asp Met Leu Pro Tyr Leu Asp Ile
    50                  55                  60

Leu Arg Ser Thr Lys Asp Ser Tyr Pro Tyr His Thr Leu Val Leu Glu
65                  70                  75                  80

Ala Met Lys Gly Phe Arg Arg Ala Gly Ala
                85                  90

<210> SEQ ID NO 138
<211> LENGTH: 88
<212> TYPE: PRT
<213> ORGANISM: Pseudomonas aeruginosa

<400> SEQUENCE: 138

Arg Asp Asp Phe Ser Arg Arg Leu Val Arg Glu Asn Val Leu Asp Met
1               5                   10                  15

Ile Thr Asn Val Arg Ile Ala Ser Ala Lys Tyr Ala Asn Lys Ala Thr
            20                  25                  30

Tyr Gln Met Asp Pro Ala Asn Ser Asp Glu Ala Leu His Glu Val Ala
        35                  40                  45

Ala Asp Leu Ala Glu Gly Ala Asp Met Val Pro Tyr Leu Asp Ile Val
    50                  55                  60

Arg Arg Val Lys Asp Glu Phe Arg Ala Pro Thr Ile Leu Glu Ser Leu
65                  70                  75                  80

Thr Ala Phe Lys Arg Ala Gly Ala
                85

<210> SEQ ID NO 139
<211> LENGTH: 88
<212> TYPE: PRT
<213> ORGANISM: Vibrio cholerae

<400> SEQUENCE: 139

```
Lys His Asp Phe Ser Arg Arg Leu Val Ala Glu Asn Gln Leu Asp Met
1               5                   10                  15

Ile Ile His Thr Gln Ile Ala Ser Ala Lys Tyr Ala Asn Lys Lys Asn
            20                  25                  30

Tyr Gln Met Asp Pro Ala Asn Ser Asp Glu Ala Leu His Glu Val Ala
        35                  40                  45

Met Asp Ile Asn Glu Gly Ala Asp Met Val Pro Tyr Leu Asp Val Val
    50                  55                  60

Arg Arg Val Lys Thr Glu Leu Gln Val Pro Thr Val Phe Glu Ser Leu
65                  70                  75                  80

Leu Cys Phe Lys Arg Ala Gly Ala
                85
```

<210> SEQ ID NO 140
<211> LENGTH: 88
<212> TYPE: PRT
<213> ORGANISM: Yersinia enterocolitica

<400> SEQUENCE: 140

```
Arg His Asp Phe Ser Arg Arg Leu Val Ala Glu Asn Gln Leu Asp Met
1               5                   10                  15

Ile Val Asn Thr Gln Ile Ala Ser Ala Lys Tyr Ala Asn Lys Lys Thr
            20                  25                  30

Tyr Gln Met Asp Pro Ala Asn Ser Asp Glu Ala Leu Gln Glu Ile Ala
        35                  40                  45

Gln Asp Leu Gln Glu Gly Ala Asp Met Val Pro Tyr Leu Asp Val Val
    50                  55                  60

Arg Arg Val Lys Asp Thr Phe Gly Val Pro Ile Val Met Glu Ser Leu
65                  70                  75                  80

Leu Cys Phe Lys Arg Ala Gly Ala
                85
```

<210> SEQ ID NO 141
<211> LENGTH: 92
<212> TYPE: PRT
<213> ORGANISM: Plasmodium falciparum

<400> SEQUENCE: 141

```
Arg Asn Lys Tyr Leu Leu Ser Leu Tyr Asn Asn Thr Asn Ile Asn Ser
1               5                   10                  15

Ile Arg Asp Ile Leu Ile Ser Thr Cys Lys Tyr Ser Lys Asn Lys Gln
            20                  25                  30

Ser Tyr Gln His Asp Phe Asn Ser Tyr Met Asp Leu Asn Asn Val Asp
        35                  40                  45

Lys His Ile Ile Glu Gly Ala Asp Ile Ile Phe Tyr Leu Asp Ile Ile
    50                  55                  60

His Lys Ile Lys Asn Arg Ile Lys Asp Asp Val Gln Ile Pro Ile Ile
65                  70                  75                  80

Thr Glu Leu Phe Lys Ser Tyr Leu Arg Ala Gly Ala
                85                  90
```

<210> SEQ ID NO 142

```
<211> LENGTH: 88
<212> TYPE: PRT
<213> ORGANISM: Toxoplasma gondii

<400> SEQUENCE: 142

Lys Asn Arg Ala Val Arg Gln Leu Val Gln Glu Asn Leu Val Ser Met
1               5                   10                  15

Val Thr Asp Thr Ser Ile Ala Ser Cys Lys Tyr Ala Asp Lys Lys Thr
            20                  25                  30

Tyr Gln Met Asp Pro Ser Asn Ser Arg Glu Ala Glu Arg Glu Ala Glu
        35                  40                  45

Ala Asp Ala Ser Glu Gly Ala Asp Met Leu Pro Tyr Leu Asp Val Leu
50                  55                  60

Ala Lys Ile Arg Glu Lys Ser Lys Leu Pro Met Val Leu Glu Val Leu
65                  70                  75                  80

Lys Ser Phe Arg Arg Ala Gly Ala
            85

<210> SEQ ID NO 143
<211> LENGTH: 88
<212> TYPE: PRT
<213> ORGANISM: Staphylococcus aureus

<400> SEQUENCE: 143

Ser Ser Lys Ser Met Arg Asn Leu Val Arg Glu Thr His Val Asp Met
1               5                   10                  15

Val Tyr Asn Val Pro Ile Ser Gly Ile Lys Tyr Ala Asp Arg Lys Thr
            20                  25                  30

Tyr Gln Met Asp Pro Ala Asn Arg Arg Glu Ala Leu Arg Glu Leu Asp
        35                  40                  45

Ser Asp Leu Arg Glu Gly Ala Asp Met Met Ser Phe Leu Asp Ile Ile
50                  55                  60

Arg Asp Val Arg Asn Thr Thr Asn Val Pro Val Val Met Glu Gln Met
65                  70                  75                  80

Thr Ser Met Lys Arg Ala Gly Ala
            85

<210> SEQ ID NO 144
<211> LENGTH: 88
<212> TYPE: PRT
<213> ORGANISM: Mycobacterium tuberculosis

<400> SEQUENCE: 144

Ser Thr Val Ala Met Arg Arg Leu Val Ala Gln Thr Ser Leu His Met
1               5                   10                  15

Val Ile Asp Val Val Ile Ala Ala Lys Phe Ala Asp Arg Arg Thr
            20                  25                  30

Tyr Gln Gln Glu Pro Gly Asn Ala Ala Glu Ala Leu Arg Glu Ile Glu
        35                  40                  45

Leu Asp Leu Asp Glu Gly Ala Asp Ile Val Gly Tyr Leu Asp Val Val
50                  55                  60

Ala Ala Ala Ala Asp Val Ser Pro Val Pro Val Leu Glu Ser Leu
65                  70                  75                  80

Thr Gly Ile Arg Arg Ala Gly Ala
            85

<210> SEQ ID NO 145
<211> LENGTH: 88
<212> TYPE: PRT
```

<213> ORGANISM: Raphanus sativus

<400> SEQUENCE: 145

| | | | | | | | | | | | | | | |
|---|---|---|---|---|---|---|---|---|---|---|---|---|---|---|
| Ala | Ser | Pro | Thr | Val | Arg | Ala | Ala | Phe | Gln | Glu | Thr | Asp | Ile | Asn | Met |
| 1 | | | | 5 | | | | | 10 | | | | | 15 | |
| Val | Gln | Asn | Val | Ser | Ile | Ser | Thr | Ala | Lys | Tyr | Ala | Asp | Lys | Lys | Thr |
| | | | 20 | | | | | 25 | | | | | 30 | | |
| Tyr | Gln | Met | Asn | Pro | Ala | Asn | Tyr | Arg | Glu | Ala | Leu | Ile | Glu | Ala | Arg |
| | | | 35 | | | | | 40 | | | | | 45 | | |
| Glu | Asp | Glu | Ala | Glu | Gly | Ala | Asp | Ile | Leu | Pro | Tyr | Leu | Asp | Ile | Ile |
| | | 50 | | | | | 55 | | | | | 60 | | | |
| Arg | Leu | Leu | Arg | Asp | Lys | Ser | Pro | Leu | Pro | Ile | Met | Met | Glu | Ser | Leu |
| 65 | | | | | 70 | | | | | 75 | | | | | 80 |
| Met | Cys | Leu | Arg | Arg | Ala | Gly | Ala | | | | | | | | |
| | | | | 85 | | | | | | | | | | | |

<210> SEQ ID NO 146
<211> LENGTH: 88
<212> TYPE: PRT
<213> ORGANISM: Glycine max

<400> SEQUENCE: 146

| | | | | | | | | | | | | | | | |
|---|---|---|---|---|---|---|---|---|---|---|---|---|---|---|---|
| Lys | Ser | Pro | Ala | Leu | Arg | Ser | Ala | Phe | Gln | Glu | Thr | Ser | Ile | Asn | Met |
| 1 | | | | 5 | | | | | 10 | | | | | 15 | |
| Val | Gln | His | Val | Ser | Ile | Ser | Thr | Ala | Lys | Tyr | Ala | Asp | Lys | Lys | Thr |
| | | | 20 | | | | | 25 | | | | | 30 | | |
| Tyr | Gln | Met | Asn | Pro | Ala | Asn | Tyr | Arg | Glu | Ala | Leu | Thr | Glu | Met | Arg |
| | | | 35 | | | | | 40 | | | | | 45 | | |
| Glu | Asp | Glu | Ser | Glu | Gly | Ala | Asp | Ile | Leu | Pro | Tyr | Leu | Asp | Ile | Ile |
| | | 50 | | | | | 55 | | | | | 60 | | | |
| Arg | Leu | Leu | Arg | Asp | Asn | Ser | Pro | Leu | Pro | Ile | Met | Met | Glu | Ser | Leu |
| 65 | | | | | 70 | | | | | 75 | | | | | 80 |
| Met | Cys | Leu | Arg | Arg | Ala | Gly | Ala | | | | | | | | |
| | | | | 85 | | | | | | | | | | | |

<210> SEQ ID NO 147
<211> LENGTH: 88
<212> TYPE: PRT
<213> ORGANISM: Pisum sativum

<400> SEQUENCE: 147

| | | | | | | | | | | | | | | | |
|---|---|---|---|---|---|---|---|---|---|---|---|---|---|---|---|
| Arg | Ser | Pro | Ala | Leu | Arg | Ser | Ala | Phe | Gln | Glu | Thr | Thr | Leu | Asn | Met |
| 1 | | | | 5 | | | | | 10 | | | | | 15 | |
| Val | Gln | His | Val | Ser | Ile | Ser | Thr | Ala | Lys | Tyr | Ala | Asp | Lys | Lys | Thr |
| | | | 20 | | | | | 25 | | | | | 30 | | |
| Tyr | Gln | Met | Asn | Pro | Ala | Asn | Tyr | Arg | Glu | Ala | Leu | Thr | Glu | Met | Arg |
| | | | 35 | | | | | 40 | | | | | 45 | | |
| Glu | Asp | Glu | Ser | Glu | Gly | Ala | Asp | Ile | Leu | Pro | Tyr | Leu | Asp | Ile | Ile |
| | | 50 | | | | | 55 | | | | | 60 | | | |
| Arg | Leu | Leu | Arg | Asp | Asn | Ser | Pro | Leu | Pro | Ile | Met | Met | Glu | Ser | Leu |
| 65 | | | | | 70 | | | | | 75 | | | | | 80 |
| Leu | Cys | Leu | Arg | Arg | Ala | Gly | Ala | | | | | | | | |
| | | | | 85 | | | | | | | | | | | |

<210> SEQ ID NO 148
<211> LENGTH: 330
<212> TYPE: PRT
<213> ORGANISM: Homo sapiens

<400> SEQUENCE: 148

```
Met Gln Pro Gln Asx Val Leu Asn Ser Gly Tyr Phe His Pro Leu Leu
1               5                   10                  15

Arg Ala Trp Gln Thr Ala Thr Thr Leu Asn Ala Ser Asn Leu Ile
            20                  25                  30

Tyr Pro Ile Phe Val Thr Asp Val Pro Asp Asp Ile Gln Pro Ile Thr
            35                  40                  45

Ser Leu Pro Gln Val Ala Arg Tyr Gly Val Lys Arg Leu Glu Glu Met
    50                  55                  60

Leu Arg Pro Leu Val Glu Glu Gln Leu Arg Cys Val Leu Ile Phe Gln
65                  70                  75                  80

Val Pro Ser Arg Val Pro Lys Asp Glu Arg Gly Ser Ala Ala Asp Ser
                85                  90                  95

Glu Glu Ser Pro Ala Ile Glu Ala Ile His Leu Leu Arg Lys Thr Phe
            100                 105                 110

Pro Asn Leu Leu Val Ala Cys Asp Val Cys Leu Cys Pro Tyr Thr Ser
            115                 120                 125

His Gly His Cys Gly Leu Leu Ser Glu Asn Gly Ala Phe Arg Ala Glu
    130                 135                 140

Glu Ser Arg Gln Arg Leu Ala Glu Val Ala Leu Ala Tyr Ala Lys Ala
145                 150                 155                 160

Gly Cys Gln Val Val Ala Pro Ser Asp Met Met Asp Gln Arg Val Glu
                165                 170                 175

Ala Ile Lys Glu Ala Leu Met Ala His Gln Leu Gly Asn Arg Val Ser
            180                 185                 190

Val Met Ser Tyr Ser Ala Lys Phe Ala Ser Cys Phe Tyr Gln Pro Phe
        195                 200                 205

Arg Asp Ala Ala Lys Ser Ser Pro Ala Phe Gly Asp Arg Arg Cys Tyr
    210                 215                 220

Gln Leu Pro Pro Gly Ala Arg Gly Leu Ala Leu Arg Ala Val Asp Arg
225                 230                 235                 240

Asp Val Arg Glu Gln Ala Asp Met Leu Met Val Lys Pro Gln Met Pro
                245                 250                 255

Tyr Leu Asp Ile Val Arg Glu Val Lys Asp Lys His Pro Asp Leu Pro
            260                 265                 270

Leu Thr Val Tyr His Val Ser Gln Glu Phe Ala Met Leu Trp His Gly
        275                 280                 285

Ala Gln Ala Gly Ala Phe Asp Leu Lys Ala Ala Val Leu Glu Ala Met
    290                 295                 300

Thr Ala Phe Arg Arg Ala Gln Ala Asp Ile Ile Ile Thr Tyr Tyr Thr
305                 310                 315                 320

Pro Gln Leu Leu Gln Trp Leu Lys Glu Glu
                325                 330
```

<210> SEQ ID NO 149
<211> LENGTH: 330
<212> TYPE: PRT
<213> ORGANISM: Pisum sativum

<400> SEQUENCE: 149

```
Ser Leu Pro Ile Gln Arg Arg Pro Arg Asn Arg Ser Pro Ala
1               5                   10                  15

Leu Arg Ser Ala Phe Gln Glu Thr Thr Leu Ser Pro Ala Asn Phe Val
            20                  25                  30

Tyr Pro Leu Phe Ile His Glu Gly Glu Glu Asp Thr Pro Ile Gly Ala
```

```
                35                  40                  45
Met Pro Gln Cys Tyr Arg Leu Gly Trp Arg His Gly Leu Leu Glu Glu
 50                  55                  60
Val Ala Lys Ala Arg Asp Val Gln Val Asn Ser Val Val Leu Pro Pro
 65                  70                  75                  80
Lys Ile Pro Asp Ala Leu Lys Thr Pro Thr Gly Asp Glu Ala Tyr Asn
                 85                  90                  95
Glu Asp Gly Leu Val Pro Arg Ser Ile Arg Leu Leu Lys Asp Lys Tyr
            100                 105                 110
Pro Asp Leu Ile Ile Tyr Thr Asp Val Ala Leu Asp Pro Tyr Ser Ser
            115                 120                 125
Asp Gln His Asp Gln Ile Val Arg Glu Asp Gln Val Ile Met Asn Asp
            130                 135                 140
Glu Thr Val His Gln Leu Cys Lys Gln Ala Val Ala Gln Ala Arg Ala
145                 150                 155                 160
Gln Ala Asp Val Val Ser Pro Ser Asp Met Met Asp Gln Arg Val Gly
                165                 170                 175
Ala Met Arg Val Ala Leu Asp Ala Glu Gln Phe Gln His Val Ser Ile
            180                 185                 190
Met Ser Tyr Thr Ala Lys Tyr Ala Ser Ser Phe Tyr Gln Pro Phe Arg
            195                 200                 205
Glu Ala Leu Asp Ser Asn Pro Arg Phe Gly Asp Lys Lys Thr Tyr Gln
            210                 215                 220
Met Asn Pro Ala Asn Tyr Arg Glu Ala Leu Thr Glu Met Arg Glu Asp
225                 230                 235                 240
Glu Ser Glu Gln Ala Asp Ile Leu Leu Val Lys Pro Gln Leu Pro Tyr
                245                 250                 255
Leu Asp Ile Ile Arg Leu Leu Arg Asp Asn Ser Pro Leu Pro Ile Ala
            260                 265                 270
Ala Tyr Gln Val Ser Gln Glu Tyr Ser Met Ile Lys Ala Gly Gln Ala
            275                 280                 285
Leu Lys Met Ile Asp Glu Glu Lys Val Met Met Glu Ser Leu Leu Cys
            290                 295                 300
Leu Arg Arg Ala Gln Ala Asp Ile Ile Leu Thr Tyr Phe Ala Leu Gln
305                 310                 315                 320
Ala Ala Arg Thr Leu Cys Gly Glu Lys Arg
                325                 330

<210> SEQ ID NO 150
<211> LENGTH: 347
<212> TYPE: PRT
<213> ORGANISM: Vibrio cholerae

<400> SEQUENCE: 150

Met Ser Val Ser Ile Gln Gly Gln Phe Pro Gly Arg Arg Leu Arg Arg
 1               5                  10                  15
Leu Arg Lys His Asp Phe Ser Arg Arg Leu Val Ala Glu Asn Gln Leu
                 20                  25                  30
Ser Val Asn Asp Leu Ile Tyr Pro Met Phe Ile Leu Met Gly Lys Asp
             35                  40                  45
Arg Arg Glu Lys Val Asp Met Ser Pro Gln Val Glu Arg Leu Ser Ile
         50                  55                  60
Asp Leu Met Leu Glu Glu Ala Gln Tyr Leu Ala Asn Leu Gln Val Pro
 65                  70                  75                  80
Ala Ile Ala Leu Phe Pro Val Val Asn Gln Asp Ala Lys Ser Leu Cys
```

85                  90                  95
Ala Ala Glu Ala Tyr Asn Pro Glu Gly Leu Val Gln Arg Ala Val Arg
            100                 105                 110

Ala Leu Lys Glu His Val Pro Gln Met Gly Val Ile Thr Asp Val Ala
            115                 120                 125

Leu Asp Pro Phe Thr Thr His Gln Asp Gln Ile Ile Asp Glu Gln
        130                 135                 140

Gln Tyr Val Leu Met Asp Glu Thr Thr Glu Val Leu Val Lys Gln Ala
145                 150                 155                 160

Leu Ser His Ala Gln Ala Gln Ala Asp Val Val Ala Pro Ser Asp Met
                165                 170                 175

Met Asp Gln Arg Ile Gly Arg Ile Arg Gln Ala Leu Glu Glu Ala Gln
            180                 185                 190

Tyr Ile His Thr Gln Ile Met Ala Tyr Ser Ala Lys Tyr Ala Ser Asn
            195                 200                 205

Tyr Tyr Gln Pro Phe Arg Asp Ala Val Gly Ser Ser Ala Asn Leu Lys
        210                 215                 220

Gly Gly Asn Lys Lys Asn Tyr Gln Met Asp Pro Ala Met Ser Asp Glu
225                 230                 235                 240

Ala Leu His Glu Val Ala Met Asp Ile Asn Glu Gln Ala Asp Met Val
                245                 250                 255

Met Val Lys Pro Gln Met Pro Tyr Leu Asp Val Val Arg Arg Val Lys
            260                 265                 270

Thr Glu Leu Gln Val Pro Thr Phe Ala Tyr Gln Val Ser Gln Glu Tyr
            275                 280                 285

Ala Met His Lys Ala Ala Ile Met Asn Gly Trp Leu Lys Glu Arg Glu
        290                 295                 300

Thr Val Phe Glu Ser Leu Leu Cys Phe Lys Arg Ala Gln Ala Asp Gly
305                 310                 315                 320

Ile Leu Thr Tyr Phe Ala Lys Glu Val Ala Glu Trp Leu Ala Glu Asp
                325                 330                 335

Ser Ala Lys Ala Ala Gln Phe Leu Pro Lys Lys
            340                 345

<210> SEQ ID NO 151
<211> LENGTH: 341
<212> TYPE: PRT
<213> ORGANISM: Pseudomonas aeruginosa

<400> SEQUENCE: 151

Met Ser Phe Thr Pro Ala Asn Arg Ala Tyr Pro Tyr Thr Arg Leu Arg
1               5                   10                  15

Arg Asn Arg Arg Asp Asp Phe Ser Arg Arg Leu Val Arg Glu Asn Val
            20                  25                  30

Leu Thr Val Asp Asp Leu Ile Leu Pro Val Phe Val Leu Asp Gly Val
        35                  40                  45

Asn Gln Arg Glu Ser Ile Pro Ser Met Pro Gln Val Glu Arg Leu Ser
    50                  55                  60

Ile Asp Gln Leu Leu Ile Glu Ala Glu Trp Val Ala Leu Gln Ile
65                  70                  75                  80

Pro Ala Leu Ala Leu Phe Pro Val Thr Pro Val Glu Lys Lys Ser Leu
                85                  90                  95

Asp Ala Ala Glu Ala Tyr Asn Pro Glu Gly Ile Ala Gln Arg Ala Thr
            100                 105                 110

Arg Ala Leu Arg Glu Arg Phe Pro Glu Leu Gly Ile Ile Thr Asp Val

```
                     115                 120                 125
Ala Leu Asp Pro Phe Thr Thr His Gln Gln Asp Gln Ile Leu Asp Asp
130                 135                 140

Asp Gln Tyr Val Leu Asn Asp Val Ser Ile Asp Val Leu Val Arg Gln
145                 150                 155                 160

Ala Leu Ser His Ala Glu Ala Gln Ala Gln Val Val Ala Pro Ser Asp
                165                 170                 175

Met Met Asp Gly Arg Ile Gly Ala Ile Arg Glu Ala Leu Glu Ser Ala
            180                 185                 190

Gln His Thr Asn Val Arg Ile Met Ala Tyr Ser Ala Lys Tyr Ala Ser
        195                 200                 205

Ala Tyr Tyr Gln Pro Phe Arg Asp Ala Val Gly Ser Ala Ser Asn Leu
    210                 215                 220

Gly Lys Gly Asn Lys Ala Thr Tyr Gln Met Asp Pro Ala Met Ser Asp
225                 230                 235                 240

Glu Ala Leu His Glu Val Ala Ala Asp Leu Ala Glu Gln Ala Asp Met
                245                 250                 255

Val Met Val Lys Pro Gln Met Pro Tyr Leu Asp Ile Val Arg Arg Val
            260                 265                 270

Lys Asp Glu Phe Arg Ala Pro Thr Phe Val Tyr Gln Val Ser Gln Glu
        275                 280                 285

Tyr Ala Met His Met Gly Ala Ile Gln Asn Gly Trp Leu Ala Glu Ser
    290                 295                 300

Val Ile Leu Glu Ser Leu Thr Ala Phe Lys Arg Ala Gln Ala Asp Gly
305                 310                 315                 320

Ile Leu Thr Tyr Phe Ala Lys Gln Ala Ala Glu Gln Leu Arg Arg Gly
                325                 330                 335

Arg Arg Ala Gln Lys
            340

<210> SEQ ID NO 152
<211> LENGTH: 348
<212> TYPE: PRT
<213> ORGANISM: Toxoplasma gondii

<400> SEQUENCE: 152

Asn Asn Asn Tyr Gly Glu Val Trp Leu Pro Ile Gln Ala Arg Pro Arg
1               5                   10                  15

Arg Asn Arg Lys Asn Arg Ala Val Arg Gln Leu Val Gln Glu Asn Leu
            20                  25                  30

Val Lys Pro Ser Ser Leu Ile Tyr Pro Leu Phe Val His Asp Glu Glu
        35                  40                  45

Thr Ser Val Pro Ile Pro Ser Met Pro Gln Gln Ser Arg Leu Ser Met
    50                  55                  60

Glu Asp Leu Leu Lys Glu Val Gly Glu Ala Arg Ser Tyr Gln Ile Lys
65                  70                  75                  80

Ala Phe Met Leu Phe Pro Lys Val Asp Asp Glu Leu Lys Ser Val Met
                85                  90                  95

Ala Glu Glu Ser Tyr Asn Pro Asp Gly Leu Leu Pro Arg Ala Ile Met
            100                 105                 110

Ala Leu Lys Glu Ala Phe Pro Asp Val Leu Leu Ala Asp Val Ala
        115                 120                 125

Leu Asp Pro Tyr Ser Ser Met Gln His Asp Gln Val Val Asp Glu Gln
    130                 135                 140

Ser Gln Lys Ile Val Asn Asp Leu Thr Val His Gln Leu Cys Lys Gln
```

```
               145                 150                 155                 160
Ala Ile Thr Leu Ala Arg Ala Gln Ala Asp Met Val Cys Pro Ser Asp
                165                 170                 175

Met Met Asp Gln Arg Val Ser Ala Ile Arg Glu Ser Leu Asp Met Glu
                180                 185                 190

Gln Cys Thr Asp Thr Ser Ile Leu Ala Tyr Ser Cys Lys Tyr Ala Ser
                195                 200                 205

Ser Phe Tyr Gln Pro Phe Arg Asp Ala Leu Asp Ser His Met Val Gly
                210                 215                 220

Gly Thr Asp Lys Lys Thr Tyr Gln Met Asp Pro Ser Asn Ser Arg Glu
225                 230                 235                 240

Ala Glu Arg Glu Ala Glu Ala Asp Ala Ser Glu Gln Ala Asp Met Leu
                245                 250                 255

Met Val Lys Pro Gln Leu Pro Tyr Leu Asp Val Leu Ala Lys Ile Arg
                260                 265                 270

Glu Lys Ser Lys Leu Pro Met Val Ala Tyr His Val Ser Gln Glu Tyr
                275                 280                 285

Ala Met Leu Lys Ala Ala Ala Glu Lys Gly Trp Ile Ser Glu Lys Asp
                290                 295                 300

Thr Val Leu Glu Val Leu Lys Ser Phe Arg Arg Ala Gln Ala Asp Ala
305                 310                 315                 320

Val Ala Thr Tyr Tyr Ala Lys Glu Ala Ala Lys Tyr Met Val Glu Asp
                325                 330                 335

Met Lys Gly Thr Gln Lys Phe Thr Glu Pro Cys Tyr
                340                 345

<210> SEQ ID NO 153
<211> LENGTH: 362
<212> TYPE: PRT
<213> ORGANISM: Plasmodium falciparum

<400> SEQUENCE: 153

Lys Asp Ile Asn Asn Asn Ile Tyr Ile Glu Thr Asn Arg Arg Glu Arg
1               5                   10                  15

Arg Ile Lys Arg Asn Lys Tyr Leu Leu Ser Leu Tyr Asn Asn Thr Asn
                20                  25                  30

Ile Lys Thr Ser Asn Phe Ile Tyr Pro Leu Phe Ile His Glu Glu Asp
                35                  40                  45

Val Glu Lys Lys Met Thr Gln Leu Glu Gln Ile Tyr Thr Tyr Asn Val
                50                  55                  60

Asp Gly Ile Ile Lys Glu Ile Glu Glu Cys Ile Lys Leu Met Ile His
65                  70                  75                  80

His Phe Met Phe Phe Pro Val Ile Arg Glu Glu Asn Lys Thr Val Tyr
                85                  90                  95

Cys Glu Glu Ser Tyr Met Glu Asn Ser Tyr Phe Cys Lys Thr Ile Ser
                100                 105                 110

Arg Ile Lys Glu Lys Phe Ser Asp Asp Ile Ile Val Tyr Thr Asp Val
                115                 120                 125

Ala Leu Asp Pro Tyr Asn Ile Tyr Gln His Asp Gln Ile Tyr Asp Asp
                130                 135                 140

Asn Lys Lys Glu Ile Leu Asn Asp Ile Thr Val His Thr Leu Val Lys
145                 150                 155                 160

Gln Ser Leu Cys Leu Ala Lys Ser Gln Ala Asp Val Val Cys Pro Ser
                165                 170                 175

Asp Ser Met Asp Lys Arg Ile Glu Leu Ile Arg Lys Asn Leu Asp Phe
```

-continued

```
                180                 185                 190
His Asn Phe Arg Asp Ile Leu Ile Leu Ser Tyr Thr Cys Lys Tyr Ser
        195                 200                 205

Ser Ser Met Tyr Lys Pro Phe Arg Ser Ile Leu Asn Ser Asn Ile Leu
        210                 215                 220

Lys Asn Phe Val Lys Asn Lys Gln Ser Tyr Gln His Asp Phe Asn Ser
225                 230                 235                 240

Tyr Met Asp Leu Asn Asn Val Asp Lys Asn Tyr Tyr Glu Gln Ala Asp
                245                 250                 255

Ile Ile Met Val Lys Pro Ser Met Phe Tyr Leu Asp Ile Ile His Lys
                260                 265                 270

Ile Lys Asn Arg Ile Lys Asp Asp Val Gln Ile Pro Ile Ala Val Tyr
        275                 280                 285

Asn Val Ser Gln Glu Tyr Met Met Ile Lys Asn Tyr Val Lys Tyr Leu
        290                 295                 300

Asn Glu Asp Ile Asn Tyr Glu Asn Glu Ile Ile Thr Glu Leu Phe Lys
305                 310                 315                 320

Ser Tyr Leu Arg Ala Gln Ala Met Ile Ile Ile Thr Tyr Phe Ala Lys
                325                 330                 335

Gln Tyr Gln Leu Tyr Met Lys Lys Leu Tyr Asp Lys Asn Ile Ile Ile
                340                 345                 350

Asp Asp Asn Ser Asn Asn Asn Phe Asn Ile
                355                 360
```

ALTERNATE MORPHEEIN FORMS OF ALLOSTERIC PROTEINS AS A TARGET FOR THE DEVELOPMENT OF BIOACTIVE MOLECULES

This application is a continuation-in-part of U.S. application Ser. No. 11/327,762, filed Jan. 6, 2006, now abandoned, which is a continuation-in-part of PCT/US04/21722, filed Jul. 7, 2004, which claims benefit of U.S. Provisional applications 60/485,253, filed Jul. 7, 2003 and 60/577,312, filed Jun. 4, 2004; and U.S. application Ser. No. 11/327,762, filed Jan. 6, 2006, which claims benefit of U.S. Provisional applications. 60/690,649, filed Jun. 15, 2005.

REFERENCE TO MATERIAL ON COMPACT DISC

The Sequence Listing submitted on compact disc is incorporated herein by reference in its entirety.

BACKGROUND OF THE INVENTION

1. Field of Invention

This invention relates to the allosteric regulation of protein function through stabilization of one or more different quaternary assemblies, herein defined as morpheein forms. The different morpheein forms of a given protein have different surface characteristics that can be targeted for the development of a broad spectrum of bioactive agents. As an example, this invention relates to the biosynthesis of tetrapyrroles, and more particularly to a mechanism for inhibiting activation of porphobilinogen synthase.

2. Description of Related Art

It is generally accepted that the three dimensional structure of a protein is determined by the sequence of that protein and that there is one structure for each protein [1]. Exceptions to this rule include prions, a term that remains controversial, but is taken to refer to proteins that can change from their biologically active globular shape to a fibrillar shape which can form an aggregate that can grow indefinitely into disease causing amyloid plaques (e.g. scrapie). The formation of the amyloid protein structure from the globular prion protein structure is believed to be irreversible. This invention does not deal with prion proteins, nor with any other irreversible transformation in protein shape, such as denaturation. A second example of a situation where one protein is known to exist in two forms, more particularly in two quaternary assemblies, occurs as the quasiequivalence of some virus capsid proteins [2,3]. The quasiequivalent virus capsid proteins are the stable components of the geodesic dome that encapsulates the virus; these stable structures exist as parts of a larger assembly and are fundamentally different from the morpheein structures introduced herein.

Allosteric effects on ligand binding and/or catalytic activity are changes in said binding or activity which are caused by binding of another molecule (the allosteric effector molecule) to a site on the protein that is different from the ligand binding site or active site. The behavior of many proteins is known to be subject to allosteric regulation. Many allosteric proteins are known to exist as homomeric multimers (oligomers made up of subunits where the sequence of each of the subunits is identical to the others). There are two well-accepted models for allosteric regulation, the Monod Wyman Changeux model and the Koshland model [4,5]. Both of these models explicitly presume that the allosteric "ON" state and the allosteric "OFF" state have a constant oligomeric multiplicity as illustrated schematically in FIG. 1. The current invention is about a third model for allosteric regulation of protein function, the morpheein model, where the oligomeric multiplicity of the "ON" state and the "OFF" state of a homo-oligomeric protein are different.

Tetrapyrrole biosynthesis is an essential pathway in animals, plants, and microbes, including bacteria, archae, fungi, and protists. The first common intermediate is 5-aminolevulinic acid (ALA). The enzymatic reactions from ALA to uroporphyrinogen are common to tetrapyrrole biosynthesis in all organisms [6,7].

The enzyme porphobilinogen synthase (PBGS, EC 4.2.1.24), also known as 5-aminolevulinic acid dehydratase (ALAD), is an ancient and highly conserved protein that catalyzes the first common step in the biosynthesis of tetrapyrroles including heme, chlorophyll, vitamin $B_{12}$, and cofactor $F_{430}$ [8,9]. PBGS catalyzes the condensation of two 5-aminolevulinic acid molecules to form the tetrapyrrole precursor porphobilinogen.

PBGS was previously understood to be a homooctameric metalloenzyme, which utilizes a variety of divalent and monovalent cations at catalytic and allosteric sites. The first 18 deposited X-ray crystal structures showed an octameric assembly [10], as illustrated for human PBGS in FIG. 2. Mammalian and yeast enzymes typically require Zn(II), some prokaryotic enzymes require either Mg(II) or Zn(II) or both for maximal activity, and plant enzymes seem to require only Mg(II) for enzymatic activity. A small number of organisms have PBGS enzymes that require neither Zn(II) nor Mg(II). The difference in the use of metal ions is caused by a variation of residues in the primary structures in at least two metal-binding regions [11]. The structure of *E. coli* PBGS is illustrated in FIGS. 3A-C and serves to illustrate the common metal binding variations in PBGS structures. Each *E. coli* PBGS monomer contains two metal ions, neither of which is phylogenetically conserved. The active site contains a zinc ion that is essential to *E. coli* PBGS activity but whose three cysteine ligands are not present in many PBGS. This zinc functions in the binding and reactivity of the second substrate molecule [12]. Details of the zinc site are illustrated in FIG. 3B. In addition, there is an allosteric magnesium that is seen bound at the interface of each alpha, beta-barrel with the N-terminal arm of a neighboring subunit; structural details are in FIG. 3C. The sequence determinants for binding the allosteric magnesium are not present in all PBGS. The PBGS have been categorized into four groups based on whether or not they have the catalytic zinc binding site and whether or not they have the allosteric magnesium binding site, as illustrated in FIG. 4.

FIG. 4 is a schematic for classifying the PBGS into four groups on the basis of whether or not they use an active site zinc and whether or not they use an allosteric magnesium [11]. The first matrix (far left) is divided into two classes: (a) active site zinc on the left (shaded), and (b) no active site zinc on the right (unshaded). The second matrix is divided into two classes: (a) no allosteric magnesium on top (white), and (b) allosteric magnesium on the bottom (squares). Combining the two matrixes provides a matrix (far right) consisting of four quadrants, wherein the northwest quadrant (QNW) represents +Zn/−Mg, the northeast quadrant (QNE) represents −Zn/−Mg, the southwest quadrant (QSW) represents +Zn/+Mg, and the southeast quadrant (QSE) represents −Zn/+Mg. The terms QNR, QNR, QSW, and QSE are used throughout this document to refer to the quadrants of FIG. 4.

The inventor has previously quantified [11] the following distribution of known sequences into the four quadrants: QNW=9; QNE=2; QSW=55 and QSE=63. Thus, approximately one-half of the currently available sequences encode an active site zinc requirement and one-half do not (i.e., QNW+QSW~QNE+QSE). In contrast to the active site metal pattern distribution, more than 90% of the PBGS sequences contain the determinants for allosteric magnesium binding (i.e., QSW+QSE>>QNW+QNE).

It has been found that the specific activity of PBGS from some sources is dependent on protein concentration, as illustrated in FIG. 5. For example, a protein concentration dependence for the specific activity has been seen for *B. japonicum, P. aeruginosa, R. capsulatus* and pea PBGS, but has not been documented for PBGS from *E. coli*, yeast, or from mammalian sources [13-15]. Prior interpretation of this phenomenon was a simple dissociation reaction of a maximally active octamer to lesser active or inactive tetramers and/or dimers (FIG. 5). Prior interpretation did not include alternative morpheein forms of PBGS.

It is known to inhibit PBGS by removing metals from an active site or from an allosteric site, e.g., by treating it with ethylenediaminetetraacetic acid (EDTA), or 1,10-phenanthroline [16,17].

Today, many consumers are demanding that personal health care products such as wet wipes, diapers, etc. have the ability to not only provide their intended function, but to cure or prevent a disease or a damage caused by contacting bacteria, archaea, and/or eucarya, for example, while not harming the consumer's health. To meet this demand, antimicrobial agents have been incorporated into a wide range of consumer products, such as wet wipes, to combat both transient and resident bacteria on skin. Antimicrobial-containing products are currently marketed in many forms such as lotions, deodorant soaps, hard surface cleaners, wet wipes, and surgical disinfectants.

Biofilms can be a problem for certain surfaces. Biofilms may be found on essentially any environmental surface in which sufficient moisture is present. Their development is most rapid in flowing systems where adequate nutrients are available. Biofilms are composed of populations or communities of microorganisms adhering to environmental surfaces and are complex aggregate of cells and polysaccharide. These microorganisms are usually encased in an extracellular polysaccharide that they synthesize. The biofilm, for example can be formed from mixed culture of *Pseudomonas aeruginosa, P. fluorescens* and *Klebsiella pneumoniae*. Biofilms may form on solid substrates in contact with moisture, on soft tissue surfaces in living organisms and at liquid air interfaces. Typical locations for biofilm production include rock and other substrate surfaces in marine or freshwater environments. Biofilms are also commonly associated with living organisms, both plant and animal. Tissue surfaces such as teeth and intestinal mucosa which are constantly bathed in a rich aqueous medium rapidly develop a complex aggregation of microorganisms enveloped in an extracellular polysaccharide they themselves produce. The ability of oral bacteria to store iodophilic polysaccharides or glycogen-like molecules inside their cells is associated with dental caries since these storage compounds may extend the time during which lactic acid formation may occur. It is this prolonged exposure to lactic acid which results in decalcification of tooth enamel.

People have made use of microbial biofilms, primarily in the area of habitat remediation. Water treatment plants, waste water treatment plants and septic systems associated with private homes remove pathogens and reduce the amount of organic matter in the water or waste water through interaction with biofilms. On the other hand biofilms can be a serious threat to health especially in patients in whom artificial substrates have been introduced. Also, biofilms are a threat to bottoms of ship wherein barnacles can grow and corrode the surface or on the external or the internal surfaces of pipes such as oil pumps or dehumidifiers.

As more has been learned about the differences in sequence and structure for various proteins/enzymes, it has become possible to target an essential pathway that is universally present in animals, plants, bacteria, and fungi. Such is the case for targeting the tetrapyrrole biosynthetic pathway through the inhibition of PBGS as the foundation for antimicrobials or herbicides. The phylogenetic variation in metal binding sites among the PBGS of various organisms provides sufficient structural differences for development of an inhibitory agent that will not be inhibitory toward human PBGS. In the case of PBGS, there are significant differences between organisms in the inherent ability of the PBGS to equilibrate between morpheein forms and in the amino acid sequence of the morpheein surfaces. In the case of the more general inhibition of protein function through the selective stabilization of one morpheein form, it may be the case that the target is a pathway that is not present in humans or it may be the case that the target simply has sufficient phylogenetic variation outside the active site that the surfaces of the morpheein forms are very different. For instance, sequence conservation in proteins is highest in the region of shared function, as in an enzyme active site. Sequence conservation is not high in regions that are not involved in shared function. Protein surfaces are the most susceptible to evolutionary changes and the least likely to be conserved between an organism (e.g. human) and it pathogen.

Accordingly, the inventor has developed bioactive compositions having universal applications, and methods for identifying such compositions, as well as methods of identifying proteins which are homo-oligomeric and allosteric in nature, and which will serve as targets for bioactive compounds that will inhibit or activate these homo-oligomeric proteins through perturbation of an equilibrium of quaternary assemblies. It is further desired to provide an agent capable of disturbing an equilibrium of units of multimeric proteins, e.g., an inhibitor capable of inhibiting tetrapyrrole biosynthesis in plants and/or bacteria through the stabilization of a lesser active quaternary assembly of porphobilinogen synthase. It is further desired to accomplish such inhibition via a mechanism that is also applicable to humans and animals, thereby creating a novel, highly specific, approach to bacteriostatic, antibiotic, or herbicide activity. As many essential proteins are homo-oligomeric and allosteric in nature, it is desired to provide bioactive compounds that will inhibit or activate these homo-oligomeric proteins through perturbation of an equilibrium of quaternary assemblies. The inventor has identified a compound, termed morphlock-1 (see FIGS. 32*a* and 32*b*) which was found to dramatically shift the equilibrium of quaternary assemblies of multimeric proteins.

All references cited herein are incorporated herein by reference in their entireties.

BRIEF SUMMARY OF THE INVENTION

Accordingly, the invention provides a composition comprising an agent adapted to affect a multimeric protein by binding to a binding site of said multimeric protein and thereby affecting an equilibrium of units, wherein said multimeric protein comprises an assembly having a plurality of said units, wherein each of said units comprises a first complementary surface and a second complementary surface and wherein the first complementary surface of one unit is associated with the second complementary surface of another unit, provided that the assembly is at least one of different quaternary isoforms on a condition that in said multimeric protein (1) a structure of each of said units determines a structure of said different quaternary isoforms, (2) said units are in the equilibrium and (3) the structure of said different quaternary isoforms influences a function of the multimeric protein. In certain embodiments, affecting said multimeric protein comprises affecting a formation of a quaternary isoform.

In certain embodiments, affecting said multimeric protein comprises affecting the function of said multimeric protein. A non-limiting example of a function of said multimeric protein is an activity and wherein affecting is at least one of inhibiting or activating.

In certain embodiments, the agent is bound to at least one of a quaternary isoform having a lesser activity or a quaternary isoform having a greater activity.

Non-limiting examples of the units include a monomer, a dimer, a trimer, a tetramer, a hexamer, and an octamer. For proteins other than PBGS, the units could be also pentamers, heptamers, nonomers, decamers, etc.

In certain embodiments, said multimeric protein is a member selected from the group consisting of porphobilinogen synthase, Class Ia ribonucleotide reductase, GDP-mannose dehydrogenase, histidine containing phosphocarrier protein kinase/phophatase, mammalian CoA transferase, purine nucleoside phosphorylase, and peroxiredoxins.

In certain embodiments, said multimeric protein is porphobilinogen synthase comprising eight porphobilinogen synthase monomers. In other embodiments, the active form of the multimeric porphobilinogen synthase has less than eight monomers.

In certain embodiments, the agent is an inhibitor bound to the quaternary isoform having the lesser activity and wherein the quaternary isoform contains less than eight porphobilinogen synthase monomers. In certain embodiments, the inhibitor is rosmarinic acid or a derivative thereof.

In certain embodiments, said multimeric protein is the Class Ia ribonucleotide reductase and the agent inhibits the Class Ia ribonucleotide reductase through selective binding to the binding site that is unique to the quaternary isoform having the lesser activity. In the case of the Class Ia ribonucleotide reductase, on the basis of the published literature, the morpheein form having lesser activity is predicted to be a tetramer, for which a structure is not yet available.

In certain embodiments, said multimeric protein is GDP-mannose dehydrogenase and the agent inhibits GDP-mannose dehydrogenase through selective binding to the binding site that is unique to the quaternary isoform having the lesser activity. The existing tetrameric crystal structure of GDP-mannose dehydrogenase [18] is predicted to be the inactive form because biochemical data predicts that the active form is a hexamer [19].

In certain embodiments, said multimeric protein is histidine containing phosphocarrier protein kinase/phophatase and the agent inhibits through selective binding to the binding site that is unique to the quaternary isoform having the lesser activity. In this case the hexameric form, for which there is a crystal structure, is predicted to have phosphatase activity and be inactive for the kinase activity [20]. Thus trapping the hexamer would trap the form less active for the kinase activity.

In certain embodiments, said multimeric protein is mammalian CoA transferase and the agent inhibits mammalian CoA transferase through selective binding to the binding site that is unique to the quaternary isoform having the lesser activity. Mammalian CoA transferase is reported to exist in both dimeric and tetrameric forms, which are separated by a large kinetic barrier [21]. It remains unclear if the tetrameric form is of equal activity or if there is a rapid reequilibration to the active dimeric form in the presence of substrate.

In certain embodiments, said multimeric protein is purine nucleoside phosphorylase and the agent inhibits purine nucleoside phosphorylase through selective binding to the binding site that is unique to the quaternary isoform having the lesser activity. Current data suggests that the morpheein forms of purine nucleoside phosphorylase are dimers, trimers, and two different hexamers [22,23], but data is insufficient to propose which are inactive forms. In certain embodiments, said multimeric protein is a peroxiredoxin and the agent inhibits the peroxiredoxin through selective binding to the binding site that is unique to the quaternary isoform having the lesser activity. The quaternary isoforms of the peroxiredoxins appear to consist of a dimer that cannot form multimers, a dimer that can form multimers, and the decamer of the latter dimer [24,25]. The inactive morpheein form is proposed to be the dimer that can form decamers.

Also provided is a composition comprising an inhibitor adapted to inhibit formation of an active form of a multimeric porphobilinogen synthase having a first number of monomers by binding to a less active form of the multimeric porphobilinogen synthase having a second number of monomers, wherein the first number of monomers is higher than the second number of monomers.

In certain embodiments, the multimeric porphobilinogen synthase is derived from bacteria, archaea, or eucarya, provided that the octameric porphobilinogen synthase contains an allosteric magnesium binding site. In one variant of this embodiment, the multimeric porphobilinogen synthase contains a catalytic zinc binding site.

In certain embodiments, the multimeric porphobilinogen synthase does not contain the allosteric magnesium binding site and does not contain the catalytic zinc binding site.

In certain embodiments, said less active form is a hexamer. In certain embodiments, said less active form is a dimer. In certain embodiments, the active form of a multimeric porphobilinogen synthase is an octamer.

In certain embodiments, the inhibitor replaces a metal ion and thereby binds at a metal ion binding site. In certain embodiments, the metal ion is zinc and/or magnesium.

In certain embodiments, the inhibitor binds at an active site.

In certain embodiments, the inhibitor is not a metal cation.

In certain embodiments, the inhibitor is adapted to inhibit formation of the active form of the multimeric porphobilinogen synthase, said active form is an octameric porphobilinogen synthase by binding to a hug-disabling domain of the less active form of the multimeric porphobilinogen synthase containing less than eight monomers.

In certain embodiments, the inhibitor is adapted to inhibit formation of the active form of the multimeric porphobilinogen synthase by binding at a site other than an active site and/or metal ion binding site.

In certain embodiments, the inhibitor is adapted to inhibit formation of the active form of the multimeric porphobilinogen synthase by a mechanism other than removing a metal ion.

In certain embodiments, the composition further comprises a delivery medium, said delivery medium is a member selected from the group consisting of a pharmaceutically-acceptable medium, an orally-acceptable carrier, an antibacterial medium, and a herbicidally-effective medium.

Advantageously, the composition is effective to inhibit or prevent formation of the active form of the multimeric porphobilinogen synthase and thereby inhibiting or preventing development or growth of bacteria, archaea, and/or eucarya.

In one variant of this embodiment, the composition is effective to cure or prevent a disease caused by contacting bacteria, archaea, and/or eucarya. In one variant of this embodiment, the composition is at least one of a drug, a toothpaste, a soap, a disinfectant, an anti-biofilm composition, and a herbicide.

In certain embodiments, the composition is effective to inhibit or prevent formation of the active form of the multimeric porphobilinogen synthase and thereby inhibiting or preventing development or growth of bacteria, archaea, and/or eucarya. In one variant of this embodiment, the composition is effective to cure or prevent a disease caused by contacting bacteria, archaea, and/or eucarya. In one variant of this embodiment, the composition is at least one of a drug, a toothpaste, a soap, and a disinfectant.

Further provided is a herbicide resistant plant adapted to be transgenic for a multimeric porphobilinogen synthase that substantially exist in a multimeric form of a hugging dimer. In certain embodiments, the multimeric porphobilinogen synthase is derived from a human. In certain embodiments, the multimeric porphobilinogen synthase contains no allosteric magnesium binding site.

Further provided is a composition comprising an inhibitor adapted to bind to a multimeric porphobilinogen synthase that does not require zinc for catalytic function.

Also provided is a method of affecting a multimeric protein, the method comprising: providing said multimeric protein comprising an assembly having a plurality of units, wherein each of said units comprises a first complementary surface and a second complementary surface and wherein the first complementary surface of one unit is associated with the second complementary surface of another unit, provided that the assembly is at least one of different quaternary isoforms on a condition that (1) a structure of said units determines a structure of said different quaternary isoforms, (2) said units are in an equilibrium and (3) the structure of said different quaternary isoforms influences a function of said multimeric protein; providing the composition of the invention comprising the agent, wherein the agent is adapted to affect the equilibrium by binding to a binding site on the assembly; and contacting the assembly with the agent, wherein the agent affects the equilibrium by binding to the binding site and thereby affecting said multimeric protein. In certain embodiments of the method, affecting said multimeric protein comprises affecting a formation of a quaternary isoform. In certain embodiments of the method, affecting said multimeric protein comprises affecting a function of said multimeric protein.

In certain embodiments of the method, the units include a monomer, a dimer, a trimer, a tetramer, a hexamer, and an octamer. For proteins other than PBGS, the units could be also pentamers, heptamers, nonomers, decamers, etc.

In certain embodiments of the method, the agent is adapted to affect a function of said multimeric protein.

In certain embodiments of the method, the function of said multimeric protein is an activity and wherein affecting is at least one of inhibiting or activating.

In certain embodiments of the method, the agent is bound to at least one of a quaternary isoform having a lesser activity or a quaternary isoform having a greater activity.

In certain embodiments of the method, the agent is bound to the quaternary isoform having a greater activity.

In certain embodiments of the method, said multimeric protein is a member selected from the group consisting of porphobilinogen synthase, Class Ia ribonucleotide reductase, GDP-mannose dehydrogenase, histidine containing phosphocarrier protein kinase/phophatase, mammalian CoA transferase, purine nucleoside phosphorylase, and peroxiredoxins.

In certain embodiments of the method, said multimeric protein is porphobilinogen synthase comprising eight porphobilinogen synthase monomers.

In certain embodiments of the method, said multimeric protein is the Class Ia ribonucleotide reductase and the agent inhibits the Class Ia ribonucleotide reductase through selective binding to the binding site that is unique to the quaternary isoform having the lesser activity.

In certain embodiments of the method, said multimeric protein is the GDP-mannose dehydrogenase and the agent inhibits the GDP-mannose dehydrogenase through selective binding to the binding site that is unique to the quaternary isoform having the lesser activity.

In certain embodiments of the method, said multimeric protein is the histidine containing phosphocarrier protein kinase/phophatase and the agent inhibits the histidine containing phosphocarrier protein kinase/phophatase through selective binding to the binding site that is unique to the quaternary isoform having the lesser activity.

In certain embodiments of the method, said multimeric protein is mammalian CoA transferase and the agent inhibits the mammalian CoA transferase through selective binding to the binding site that is unique to the quaternary isoform having the lesser activity.

In certain embodiments of the method, said multimeric protein is purine nucleoside phosphorylase and the agent inhibits the purine nucleoside phosphorylase through selective binding to the binding site that is unique to the quaternary isoform having the lesser activity.

In certain embodiments of the method, said multimeric protein is peroxiredoxins and the agent inhibits peroxiredoxins through selective binding to the binding site that is unique to the quaternary isoform having the lesser activity.

Further provided is a method of modulating a physiological activity in a cell, a tissue or an organism, the method comprising: providing the cell, the tissue or the organism, wherein the cell, the tissue or the organism comprise a multimeric protein comprising an assembly having a plurality of units, wherein each of the units comprises a first complementary surface and a second complementary surface and wherein the first complementary surface of one unit is associated with the second complementary surface of another unit, provided that the assembly is at least one of different quaternary isoforms on a condition that (1) a structure of said units determines a structure of said different quaternary isoforms, (2) said units are in an equilibrium and (3) the structure of said different quaternary isoforms influences a function of the multimeric protein; and providing to the cell, the tissue or the organism the composition of the invention comprising the agent, wherein the agent is adapted to affect the equilibrium by binding to the binding site on the unit and thereby affecting the formation of a quaternary isoform and thereby modulating the physiological activity.

Further provided is a method of inhibiting a multimeric porphobilinogen synthase from forming an active form, the method comprising: applying the composition of the invention to the multimeric porphobilinogen synthase; associating the composition with the less active form; inhibiting the less active form from assembling into the active form and thereby inhibiting the multimeric porphobilinogen synthase from forming the active form.

Further provided is a method for manipulating growth or development of a plant comprising applying the composition of the invention which is a herbicide to the plant, wherein the plant is herbicide resistant and is adapted to be transgenic for a multimeric porphobilinogen synthase that substantially exist in a multimeric form of a hugging dimer. In one variant of the method, the multimeric porphobilinogen synthase contains no allosteric magnesium binding site.

Further provided is a method of making an antibacterial surface, the method comprising: (1) providing the composition of the invention wherein the composition is effective to inhibit or prevent formation of the active form of the multimeric porphobilinogen synthase and thereby inhibiting or preventing development or growth of bacteria, archaea, and/or eucarya, provided that the active form of the multimeric porphobilinogen synthase contains an allosteric magnesium binding site and the composition is at least one of a drug, a toothpaste, a soap, a disinfectant, an anti-biofilm composition, and a herbicide; (2) providing a surface-forming matrix; and (3) combining the composition with the surface-forming matrix and thereby making the antibacterial surface. In one variant of the method, the antibacterial surface is adapted to prevent or inhibit a formation of a biofilm.

The invention provides an isolated nucleic acid sequence selected from the group consisting of SEQ ID NO: 1, SEQ ID NO: 2, SEQ ID NO: 4, fragments thereof, variants thereof, and muteins thereof. The invention provides an isolated nucleic acid sequence encoding a polypeptide selected from the group consisting of SEQ ID NO: 3, fragments thereof, muteins thereof, and variants thereof. In certain embodiments, the nucleic acid further comprises a nucleic acid sequence selected from the group consisting of SEQ ID NO: 1-2, fragments thereof, variants thereof, and muteins thereof. In certain embodiments, the nucleic acid further comprises a nucleic acid encoding a tag polypeptide covalently linked thereto. In certain embodiments the tag polypeptide is selected from the group consisting of a myc tag polypeptide, a glutathione-S-transferase tag polypeptide, a green fluorescent protein tag polypeptide, a myc-pyruvate kinase tag polypeptide, a His6 tag polypeptide, an influenza virus hemagglutinin tag polypeptide, a flag tag polypeptide, and a maltose binding protein tag polypeptide. In certain embodiments the isolated nucleic acid further comprises a nucleic acid specifying a promoter/regulatory sequence operably linked thereto. The invention provides a host cell comprising the nucleic, and further wherein the host cell is a member selected from the group consisting of eukaryotic cells and prokaryotic cells. The invention provides a cell line stably transfected with the nucleic.

The invention provides a substantially purified polypeptide selected from the group consisting of SEQ ID NO: 3, fragments thereof, muteins thereof, and variants thereof. The invention provides an immunogenic peptide selected from the group consisting of SEQ ID NO: 3, fragments thereof, muteins thereof, and variants thereof. In certain embodiments the isolated polypeptide further comprises a tag polypeptide covalently linked thereto. In further embodiments the tag polypeptide is selected from the group consisting of a myc tag polypeptide, a glutathione-S-transferase tag polypeptide, a green fluorescent protein tag polypeptide, a myc-pyruvate kinase tag polypeptide, a His6 tag polypeptide, an influenza virus hemagglutinin tag polypeptide, a flag tag polypeptide, and a maltose binding protein tag polypeptide. The invention provides an isolated nucleic acid encoding an immunogenic peptide selected from the group consisting of SEQ ID NO: 3, fragments thereof, muteins thereof, and variants thereof.

The invention provides an isolated antibody, wherein said antibody selectively binds: a) a polypeptide with an amino acid sequence of SEQ ID NO: 3, fragments thereof, muteins thereof, and variants thereof; b) a polypeptide that is encoded by a nucleic acid molecule that hybridizes to the nucleic acid sequence of SEQ ID NO: 1 under stringent conditions, comprising 50% formamide, 0.1% bovine serum albumin, 0.1% Ficoll, 0.1% polyvinylpyrrolidone, 50 mM sodium phosphate (pH 6.5), 750 mM NaCl, and 75 mM sodium citrate at 42° C., with washes at 42° C. in 0.2×SSC and 0.1% SDS; c) a fragment of said antibody, wherein said antibody and antibody fragment selectively bind to said polypeptide. In certain embodiments the antibody is of polyclonal or monoclonal origin.

The invention provides a method of identifying a potential therapeutic agent which inhibits formation of the active form of a multimeric protein by binding at a site other than an active site and/or metal ion binding site of the multimeric protein comprising an assembly having a plurality of units, wherein each of said units comprises a first complementary surface and a second complementary surface and wherein the first complementary surface of one unit is associated with the second complementary surface of another unit, provided that the assembly is at least one of different quaternary isoforms on a condition that (1) a structure of said units determines a structure of said different quaternary isoforms, (2) said units are in an equilibrium and (3) the structure of said different quaternary isoforms influences a function of said multimeric protein comprising the steps of: (a) providing a multimeric protein, wherein the multimeric protein comprising an assembly having a plurality of units, wherein each of said units comprises a first complementary surface and a second complementary surface and wherein the first complementary surface of one unit is associated with the second complementary surface of another unit; (b) providing a test agent; (c) combining the multimeric protein and the test agent; (d) measuring the formation of the active form of a multimeric protein in the presence of test agent; (e) measuring formation of the active form of a multimeric protein in a control sample; and (f) comparing formation of the active form of a multimeric protein in the control sample compared to the test sample, to identify a compound which modulates formation of the active form of a multimeric protein. In certain embodiments the multimeric protein is in a stably transfected cell line, and further wherein the cell is a member selected from the group consisting of eukaryotic cells, and prokaryotic cells. In certain embodiments, the multimeric protein comprises a protein tag. In certain embodiments, the tag polypeptide is selected from the group consisting of a myc tag polypeptide, a glutathione-S-transferase tag polypeptide, a green fluorescent protein tag polypeptide, a myc-pyruvate kinase tag polypeptide, a His6 tag polypeptide, an influenza virus hemagglutinin tag polypeptide, a flag tag polypeptide, and a maltose binding protein tag polypeptide.

The invention provides a kit comprising a multimeric peptide selected from the group consisting of SEQ ID NO: 3, fragments thereof, muteins thereof, and variants thereof. The invention provides a kit for the detection of PBGS antigen comprising a container; and at least one antibody wherein the at the least one antibody specifically binds to an epitope of PBGS. In certain embodiments the kit further comprises a solid support, wherein said solid support is selected from the group consisting of wells of reaction trays, test tubes, polystyrene beads, strips, membranes and microparticles. In certain embodiments the kit further comprises a label, wherein said label is selected from the group consisting of enzymes, radioisotopes, fluorescent compounds and chemiluminescent compounds. In certain embodiments the enzymatic label is horseradish peroxidase. In certain embodiments the kit further comprises a hapten and labeled anti-hapten system wherein the hapten is conjugated to a labeled murine monoclonal antibody.

The invention provides an in silico method for identifying a compound that inhibits formation of the active form of a multimeric protein by binding at a site other than an active site and/or metal ion binding site of the multimeric protein comprising an assembly having a plurality of units, wherein each of said units comprises a first complementary surface and a second complementary surface and wherein the first complementary surface of one unit is associated with the second complementary surface of another unit, provided that the assembly is at least one of different quaternary isoforms on a condition that (1) a structure of said units determines a structure of said different quaternary isoforms, (2) said units are in an equilibrium and (3) the structure of said different quaternary isoforms influences a function of said multimeric protein, comprising the steps of: (a) providing atomic co-ordinates of said multimeric protein in a storage medium on a computer; (b) providing the atomic coordinates of a compound; (b) using said computer to apply molecular modeling techniques to said co-ordinates; and (c) identifying a compound that inhibits formation of the active form of the multimeric protein. In further embodiments the molecular modeling techniques involve de novo compound design. In further embodiments the de novo compound design comprises the steps of (i) the identification of functional groups or small molecule fragments which can interact with sites in the binding surface of multimeric protein; and (ii) linking these in a single compound. In further embodiments the molecular modeling techniques use automated docking algorithms. In further embodiments the multimeric protein is selected from the group consisting of PBGS, acetyl-CoA carboxylase, adenylosuccinate lyase, alpha-acetylgalactosaminidase, aristolochene synthase, asparaginase, aspartokinase III, ATPase of the ABCA1 Transporter, biotin holoenzyme synthetase, choline oxidase, chorismate mutase, citrate synthase, cyanovirin-N, D-3-Phosphoglycerate dehydrogenase, d-Amino Acid oxidase, dihydrolipoamide dehydrogenase, dopamine b-monooxygenase, glutamate dehydrogenase, glutamate racemase, glyceraldehyde-3-phosphate dehydrogenase, glycerol kinase, histidine decarboxylase, hemocyanins, lactate dehydrogenase, Lon protease, malic enzyme, phenylalanine hydroxylase, phosphoenolpyruvate carboxylase, phosphofructokinase, polyphenol oxidase, pyruvate kinase, S-adenosyl=-L-homocysteine hydrolase, threonine dehydratase aka threonine deaminase, uracil phosphoribosyltransferase, isocitrate dehydrogenase, and variants thereof. In further embodiments the method further comprises the additional steps of: i) providing a compound identified by said molecular modeling techniques; and ii) contacting said compound with the multimeric protein and detecting the interaction between them.

The invention provides a method of identifying a compound that inhibits formation of the active form of a multimeric protein by binding at a site other than an active site and/or metal ion binding site of the multimeric protein comprising an assembly having a plurality of units, wherein each of said units comprises a first complementary surface and a second complementary surface and wherein the first complementary surface of one unit is associated with the second complementary surface of another unit, provided that the assembly is at least one of different quaternary isoforms, the method comprising: a) providing at least one multimeric protein with the biochemical function; (b) identifying a compound that binds to the protein; and (c) testing for the ability of the compound to affect the biochemical function in at least one member of the multimeric protein. In further embodiments the biochemical function of said multimeric protein correlates to a human disease or condition. In further embodiments the effect of the compound on the biochemical function is selected from the group consisting of inhibition, activation, enhancement, modulation, binding, and allosteric effect.

In further embodiments the multimeric protein is selected from the group consisting of PBGS, acetyl-CoA carboxylase, adenylosuccinate lyase, alpha-acetylgalactosaminidase, aristolochene synthase, asparaginase, aspartokinase III, ATPase of the ABCA1 Transporter, biotin holoenzyme synthetase, choline oxidase, chorismate mutase, citrate synthase, cyanovirin-N, D-3-Phosphoglycerate dehydrogenase, d-Amino Acid oxidase, dihydrolipoamide dehydrogenase, dopamine b-monooxygenase, glutamate dehydrogenase, glutamate racemase, glyceraldehyde-3-phosphate dehydrogenase, glycerol kinase, histidine decarboxylase, hemocyanins, lactate dehydrogenase, Lon protease, malic enzyme, phenylalanine hydroxylase, phosphoenolpyruvate carboxylase, phosphofructokinase, polyphenol oxidase, pyruvate kinase, S-adenosyl=-L-homocysteine hydrolase, threonine dehydratase aka threonine deaminase, uracil phosphoribosyltransferase, isocitrate dehydrogenase, and variants thereof.

The invention provides a compound identified by the method that specifically interacts with a target protein. The invention provides a method of treating a disease or condition by administering a therapeutically effective amount of the compound. The invention provides a method of treating a disease or condition by administering a therapeutically effective amount of the compound. The invention provides a method of identifying a compound, wherein the effect of the compound on the biochemical function is selected from the group consisting of inhibition, activation, enhancement, modulation, binding, and allosteric effect.

The invention provides a method of identifying a compound capable of inhibiting the formation of the active form of a multimeric protein by binding at a site other than an active site and/or metal ion binding site of the multimeric protein a multimeric protein, providing said multimeric protein comprises an assembly having a plurality of units, wherein each of said units comprises a first complementary surface and a second complementary surface and wherein the first complementary surface of one unit is associated with the second complementary surface of another unit, provided that the assembly is at least one of different quaternary isoforms on a condition that (1) a structure of said units determines a structure of said different quaternary isoforms, (2) said units are in an equilibrium and (3) the structure of said different quaternary isoforms influences a function of said multimeric protein, the method comprising: (a) providing a three-dimensional structure of said multimeric protein; and (b) using information comprising the three-dimensional structure of the multimeric protein to identify a compound that specifically interacts with the protein. In certain embodiments the information for the three-dimensional structure of the functional domain further comprises amino acid residues related to a biochemical function selected from the group consisting of inhibition, activation, enhancement, modulation, binding, and allosteric effect on the protein of interest. In certain embodiments the method is performed computationally. In certain embodiments the biochemical function is related to a human disease or condition. In certain embodiments the multimeric protein is selected from the group consisting of PBGS, acetyl-CoA carboxylase, adenylosuccinate lyase, alpha-acetylgalactosaminidase, aristolochene synthase, asparaginase, aspartokinase III, ATPase of the ABCA1 Transporter, biotin holoenzyme synthetase, choline oxidase, chorismate mutase, citrate synthase, cyanovirin-N, D-3-Phosphoglycerate dehydrogenase, d-Amino Acid oxidase, dihydrolipoamide dehydrogenase, dopamine b-monooxygenase, glutamate dehydrogenase, glutamate racemase, glyceraldehyde-3-phosphate dehydrogenase, glycerol kinase, histidine decarboxylase, hemocyanins, lactate dehydrogenase, Lon protease, malic enzyme, phenylalanine hydroxylase, phosphoenolpyruvate carboxylase, phosphofructokinase, polyphenol oxidase, pyruvate kinase, S-adenosyl=-L-homocysteine hydrolase, threonine dehydratase aka threonine deaminase, uracil phosphoribosyl-transferase, isocitrate dehydrogenase, and variants thereof.

BRIEF DESCRIPTION OF SEVERAL VIEWS OF THE DRAWINGS

The invention will be described in conjunction with the following drawings in which like reference numerals designate like elements and wherein:

FIG. 2 illustrates the differential assembly of octameric and hexameric human PBGS.

FIG. 15A represents an alignment of active site metal binding residues for the PBGS sequences of Eukaryota and Archaea, which were obtained from GenBank and other web-searchable genomes available as of April 2002. FIG. 15A, SEQ ID NOs: 5-46.

FIGS. 15B and 15C represents an alignment of active site metal binding residues for the PBGS sequences of Eubacteria, which were obtained from GenBank and other web-searchable genomes available as of April 2002. FIG. 15B, SEQ ID NOs: 47-89, FIG. 15C, SEQ ID NOs: 90-135.

FIG. 18B shows the subunit interfaces of human PBGS octamer (left) relative to the hexamer (right). The first dimer is illustrated using space fill (gray and black) and the remaining subunits are shown in a strand representation. The black bordered white arrow shows the locations comparable to the allosteric magnesium in FIG. 18A. This binding site is present in the octamer and absent in the hexamer.

FIG. 25A is a graph demonstrating porphobilinogen formation during the equilibrium dialysis of Pools I and II (as per FIG. 17A) against buffer containing ALA. (◇) Pool II, pH 7.0; (Δ) Pool I, pH 7.0; (□) Pool II, pH 9.0. (○) Pool I, pH 9.0.

FIG. 25B is a picture of native electrophoresis gels of WT+F12L Pool I and Pool II during dialysis at 37 C in the presence and absence of ALA at various times. In the absence of ALA the percentage of octamer and hexamer remain unchanged. In the presence of ALA, the equilibrium of all Pools shifts toward the octamer.

FIG. 25C is a graph demonstrating densitometric analysis of the native gel data shown in FIG. 25B. (■) Pool II, pH 9.0; (▲) Pool I, pH 7.0; (●) Pool I, pH 9.0. The lines are the best fit to a single rate exponential equation.

FIG. 26A is a picture of gels obtained in native gel electrophoresis of the Pools before dialysis, after 24 hours of dialysis against ALA at pH 7, and after chromatographic separation on the Mono-Q column.

FIG. 30 illustrates two orientations of the crystal structure of *Lactobacillus casei* HPrK/P, in the hexameric assembly (ribbons in white), complexed with the HPr protein of *Bacillus subtilus* (ribbons in gray). The tryptophan illustrated using the space filling representation (dark gray) is the only tryptophan in HPrK/P of both *L. casei* and *B. subtilus*. The putative drug-binding site is illustrated with an arrow.

FIG. 32 illustrates that the oligomer-trapping inhibitor, morphlock-1, stabilizes the hexameric assembly of pea PBGS. FIG. 32(a) The inhibitor morphlock-1 is illustrated as posed by Glide. The subunits A, B, and E are illustrated as ribbon diagram. Morphlock-1 is shown with carbon atoms and illustrated as ball and stick. FIG. 32(b) The chemical structure of morphlock-1. FIG. 32(c) Pea PBGS (1 mg/mL) resolves on native PAGE into its octameric and hexameric components. Pea PBGS was incubated with various concentrations of morphlock-1 (in a DMSO solution). Each concentration of morphlock-1 with a fixed amount of DMSO was incubated with protein for 30 minutes at 37° C. prior to resolution on 12.5% polyacrylamide native PhastGels. Morphlock-1 draws the pea PBGS morpheein equilibrium entirely to the hexamer in a dose dependent fashion. (d) The protein concentration dependence of pea PBGS specific activity is illustrated. PBGS (at varied concentrations) was incubated in the presence of DMSO (●) or 50 µM morphlock-1 in DMSO (○) for 30 minutes at 37° C. prior to assay. The final concentration of morphlock-1 in the inhibited assay was 5 µM, and the concentration of PBGS in the inhibited and control assays ranged from 0.05-50 µg/mL (0.014-1.4 µM).

FIG. 33(b). The $IC_{50}$ for morphlock-1 is a function of pea PBGS concentration. $IC_{50}$ values were determined as per part (a) using the noted concentrations of pea PBGS. (c) Native PAGE evaluation of the effect of morphlock-1 on the quaternary structure equilibria of PBGS (~1 mg/ml) from *D. melanogaster, P. aeruginosa, V. cholerae*, and *H. sapiens*. Note that the charge/mass ratio is not the same for PBGS from different species.

FIG. 34 illustrates morphlock-1 and substrate induced interconversion of PBGS quaternary structure assemblies—FIG. 34(a) Matched Coomassie (left) and PBGS activity (right) stained native PAGE (at 1 mg/ml PBGS) illustrates specific binding of morphlock-1 (at 2 mM) to the hexameric assembly. Enzyme-bound morphlock-1 prevents the in-gel transition of inactive hexamer to active octamer (see Fig S2).

FIG. 34(b) Hexameric pea PBGS (1 mg/mL, prepared by dialysis against low ionic strength) was incubated with DMSO (left) or 500 µM morphlock-1 (right) for 30 minutes at 37° C. ALA was added at the indicated concentrations, and the incubation was continued for 30 minutes prior to resolution on 12.5% polyacrylamide native PhastGels. FIG. 34(c) Morphlock-1 induced stabilization of the pea PBGS hexameric assembly. Morphlock-1 concentrations are listed at the top of each lane. Protein samples for left-most gel were at 50 µg/ml (1.4 µM subunit) and 1 mM ALA; protein detection is by silver staining. Samples for the middle gel were also at 50 µg/ml (1.4 µM subunit) and 1 mM ALA; the gel was activity stained. Samples for the right-most gel were at 5 µg/ml (0.14 µM subunit) and 10 mM magnesium; protein detection is by Krypton Infrared staining.

FIG. 35(a) A reaction coordinate diagram of the following equilibrium: PBGS hexamer ⇌ pro-hexamer dimer ⇌ pro-octamer dimer ⇌ octamer There is substantial uncertainty in the heights of the thermodynamic barriers, which are shown as dashed lines to illustrate this concept. The energy difference between the hexamer and the octamer is proposed to be small and is known to respond to the binding of ligands (4, 5). FIG. 35(b) A typical time-course monitoring the increase in specific activity as the metastable hetero-hexamer converts to the higher activity hetero-octamer upon substrate turnover. The illustrated data was obtained at 37° C. FIG. 35(c) Arrhenius plots of the first order rate constants (k, min-1) for the conversion hetero-hexamers to hetero-octamers (squares right axis) and of initial rates expressed as specific activities (µmol h-1 mg-1, left axis) of WT (circles), F12L (diamonds) and WT+F12L hetero-octamers (triangles). In all experiments the concentration of ALA-HCl was 10 mM and the pH was 7.0.

FIG. 37 illustrates a structural explanation for the kinetic behavior of octameric and hexameric PBGS—On the left is an overlay of the pH activity profiles for the wild type octameric human PBGS and the hexameric F12L variant. Published studies establish that the kinetic differences are due to the quaternary structure assembly, and not the specific mutation. As shown, these two assemblies differ in the pH dependence of the specific activity (at 10 mM substrate) and in the $K_m$ values. These differences are attributed to a difference in the stability of the active site lid. Illustrated on the right is an overlay of the octameric wild type human PBGS crystallographic unit (PDB code 1 e51) and the hexameric F12L crystallographic unit (PDB code 1 pv8). Both crystallographic dimers are themselves asymmetric. The bulk of the asymmetry lies in what is seen to be ordered vs. disordered in the structures. Exceptionally good overlap is seen in the core of the two assemblies, including the active site, which lies in the center of the alpha-beta-barrels. The differences lie in the conformation, location, and order seen in the N-terminal 24 amino acids (the N-terminal arm) and in that region of the protein that constitutes a flexible active site lid. In short, when the N-terminal arm is "up", as in the hexameric assembly, an arm-to-barrel interaction seen in the octameric assembly is missing, and the active site lid is seen to be disordered. Without a highly ordered active site lid, the active site is open to solvent and a high external pH is essential to deprotonate an active site lysine that must form a Schiff base with the substrate for the PBGS catalyzed reaction). In the crystallographic asymmetric unit of the octamer, one active site lid is seen to be ordered. Many crystal structures show an interaction between the Km determining substrate and the active site lid. Without this stabilizing interaction, the Km is much higher.

FIG. 38(a) The pea PBGS equilibrium ensemble of quaternary structure forms is illustrated using homology models. For most species, the asymmetric unit of the crystal structure is an asymmetric homodimer [8, 12, 14, 44]. The hexamer and its asymmetric unit, the detached dimer (based on PDB code 1PV8) are shown. The octamer and its asymmetric unit, the hugging dimer (based on PDB code 1GZG) are shown. For the octamer, the dimers assemble at a 90° rotation around a central axis; for the hexamer, the dimers assemble at a 120° rotation around a central axis. The octamer contains a phylogenetically variable binding site 31 for an allosteric magnesium ion. This ion binds to the arm-to-barrel interface that is unique to the octamer; the allosteric magnesium binding site is not present in the hexamer [8,20]. The hexamer contains a surface cavity that is not present in the octamer and is predicted to be a small molecule binding site. The small molecule inhibitor (illustrated schematically by the balls) draws the equilibrium toward the hexamer. FIG. 38(b) Left panel—The small molecule binding site in the pea PBGS hexamer model contains components from three subunits, shown as ribbons. The GLIDE docking box is superimposed at the subunit interface. The box into which ligands must fit and the box in which the center of the docked small molecules must fit are shown. Right panel—The three subunits forming the docking site are shown as ribbons in the context of the hexameric assembly with the remaining subunits shown as surfaces, subunit labels correspond to subunits. FIG. 38(c) A multiple sequence alignment of the regions of PBGS contained within the hexamer-specific inhibitor docking site of pea PBGS is shown with the highly conserved residues shaded in grey SEQ ID NOs: 136-147). Sequence conservation was determined from an alignment of 33 PBGS sequences (not shown), and a residue was defined as "highly conserved" if it was present in at least 32 sequences. Numbers correspond to the pea PBGS sequence. Residues highlighted of the *P. sativum* PBGS are within 4 Å of docked morphlock-1. Residues marked with an "A", "B", or "E" indicate a sidechain interaction between subunits A, B, or E of pea PBGS and docked morphlock-1.

FIG. 40(a) pea PBGS resolves into ~70% octamer and ~30% hexamer after electrophoresis in the 1st dimension. The resolved gels were then incubated in following conditions: FIG. 40(b) no incubation, FIG. 40(c) 0.1 M BTP, pH 8.5 at 37° C. for 20 min, d. 0.1 M BTP, pH 8.5, 10 mM ALA, 10 mM Mg2+ (assay conditions) at 37° C. for 20 min. Following these incubations, the 2nd dimension separation was carried out immediately. All gels were then stained for PBGS activity (right panels) followed by Coomassie staining (left panels). In panel b. the hexamer ran as hexamer in the second dimension. In panel c. there is a minimal conversion of hexamer to octamer during the buffer incubation step. In panel FIG. 40(d), where the gel is incubated with substrate under turnover conditions, there is nearly total conversion of hexamer to octamer during the incubation step. The protein mobility difference observed for the 2nd dimension separation for gels c and d versus gel b is due to the effect of incubation buffer on gel matrix.

FIG. 43(c) The proposed biologically relevant dimers (the pro-octamer and pro-hexamer dimers) are composed of one subunit from each of two neighboring asymmetric units, and are illustrated as described for A. Interconversion between the pro-octamer and pro-hexamer dimers, which is proposed to mediate the equilibrium between octamers and hexamers, involves backbone rotations at only a few amino acids. A 90° rotation of the oligomers about the x-axis yields the "pinwheel" view that further illustrates oligomeric assembly (bottom panels).

FIG. 45(a) In a classic enzyme-catalyzed reaction, the catalytic rate increases as a hyperbolic function of substrate concentration (grey squares and dashed line) system. In the event that two kinetically distinct forms of an enzyme coexist, the data (black circles) cannot be fit to a single hyperbola (dotted black line). Instead, the data fit to a double hyperbola (solid line), where the sum of two Michaelis-Menten equations describes the contributions from both species. FIG. 45(b). In a classic enzyme-catalyzed reaction (dashed grey line) the product increases linearly with time as long as substrate is saturating. For an enzyme that exists as an equilibrium of morpheein forms (solid black line), a lag time can reflect an inactive form dissociating, equilibrating, and re-associating into a more active form in the presence of substrate. Alternatively, in the presence of an inhibitor, a rapid initial rate can slowly approach a final steady state rate as the ensemble of morpheein forms reequilibrates to the less active assembly (not shown). FIG. 45(c) The activity per enzyme unit (specific activity) is a fixed property that does not vary with enzyme concentration for standard enzymes (dashed grey line). In a morpheein system in which a higher protein concentration favors a more active assembly, the specific activity increases as a function of enzyme concentration (solid black line). Alternatively, if the lower stoichiometry assembly is more active, one might see an inverse relationship between enzyme concentration and specific activity (not shown).

FIG. 46(a) In the Monod, Wyman, Changeux (MWC, or concerted) model of allostery, each oligomer exists in the inactive (composed of round subunits) or active (composed of square subunits) states. The oligomers are in equilibrium with each other, and binding of an allosteric activator (shown as jagged black squares), draws the equilibrium towards the active state. FIG. 46(b) In the Koshland, Nemethy, Filmer (KNF, or sequential) model of allostery, the individual subunits of the oligomers exist in the inactive (round) or active (square) state. Binding of an allosteric activator to a subunit within an oligomer induces a conformational change of an adjacent subunit to the active state. FIG. 46(c) In the example of the morpheein model, allosteric control involves dissociation of the oligomers. The inactive form is a trimer of pie-wedge subunits, the active form is a tetramer of square subunits; the trimers, pie-wedges, squares, and tetramers all coexist in equilibrium. The allosteric activator binds to the square subunits and draws the equilibrium towards the active tetramer. For example, in the case of plant PBGS, the allosteric activator is a magnesium ion.

DETAILED DESCRIPTION OF THE INVENTION

Figure 1:
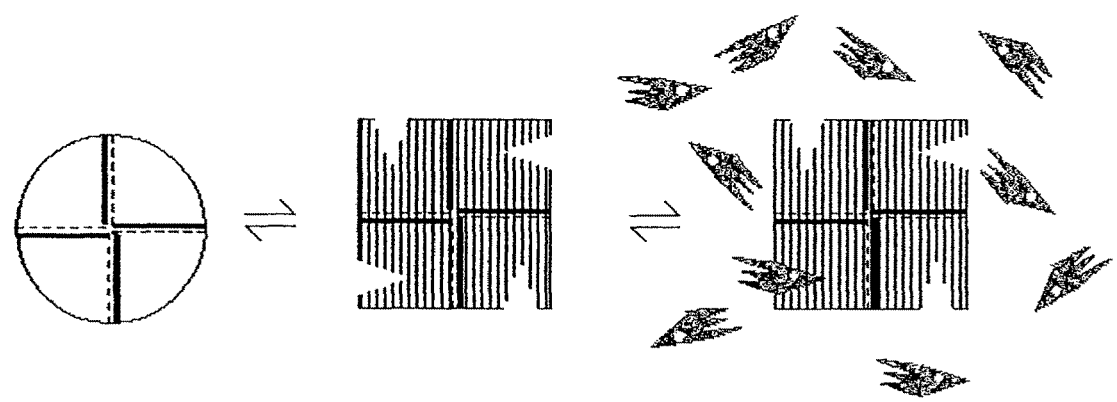
FIG. 1 (prior art) is a classic model for allosteric regulation of protein function. An equilibrium of allosteric states (ON state and OFF state) is illustrated. The allosteric regulators (objects in a shape of a granite fish) can bind to the square tetramer and pull the equilibrium in that direction; oligomer dissociation is not an obligatory part of the equilibration process. This classic model presumes that the stoichiometry of the quaternary assembly of the allosteric protein is constant between the ON state and the OFF state. In this figure, both are tetramers.
Figure 6:
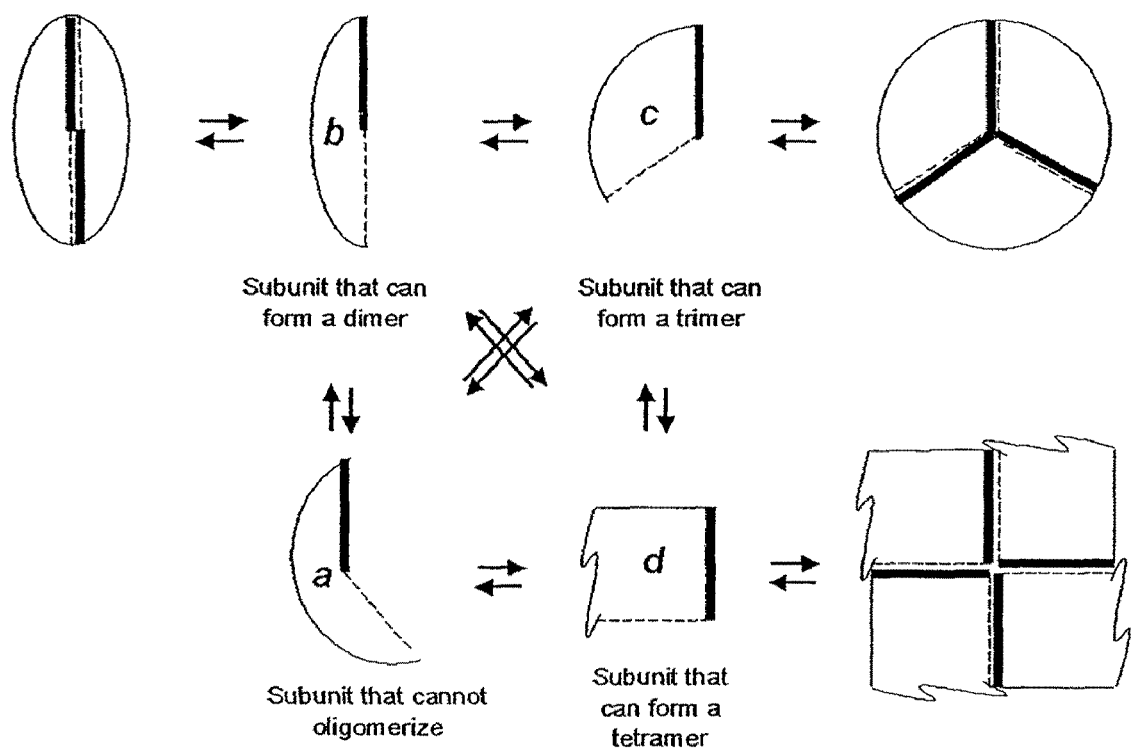
FIG. 6 is a 2-D schematic representation of the morpheein concept of an equilibrium ensemble of protein oligomers—Different conformations of a protein monomer are represented by different shapes (labeled a-d); each shape has one surface that is a dashed line and one surface that is a thick line. For oligomeric assembly, the rule of engagement between any two monomers is the association of the dashed line with the thick line. Four possible alternative conformations are shown for the monomer and each of these conformations dictates a different quaternary structure. Conformation (a) cannot oligomerize because it is not geometrically possible to satisfy the rule of engagement in two dimensions. Conformation (b) can completely satisfy the rule of engagement by forming a dimer after which oligomerization is complete. Conformation (c) can completely satisfy the rule of engagement by forming a trimer. Conformation (d) can completely satisfy the rule of engagement by forming a tetramer. Within this framework, the dimerization of a protein involves an equilibrium between three species. These are the monomer conformation that cannot form a dimer (a), the monomer conformation that can form a dimer (b), and the dimer (of b).
Figure 7:
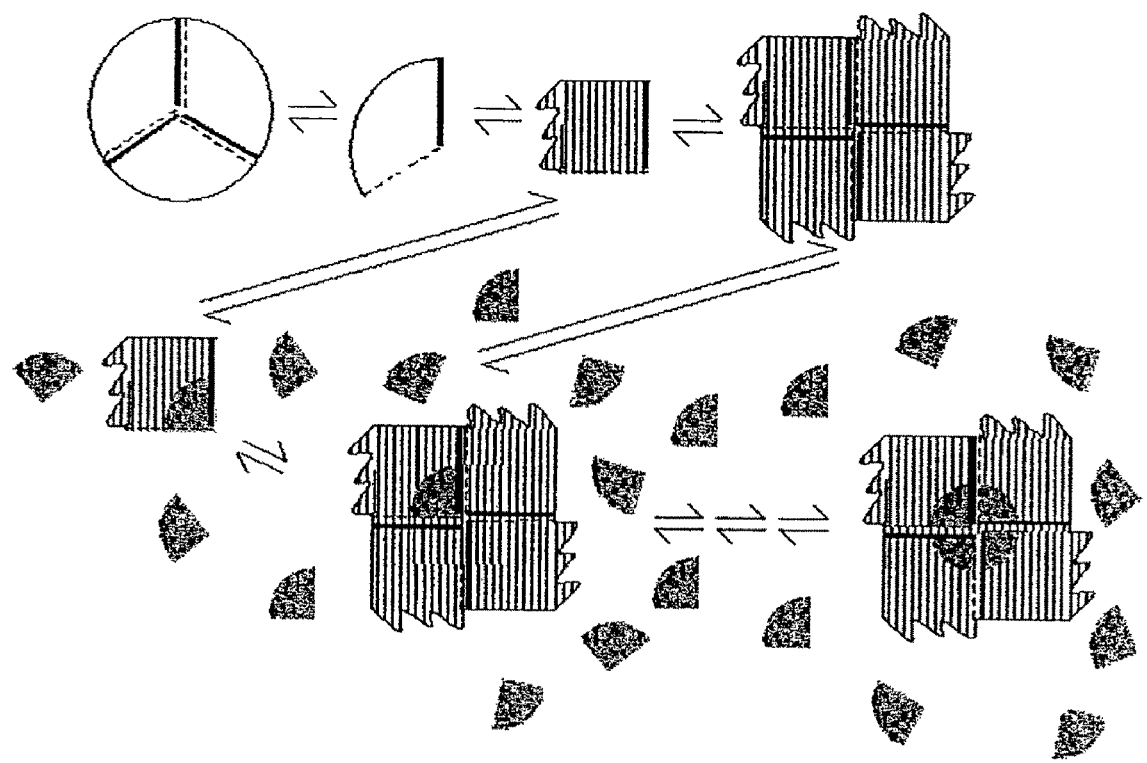
FIG. 7 illustrates the alternate representation of allosteric regulation as an equilibrium of morpheein forms. The defining characteristics of this MORPHEEIN MODEL OF ALLOSTERIC REGULATION are that 1) the structure of the monomer dictates alternate assemblies for the oligomers (round trimer, square tetramer) and 2) there is a requisite dissociation and reassociation of fundamental units. The granite substance represents the allosteric regulator, which functions to draw the equilibrium toward the square forms by acting as a wedge and inhibiting the interconversion of monomeric forms. In the morpheein representation the change in oligomeric state is more complex than a simple association/dissociation phenomenon. A morpheein equilibrium involves a dramatic change in the conformation of the (at least partially dissociated) monomeric unit. The morpheein concept provides a novel structural paradigm for allosteric regulation, which is fundamentally different from that which is illustrated in FIG. 1.

The present invention was prompted by the inventor's studies relating to the basic science of tetrapyrrole biosynthesis. The unexpected behavior of the enzyme porphobilinogen synthase led the inventor to propose that this, and perhaps also other, proteins could defy the Anfinsen paradigm (one protein one structure) [1] and could exist as more than one physiologically relevant quaternary assembly where each quaternary assembly was the natural outcome of an alternate conformation for the monomeric unit. These alternate quaternary assemblies are given the name morpheein forms. A two dimensional schematic representation of morpheein forms as alternate quaternary assemblies of homo-oligomeric proteins is shown in FIG. 6. The morpheein forms of PBGS, the structures of which are described in detail below, and the inventor's knowledge that some PBGS are subject to allosteric regulation, led to the proposal of the morpheein model of allosteric regulation of protein function, which is illustrated in FIG. 7, and is fundamentally different from all previously proposed models for allosterism (as illustrated in FIG. 1). The morpheein model for allosteric regulation requires that the oligomeric protein must dramatically rearrange as part of the allosteric transition from the ON state to (or from) the OFF state.

Morpheeins are homo-oligomeric proteins that can come apart and change conformation in the dissociated form such that they can no longer reassociate to the same assembly, this is illustrated in FIG. 6. In some cases the altered conformation of the dissociated form can reassemble to a different assembly. Individual components of morpheein proteins can be referred to as alternate morpheein forms or alternate quaternary (structure) assemblies.

Figure 8:
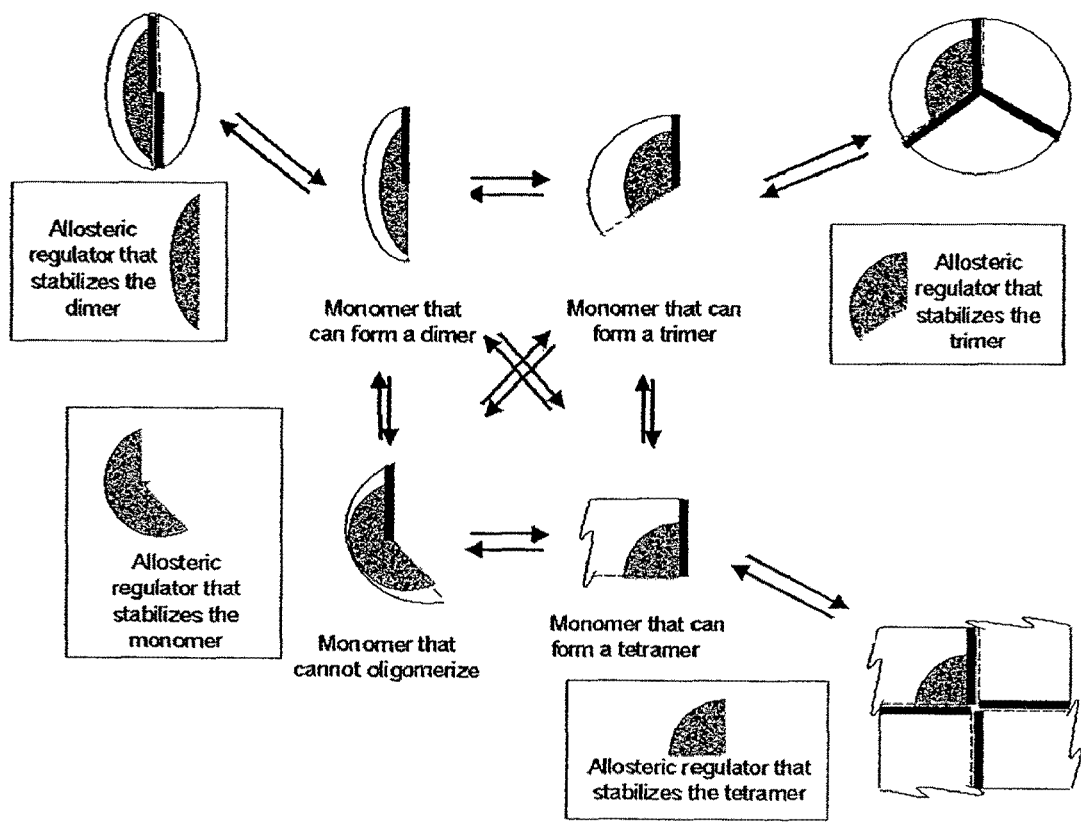
FIG. 8 is a two-dimensional schematic representation of the equilibrium between units and oligomers involving an allosteric regulator (agent). The allosteric regulator is shown as a filled gray shape bound to either a unit or to a multimeric protein. The allosteric regulator is capable of perturbing the equilibrium between oligomeric states. This figure illustrates wedges that will shift the equilibria illustrated in FIG. 6.

This invention provides a novel way to think about how different oligomerization states, such as those involved in signaling and cell cycle control, can up-regulate or down-regulate pathways. In accordance with the invention, the activity of any protein whose allosteric regulation can be defined by an equilibrium among "morpheein forms" can be modulated by agents (e.g., small molecules) that bind to the unique surface features of one or another of these morpheein forms and thus shift the equilibrium of quaternary forms, as illustrated in FIG. 8. Because the binding sites for these agents can be surface pockets that are peculiar to a specific morpheein shape, they are not generally expected to contain phylogenetically conserved sequences, thus allowing species specificity. Porphobilinogen synthase is presented as the prototype morpheein system subject to allosteric regulation and the most specific embodiments of the invention are related to inhibition of porphobilinogen synthase through stabilization of one or more less active (OFF state) morpheein forms.

According to certain embodiments of the invention, tetrapyrrole biosynthesis can be modulated by modulating the equilibrium among the morpheein forms of PBGS. According to certain embodiments of the invention, inhibitor molecules can be discovered that will preferentially interact with the unique surface components of the PBGS hexamer and displace the distribution of morpheein forms toward the hexameric form (which in the case of plant and some bacterial PBGS is believed to be the inactive form).

Advantageously, the invention provides a composition comprising an agent adapted to affect a multimeric protein by binding to a binding site of said multimeric protein and thereby affecting an equilibrium of units, wherein said multimeric protein comprises an assembly having a plurality of said units, wherein each of said units comprises a first complementary surface and a second complementary surface and wherein the first complementary surface of one unit is associated with the second complementary surface of another unit, provided that the assembly is at least one of different quaternary isoforms on a condition that in said multimeric protein (1) a structure of each of said units determines a structure of said different quaternary isoforms, (2) said units are in the equilibrium and (3) the structure of said different quaternary isoforms influences a function of the multimeric protein. The composition of the invention can be used for inhibiting or preventing development or growth of bacteria, archaea, and/or eucarya in a host organism. For example, the composition of the invention can be used in form of a drug, a toothpaste, a soap, a disinfectant, an anti-biofilm composition, and a herbicide. The invention provides guidance to selection of a target organism and influencing it to achieve a desired effect.

The unit of the multimeric protein can be, for example, a monomer, a dimer, a trimer, a tetramer, a hexamer, and an octamer. In certain embodiments, affecting said multimeric protein comprises affecting a formation of a quaternary isoform. In certain embodiments, affecting said multimeric protein comprises affecting the function of said multimeric protein. A non-limiting example of a function of said multimeric protein is an activity and wherein "affecting" is at least one of inhibiting or activating. As described further below, depending on the application, the agent can be bound to at least one of a quaternary isoform having a lesser activity or a quaternary isoform having a greater activity, thus inhibiting or activating the multimeric protein.

Exemplary multimeric proteins are porphobilinogen synthase and a ribonucleotide reductases, such as Class Ia ribonucleotide reductase (highly regulated enzymes responsible for balancing the deoxyribonucleotides that are required for DNA replication).

The following five systems have been identified as potential morpheein systems. The first is *Pseudomonas aeruginosa* GDP-Mannose dehydrogenase, which is a key regulatory enzyme in the biosynthesis of alginate, the polysaccharide that encapsulates the human pathogen *P. aeruginosa*, thus helping to create a protective biofilm. The second is *Bacillus subtilis* HPr (histidine containing phosphocarrier protein), kinase/phosphatase (HPrK/P) of most gram-positive (and some gram negative) bacteria, which is involved in the regulation of carbon catabolite repression/activation. Regulation of this enzyme allows bacteria to adapt rapidly to environmental changes in carbon sources. The third is mammalian CoA transferase, which is a mitochondrial enzyme essential for the metabolism of ketone bodies. The fourth is purine nucleoside phosphorylase (PNP) enzymes, which play a key role in the purine salvage pathway and are reported to have a variety of oligomeric stoichiometries. The fifth is the family of peroxiredoxins, which are a phylogenetically diverse family of proteins that act as antioxidants and in the regulation of cell signaling pathways, apoptosis, and cellular differentiation.

Thus, in certain embodiments, the agent is an inhibitor bound to the quaternary isoform having the lesser activity and wherein the quaternary isoform contains less than eight porphobilinogen synthase monomers. Similarly, when the multimeric protein is the Class Ia ribonucleotide reductase or another morpheein system, the agent inhibits the Class Ia ribonucleotide reductases through selective binding to the binding site that is unique to a less active quaternary isoform.

The invention will now be described using PBGS as an example of a multimeric protein. Thus, the invention provides a composition comprising an inhibitor adapted to inhibit formation of an active form of a multimeric porphobilinogen synthase having a first number of monomers by binding to a less active form of the multimeric porphobilinogen synthase having a second number of monomers, wherein the first number of monomers is higher than the second number of monomers.

Figure 2:
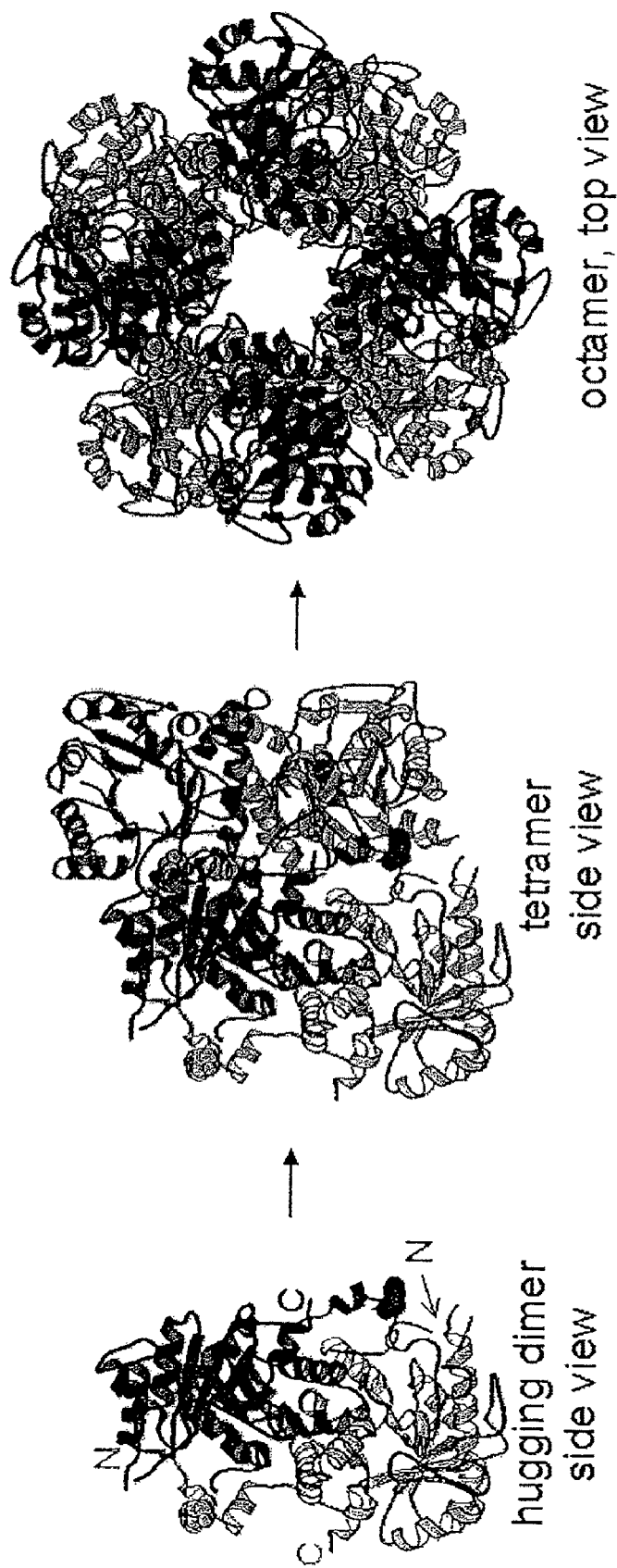
FIG. 2 (prior art) shows the assembly of octameric human PBGS (PDB code 1e51) using ribbon representation. To the left is the hugging dimer; in the middle is the tetramer (same orientation as the hugging dimer), and on the right is a top down view of the octamer. For each dimer, one monomer is light gray and the other is dark gray.
Figure 3A:
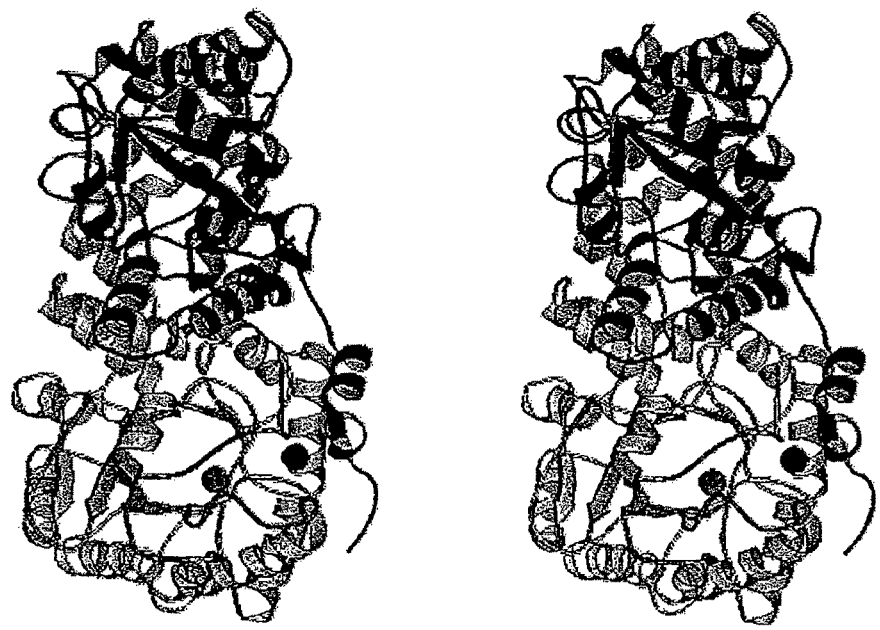
FIG. 3A (prior art) shows a stereo diagram of one dimer of E. coli PBGS, where the protein subunits are shown as ribbon diagram and colored black and light gray. The active site zinc ions are shown as gray spheres, and the allosteric magnesium ions are shown as black spheres. Active site ligands are not illustrated.
Figure 3B:
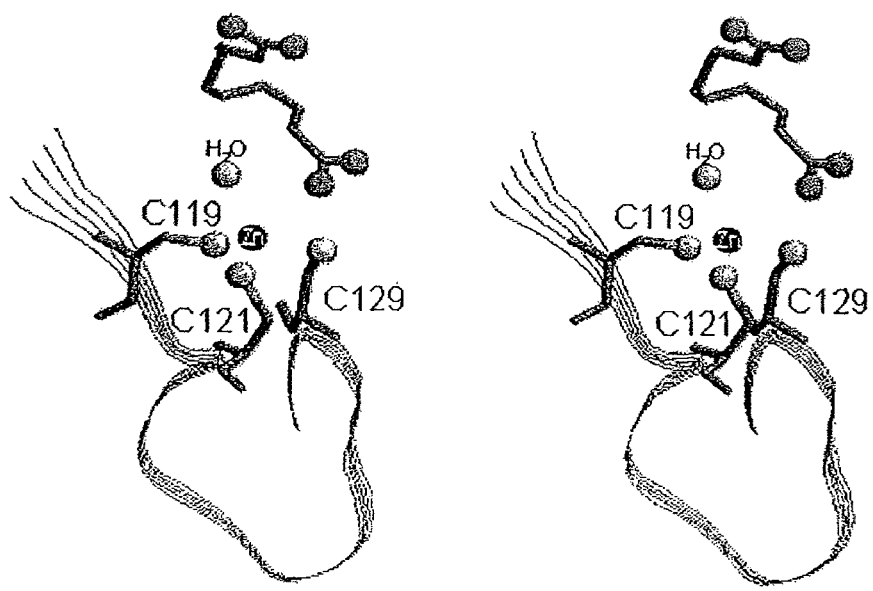
FIG. 3B (prior art) shows a stereo diagram of the structural details of the active site zinc of E. coli PBGS. The cysteine ligands are labeled and the cysteine sulfur atoms are shown as white balls. The water is labeled. The active site ligand 4,7-DOSA is shown in gray, with oxygen atoms as balls.
Figure 3C:
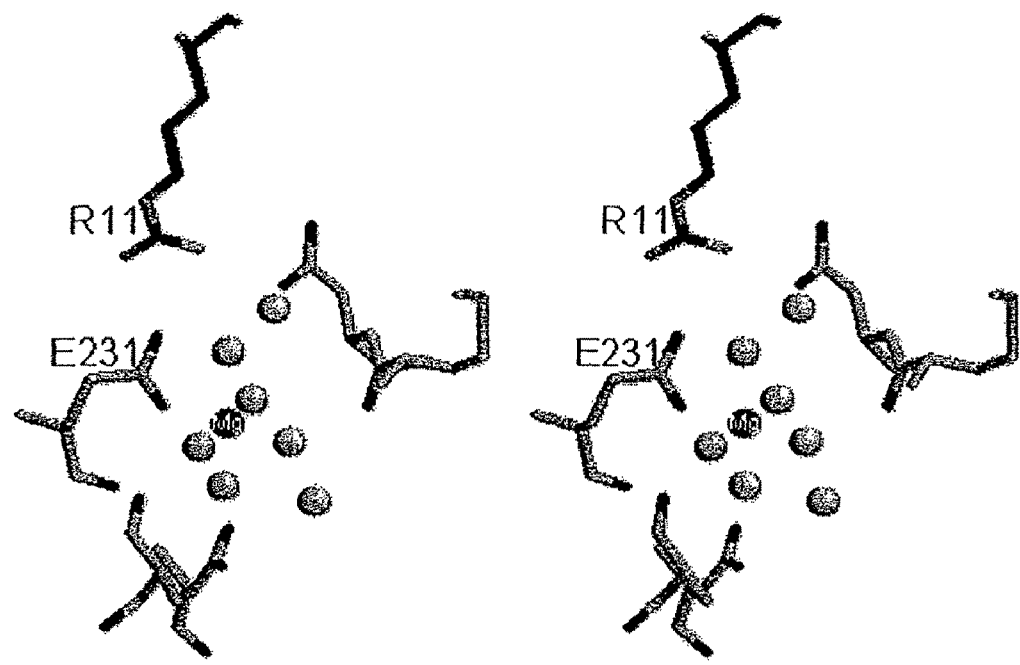
FIG. 3C (prior art) shows a stereo diagram of the structural details of the allosteric magnesium binding site of E. coli PBGS. The white balls indicate water molecules, which form an extended ligation network between the magnesium and oxygen and nitrogen atoms of neighboring residues. The amino acids involved in this network are shown as stick diagrams, with carbons colored light or dark according to the chains of FIG. 3A. Oxygen or nitrogen atoms that are involved in the ligation network are shown in a contrasting shade. The labeled amino acid E231 is the only amino acid in the first coordination sphere of the magnesium. R11 derives from the N-terminal arm of the neighboring subunit of the hugging dimer shown in FIG. 3A.
Figure 9:
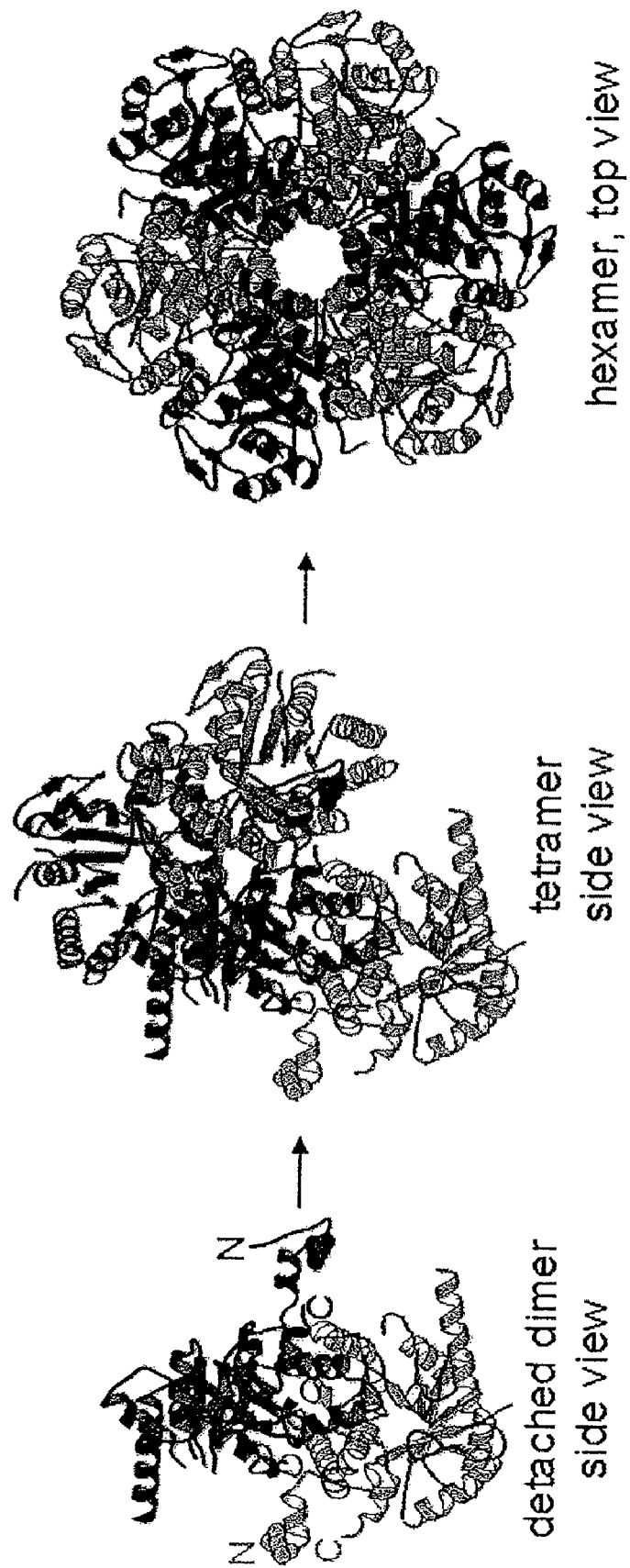
FIG. 9 shows the assembly of hexameric human PBGS variant F12L (PDB code 1PV8). To the left is the detached dimer; in the middle is the tetramer (same orientation as the detached dimer), and on the right is a top down view of the hexamer. For each dimer, one monomer is light gray and the other is dark gray. A comparison of FIG. 9

The inventor has discovered that PBGS can exist in at least two alternate quaternary structures, octamer and hexamer. The multimeric PBGS having a lesser number of monomers of PBGS is also encompassed by this invention. Previously, only the octameric form was known to exist. In both forms, the monomer contains an $\alpha 8\beta 8$ barrel comprised of the C-terminal 300 amino acids, wherein the center of the $\alpha 8\beta 8$ barrel contains the active site. A variable length N-terminal portion of the subunit forms an extended arm structure that is involved in extensive inter-subunit interactions in both oligomeric forms, i.e., octamer and hexamer. A major difference between the two quaternary structures is the conformation of the N-terminal arm. FIG. 2 shows the assembly of octameric PBGS as a tetramer of hugging dimers. FIG. 9 shows the assembly of hexameric PBGS as a trimer of detached dimers.

In certain embodiments, the multimeric porphobilinogen synthase is derived from bacteria, archaea, or eucarya, provided that the octameric porphobilinogen synthase contains an allosteric magnesium binding site. In one variant of this embodiment, the multimeric porphobilinogen synthase contains a catalytic zinc binding site.

Figure 4:
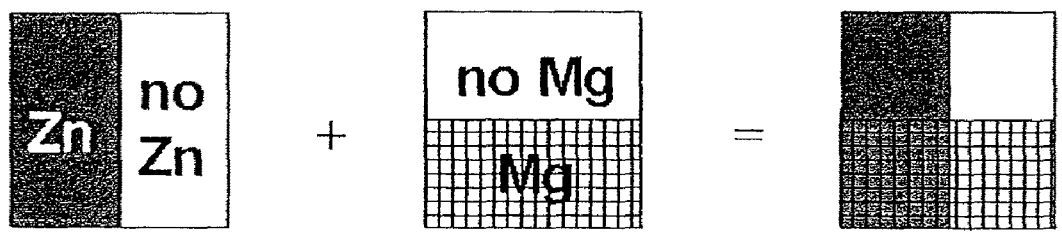
FIG. 4 shows a schematic classification of PBGS according to the independently segregating criteria of the presence of active site zinc (dark gray area, far left), and the absence of active site Zn (white area, left box), the presence of allosteric magnesium (Mg++) (checkered area, middle box), the absence of allosteric Mg++ (middle box). The resulting matrix (far right) consists of four quadrants, wherein the northwest quadrant (QNW) represents +Zn/−Mg++, the northeast quadrant (QNE) represents −Zn/−Mg++, the southwest quadrant (QSW) represents +Zn/+Mg, and the southeast quadrant (QSE) represents −Zn/+Mg++.
Figure 5:
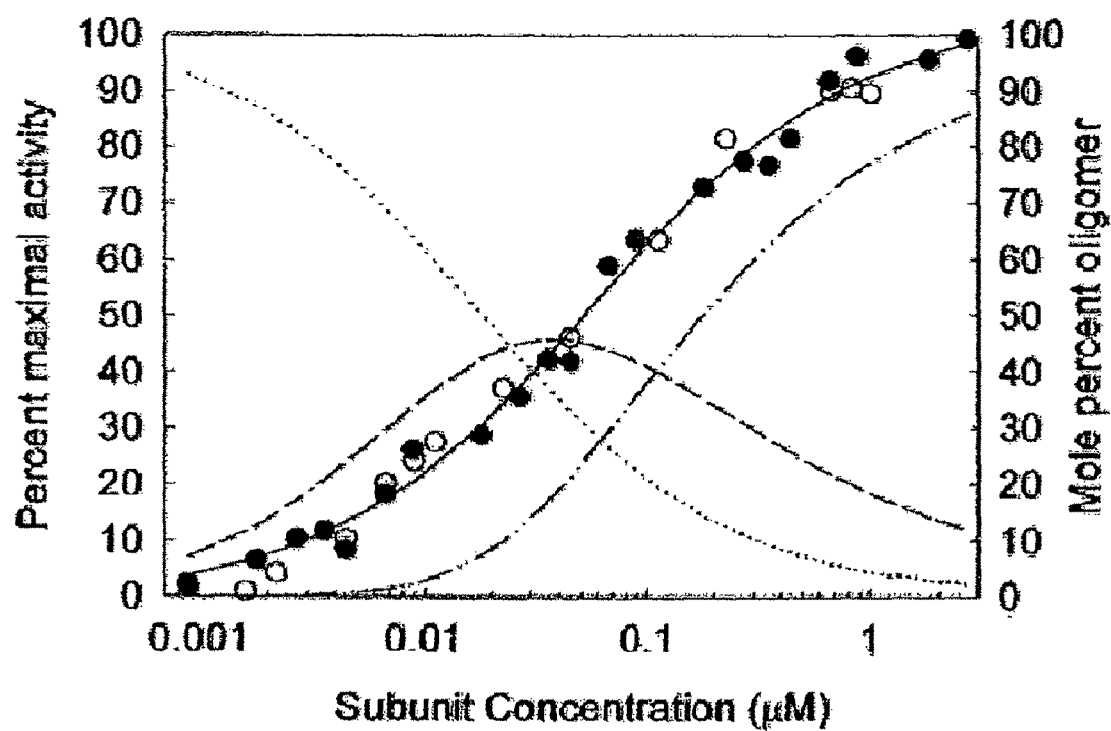
FIG. 5 (prior art) (taken directly from reference [13]) shows the combined data on the protein concentration dependence of PBGS from P. sativum (common garden pea, open circles) and B. japonicum PBGS (filled circles). The solid line is a simple hyperbolic fit to the data. The other lines depict the mole percent of various oligomers according to a published interpretation of the data wherein the octamer dissociates to tetramers and dimers. The model presumed that the dimer (a dotted line) is inactive, half of the asymmetric units of the tetramer (a dashed line) are active, and all the asymmetric units of the octamer (a dash-dot line) are active.
Figure 10:
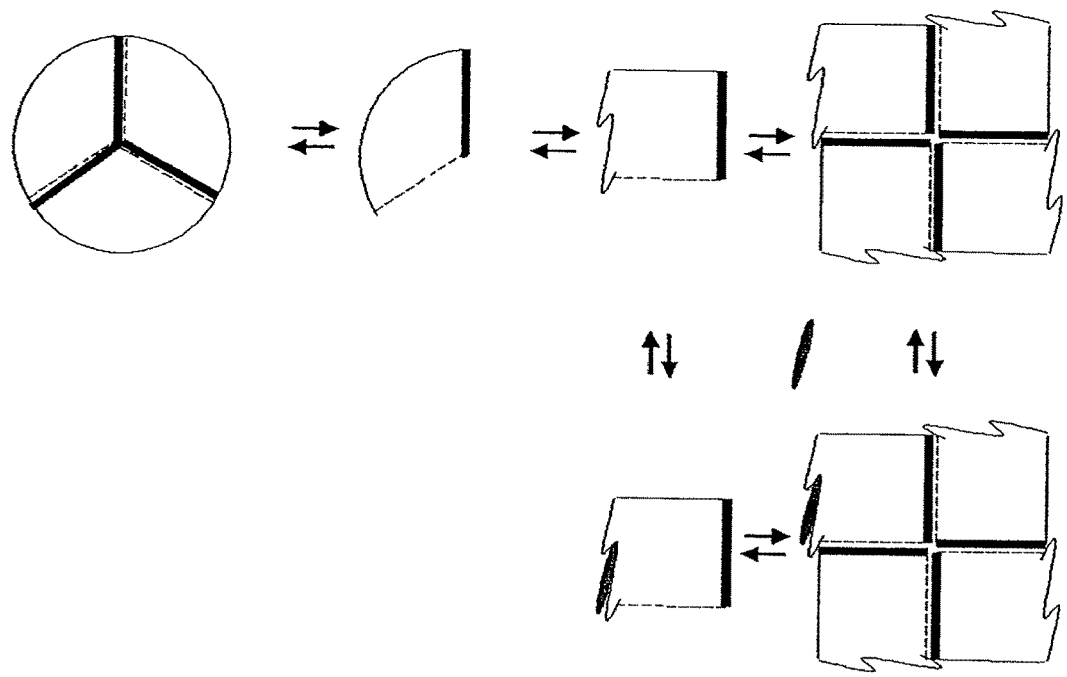
FIG. 10 is a two-dimensional schematic representation of the equilibrium between two isoforms of a protein demonstrating that an agent that is capable of affecting a function of the protein has a binding site on one form of a unit but not on another. In each case, the rules for multimerization are to juxtapose one thick line with one dashed line.
Figure 11:
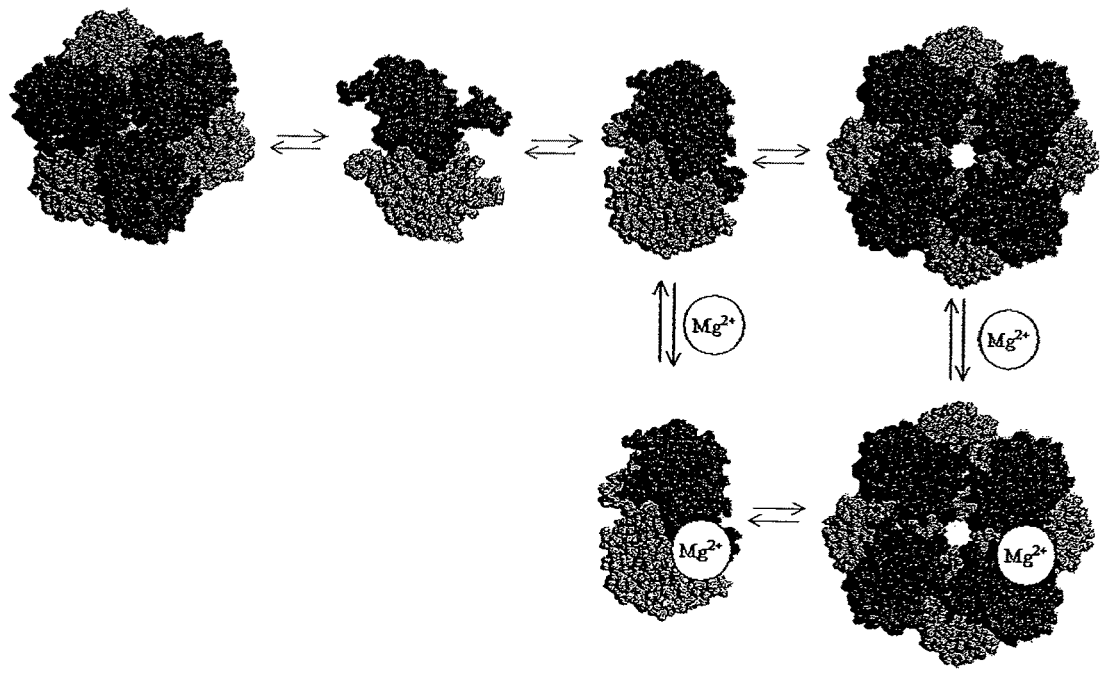
FIG. 11 uses space filling representations to illustrate the equilibrium of PBGS morpheein forms, which are (from left to right) the hexamer, the detached dimer, the hugging dimer, and the octamer. The lower portion of the figure illustrates how magnesium stabilizes the morpheein forms made up of hugging dimers by stabilizing the arm-to-side-of-barrel interface.
Figure 12:
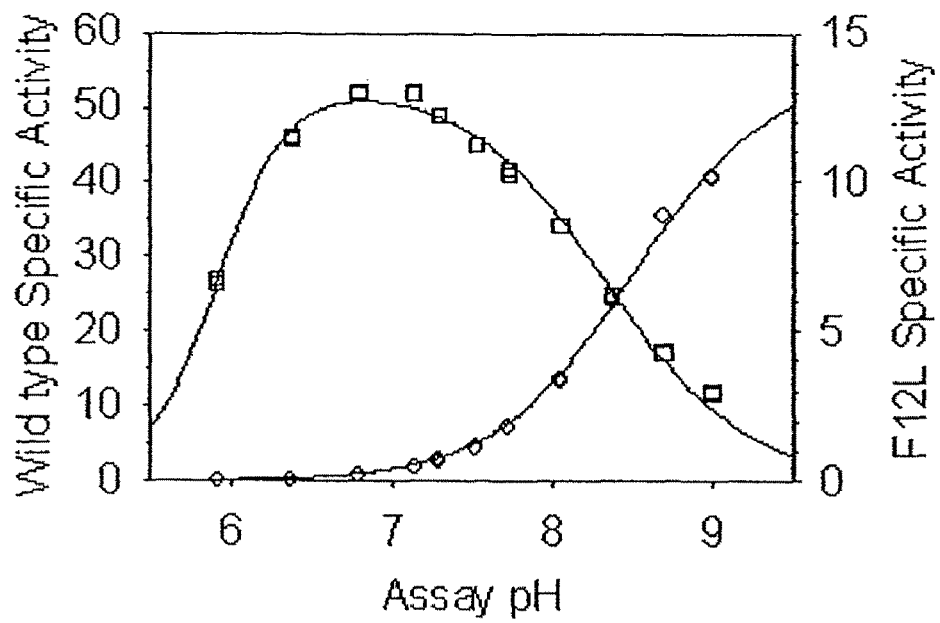
FIG. 12 shows the functional difference between human PBGS WT (open squares) and F12L (open diamonds) in terms of their pH activity profiles.
Figure 14:
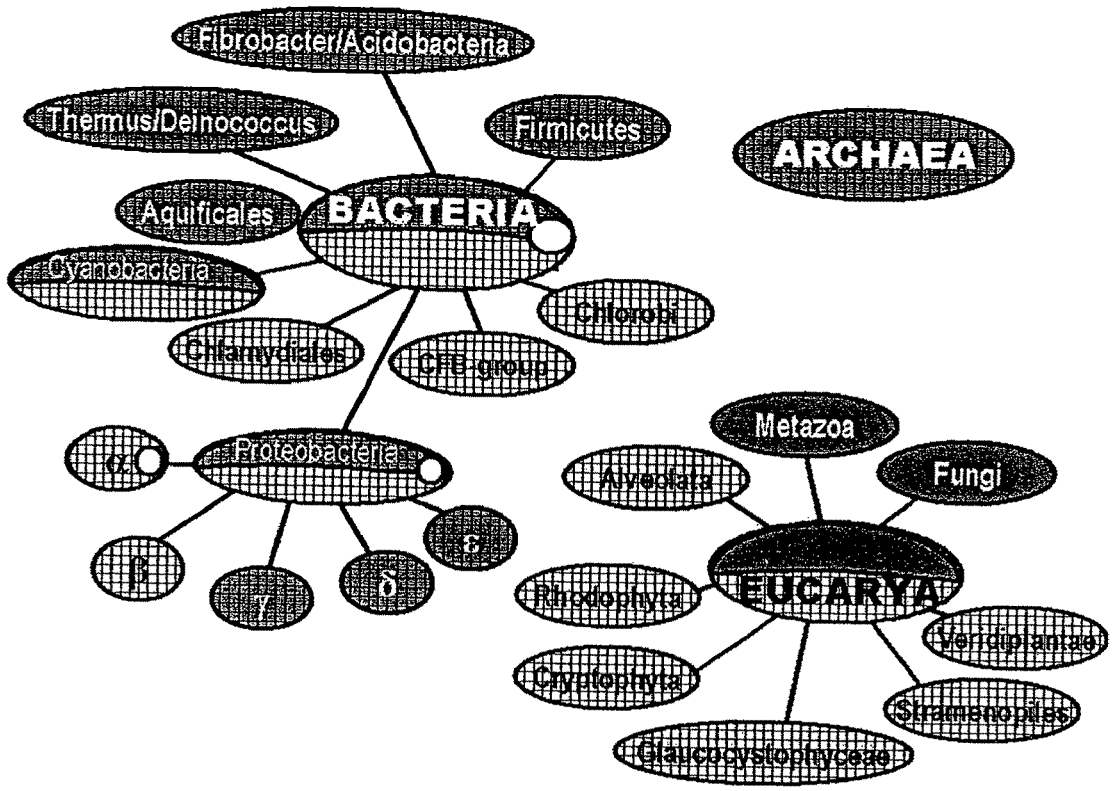
FIG. 14 is a classification of sources for PBGS including bacteria, archaea, and eucarya, wherein distribution of metal binding properties of PBGS is coded in accordance with FIG. 4. From the inventor's experience with PBGS from various sources, the organisms with the white background (checkered or not) are expected to rapidly equilibrate between morpheein forms and thus be susceptible to the inhibitors of this invention.
Figure 16A:
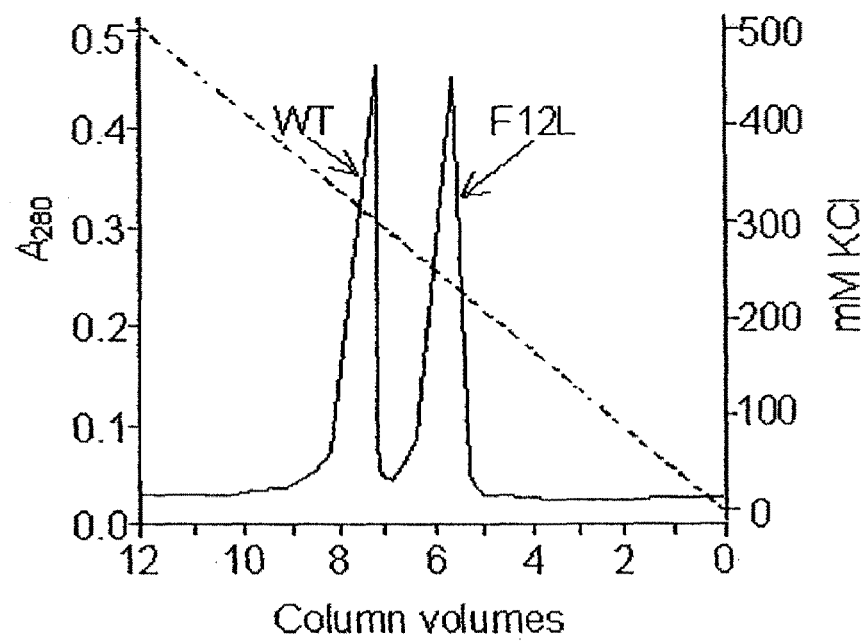
FIG. 16A shows the chromatographic separation of wild type human (WT) PBGS and F12L on a mono-Q column using a salt gradient (dashed line).
Figure 16B:
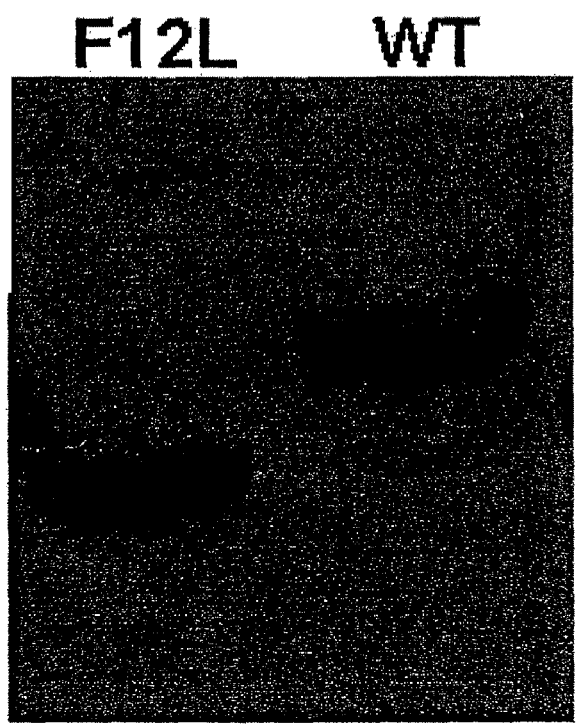
FIG. 16B shows the differential mobility of wild type (WT) human PBGS and F12L on 12.5% polyacrylamide native gel electrophoresis.
Figure 38:
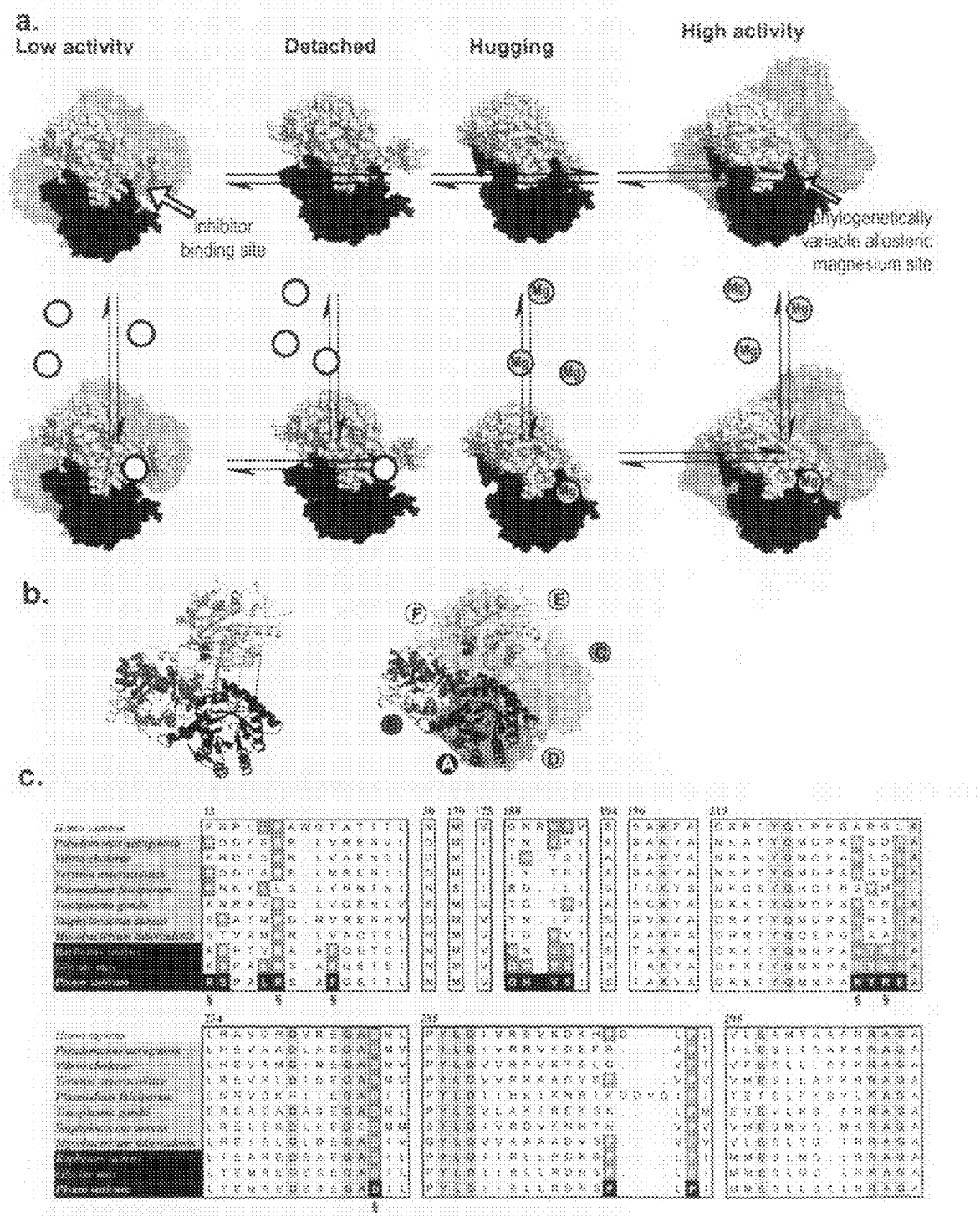
FIG. 38 illustrates that Porphobilinogen synthase (PBGS) is the prototype morpheein ensemble.

Porphobilinogen Synthase as an Example of a Morpheein:

The following describes the discovery that PBGS can exist in alternate quaternary states, which are called herein "morpheein forms" (FIGS. 2, 6, 9, 36), that an equilibrium of morpheein forms can be a structural basis for allosteric regulation (FIGS. 7, 8, 10), and that the interconversion of these states forms the structural basis for allosteric regulation of this PBGS in some species (FIGS. 11, 14, 38). The well known quaternary state for PBGS is the octamer made up of hugging dimers (FIG. 2). Also known was that some PBGS, particularly those in the QSE of FIG. 4, exist as equilibrium of quaternary forms as shown by a protein concentration dependence to the specific activity (FIG. 5). The protein concentration dependence to the specific activity indicates that a maximally active oligomer can dissociate or re-associate into smaller less active forms. It was previously believed that the smaller, less active forms, were also multiplicities of hugging dimers (modeled in FIG. 5). Observation and characterization of a stable oligomer of detached dimers was made possible by the fact that PBGS in the QNW do not readily equilibrate between quaternary isoforms. Hence the F12L mutation of human PBGS allowed the inventor to study a stable form of the hexamer and to establish that it was the hexameric property (and not the specific F12L mutation) that dictated the dramatically different functional properties of F12L relative to wild type human PBGS. F12L is a naturally occurring rare allele for human PBGS [26,27]. Described in EXAMPLE 1 below are studies of human PBGS (both wild type and F12L) that were heterologously expressed in *E. coli* and purified by conventional techniques. The different physical and kinetic properties of wild type and F12L are illustrated in FIG. 12, Table 1, and FIGS. 16A and 16B.

The data presented on wild type human PBGS, the F12L variant, and the WT+F12L heteromers definitively establishes that the kinetic differences between the wild type protein and the F12L variant are primarily due to the difference in quaternary structure as described in detail in EXAMPLE 2 below. Further work on other select human PBGS mutants (R240A, T23P, and T23P/F12L) confirm that the kinetics of the hexamer are like the kinetics of F12L and that the kinetics of the octamer are like that of the wild type protein.

The interconversion of human PBGS morpheein forms during turnover (catalytic activity) was hypothesized based on the physical and kinetic characteristics of the heteromeric WT+F12L oligomers, as illustrated in FIGS. 17A-D and Table 3, as described in detail in EXAMPLE 2 below. The disproportionation of these hetero-oligomers during extended turnover proves that the morpheein forms of human PBGS can exist in a dynamic equilibrium, as illustrated in EXAMPLE 3.

In light of the structures of octameric vs. hexameric human PBGS, a hypothesis can be formulated concerning the dramatic difference in pH optimum for these two forms of PBGS. The chemistry of the PBGS catalyzed reaction requires the formation of at least two Schiff base intermediates [28]. Formation of the carbinolamine precursors to these Schiff bases requires that the participating amino groups are uncharged, or that the local pH is above the $pK_a$ of the amino groups. One significant structural difference between hexameric and octameric PBGS is the degree of order found in the amino acids that comprise the active site lid. The crystal structure of hexameric PBGS F12L is lacking in density from most of the residues that make up the active site lid, thus implying that the hexamer structure destabilizes the closed lid configuration. In the absence of a closed lid to isolate the active site from bulk solvent, the PBGS catalyzed reaction cannot proceed until the external pH is above the $pK_a$ of the amino groups that participate in Schiff base formation. Hence, the hexameric structure is proposed to exhibit activity only when the external pH is sufficiently basic to facilitate Schiff base formation. The high Km can also be attributed to destabilization of the active site lid since crystal structures of the PBGS octamer show stabilizing interactions between residues on the lid and the substrate molecule that determines the Km value. This provides a novel approach to understanding the regulation of PBGS function. As described below, the insight provided from identification of a PBGS hexamer has considerable significance for rethinking the allosteric regulation of PBGS activity in non-human species.

Figure 18A:
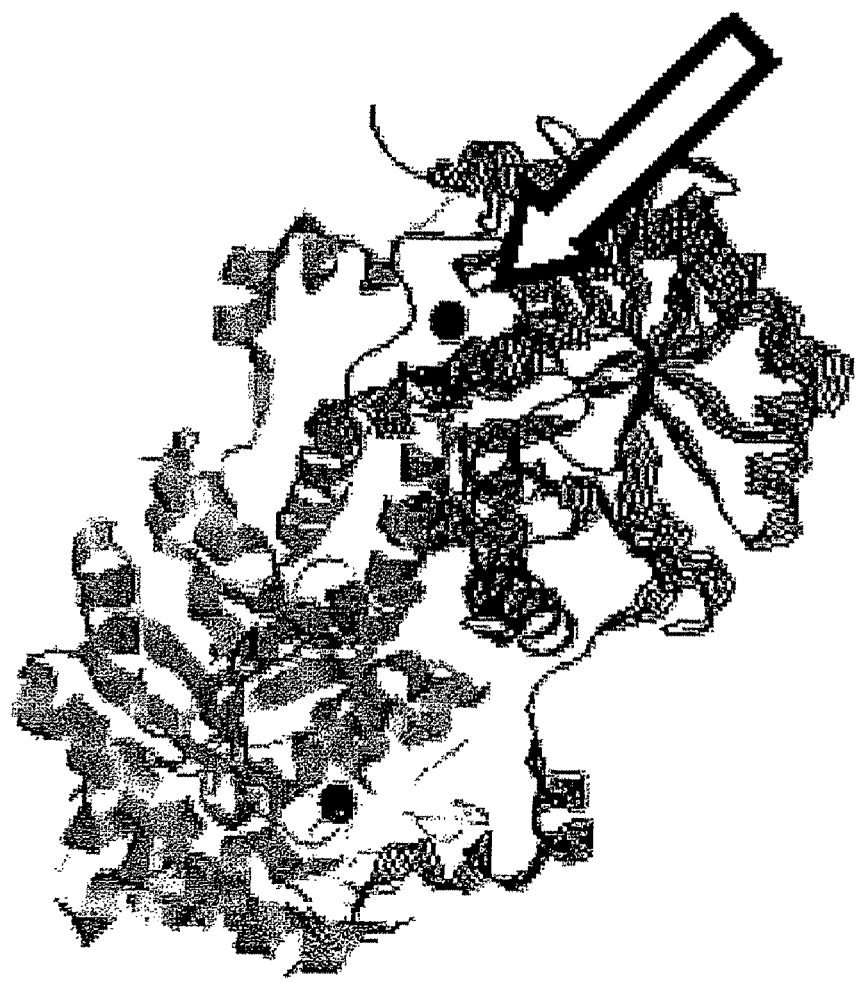
FIG. 18A shows a ribbon diagram representation of the crystal structure of the hugging dimer of E. coli PBGS; the arrow indicates the location of the allosteric magnesium.
Figure 19A:
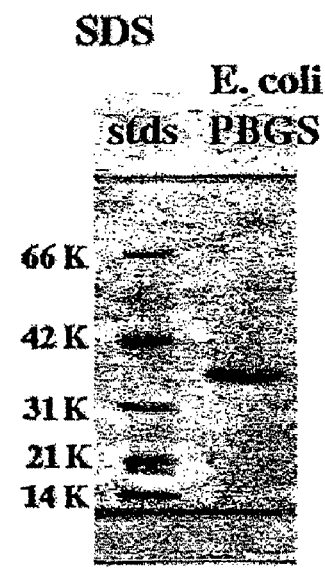
FIG. 19A shows an SDS gel of purified E. coli PBGS.
Figure 19B:
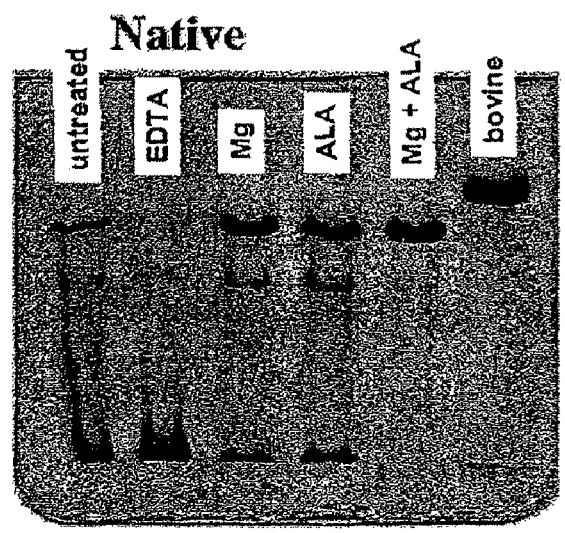
FIG. 19B shows a native gel of E. coli PBGS (12.5% acrylamide). Untreated protein is shown in the far left lane. The bands have mobility consistent with (top to bottom) octamer, hexamer, tetramer, and dimer. The following lanes shows that addition of the magnesium chelator EDTA, magnesium, ALA, or magnesium plus ALA can shift the equilibrium of E. coli PBGS morpheein forms in the native gel environment. Removal of magnesium by EDTA favors the dimer. Addition of excess magnesium or the substrate ALA or both favors formation of the octamer. The far right lane shows bovine PBGS, which like human PBGS runs as a single band. The octamer of bovine PBGS has a different charge than the octamer of E. coli PBGS and thus runs at a different mobility on the gel.

Allosteric Regulation of PBGS can be Attributed to the Octamer to Hexamer Equilibrium:

Comparison of the PBGS octamer and hexamer reveals a basis for allosteric regulation of PBGS. Despite the fact that all the obvious components of the PBGS active site are contained in the monomer, most PBGS proteins contain a binding site for an allosteric magnesium that is located at the arm-to-barrel interface of the hugging dimer [11,29]. The position of the allosteric magnesium is seen in the crystal structures of both *Pseudomonas aeruginosa* [29] and *E. coli* PBGS [30], as illustrated for the latter in FIG. 18A. FIG. 18A shows the hugging dimer (light ribbon, dark strand) with the allosteric magnesium as black balls, one of which is illustrated with a large white-on-black arrow. The structures of yeast and human PBGS show that the guanidinium group of an arginine resides in the place of the allosteric magnesium as illustrated previously [9]. This is Arg240 of human PBGS. If one presumes that all PBGS can exist in the hexameric state under appropriate conditions, then the position of the allosteric magnesium is pertinent to a hexamer-octamer transition because this metal binding site is present in the octamer (made up of hugging dimers) and absent in the hexamer (made up of detached dimers). FIG. 18B shows the three subunit to subunit interfaces in the PBGS octamer. The black-on-white arrow shows the barrel-to-barrel interface, which is common to both octameric and hexameric PBGS assemblies. The dots-on-black arrow shows the arm-to-base-of-barrel interaction, which is also common to both octameric and hexameric PBGS assemblies. The white-on-black arrow, which is analogous to the allosteric magnesium binding site, shows the arm to barrel interaction that is present in the octamer (hugging dimer) and absent in the hexamer (detached dimer). Consistent with the notion that the allosteric magnesium mediates a hexamer-octamer equilibrium is the effect of magnesium on the kinetic parameters of *E. coli* PBGS. In this case, the addition of the allosteric magnesium causes the $K_m$ value to decrease from ~2 mM to ~200 μM [31], which is remarkably reminiscent of the difference between the $K_m$ values of the hexameric and octameric forms of human PBGS (Table 1). Also of note is the inventor's prior observation that homogeneously pure *E. coli* PBGS shows multiple bands during native gel electrophoresis, that the mobility of these bands is consistent with the molecular size of octamer, hexamer, tetramer and dimer, and that addition of magnesium favors the largest (octameric) form [31] (reproduced in FIG. 19). Also of note is the recent finding that the human PBGS variant R240A purifies ~80% as the hexamer and 20% as the octamer, and that the latter oligomer is unstable and rearranges to the hexamer with time.

Observation of Protein Concentration-Dependent Specific Activity is One of the Diagnostic Tools for the Presence of an Equilibrium of Morpheein Forms Interconversion of PBGS between hexamer and octamer is proposed as the mechanism responsible for the protein concentration-dependent specific activity of PBGS from some species. To date, the inventor has characterized four different PBGS that contain the allosteric magnesium. The enzymes are from the species *E. coli* (a γ-proteobacter), *B. japonicum* (an α-proteobacter), *P. aeruginosa* (a γ-proteobacter), and Pisum sativum (a green plant). The last three are different from human PBGS in that they do not use an active site catalytic zinc [11] and they also share the unusual property of protein concentration dependent specific activity [13,14,32] (see FIG. 5). The latter property indicates that a maximally active oligomer can dissociate into less active or inactive smaller forms. Published mathematical models, as illustrated in FIG. 5, have considered maximally active octamers dissociating into less active or inactive tetramers and/or dimers [13,14].

Figure 20A:
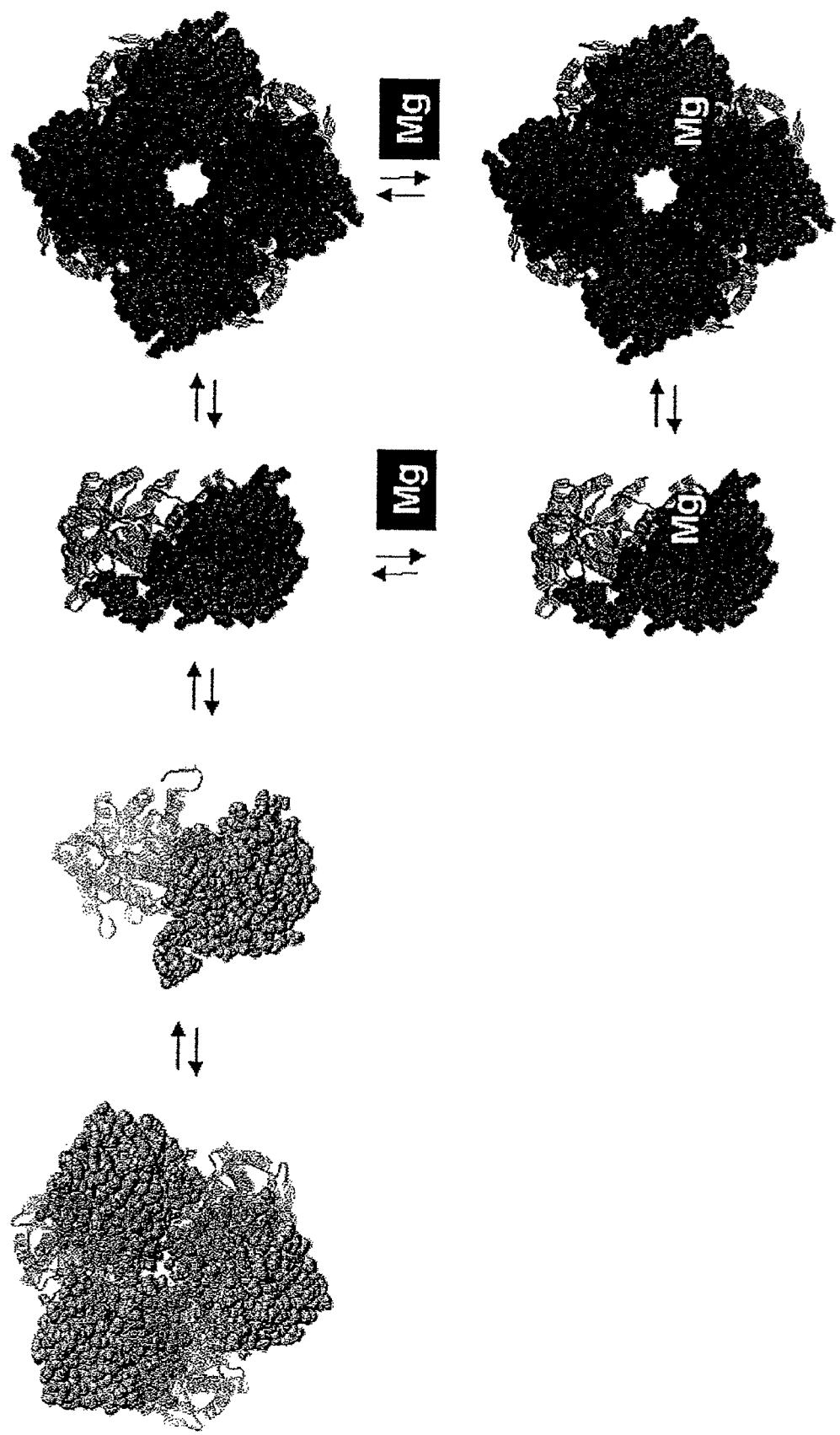
FIG. 20A shows a schematic of the equilibrium of pea PBGS morpheein forms, using darker shades for the hugging dimer forms and lighter shades for the detached dimer forms. This figure utilizes models of pea PBGS.
Figure 20B:
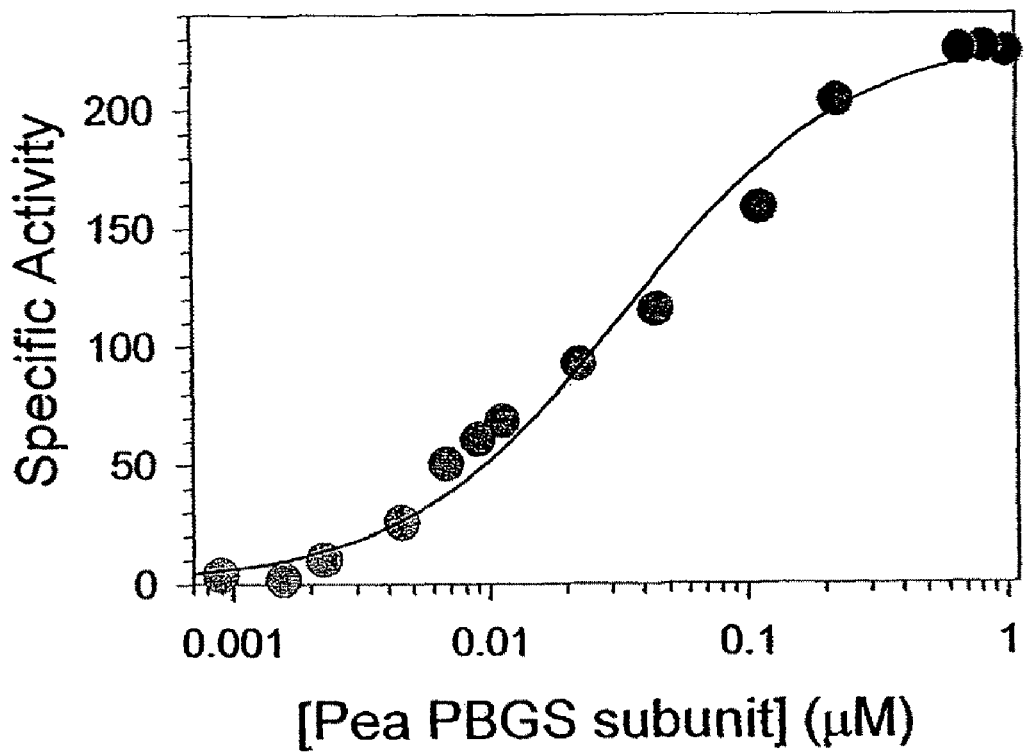
FIG. 20B shows the protein concentration dependence of pea PBGS, coloring the data points according to the interpretation that low activity corresponds to the detached dimer forms and high activity corresponds to the hugging dimer forms (as per FIG. 20A).
Figure 20C:
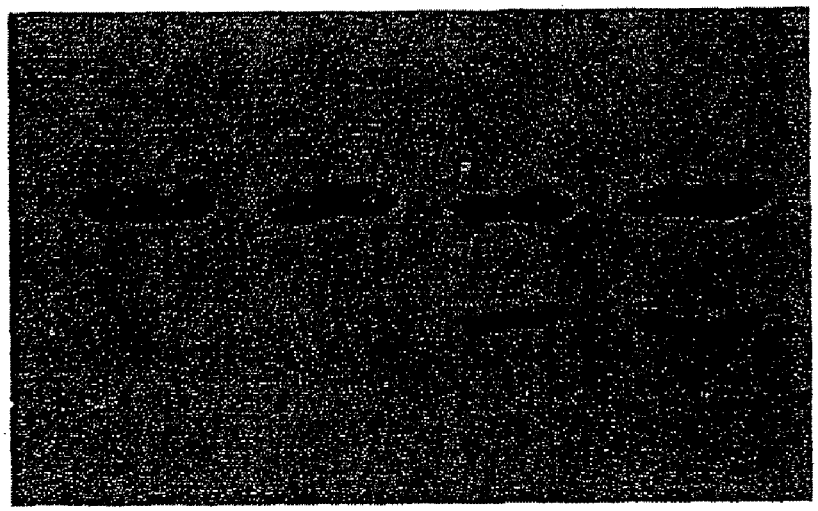
FIG. 20C shows a native gel illustrating the effect of EDTA on the equilibrium of octameric and hexameric pea PBGS. As per FIG. 20A, removal of magnesium by EDTA destabilizes the hugging dimer forms.

The hexameric structure of human PBGS variant F12L leads the inventor to believe that the protein concentration dependence of plant and certain bacterial PBGS is rather due to an equilibrium between a less active hexameric form and a more active octameric form, as illustrated in FIGS. 20A and 20B. The existence of such an equilibrium is supported by sedimentation equilibrium studies on pea PBGS. Because magnesium is integral to the difference between the hugging-dimer and the alternative detached-dimer, this ion is believed to favor formation of the hugging-dimer and, hence, the octamer. FIG. 20C illustrates that removal of magnesium from pea PBGS disfavors the largest form in favor of a smaller form, where the mobility of the two forms is consistent with that of octamer and hexamer. In the model, the hexamer is a putative storage form of the PBGS protein because it is less active at physiologic pH and is characterized by a $K_m$ value that is well above the physiological concentration of ALA. By contrast, the octamer is active at physiological pH and has a $K_m$ value that is in the proper range of ALA concentrations during active tetrapyrrole biosynthesis.

Together, these studies support the belief that there is a role for PBGS in the complex control of chlorophyll biosynthesis [33-35]. One documented occurrence during the greening of plants is a dramatic increase in the magnesium concentration in the chloroplast from <1 mM to >10 mM [36]. The Kd for the allosteric magnesium of pea PBGS is physiologically reasonable at 2.5 mM [13]. One can imagine that an inactive hexameric storage form allows rapid activation of PBGS as part of a cascade of biochemical changes that accompanies the greening process. Several gel filtration studies on the quaternary structure of plant and algae PBGS concluded that the oligomer was a hexamer [37], but these studies preceded determination of the crystal structure of the octamer and they did not consider that an octamer-hexamer equilibrium might exist. Literature support for the existence of interconvertible quaternary forms of PBGS separable by anion exchange chromatography can be found in an early report on PBGS from Chlorella regularis [38], but again these investigators were reporting on an unusual phenomenon and did not indicate any premonition of the existence of morpheein forms.

Hexameric human PBGS reveals a novel structural paradigm for allosteric regulation of protein function and is the first example of a protein that can exist as a morpheein.

Characterization of the human PBGS variant F12L reveals that this point mutation causes a dramatic change in the structure and function of PBGS. This mutation can serve as a precedent for a single amino acid change resulting in significant changes in protein behavior during evolution. The F12L mutation destabilizes the PBGS octamer and leads to formation of hexamers. The structural transition between octamer and hexamer must proceed through an unprecedented equilibrium containing two different dimer structures. The allosteric magnesium, present in most PBGS has a binding site in the octamer, but not in the hexamer. Native gel data indicate that removal of the allosteric magnesium favors formation of the hexamer over the octamer (see FIG. 20C). The octamer-hexamer transition defines a novel mechanism for metal ion-dependent allosteric regulation of protein function.

This invention describes inhibition of protein function through stabilization of the inactive morpheein form of PBGS and/or any other protein that might be regulated by the interconversion of morpheein forms. In order to decipher molecules that will selectively bind to and stabilize the hexameric form of PBGS, the inventor is taking the following approach. PBGS in QSE (see FIGS. 4 and 14) are currently being considered as targets because these PBGS have been shown to be active as octamers but they exhibit the protein concentration dependent specific activity phenomenon. The target molecule is one that will selectively bind to the "arm pit" of the hexamer as illustrated by the balls in FIG. 13. The inventor is taking an "in silico" approach of searching molecular libraries for molecules that will bind to the hexameric form of PBGS from the target organisms.

A similar approach can be used for other proteins that can be regulated by the interconversion of morpheein forms. It is necessary to have a crystal structure of the less active morpheein, or model thereof, and the localization of a unique surface binding pocket on this target morpheein form that is not present on the active morpheein form. In some cases it will be required to have crystal structures representative of both the active and inactive morpheein forms in order to localize a unique binding pocket. In other case, it may be possible to consider the structure of the inactive morpheein form in conjunction with biochemical or biophysical data on the active morpheein form to predict the unique surface binding pocket. Examples 5 and 6 describe the proposed unique surface binding pocket for GMD and for HPrP/K.

Homology Model Building for Target Hexameric PBGS

As of 2005, the only existing crystal structure on which the inventor bases a model of target hexameric PBGS is that of human PBGS clinical variant F12L, PDB code 1PV8 [39] Unfortunately, the crystal structure of F12L shows significant disorder, which limits its use as the sole foundation for homology model building. However, comparison of human PBGS octameric and hexameric structures (PDB codes 1E51 and 1PV8) show near identity for the ~300 amino acids that comprise a TIM-like alpha, beta-barrel domain. For human PBGS, the difference between octamer and hexamer lies in the structure of the 24 amino terminal amino acids and various regions that are more disordered in the hexamer [39]. Hence, one can use a higher quality crystal structure of a PBGS octamer for homology model building the alpha, beta-barrel domain of target PBGS. The chosen structure is PDB code 1GZG [40] describes a highly ordered, high resolution crystal structures of Pseudomonas aeruginosa PBGS, itself a target for inhibitors that would "trap" the PBGS hexamer. A hexameric form of P. aeruginosa PBGS was built using various capacities of Swiss-PDB Viewer and other programs. To build the P. aeruginosa PBGS hexamer, the N-terminal arms were removed from the structure file for the 1GZG dimer. The resulting alpha, beta-barrel domains (residues 32-335) were successively overlaid upon the three dimers of hexameric 1PV8 to create a hexameric assembly of P. aeruginosa PBGS alpha, beta-barrels. There is no significant sequence identity between the N-terminal arms of human and P. aeruginosa PBGS, but there is a conserved alpha-helix in the structure of the N-terminal arm. Hence, a structure alignment of octameric forms of human PBGS and P. aeruginosa PBGS was used to determine the proper sequence alignment for this alpha-helical segment. This information was used to spatially position the amino acids 22-29 of P. aeruginosa PBGS in the hexamer. The program Loopy [41] was used to model amino acids 29-32, so as to connect the N-terminal alpha-helix to the alpha, beta-barrel domain of each subunit. Finally, the remaining N-terminal amino acids, which are present in file 1PV8, were built onto the *P. aeruginosa* PBGS structure using phi, psi, and omega angle information for the corresponding amino acids of hexameric human PBGS. Due to disorder in some of the N-terminus of the human PBGS hexamer (1PV8), the hexamer model for *P. aeruginosa* PBGS is missing residues 1-9 of subunits A, C, and E as well as residues 1-11 of subunits B, D, and F. The hexameric *P. aeruginosa* PBGS was the foundation structure for building a model of hexameric pea PBGS using well established published methods as has been done before [16].

Figure 21:
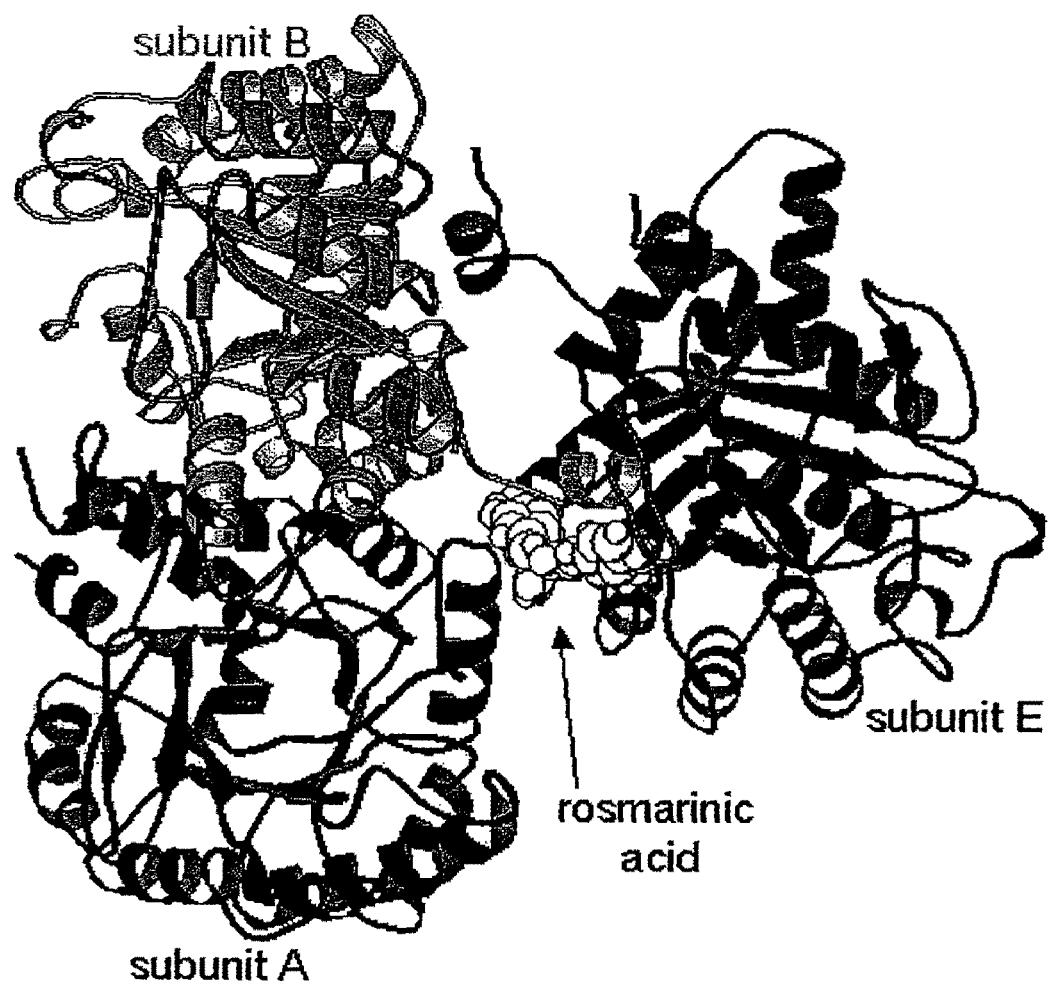
FIG. 21 shows three subunits of the model of the hexameric morpheein form of pea PBGS. Rosmarinic acid is shown docked into the putative drug (one example of this invention) binding site.

In searching for molecules that will preferentially bind to hexameric PBGS, the following was discovered. Analysis of the hexamer of PBGS shows that the putative "inhibitor" binding site (also referred to as the arm-pit) contains elements of the three subunits A, B, and E. Subunits A and B comprise the already defined "detached dimer", where the bottom subunit (subunit A, FIG. 21) is typically depicted such that the reader is looking directly into the active site, which is in the center of the alpha, beta-barrel. Subunit B shares a barrel-to-barrel interface with subunit A. Subunit E shares a mutual interaction with subunit B wherein the N-terminal arm of one subunit is nested into the base of the alpha-beta-barrel of the other subunit. The arm-pit of the trimer shown was used as the "binding site" in a computational search of small molecules. The process of using a computational approach to fit small molecules into this site is called docking. The docking program that was used is Glide [42,43], which holds the protein as a rigid body and allows the small molecules to sample many conformations in search of the best complement (shape, charge) to the binding site. This process is called docking. FIG. 21 shows the docked inhibitor, rosmarinic acid, described below. In this docking result, rosmarinic acid has direct interactions with all three subunits shown in FIG. 21.

A variety of "Small Molecule" molecular libraries was used, which have been assembled by the collaborator George Markham, and the docking process attempts to discover molecules that will trap PBGS in the hexameric form. Initial library screening focused on metabolites and natural products. At the time or original filing, out of a molecular library of ~1,000,000 molecules, ~30,000 had been screened for molecules that will bind to the "arm pit" of the hexameric model of pea PBGS. Several molecules with high docking scores were purchased and tested for whether they would inhibit pea PBGS; originally the best results were with the natural product rosmarinic acid. Later use of the Life Chemicals Inc. libraries provided superior in vitro results with a compound we have named morphlock-1.

The following concepts and definitions are provided in order to aid those skilled in the art in understanding the detailed description of the present invention.

The term "promoter" or "promoter region" refers to a nucleic acid sequence usually found upstream (5') to a coding sequence that controls expression of the coding sequence by controlling production of messenger RNA (mRNA) by providing the recognition site for RNA polymerase or other factors necessary for start of transcription at the correct site. As contemplated herein, a promoter or promoter region includes variations of promoters derived by means of ligation to various regulatory sequences, random or controlled mutagenesis, and addition or duplication of enhancer sequences. The promoter region disclosed herein, and biologically functional equivalents thereof, are responsible for driving the transcription of coding sequences under their control when introduced into a host as part of a suitable recombinant vector, as demonstrated by its ability to produce mRNA.

"Regeneration" refers to the process of growing a plant from a plant cell (e.g., plant protoplast or explant).

"Transformation" refers to a process of introducing an exogenous nucleic acid sequence (e.g., a vector, recombinant nucleic acid molecule) into a cell or protoplast in which that exogenous nucleic acid is incorporated into a chromosome or is capable of autonomous replication.

A "transformed cell" is a cell whose DNA has been altered by the introduction of an exogenous nucleic acid molecule into that cell.

The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression.

The phrase "DNA segment heterologous to the promoter region" means that the coding DNA segment does not exist in nature in the same gene with the promoter to which it is now attached.

The term "encoding DNA" refers to chromosomal DNA, plasmid DNA, cDNA, or synthetic DNA that encodes any of the enzymes discussed herein.

The term "genome" as it applies to bacteria encompasses both the chromosome and plasmids within a bacterial host cell. Encoding DNAs of the present invention introduced into bacterial host cells can therefore be either chromosomally integrated or plasmid-localized. The term "genome" as it applies to plant cells encompasses not only chromosomal DNA found within the nucleus, but organelle DNA found within subcellular components of the cell. DNAs of the present invention introduced into plant cells can therefore be either chromosomally integrated or organelle-localized.

The term "herbicide" refers to a chemical substance used to kill or suppress the growth of plants, plant cells, plant seeds, or plant tissues.

The term "inhibitor" refers to a chemical substance that inactivates the activity of a protein such as a biosynthetic enzyme, receptor, signal transduction protein, structural gene product, or transport protein that is essential to the growth or survival of the organism. In the context of the instant invention, an inhibitor is a chemical substance that inactivates the enzymatic activity of porphobilinogen synthase. The term "herbicide" is used herein to define an inhibitor when applied to plants, plant cells, plant seeds, or plant tissues.

The terms "microbe" or "microorganism" refer to algae, bacteria, archae, fungi, and protozoa.

"Overexpression" refers to the expression of a polypeptide or protein encoded by a DNA introduced into a host cell, wherein said polypeptide or protein is either not normally present in the host cell, or wherein said polypeptide or protein is present in said host cell at a higher level than that normally expressed from the endogenous gene encoding said polypeptide or protein.

The term "plant" refers to any plant or part of a plant at any stage of development. Therein are also included cuttings, cell or tissue cultures and seeds. As used in conjunction with the present invention, the term "plant tissue" includes, but is not limited to, whole plants, plant cells, plant organs, plant seeds, protoplasts, callus, cell cultures, and any groups of plant cells organized into structural and/or functional units.

The term "plastid" refers to the class of plant cell organelles that includes amyloplasts, chloroplasts, chromoplasts, elaioplasts, eoplasts, etioplasts, leucoplasts, and proplastids. In organisms of the genus *Plasmodia* and *Toxo-*

*plasma*, PBGS resides in the apicoplast, thus examples of targets include malaria, and toxoplasmosis. These organelles are self-replicating and contain what is commonly referred to as the "chloroplast genome," a circular DNA molecule that ranges in size from about 120 kb to about 217 kb, depending upon the plant species, and which usually contains an inverted repeat region.

The term "tolerance/resistance" refers to the ability to continue normal growth or function when exposed to an inhibitor or herbicide.

The term "transformation" refers to a process for introducing heterologous DNA into a cell, tissue, or plant. Transformed cells, tissues, or plants are understood to encompass not only the end product of a transformation process, but also transgenic progeny thereof.

The "oral composition" is a product, which in the ordinary course of usage, is not intentionally swallowed for purposes of systemic administration of particular therapeutic agents, but is rather retained in the oral cavity for a time sufficient to contact substantially all of the dental surfaces and/or oral tissues for purposes of oral activity. The oral composition may be a single phase oral composition or may be a combination of two or more oral compositions.

The term "orally-acceptable carrier" as used herein means a suitable vehicle, which can be used to apply the present compositions to the oral cavity in a safe and effective manner. Such vehicle may include materials such as fluoride ion sources, additional anticalculus agents, buffers, other abrasive materials, peroxide sources, alkali metal bicarbonate salts, thickening materials, humectants, water, surfactants, titanium dioxide, flavor system, sweetening agents, xylitol, coloring agents, and mixtures thereof.

Morpheein Concept

Morpheeins are proteins that exist as an ensemble of non-additive, functionally distinct, quaternary structure isoforms. The term "morpheein forms" is used in this disclosure by the inventor to describe different quaternary isoforms of a protein, which are described in detail below. Morpheein forms of a given protein are in equilibrium with each other, and in some cases morpheein forms can form the basis for allosteric regulation. In the case of plant and some bacterial PBGS, the stimulus for transition between morpheein forms is the allosteric regulator, i.e., an agent (e.g., magnesium).

One dogma of modern biochemistry is that the three dimensional structure of a protein is a direct consequence of the amino acid sequence of that protein. Consequently, it is taught that one protein sequence makes one native structure. The discovery of prions challenges the one structure concept, but not if one believes these to be "misfolded". The current invention draws on a new discovery, that of morpheein forms, which are alternate protein quaternary structures that are a physiologically relevant consequence of a conformational change in the monomeric unit. In the case of morpheein forms, the alternate native states are close in energy to each other, but each state dictates a different finite quaternary assembly and may have different multiplicity, as illustrated schematically in FIG. 6.

The morpheein forms of a given protein have partial differences in secondary and tertiary structure, and these differences dictate a difference in quaternary structure. In certain aspects, morpheeins are like prions; one protein sequence that can undergo a conformational change which results in an altered quaternary structure (aggregation state). However, in other aspects, morpheeins are unlike prions in that the oligomer is of finite multiplicity and the quaternary structure change is reversible, non-pathologic, and part of a normal physiologic control process.

Figure 36:
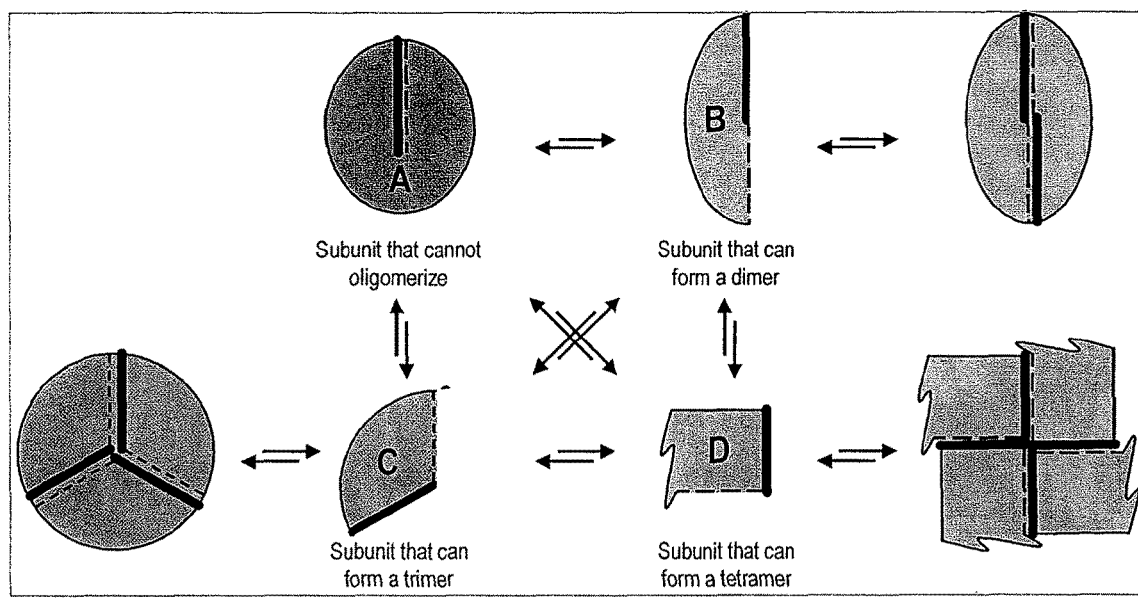
FIG. 36 illustrates a two-dimensional schematic of an equilibrium of morpheein forms. Four possible conformations of the monomer are shown. A protein that functions as a morpheein need only support two of these monomer conformations. Following a "rule of engagement" where oligomerization must occur by an association of a dashed line with a thick line, the subunits can self-engage to monomers of A or oligomerize to dimers of B, trimers of C, or tetramers of D. Monomer A is comparable to what have previously been termed "auto-inhibited" conformations of some proteins that are active as dimers.

In FIG. 6, the fundamental structural unit is monomeric and the association of any two units is driven by the placement of a dashed line adjacent to a thick line. This is the rule of assembly. FIG. 6 is a two dimensional illustration of the concept that the multiplicity of the assembly is directed by the shape of the fundamental structural unit (shown as a monomer) and the rule of assembly. In FIG. 6, there are four different shapes for the fundamental unit. The monomeric pac-man-like shape in the lower left cannot come together with itself in a way that places the dashed line adjacent to the thick line, this monomer cannot oligomerize. The half-oval monomer shape is capable of coming together with itself to form a dimer. Once the dimer is formed, all of the dashed lines are adjacent to all of the thick lines and oligomerization stops at the dimer. The pie-wedge shape can come together with itself in the same fashion, but three units are needed in order to have all the dashed lines adjacent to all the thick lines. Thus, the pie-wedge monomer is destined to multimerize into a trimer. Finally, following the same logic, the square monomer form is destined to form a tetrameric assembly. In addition, FIG. 36 is a two dimensional schematic describing the general phenomenon of morpheein equilibria. As the fundamental unit of the PBGS morpheein equilibrium is a dimer, this system is analogous to the equilibrium between tetramers and trimers.

Working within the morpheein concept, each multimer has different physiologically relevant functional characteristics, such as different $K_m$ and $V_{max}$ values. For instance, one multimer might be the allosteric "ON state" with high enzymatic activity and another multimer might be the allosteric "OFF state" with low activity. Alternatively, the function of the different oligomers might be a result of differences in the molecular surface of the oligomer. For instance, the rounded surface of the trimer in FIG. 6 would interact with different receptors or binding partners than the oval surface of the dimer or the pointed surface of the tetramer. These molecular surface differences could dictate the cellular localization for the complex. FIG. 8 is a two dimensional schematic of agents that can stabilize one or the other of the morpheein assemblies in FIG. 6.

Figure 24:
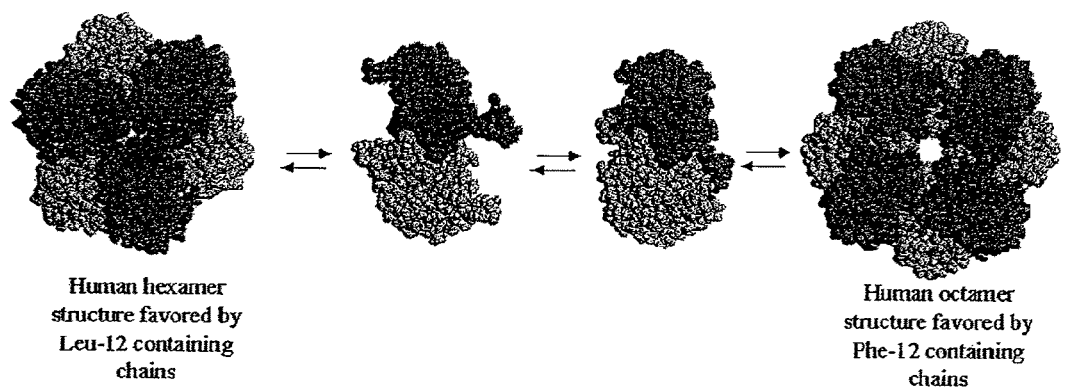
FIG. 24 shows the interconversion of human PBGS octamer and hexamer. The interconversion and disproportionation of human PBGS hexamer and octamer is proposed to proceed through a dissociation of the oligomers to their component dimers, interconversion of the dimeric forms, and a reassociation of the oligomers. The disproportionation reaction shown in FIGS. 25-27 prove this reaction occurs.

One example of a morpheein is the porphobilinogen synthase (PBGS) system where discovery of the alternate quaternary assemblies arose from characterization of the naturally occurring human PBGS variant F12L, which was found to have very different catalytic properties relative to the wild type (predominantly) octameric protein. The assembly of hexameric PBGS is illustrated in FIG. 9, and is dramatically different from the assembly of the PBGS octamer (FIG. 2). Fortunately, there is a vast phylogenetic variation in the amino acid sequence of the N-terminal arm segment of PBGS. This sequence variation provides a significant phylogenetic variation in the rate with which the alternate quaternary isoforms of PBGS will interchange. In human PBGS, particularly in the absence of turnover, the rate of interconversion of the quaternary isoforms is so slow as to be unmeasurable, thus providing us with the ability to observe stable crystal structures of the octameric and hexameric forms of the human protein. The discovery of the two forms of human PBGS is the first concrete example of morpheein forms and is described in detail in EXAMPLE 1. EXAMPLE 1 describes the discovery of the hexameric structure for F12L, and its unique properties. EXAMPLE 2 describes experiments demonstrating that the quaternary structure, rather than the specific mutation is responsible for the unusual properties of F12L. EXAMPLE 3 describes experiments demonstrating that the octameric and hexameric morpheein forms of human PBGS can exist in a dynamic equilibrium, thus proving that morpheein equilibria, such as are illustrated in FIG. 6 and FIG. 24, can exist.

There are two views of the structures of the functional dimeric intermediates in the PBGS morpheein equilibrium. The published reaction scheme for the equilibrium between hexameric and octameric PBGS uses the structures illustrated in FIG. 38. Interconversion between the hexamer and the octamer requires dissociation to a smaller state, which we hold to be dimeric. The dimer is the smallest state we have observed using size exclusion chromatography, analytical ultracentrifugation, or native gel electrophoresis. In FIG. 38 the hugging dimer and the detached dimer represent the asymmetric units of the crystal structures [2,15]. PBGS crystal structures from all organisms, except those of yeast [20-22, 26-29], contain one of these two asymmetric dimers as the asymmetric unit [2, 16-19, 30-32]. However, these structures are unlikely to represent the dimeric components of the equilibrium in solution because they expose significant hydrophobic surfaces to bulk solvent. In contrast, a detailed analysis of PBGS crystal structures shows that the subunit-subunit interface in each of these asymmetric units is rich in hydrophilic contacts and ordered water molecules. Hence our updated view of the morpheein equilibrium for PBGS is illustrated in FIG. 38, which introduces the existence of a pair of alternate dimers, which we call the pro-octamer dimer and the pro-hexamer dimer. The pro-octamer and pro-hexamer dimers are each composed of two subunits that are not from the same crystallographic asymmetric unit. Rather, the two subunits are from adjacent dimers in the crystal lattice. FIG. 38 illustrates how the crystallographic dimers fit into a side view of the octameric and hexameric assemblies. The pro-octamer and pro-hexamer dimers have buried surfaces that are more hydrophobic and exposed surfaces that are more hydrophilic than the hugging and detached dimers illustrated in FIG. 38.

Two morpheein forms of human PBGS that have been characterized separately include the high activity octamer and the low activity hexamer [2-4]. The destabilization of the active site lid in the hexamer can explain both the perturbed pH rate profile seen in this form and the high Km (see FIG. 37). Of the four assemblies illustrated in FIG. 38, only the octamer has the arm-to-barrel interface that stabilizes the closed conformation of the active site lid. Neither the pro-octamer dimer nor the pro-hexamer dimer contain this interaction; thus both would be expected to require high pH for activity and exhibit a high Km value. Our preliminary results with *P. aeruginosa* PBGS show a dramatic protein concentration-dependent specific activity (see below), but purification in the absence of magnesium results in purification of a dimeric assembly, not a hexamer. This purified dimer can be converted to the octamer upon dialysis against magnesium. Thus, we conclude that the hexameric assembly is disfavored by the sequence of *P. aeruginosa* PBGS and magnesium modulates the equilibrium between a low activity pro-octamer dimer and a high activity octamer. The general approach for our drug discovery efforts is to find compounds that preferentially bind to and stabilize a low activity morpheein form (e.g. hexamer and/or pro-octamer dimer) of PBGS from the selected human pathogens.

The existence of morpheeins expands the concept of autoinhibition beyond the monomer—dimer situation. FIG. 36 is a two dimensional schematic describing the general phenomenon of morpheein equilibria. As the fundamental unit of the PBGS morpheein equilibrium is a dimer, this system is analogous to the equilibrium between tetramers and trimers. However, the general schematic also includes the previously established phenomenon wherein a protein can exist in a three-part equilibrium between an autoinhibited monomer that cannot dimerize, a conformation of the subunit that can dimerize, and the dimer. A prime example is the epidermal growth factor (EGF) receptor. In that case the monomer has two possible structures; one is a closed form that cannot dimerize and the other is an open form whose most stable assembly is dimeric. The EGF binding site is present in the open form of the monomer, but not the closed form of the monomer. EGF binding stabilizes the open form of the receptor, thereby promoting dimer formation. Many cell surface receptors may function this way; this is a distinctly different mechanism than the one wherein the dimeric form of the receptor is tethered together by the effector molecule. One can consider the autoinhibited monomer as the "self-associated" morpheein form and one can draw a correlation between the dimer and various domain swapped dimeric structures for which there are now many examples such as ribonuclease and catalase.

The inventor's prior knowledge of the allosteric effect of magnesium binding on some PBGS and on the location of the allosteric magnesium binding site suggested that for some PBGS, the quaternary structure equilibrium between octameric and hexameric PBGS forms the structural basis for the phenomenon of allosterism. This lead to the formulation of the morpheein model for allosteric regulation (FIG. 7), which is fundamentally different from classic models for allosterism.

Allosterism is a general concept wherein the activity of an enzyme is affected by the binding of an allosteric regulator molecule to a binding site on the protein that is not the catalytic site. Most models of allosteric regulation propose that the active and the inactive state are oligomers of the same multiplicity, that these two forms are in equilibrium with each other, and that binding of an allosteric regulator molecule can shift this equilibrium (see FIG. 1). In some cases, this classic model is well supported or even proven by X-ray crystal structures of the ON and OFF states. In general however, there is insufficient structural information (three dimensional X-ray crystal structures for instance) in order to allow an understanding of where the allosteric regulator binds, how the ON and OFF states differ from each other, or why one form is more active than the other. The inventor's recent discovery of two different quaternary forms of PBGS allows one to examine these forms and to deduce a rational explanation for the allosteric regulation of the PBGS of some organisms by magnesium. Moreover, the observation of alternate quaternary forms of PBGS leads to a general description of the concept of morpheeins as a regulatory mechanism for protein function and the description of agents that can trap one or another of the morpheein forms such as to direct protein function. This is the morpheein model for allosteric regulation, as illustrated in FIG. 7. FIG. 10 illustrates this concept using, for example, the tetramer and trimer shown in FIG. 7, but adds a "splinter" to illustrate the allosteric regulator that can only bind to the tetramer. Binding of the splinter perturbs the quaternary structure equilibrium and draws the system toward the tetrameric form. FIG. 8 illustrates the concept of agents (shown as "wedges") that can trap a desired quaternary state of the protein and thus act to draw the equilibrium toward that state. Thus, these agents, which will perturb the quaternary structure equilibrium of morpheein forms, can inhibit or activate the protein. In one embodiment of the invention, the agent is an inhibitor, which traps the inactive form and therefore prevents formation of the active form. In one embodiment, the protein is PBGS, the inactive form is a hexamer and the active form is an octamer. A non-limiting example of the inhibitor is a rosemarinic acid or a derivative thereof. Another non-limiting example of the inhibitor is morphlock-1 or a derivative thereof. In another embodiment of the invention, the agent is an activator, which traps the active form of the protein.

Accordingly, in this the invention, a general mechanism for allosteric regulation using morpheein forms (quaternary structure isoforms) is proposed. In this mechanism, the monomeric structures are different in some aspect of their secondary/tertiary structure, and these differences dictate an assembly into one or the other morpheein. This morpheein utilizing allosteric mechanism is illustrated schematically in FIG. 7.

FIG. 10 is a two dimensional representation of the equilibrium between two forms of a protein (morpheein forms). A unit (e.g., a monomer) of one form (shown herein as a square) contains four different surfaces, which are a line, a thick line, a dashed line, and a squiggly line. The complementary surfaces that naturally associate are illustrated herein as the thick line with the dashed line. This association defines the rule of engagement between the units. When the subunit association potential of the square is satisfied (in another words when all thick lines are associated with all dashed lines), the optimal resulting assembly is a tetramer. Thus, the oligomeric assembly is dictated by the structure of the monomer and the rule of engagement. As shown in FIG. 10, the square structure can associate with a "splinter", which is a schematic representation of an agent (e.g., an allosteric regulator molecule); association of the square monomer and the square tetramer with the splinter affect a function of the multimeric protein, for example, in the case of plant and some bacterial PBGS, magnesium provides stability to these forms of the protein.

The square unit is in equilibrium with another structure, which shares some, but not all of its secondary and tertiary structure and consequently shares only some of the surface characteristics. The alternate unit is illustrated in FIG. 10 as a "segment". This monomer contains the surfaces depicted by the thick line and the dashed line; the rule of engagement between these surfaces is the same as for the square unit. Consequently, following this rule of engagement, the alternate unit assembles into a trimer. It is important that the trimeric structure and its individual components do not contain the binding site for the allosteric regulator molecule (the splinter). Since the splinter stabilizes the square and its oligomer, the presence of the splinter will pull the equilibrium of quaternary structures toward the square and its oligomers.

The observation of hexameric PBGS provided the first example of how quaternary structure can serve as a structural basis for allosteric regulation of protein function. In PBGS from photosynthetic organisms and some bacteria, a protein concentration dependence of the specific activity provides evidence for an equilibrium between a fully active (presumably octameric) form and an inactive (presumably hexameric) form (See FIGS. 5, 20A and 20B).

FIG. 10 is a schematic description of the behavior of PBGS, which is better illustrated using space filling diagrams in FIG. 11. In the case of PBGS, the square in FIG. 10 is the hugging dimer and the segment in FIG. 10 is the detached dimer. In each case, the structures share some, but not all surface characteristics and the rule of engagement between surfaces is to a first approximation shared between the two alternate structures. In the case of PBGS, the differences in oligomeric structure translate to different functional characteristics, such as the pH rate profiles illustrated in FIG. 12 and the $K_m$ values (in units of mM) and $V_{max}$ values (in units of μM h-1 mg-1) illustrated in Table 1. It is reasonable to assume that different quaternary structures of other proteins also translate to different functional characteristics. It is well known that dimerization of receptors is associated with signal transduction. What has not been appreciated prior to this invention is that the structures of the monomer within the dimer structure may not be the same as the structures of the monomer when they are not in the dimer structure.

TABLE 1

Kinetic parameters at pH 7 and pH 9 for wild type human PBGS as an example of an octameric PBGS and the human PBGS variant F12L as an example of the hexameric PBGS morpheein

| | pH | $K_{m1}$ | $V_{max1}$ | $K_{m2}$ | $V_{max2}$ |
|---|---|---|---|---|---|
| F12L hexamer | 7 | 17.7 ± 1.1 | 1.14 ± 0.05 | | |
| | 9 | 4.6 ± 0.1 | 18.2 ± 0.02 | | |
| wild type octamer | 7 | 0.25 ± 0.01 | 55.5 ± 0.2 | | |
| | 9 | 0.015 ± 0.001 | 8.16 ± 0.13 | 4.46 ± 0.80[a] | 6.67 ± 0.36[a] |

Figure 28:
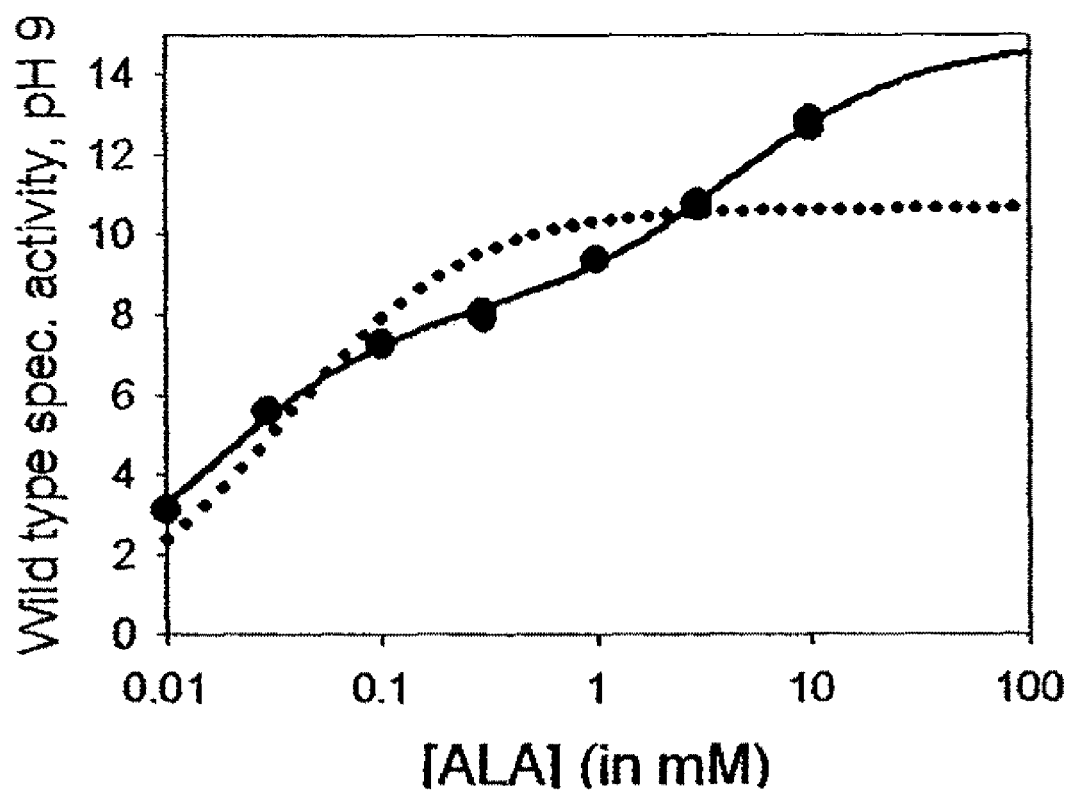
FIG. 28 illustrates the dependence of wild type human PBGS activity on the concentration of the substrate ALA at pH 9. The dotted line is the fit to the single hyperbolic Michaelis Menton equation. The solid line is the fit to a double hyperbolic equation, indicative of catalysis by two morpheein forms, one with a low $K_m$ value and one with a high $K_m$ value.

[a] At pH 9 the wild type human PBGS shows some propensity to form the hexamer (see below and FIG. 28).

Figure 13:
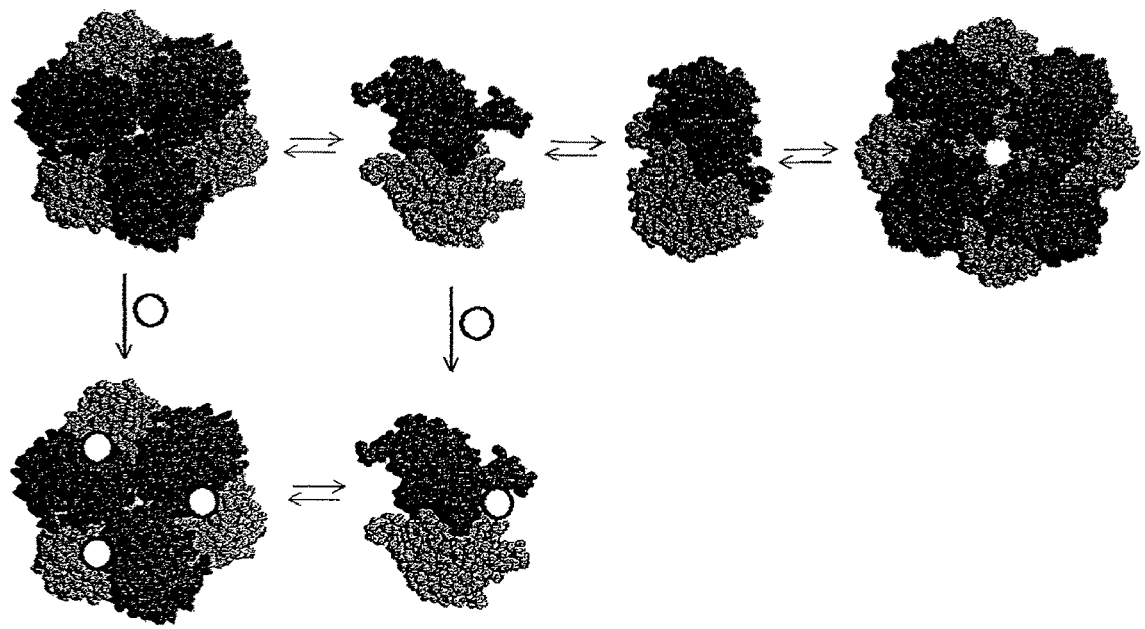
FIG. 13 shows a schematic representation of an embodiment of the inventive inhibition process, wherein an inhibitor of the invention (represented by circles) binds to one or more domains of the dimeric or hexameric PBGS to inhibit the formation of the octamer, stabilize bound forms and shift equilibrium. In this case, the inhibitor is a circle that binds to the arm-pit of the hugging dimer/hexamer forms.

FIG. 11 illustrates how Mg++ serves as an allosteric activator of PBGS from some species, FIG. 13 illustrates an agent that would serve as an inhibitor of PBGS through stabilization of the less active hexameric form. This schematic agent, illustrated as a ball that would fit into the arm-pit of the detached dimer, is an illustration of an agent of this invention.

Another non-limiting example of a protein which is a morpheein is Class Ia ribonucleotide reductase. The recent model put forth for allosteric regulation of Class Ia ribonucleotide reductase describes an equilibrium between a tetramer and a hexamer [44]. In this case, the model is schematic only and authors do not have protein structures that define the differences in the putative morpheein forms. However, ribonucleotide reductase is essential for de novo DNA biosynthesis, the Class Ia enzymes are found in all eukaryotes, and inhibition of de novo DNA biosynthesis is a rational approach to cancer chemotherapy. Thus, affecting a function of Class Ia ribonucleotide reductases (e.g., the inhibition) can be achieved through selective binding of an effector to a surface that is unique to the less active morpheein.

Examples of proteins which are morpheeins include, but are not limited to, acetyl-CoA carboxylase, adenylosuccinate Lyase, alpha-Acetylgalactosaminidase, aristolochene synthase, Asparaginase, aspartokinase III, ATPase of the ABCA1 Transporter, biotin holoenzyme synthetase, choline oxidase, chorismate mutase, citrate synthase, cyanovirin-N, D-3-Phosphoglycerate dehydrogenase, d-Amino acid oxidase, dihydrolipoamide dehydrogenase, dopamine b-monooxygenase, glutamate dehydrogenase, glutamate racemase, Glyceraldehyde-3-phosphate dehydrogenase, glycerol kinase, histidine decarboxylase, hemocyanins, lactate dehydrogenase, lon protease, malic enzyme, phenylalanine hydroxylase, phosphoenolpyruvate carboxylase, phosphofructokinase, polyphenol oxidase, porphobilinogen synthase, pyruvate kinase, S-adenosyl-L-homocysteine hydrolase, threonine dehydratase aka threonine deaminase, uracil phosphoribosyl-transferase, isocitrate dehydrogenase.

Although PBGS is the first example for which crystal structures are available for both of the two alternate quaternary forms, there are other systems described in the literature for which the morpheein concept appears to be applicable. As metastable states, it is not surprising that morpheeins have not previously been seen as alternate crystal structures of the same protein. Clues to the existence of homo-oligomeric enzymes that are morpheeins come from kinetic phenomena such as a protein concentration dependence to an enzyme's specific activity, from non-Michaelis behavior that fits to a double hyperbolic equation, from kinetic hysteresis, from dependence of activity upon the order of addition of reaction components, or from various protein sizing methods that suggest more than one quaternary isoform. None of these characteristics is in itself diagnostic of a morpheein equilibrium.

The multimeric protein of the invention should have at least one characteristic such as a protein concentration dependent specific activity or an ability to separate into different assemblies by e.g., ion-exchange chromatography, native gel electrophoresis; analytical ultracentrifugation, size-exclusion chromatography (on the basis of size); To demonstrate the equilibrium, kinetic studies can be conducted to show, e.g., $K_m$ and $V_{max}$; activity as a function of substrate concentration fit to MM equation; morpheeins will not fit well to a hyperbolic curve but rather a double hyperbolic curve, as seen for wild type human PBGS at pH 9 as illustrated in FIG. 28. Non-limiting example of a function of the multimeric protein is an enzymatic activity and an ability to interact with other molecules such as, for example, an ability to bind a different protein. The function can be inhibited or enhanced (or activated). Monitoring of changes in the function can be conducted by, for example, monitoring kinetic parameters $K_m$ and $V_{max}$ as a skilled artesian would appreciate. In certain embodiments of the invention, inhibition of a protein function is through stabilization of a less active morpheein.

In certain embodiments, the agent is adapted to affect a function of the multimeric protein. Non-limiting examples of the function of the multimeric protein is an activity and wherein affecting is at least one of inhibiting or activating. In certain embodiments, the agent is associated with the quaternary isoform having a lesser activity. In certain embodiments, the agent is bound to the quaternary isoform having a greater activity. A non-limiting example of an agent inhibiting octameric PBGS is described further below.

The octameric form of PBGS binds to substrate in a physiologically relevant concentration range and is active at physiological pH. The octamer is composed of four hugging dimers, where the arms of one subunit hug the barrel of an adjacent subunit with which there are strong barrel-to-barrel interactions (see FIG. 2).

The newly discovered hexameric form of PBGS is proposed to be an essential component of the regulation of tetrapyrrole biosynthesis in a subset of organisms, including plants and some pathogenic bacteria, but not including humans, animals or fungi. The hexameric form is substantially inactive under physiological conditions. In particular, the hexamer cannot bind substrate in the physiologically relevant concentration range because its $K_m$ value is at least two orders of magnitude larger than the $K_m$ of the octamer. The hexamer is composed of three detached dimers, where the N-terminal arms do not interact with the adjacent subunit with which there are strong barrel-to-barrel contacts (see FIG. 9).

The transition between the hexameric form and the octameric form involves a significant change in the protein structure, which is a dramatic reorientation of the N-terminal arm relative to the α8β8-barrell. Certain embodiments of the invention relate to the inhibition of the structural change from a hexamer to an octamer (as illustrated in FIG. 13) to inhibit the activation of PBGS and tetrapyrrole biosynthesis in plants and/or bacteria and/or animals. Certain embodiments of the invention relate to discovery of agents that inhibit in a species specific fashion, as has been done, for example, with morphlock-1.

The invention provides a novel approach to bacteriostatic, antibiotic, and herbicide applications by targeting PBGS, a universally conserved protein, because the inhibitor binding site is not conserved between humans and pathogens or plants. The invention provides a novel approach to bacteriostatic, antibiotic, and herbicide applications by targeting the stabilization of a low activity quaternary structure assembly of a morpheein. Since the inhibition mechanism is effective for plants, bacteria, and animals, thus the invention provides a novel approach to bacteriostatic, antibiotic and herbicide applications.

Thus, in certain embodiments, the invention comprises an inhibitor of the hexamer-to-octamer transition for those PBGS that are physiologically regulated by magnesium. Although PBGS that use the allosteric magnesium appear to equilibrate more rapidly between morpheein forms, the human protein also undergoes this equilibration, at a slower rate. However, with a long enough incubation of inhibitor, human PBGS and all PBGS are targets. The inhibitor can be a known or novel compound. The inhibitor is effective at inhibiting tetrapyrrole biosynthesis in plants and bacterial pathogens at that point in their growth and development where the hexamer-to-octamer transition is physiologically significant. Inhibition of the quaternary structure transition from hexameric PBGS to octameric PBGS is a novel target for the development of antibiotics and herbicides.

Identification of Morpheeins

Prior to the introduction of covalent appendages to facilitate protein purification (purification tags), the standard approach for purification of an enzyme from a cellular lysate typically involved a multi-stage fractionation scheme that eliminated other proteins from the sample while retaining the protein of interest. This approach is still in use and a reasonable hypothetical purification scheme is as follows: after disruption of the source cells/tissues, a centrifugation step is used to eliminate insoluble components, a salt cut is used to fractionate proteins with different solubility properties, and a series of column chromatography steps are used to separate the proteins into discrete fractions based on their surface charge, hydrophobicity, or size. The fraction(s) containing the protein of interest are identified by a PAGE procedure (SDS, native, or blot) or an activity screen, and the identified protein peak is pooled for the next purification step while the remainder of the sample is discarded. While this approach is effective, and has certainly withstood the test of time, it involves the assumptions that the surface charge, hydrophobicity, and/or size of a given enzyme are constants such that all of the physiologically relevant forms of the protein-of-interest will chromatograph identically. In the case of an ensemble of morpheein forms in equilibrium with each other, all of these assumptions may be false.

Unfortunately, this standard approach to protein purification disfavors the discovery of morpheeins. For instance, if the protein-of-interest is discovered in two chromatographic peaks by PAGE analysis, but the associated activity is only identified in one peak, the "other peak" is usually discarded as a misfolded form or a non-physiological aggregate. In the case of PBGS, the hexamer and octamer differ sufficiently in surface charge to be separated by ion exchange chromatography, and the size difference allows at least partial separation by gel filtration chromatography [14]. Prior to characterization of the inactive PBGS hexamer, this form was discarded rather than identified as a physiologically relevant form of the enzyme that can be activated under appropriate conditions. With any novel purification scheme, it is prudent to examine every peak carefully before discarding what at first may appear to be a misfolded form or aggregate of the protein of interest.

Among the wonders of molecular biology was the dramatic shift from traditional purification methods described above to the use of purification tags, such as the now ubiquitous GST-tag and His-tag. In this approach, the DNA sequence coding for the protein of interest is modified so that the resulting protein is produced with a "tag" of amino acids attached at one terminus. Depending on the system used, the tag can be a small number of residues, or larger than the protein of interest itself. These tagged proteins are then purified using a resin that specifically binds the tag, which can be either cleaved after purification (in the case of large tags) or left in place with the assumption that a few extra residues at the N or C terminus will not impact the function of the protein of interest. However, in the case of an equilibrium of morpheein forms, the use of a tag for purification may mask the potentially valuable chromatographic separation of morpheein forms. Furthermore, the use of a tag might also shift the morpheein equilibrium toward or away from one of the alternate oligomeric forms, potentially locking the protein in an inactive form which might be taken as "misfolded".

Figure 45:
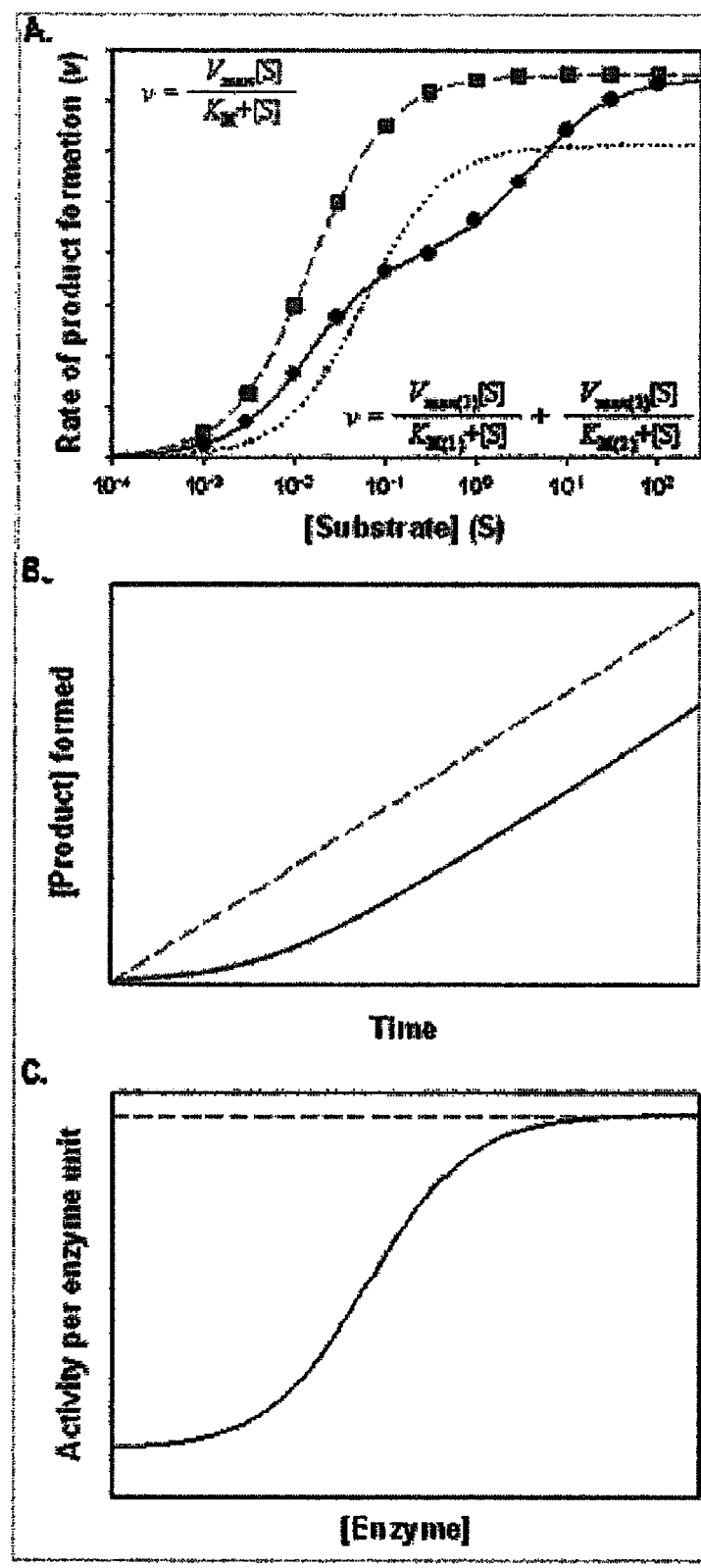
FIG. 45. Examples of atypical kinetics that can be associated with morpheeins.

Non-Michaelis Menten kinetics—That an enzyme is a morpheein can explain deviations from Michaelis-Menten kinetics, kinetic hysteresis, and a protein concentration dependence to an enzyme's specific activity. In fact, observation of such anomalous kinetic behavior can be a clue that an enzyme may function as a morpheein. In the standard approach for determining kinetic constants such as $K_m$ and $V_{max}$, we generally instruct that to get good kinetic values, one determines the rate while varying substrate concentration within the range of the $K_m$. But what if the protein exists as an equilibrium of morpheein forms where one assembly has a $K_m$ value of 20 μM and the other assembly has a $K_m$ of 5 mM, and both forms are present under assay conditions? Determination of both $K_m$ values requires varying substrate concentration over at least three orders of magnitude, which is not currently a standard procedure. Furthermore, the results will not be described by standard Michaelis-Menten kinetics for a single enzyme species (FIG. 45A). At low substrate concentration the activity results predominantly from the low $K_m$ morpheein form; but as substrate concentration approaches the $K_m$ of the higher $K_m$ morpheein form, it becomes a significant contributor to the overall rate of product production. On first glance, this situation could be mistaken as indicative of negative cooperativity; Segel's classic text on enzyme kinetics describes just such a situation for a mixture of isozymes with different kinetic constants [17]. In either case, the appropriate equation for fitting the kinetic data is the sum of two hyperbolic equations. However, the apparent $V_{max}$ obtained from such a fit for each morpheein form is actually the product of the mole fraction of that morpheein form and the true $V_{max}$ for that morpheein form. To obtain the latter value, one requires an independent assessment of the mole fraction of each morpheein form [12, 18].

Kinetic hysteresis—Kinetic hysteresis is another potential indicator of an equilibrium of morpheein forms (FIG. 4B). Kinetic hysteresis is a slow change in the rate of an enzyme catalyzed reaction in response to a rapid change in reaction conditions (e.g. addition of ligand, change in pH) [19]. This phenomenon has typically been attributed to slow conformational changes as well as experimental factors such as viscosity or mixing effects. We propose that another viable explanation for a slow approach to steady state may be that an enzyme (as it is added to the reaction mix) is predominantly in one morpheein form (e.g. low activity) and that turnover in the new environment triggers dissociation, conformational change, and reassembly to an altered morpheein form (e.g. high activity). Following a hysteretic approach to a new equilibrium of morpheein forms, the reaction proceeds at the expected linear rate until substrate becomes depleted. The slow hysteretic activation of one human PBGS construct has been demonstrated to arise from a hexamer to octamer transition, the time scale of which is about 0.017 per minute (half-life ~1 h), depending on conditions (e.g. variant, pH, etc.) [14].

Enzyme-concentration dependent specific activity—Yet another characteristic that can be diagnostic of a morpheein is a specific activity that varies as a function of enzyme concentration (FIG. 45C). The specific activity (typically expressed in □moles product formed/unit time/mg enzyme) is generally taught to be a fixed property of an enzyme and is often a criterion applied to pooling column fractions during a purification (see above). In the case of a morpheein system such as PBGS where the higher-order oligomer is the more active form, the specific activity increases as a function of enzyme concentration (as in FIG. 45C) since the octamer is favored over the hexamer under these conditions. This phenomenon has been documented for PBGS from plant and bacterial species [20].

Morpheeins Provide a New Structural Basis for Allostery

Figure 46:
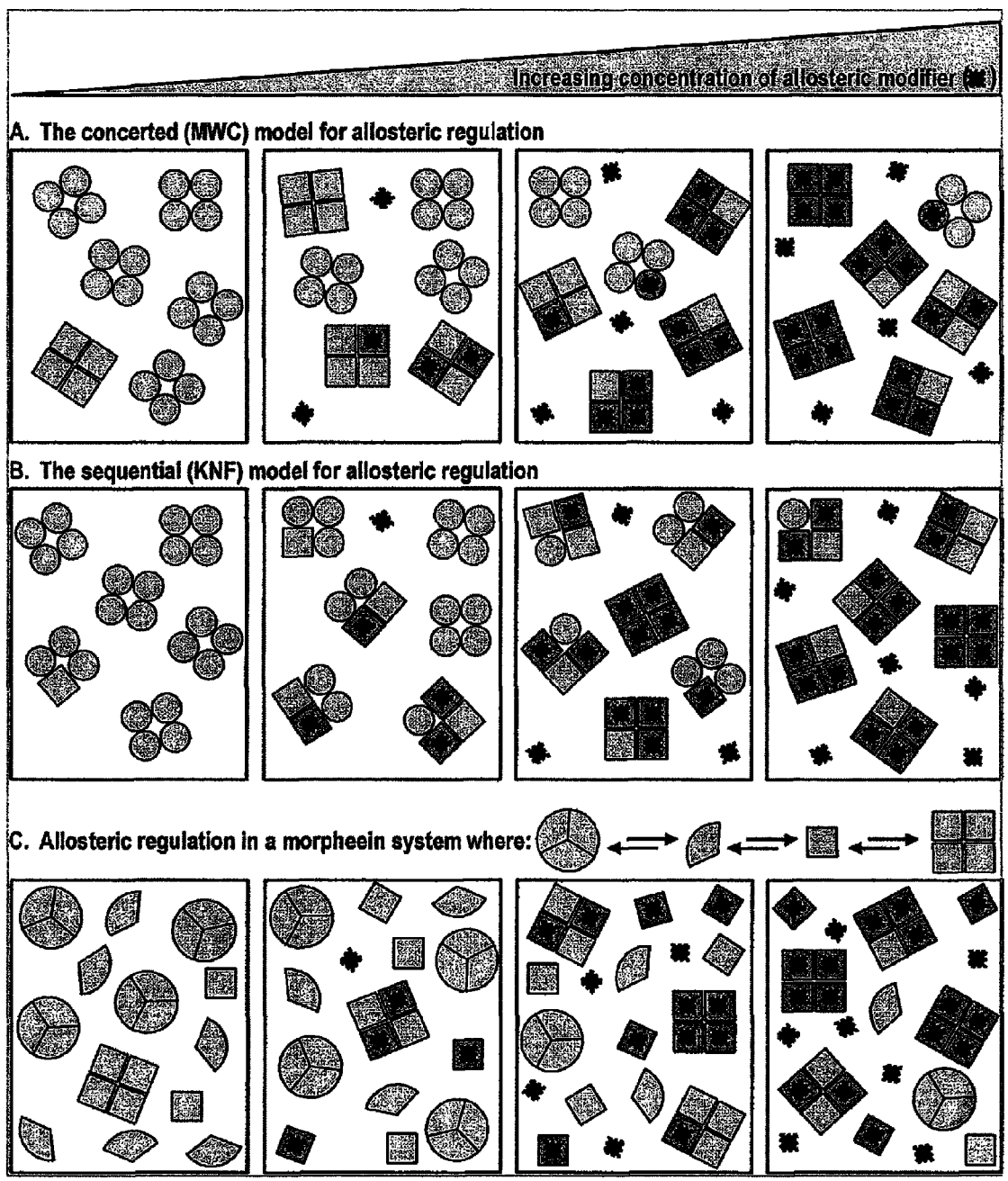
FIG. 46. Morpheeins introduce a third model for allostery.

From a historical perspective, fixed oligomeric stoichiometry was a deliberate and simplifying assumption of the development of both the Monod, Wyman, Changeux (MWC, or concerted) and Koshland, Nemethy, Filmer (KNF, or sequential) models for allosteric regulation [7,8]. With few exceptions this assumption has become a part of the fabric of how we think and teach about protein structure. The basic premises for each of these models are illustrated in terms of the relevant ensemble of structures in FIGS. 46A and B; allosteric regulation in a morpheein system is introduced in FIG. 46C. Similarities in all three models are that the enzyme subunits can exist in both a less active and a more active conformation, and that a regulatory molecule influences which conformation the subunits assume. The MWC model requires that all subunits of one oligomer are in the same conformation, while the KNF model allows for an oligomer composed of mixed subunits; both models assume that the conformational change occurs within the context of the fixed oligomeric stoichiometry. The required oligomer disassembly step differentiates the morpheein model for allosteric regulation from the classic MWC and Koshland models [6-8]. In the morpheein model, dissociation of the subunits is required for the conformational change to occur. The new subunit conformation then drives assembly to a different oligomeric state. Like the MWC model, the morpheein model requires all of the subunits of one oligomer to exist in the same conformation. Most importantly, the morpheein model explains why all of the subunits of one oligomer must be in the same conformation. In the morpheein model for allosteric regulation, it is not possible to have an asymmetric assembly where one subunit is different from all the other subunits. They just don't fit together!

We have introduced the interconversion of morpheein forms as a third general mechanism for allosteric regulation of protein function [6]. Furthermore, we have proposed that the morpheein mechanism for allosteric regulation may be relatively common, though under-recognized because oligomer dissociation runs counter to the traditional view of stable quaternary structure assemblies [6].

Morpheeins should not be Confused with Isozymes.

Different morpheein forms of the same protein share some commonalties with isozymes. For instance, different morpheein forms catalyze the same chemical reaction but may be characterized by different $K_m$ and $V_{max}$ values. Consequently it is important to differentiate morpheeins from isozymes. A morpheein is a protein that can exist in functionally and structurally distinct morpheein forms. Isozymes are two different proteins (different primary sequence) that can catalyze the same reaction (usually with some functional distinctions).

Morpheeins are Distinct from Other Examples of Alternate Quaternary Structures Such as the Amyloid Forming Proteins and Quasiequivalent Virus Coat Proteins.

The assembly of alternate oligomers plays a role in the pathologic process of amyloid plaque formation in Alzheimer's disease and prion infections like scrapie and Creutzfeld-Jacob disease. Like morpheeins, these examples also involve a single protein that can take on different conformations leading to alternate oligomeric states. The critical difference between morpheeins and amyloid-forming proteins is that the oligomeric interconversions of morpheeins are non-pathologic, reversible, and limited to oligomers of finite stoichiometry (FIG. 36). The proteins involved in amyloid plaque formation, however, assemble irreversibly into insoluble polymers of indefinite size.

The assembly of one protein into alternate quaternary assemblies has also been demonstrated for some icosahedral virus coat proteins where the structural variation has been called quasiequivalence [26,27]. However, these quasiequivalent forms differ from morpheeins in that the coexistence of the different forms in a single assembly is necessary for function, the ratio of the alternate oligomers must be fixed to build the higher-order geometric viral coats, and there is no evidence for a dynamic interchange of subunits between alternate oligomeric forms. Furthermore, the assembly of the oligomers of the viral coat proteins does not occur spontaneously.

Morpheeins are homo-oligomeric proteins whose function is controlled through reversible transitions between alternate non-additive quaternary structure assemblies. Morpheeins can deviate from classical Michaelis-Menten kinetics. Morpheeins provide a structural basis for allostery. The required oligomer disassembly process differentiates the morpheein model of allostery from the classic MWC and Koshland models. The morpheein model also accounts for why all of the subunits of a given oligomer must be in the same conformation. Hydrophilic subunit interfaces may indicate that an oligomeric protein can readily dissociate and possibly adopt alternate morpheein forms. Morpheeins are distinct from isozymes because isozymes have different primary structures. Morpheeins are distinct from amyloid-plaque forming proteins because morpheein forms are of finite stoichiometry. Morpheeins are distinct from quasi-equivalent virus coat proteins because alternate forms interconvert spontaneously in the absence of a scaffold or chaperone. Trapping of alternate morpheein oligomers provides a novel mechanism of drug action.

Determining which PBGS Proteins are the Most Likely Targets for Rapid Inhibition There is a phylogenetic variation in PBGS proteins where some have allosteric magnesium and others do not. The PBGS that have the allosteric magnesium are comprised of the archaea, all the bacteria with the exception of the genus *Rhodobacter*, and all of the photosynthetic eucarya (e.g., green plants) [11] (FIGS. 4 and 14). Another more recent exception appears to be the malaria parasite *Plasmodium falciparum* [45]. Based on the inventor's previously determined crystal structure for *E. coli* PBGS and the structure of hexameric PBGS disclosed herein, it appears that the role of the allosteric magnesium is to induce a structural change between the low activity hexamer and the high activity octamer (see FIGS. 11 and 20C). The hexamer-octamer transition for Mg++ acting on PBGS is a novel structural paradigm for allosteric regulation of protein function.

An inhibitor that stabilizes a hexamer will be most effective against a subset of PBGS that contain the allosteric magnesium but do not contain the active site zinc (i.e., PBGS within QSE, see FIG. 4). These are the photosynthetic eucaryotes and a subset of bacteria, including pathogens such as *Pseudomonas aeruginosa*. These PBGS proteins elicit the property of protein concentration dependent specific activity, which indicates a rapid interconversion between large active quaternary forms and smaller less active quaternary forms (see FIGS. 5, 20A and 20B). Also seen for NE quadrant [15].

Figure 15A:
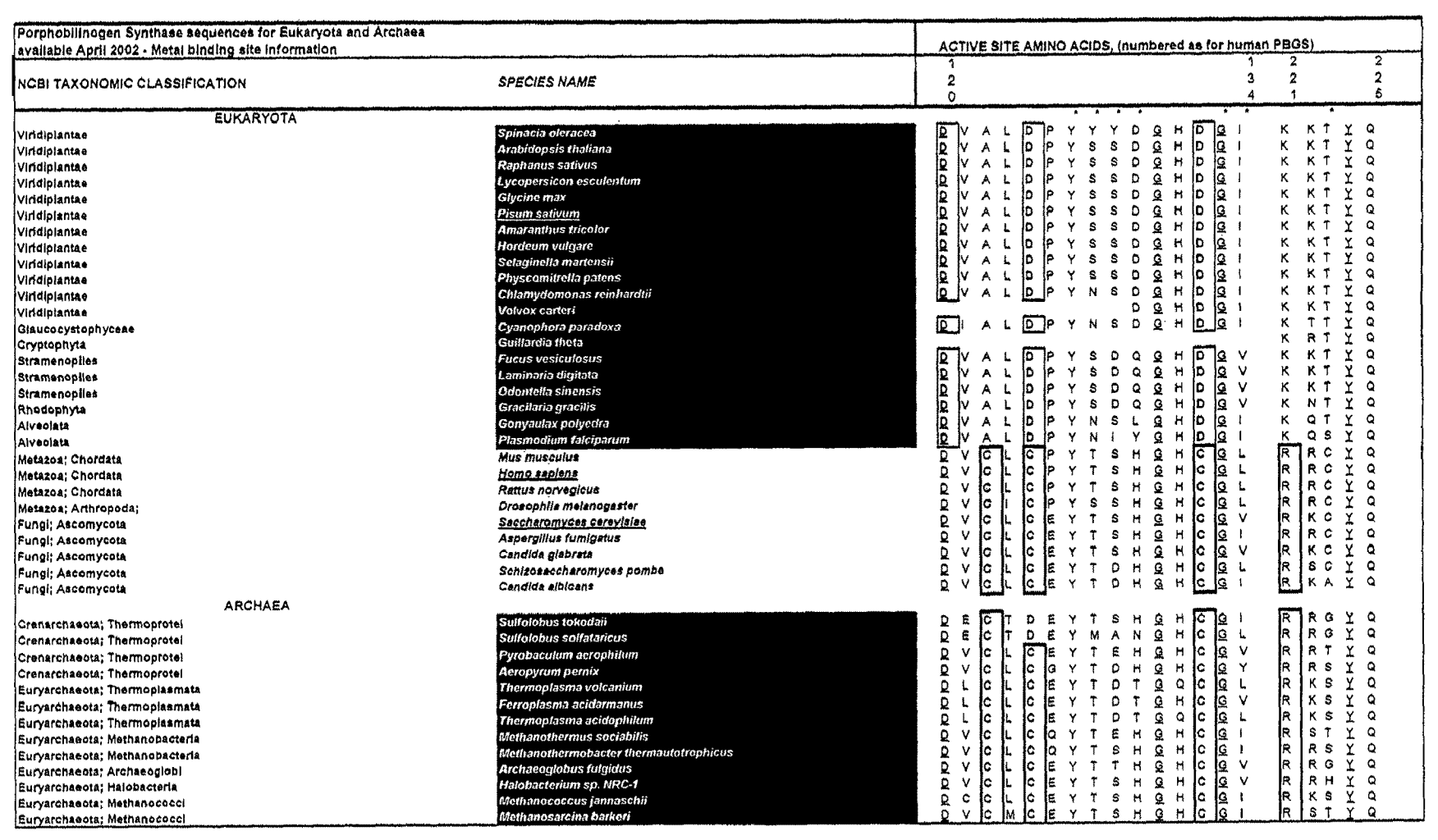
Figure 15C:
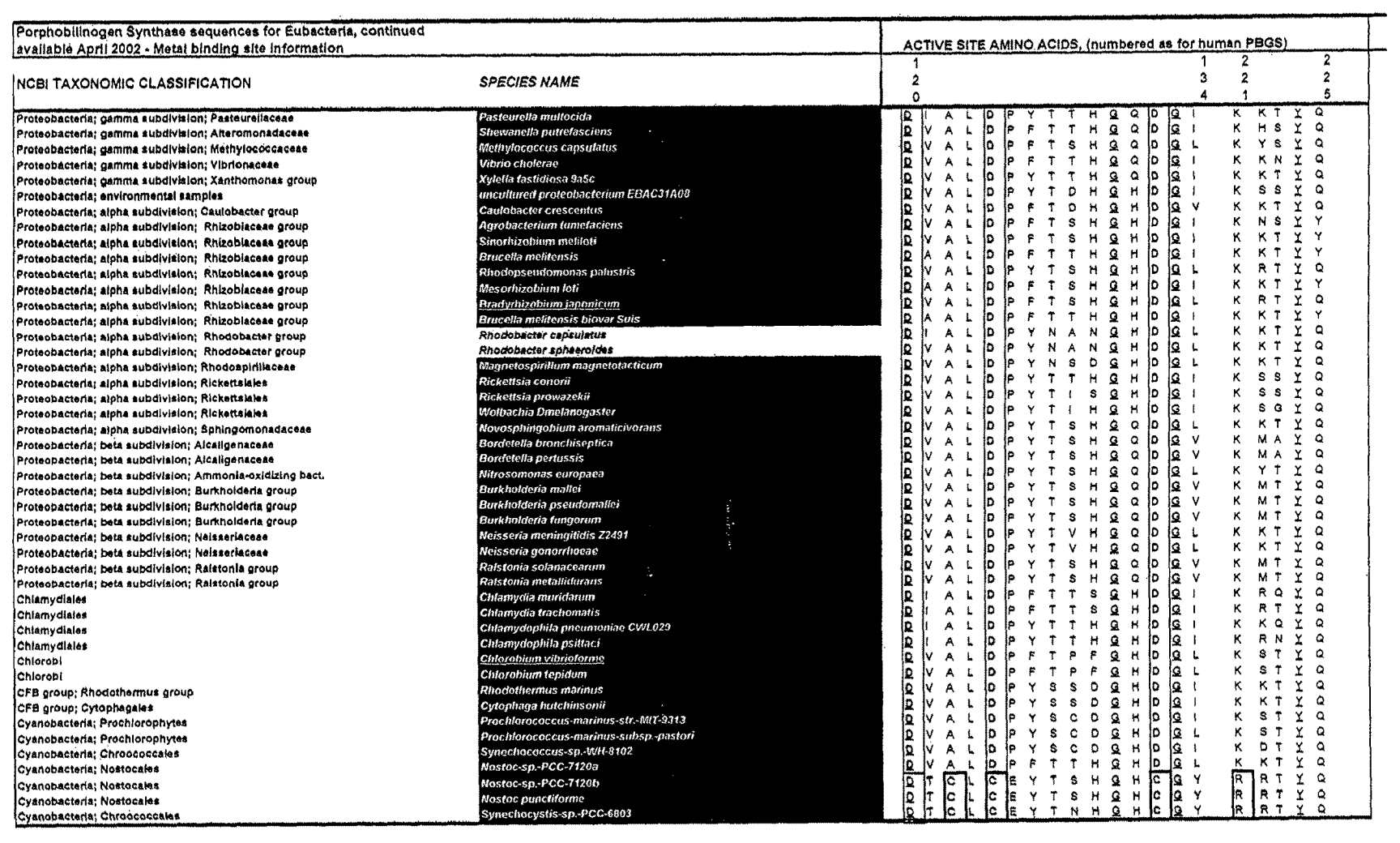

Thus, in certain preferred embodiments, the inhibitor of the invention is effective to inhibit the formation of octameric PBGS derived from bacteria, archaea, or eucarya, provided that the octameric PBGS contains an allosteric magnesium binding site. A non-limiting list of sources of the octameric PBGS, which can be inhibited by the composition of the invention, is shown in FIG. 14, which is a classification of organisms including bacteria, archaea and eucarya. FIGS. 15A and 15B and 15C represent an alignment of active site metal binding residues for the PBGS sequences obtained from GenBank and other web-searchable genomes available as of April 2002. The assignment of an organism into one of the four quadrants of FIG. 4 is based on the sequence information presented in FIGS. 15A-C. The presence of the active site zinc binding site is indicated by a cysteine rich cluster (positions 122, 124, and 132 of human PBGS) in association with an arginine residue on the active site lid (position 221 of human PBGS). Species that do not have the cysteine rich active site zinc binding cluster, contain instead an aspartic acid rich region and the active site lid residue is a lysine.

In certain embodiments of the invention, the inhibitor replaces a metal ion and thereby binds at a metal ion binding site, preferably, the metal ion is zinc or magnesium. In certain embodiments of the invention, the inhibitor binds at an active site. The inhibitor can bind anywhere, but the binding site must stabilize one quaternary structure. Binding is preferable to a site that is present in one morpheein form but not the other.

Inhibitors of the invention can be identified using the following protocol. First, a model is provided for a hexameric form of a PBGS. Example 4 describes the method used to build a model for a hexamer of *Pseudomonas aeruginosa* PBGS, which can serve as a template for more routine building of other hexameric PBGS proteins [15]. The initial model can, e.g., be one of pea PBGS. Second, small molecule databases are screened in silico for molecules that will fit into a hug-disabling domain adjacent to the N-terminal portion of the subunit. Some small molecule databases are available online [46] and others are being built in-house at Fox Chase Cancer Center. The hug-disabling domain is at least one area of the detached dimer on which binding of the inhibitor inhibits the arms of the dimer from hugging the barrel of that dimer which is necessary to form the active octamer. See FIG. 13, wherein circles represent inhibitors. A likely site of a hug-disabling domain is underneath the joint at which a hugging arm joins the body of the subunit (i.e., at the "arm-pit"). Theoretically suitable molecules will be empirically tested in vitro by determining their effect on the protein concentration dependent specific activity of pea PBGS, which is available using an artificial gene construct. Those molecules that inhibit the specific activity of the protein in a protein concentration dependent fashion are good inhibitor candidates (see FIG. 5).

Inhibitors of the invention can be identified for other morpheeins as targets using a similar in silico screening approach provided that a crystal structure or model structure can be prepared for the inactive quaternary isoforms of the target protein.

The following method will allow identifying inhibitors that will bind anywhere, not necessarily in the hug-disabling domain on PBGS to inhibit octamer formation. A functional assay for specific activity of PBGS will be used first to select potential inhibitors from available molecules that are identified in the computational screen, e.g., substances that are not harmful to humans. After potential inhibitors are selected, they will be further screened for affecting specific activity based on protein concentration. This traditional screening for inhibitors does not have any special propensity to select inhibitors that bind in a quaternary-structure-specific fashion.

Accordingly, this invention provides a method of affecting a multimeric protein, the method comprising: providing said multimeric protein comprising an assembly having a plurality of units, wherein each of said units comprises a first complementary surface and a second complementary surface and wherein the first complementary surface of one unit is associated with the second complementary surface of another unit, provided that the assembly is at least one of different quaternary isoforms on a condition that (1) a structure of said units determines a structure of said different quaternary isoforms, (2) said units are in an equilibrium and (3) the structure of said different quaternary isoforms influences a function of said multimeric protein; providing the composition of the invention comprising the agent, wherein the agent is adapted to affect the equilibrium by binding to a binding site on the assembly; and contacting the assembly with the agent, wherein the agent affects the equilibrium by binding to the binding site and thereby affecting said multimeric protein. In certain embodiments of the method, affecting said multimeric protein comprises affecting a formation of a quaternary isoform. In certain embodiments of the method, affecting said multimeric protein comprises affecting a function of said multimeric protein.

Further provided is a method of inhibiting a multimeric porphobilinogen synthase from forming an active form, the method comprising: applying the composition of the invention to the multimeric porphobilinogen synthase; associating the composition with the less active form; inhibiting the less active form from assembling into the active form and thereby inhibiting the multimeric porphobilinogen synthase from forming the active form. A non-limiting example of the inhibitor is a rosmarinic acid or derivatives thereof, whose characterization as an inhibitor of pea PBGS is described in EXAMPLE 5.

In Silico Drug Discovery

The in silico approach is an approach to drug discovery. In most cases the target is an enzyme active site whose structure is known and the object is to find an inhibitor that functions by competing for the active site. The in silico approach has three components. These are the small molecule virtual libraries, the protein structure models to which these libraries are docked, and the computational docking software. The development of software for virtual library screening by docking small molecule structures to protein structures is being intensely developed by many groups [cf. 34]. Programs at present are estimated to provide at least a 50-fold increase in the probability of finding a ligand compared to random screening, although our experience has been much better. An exemplary docking program is the commercially available program Glide (Schrödinger Inc., 2003).

Preparation of the Protein Structure Model Used for in Silico Docking

A three-dimensional protein structure model was prepared for the hexameric assembly of pea PBGS. Of necessity, building this model was an iterative process that depended on multiple crystal structures. As a basis for this model, high resolution structures (better than 1.8 Å) were available for octameric PBGS from yeast, E. coli, and P. aeruginosa. Of these choices, P. aeruginosa PBGS has the highest sequence identity with pea PBGS and that of the selected pathogens. On the other hand, only one crystal structure is available for hexameric PBGS, and that is the human PBGS structure 1PV8 [2]. As shown in FIG. 37, the unit cell of 1PV8 contains an asymmetric dimer at 2.2 Å resolution. Subunit A is disordered in the N terminal ten residues, and in residues 83 96, 125-139, 170-171, and 213-225 of the α8β8 barrel. Subunit B is disordered in the N terminal two residues, the C terminal two residues, as well as residues 83-96, 123-139, 170-171, and 213-225 of the α8β8 barrel. FIG. 37, which contains a structural overlay of the hugging dimer of octameric human PBGS and the detached dimer of hexameric human PBGS, illustrates that the amino acids of the barrel domain do not move significantly in the transition between these two structures. The hugging dimer structure of P. aeruginosa PBGS was used as a basis for the barrel domain of the modeled PBGS hexamer. The primary difference shown in FIG. 37 is the orientation of the N terminal 23 amino acids. This region of the structure of human PBGS is needed to form the basis for the N terminal arm region of our models. The other apparent differences between the two structures in FIG. 37 arise from disordered regions that are not visible in the crystal structure of the detached dimer of human PBGS. Many of these are in the barrel domain and these portions of the model were derived from the more complete hugging dimer structure of P. aeruginosa PBGS.

The modeling approach was based on the construction of a hexamer for P. aeruginosa PBGS. This hexamer serves as the template for the model of hexameric pea PBGS, and the template for the hexameric assembly of PBGS from the selected pathogens. The publicly available Swiss PDB Viewer, or DeepView package (us.expasy.org/spdbv/) was used. This software provides a user-definable structure alignment and manipulation of coordinates through alteration of dihedral angels. The program SCWRL, created by Dunbrack, which uses state-of-the-art amino acid side chain rotamer libraries was used to orient the side chains for those amino acids which are modeled. The program LOOPY can be used when it was necessary to model loop regions. The first step was the construction of a hexamer from the hugging dimer of P. aeruginosa PBGS. Three copies of the P. aeruginosa PBGS hugging dimer 1GZG were superimposed upon the human hexameric structure 1PV8. Fusing the output files creates a rudimentary hexamer model of P. aeruginosa PBGS that contains the correct orientation of the barrels, but the incorrect orientation of the N terminal arms. The structure 1GZG, upon which this model is based, is an asymmetric dimer at 1.66 Å resolution. Subunit A is complete through the barrel domain, with the exception of the C terminal two amino acids. The N terminus of subunit A is missing residues 16. Subunit B is not complete throughout the barrel domain. It is missing the C terminal two amino acids as well as eight amino acids (221-228) that comprise part of a flexible lid over the active site. The B subunit is missing only four N terminal amino acids. Like other PBGS structures, the thermal factors of 1GZG shows that the well ordered structural unit of the dimer is comprised of the barrel of subunit A and the arm of subunit B. For the octameric assemblies, the ordered structural components are the four barrels of the bottom subunits (which are called A, C, E, and G) and the four arms of the top subunits (which are called B, D, F, and H).

The next steps focused on modeling the arms of this rudimentary hexamer model. FIG. 37 illustrates that the arms of both the hugging and detached dimer share an α-helix, which is located between residues 12 and 23 of human PBGS. We strove to correctly place this helix so that it sat properly at the base of the barrel for a neighboring dimer. For each arm of the rudimentary hexamer model, the amino acids of this helix of *P. aeruginosa* PBGS were superimposed on the corresponding helix of 1PV8. The resulting arm configurations were used to reposition the arms of the rudimentary hexamer model. Since there is virtually no sequence identity between the arm regions of *P. aeruginosa* and human PBGS (see below), we relied on a structure alignment for overlaying the helices. Once the helices were properly positioned, the program LOOPY was used to position the four amino acids of *P. aeruginosa* PBGS that lie between this helix and the barrel. The resulting intermediate model of the *P. aeruginosa* PBGS hexamer is a good first approximation. The missing N-terminal structure was modeled from the available N-terminal structure information in 1PV8. For these residues, DeepView was used to set the phi, psi, and omega angles of the model to the corresponding amino acids of 1PV8. The model does not contain the N terminal residues of *P. aeruginosa* PBGS that correspond to the missing N-terminal residues of 1PV8. These residues are not in a position that would contribute to the putative drug binding site. The result was the second intermediate hexamer model, which contained a good representation of the backbone configuration for the arm, but the side chains required attention. To orient these side chains and avoid intersubunit conflicts, the SCRWL program was used to orient the side chains for all of the residues of the arm for which the backbone conformations have been adjusted. The resulting model of the hexamer of *P. aeruginosa* PBGS was imported into the Maestro component of the Schrödinger package to identify any portions of the model that were inconsistent with the force fields used by Glide and resolved them by energy minimizations. This energy-minimized structure then served as the template for formation of a homology model for the hexameric assembly of pea PBGS using the MolIDE software [65]. Using these same techniques, models have been prepared for the hexameric assemblies of PBGS from the NIAID high priority human pathogens *Burkholderia mallei, Plasmodium falciparum, Brucella melitensis, V. cholerae, Yersinia enterocolitica,* and *Bulkholderia pseudomallei.*

Models may be constructed to enable the determination of different side chain conformations as the pro-octamer dimer in the absence of the other subunits, or to enable the determination of the octamer from the pro-octamer dimer is extracted. The Inventors have already used MolIDE to prepared models for the hexameric assembly of *V. cholerae* PBGS and *P. falciparum* PBGS. The preparation of the pea PBGS hexamer, as documented above, and the successful identification of morphlock-1 show the utility of the model building approach.

Defining the Inhibitor Binding Site

The model of hexameric pea PBGS is comprised of three copies of an asymmetric dimer. The putative inhibitor binding site contains components from three subunits of the hexamer, i.e. one detached dimer and one subunit of an adjacent dimer (FIG. 38*b*). The asymmetry in each dimer results in the hexameric model containing two sequence-identical but structurally distinct inhibitor binding sites. Rotating counter-clockwise around the central axis, the detached dimers are comprised of subunits A and B, C and D, and E and F. One inhibitor binding site is at the junction of subunits A, B, and E (ABE) and the other site is at the junction of subunits B, A, and D (BAD). Each hexamer has three sites equivalent to the ABE site and three sites equivalent to the BAD site. The putative inhibitor binding site on the hexameric assembly contains components from three subunits, which are one detached dimer and one subunit of an adjacent dimer (see FIG. 39). The asymmetry in each dimer results in the model containing two sequence-identical but structurally distinct potential inhibitor binding sites, which was named ABE and BAD for the subunits that comprise the sites. Each hexamer has three sites equivalent to the ABE site and three equivalent to the BAD site.

Figure 39:
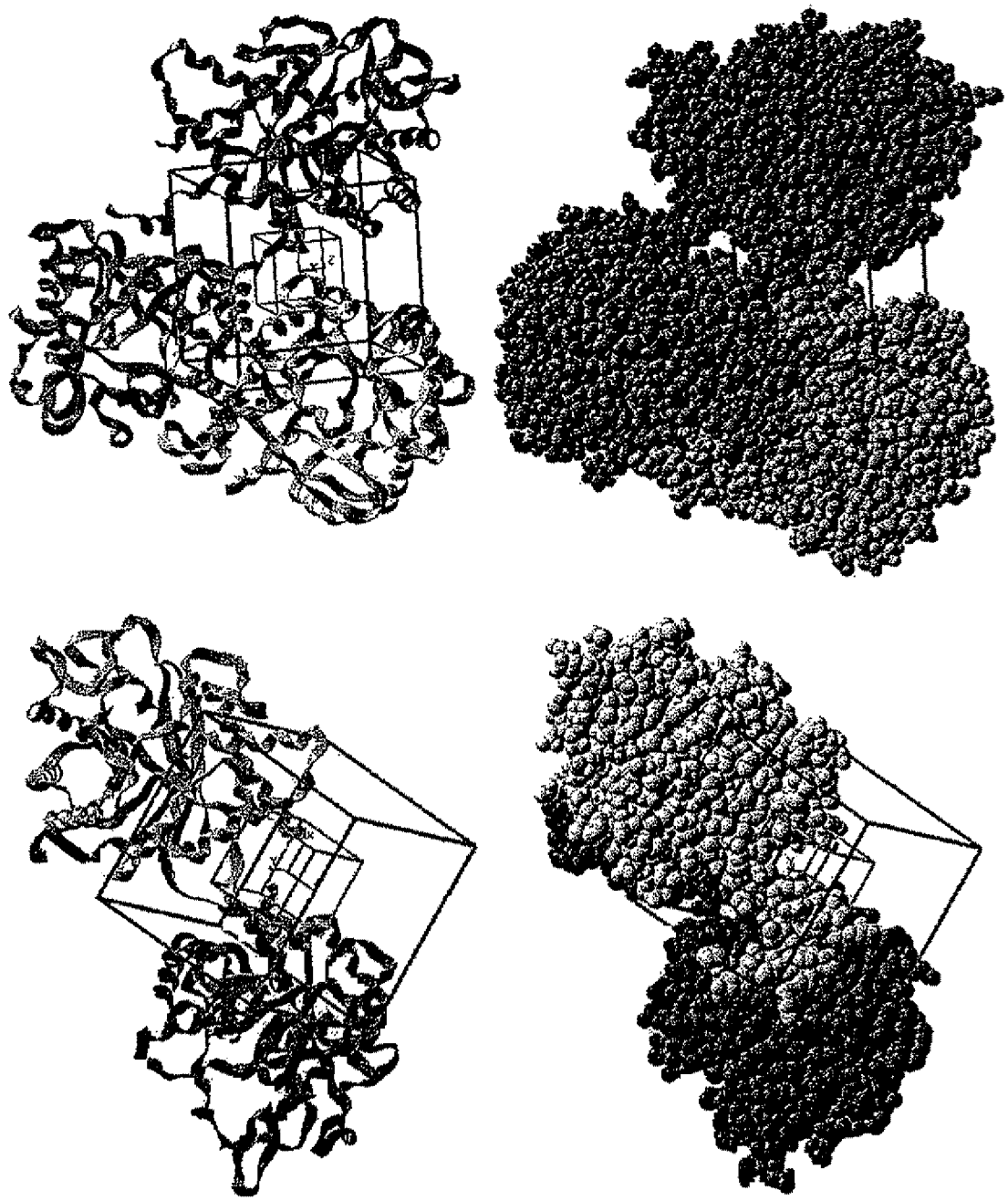
FIG. 39 illustrates the boxes used by Glide in the search for morphlocks are illustrated both as a ribbon representation (left) and as a spacefill representation (right). The top structures illustrate the placement of the docking box for the hexameric pea PBGS assembly. The bottom structures show the placement of the docking box for the pro-octamer dimer of *P. aeruginosa* PBGS.
Figure 43:
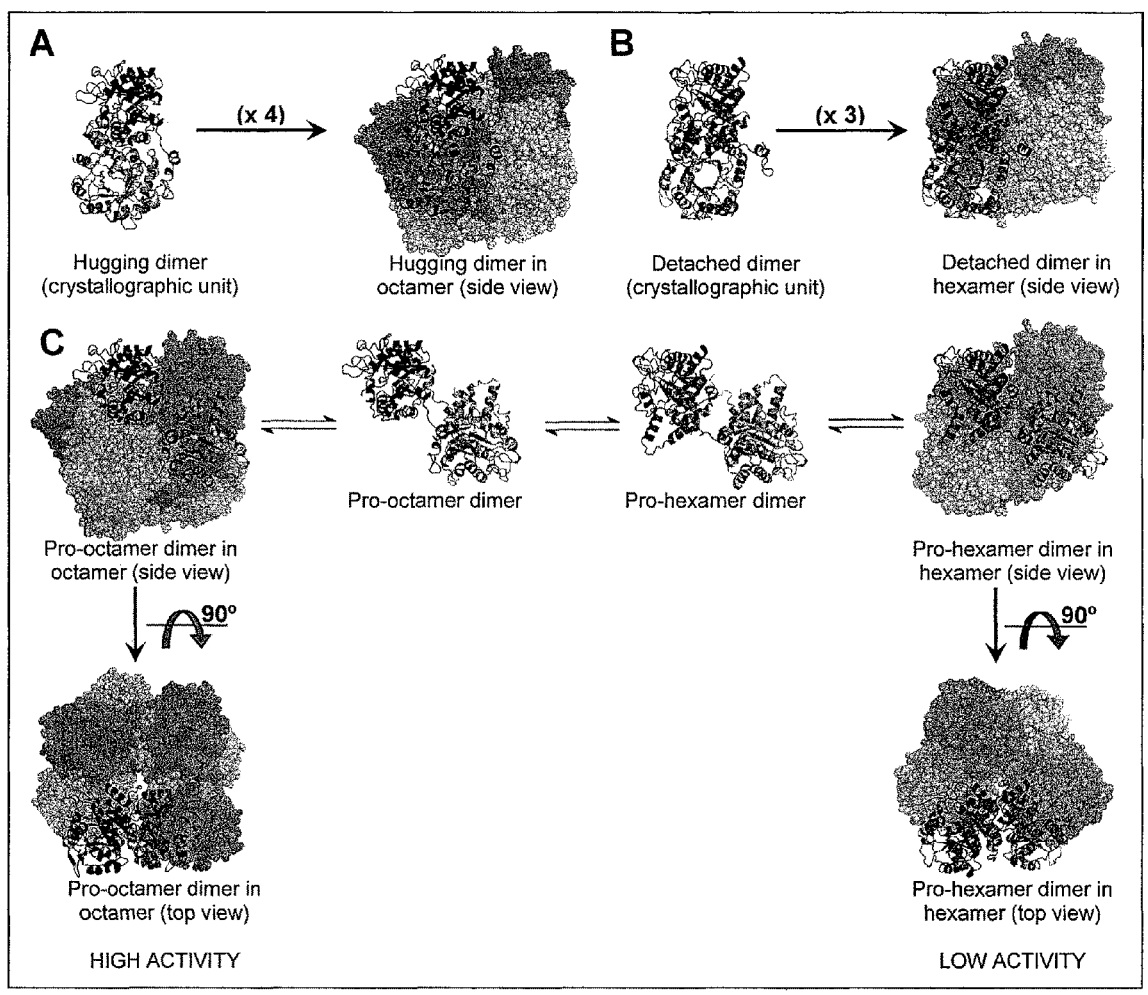
FIG. 43 illustrates alternate views of dimers that assemble into the PBGS oligomers—FIG. 43(a) and FIG. 43(b) The crystallographic asymmetric units of PBGS octamers and hexamers are hugging and detached dimers, respectively. The dimers are shown as ribbons with one subunit in a light shade and the other in a dark shade. Each dimer is shown in the context of its oligomer with the remaining subunits shown as spheres.
Figure 44:
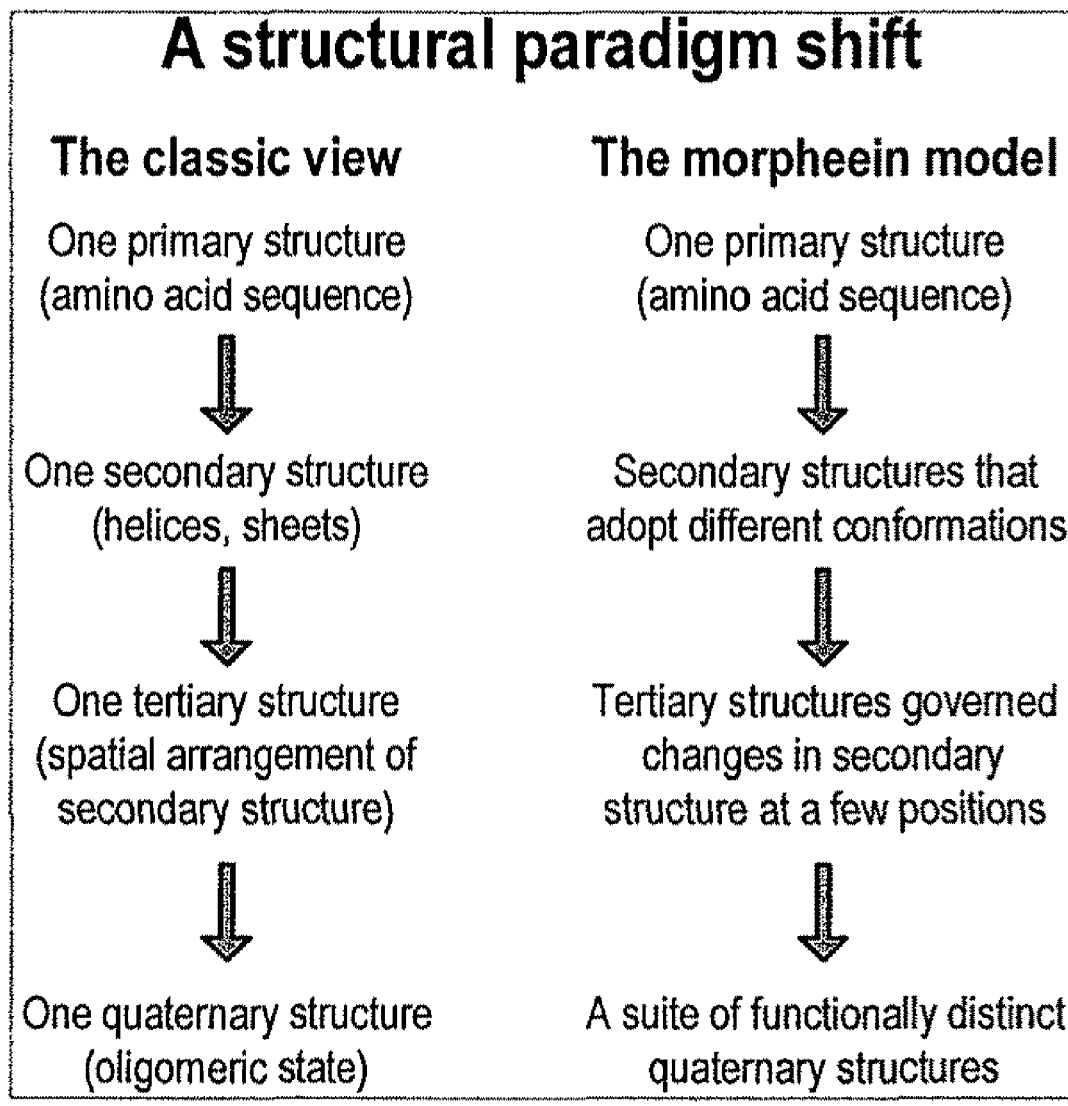
FIG. 44. Morpheeins challenge protein folding paradigm. The similarities and differences of the classic protein folding paradigm (left), versus the morpheein model (right).

Selection of Drug Binding Sites, Including Phylogenetic Analysis of the "Morphlock" Binding Sites The inactive or low activity morpheein forms of PBGS are represented by the dimeric and hexameric assemblies illustrated in FIG. 38. The hexameric assembly of PBGS has a unique "drug"-binding site. Because extensive characterization of the wild type human PBGS shows a low but finite mole fraction in this hexameric assembly, it is important that the drug binding site for PBGS of pathogens have a different constellation of amino acids in this site than does the human protein. The morphlock docking boxes are illustrated in FIG. 39. It is apparent from this figure that there is low sequence similarity in most of these amino acids between human PBGS and the target organisms. The amino acids that are within 3 Å of the docked position of morphlock-1, but morphlocks directed at other PBGS may be found to interact with any constellation of residues within the box. Some human pathogens, e.g. *P. aeruginosa*, express a PBGS that also has a low propensity to take on the hexameric assembly. In these cases the observed protein concentration-dependent specific activity, shown in FIG. 32 for *P. aeruginosa* PBGS, is interpreted as an equilibrium between the high activity octamer and the pro-octamer dimeric assembly. The drug binding site in the pro-octamer dimer is illustrated in FIG. 44, set subunits A, C, E, and G, and the octamer is then comprised of hugging dimers AB, CD, EF, and GH or pro-octamer dimers BC, DE, FG, and HA. The putative drug-binding site that would disallow assembly of pro-octamer dimer is then the site of interaction between the B,C-pro-octamer dimer and subunit D. The asymmetry of the known octameric assemblies is not significant in this region; thus docking to the pro-octamer need only use one kind of morphlock binding site. The docking box to be used is illustrated in FIG. 43; with this strategy, drug binding is proposed to interfere with assembly of the active octamer. The sequence alignment in FIG. 43 also shows the phylogenetically variable nature of the morphlock binding site on the pro-octamer dimer. The N-terminal arm of the PBGS subunit, which is a significant component of this binding site on the pro-octamer dimer, is one of the least conserved regions of the PBGS sequence. In contrast, the complementary barrel-to-barrel contact region of the hugging and detached dimers is also contained in this binding box and is a highly conserved region of PBGS, see FIG. 39.

Building the in Silico Library of Compounds for Docking

The computational docking studies require preparation of the in silico libraries of small molecules and the docking using Glide. The compounds available from Life Chemicals, Inc. are predominantly molecules of molecular mass ~500 Daltons, and are designed to be relatively "drug-like" (e.g. adhering to Lipinski's rule of five). Two dimensional representations of compounds available from Life Chemicals, Inc. were obtained in SD format from the vendor. Scripts supplied by Schrödinger Inc. were used to convert these into three dimensional, energy minimized representations in a file format used by Glide. In this process the structures were converted to Maestro format, and entries that contained metal ions or atom types other than H, C, N, O, P, S and halogens were discarded. Hydrogens were then added to all atoms as appropriate for the structures, generating a single stereoisomer per compound. The structures were energy minimized using MacroModel with the MMFFs force field and then expanded to include all forms likely to be present in the pH range 5-9 using Schrödinger's Ionizer utility. The structures were again energy minimized using MacroModel, which yielded output files that were suitable for docking with Glide.

Docking

Docking studies used Life Chemical, Inc.'s compound libraries, which are comprised of small molecules (molecular weight ~500) that are designed to be relatively "drug-like" (e.g. adhering to Lipinski's Rule of Five [Lipinski, 2001]). Two libraries, named "G-protein coupled receptor-targeted" and "Kinase-targeted" were used. For each of the proposed binding sites, ABE and BAD, a cubic region 25 Å in length was defined at the interface of the three subunits (shown for ABE in FIG. 38b). This box was used by Glide as the search region within which each entire docked molecule must fit in order to be scored. A second concentric cubic region with length 14 Å was defined and used to restrict the location of the center of each docked molecule (FIG. 38b). The docking process used the default settings of Glide (version 3.5) Standard Precision (SP) mode, which produced a "Glide score" for each molecule; the Glide score is based on a proprietary modification of the chemscore algorithm [Eldridge, 1997] that quantitatively accounts for characteristics of the binding interaction between each docked small molecule and the protein. The Glide SP mode scores goodness of fit based predominantly on geometries. For each library and each binding site, we found that the Glide scores of approximately 80% of the docked compounds were similar to each other; 10% were significantly lower (better fit), and 10% were significantly higher (inferior fit). Compounds with the best SP Glide scores, ~10% for each library, were then docked a second time using the Extra Precision (XP) mode of Glide, resulting in a set of new, quantitatively unrelated Glide scores. XP mode scoring is more rigorous as it takes into account polarity and hydrophobicity, and penalizes mismatches of hydrophobic-hydrophilic contacts or charges. Again, roughly 80% of the molecules had similar scores. Molecules with XP Glide scores in the top ~10% (about 1% of the starting library) were then analyzed further to select for predicted solubility, interactions with each of the three subunits, and variety in both chemical structure and binding interactions. This resulted in the selection of a set of ~100 diverse, putatively soluble, small molecules for purchase and in vitro testing from Life Chemicals, Inc. The selected compounds represented an equal distribution of fits to ABE and BAD. The compounds are shown in their docked orientation in Lawrence et al., Shape Shifting Leads to Small-Molecule Allosteric Drug Discovery, Chemistry & Biology (2008) doi:10.1016/j.chembiol.2008.04.012).

Post-Docking Processing

Molecules with XP Glide scores in the top ~10% (about 1% of the starting library, ~3500 compounds) were then analyzed further to select compounds. Compounds may be selected for testing based on, for example, the following criteria. Each selected molecule must make van der Waals contacts or hydrogen bonds with all three of the subunits. it is preferred that each selected compound must have a predicted solubility (Log S) estimate of at least −6, which was calculated using QikProp. The set of selected molecules must contain a broad sampling of dissimilar structures. The set of selected molecules must represent diverse positions within the docking box (see FIG. 39).

Initial Screening of Compounds

Figure 41:
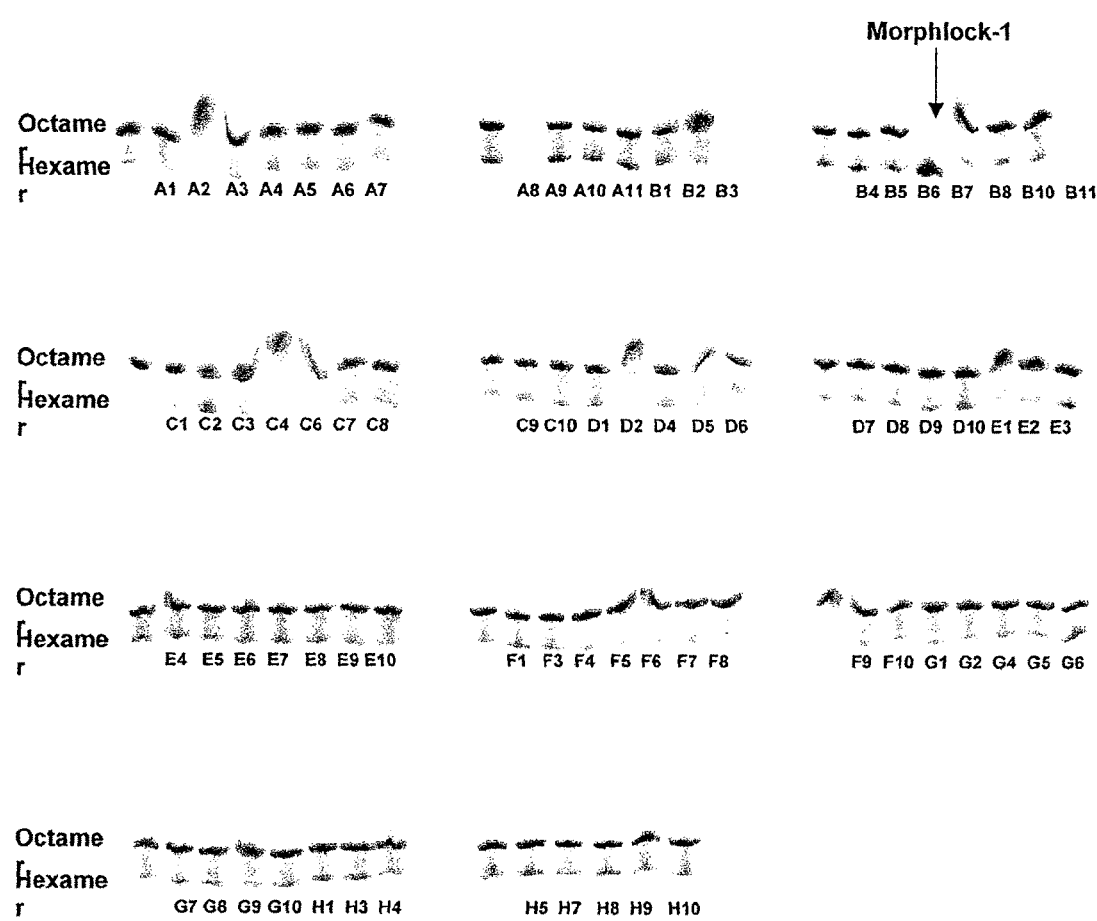
FIG. 41 illustrates native PAGE screening of compounds. Octameric PBGS (1 mg/mL) was incubated with DMSO or 2 mM of each compound for 30 minutes at 37° C. prior to resolution on 12.5% polyacrylamide native PhastGels. The gels are divided laterally by double lines, and the first lane of each shows the effects of DMSO as a control. Each compound is identified by its box address. The compound B6 is morphlock-1. Some compounds caused PBGS to precipitate out of solution, and these lanes appear empty.
Figure 42:
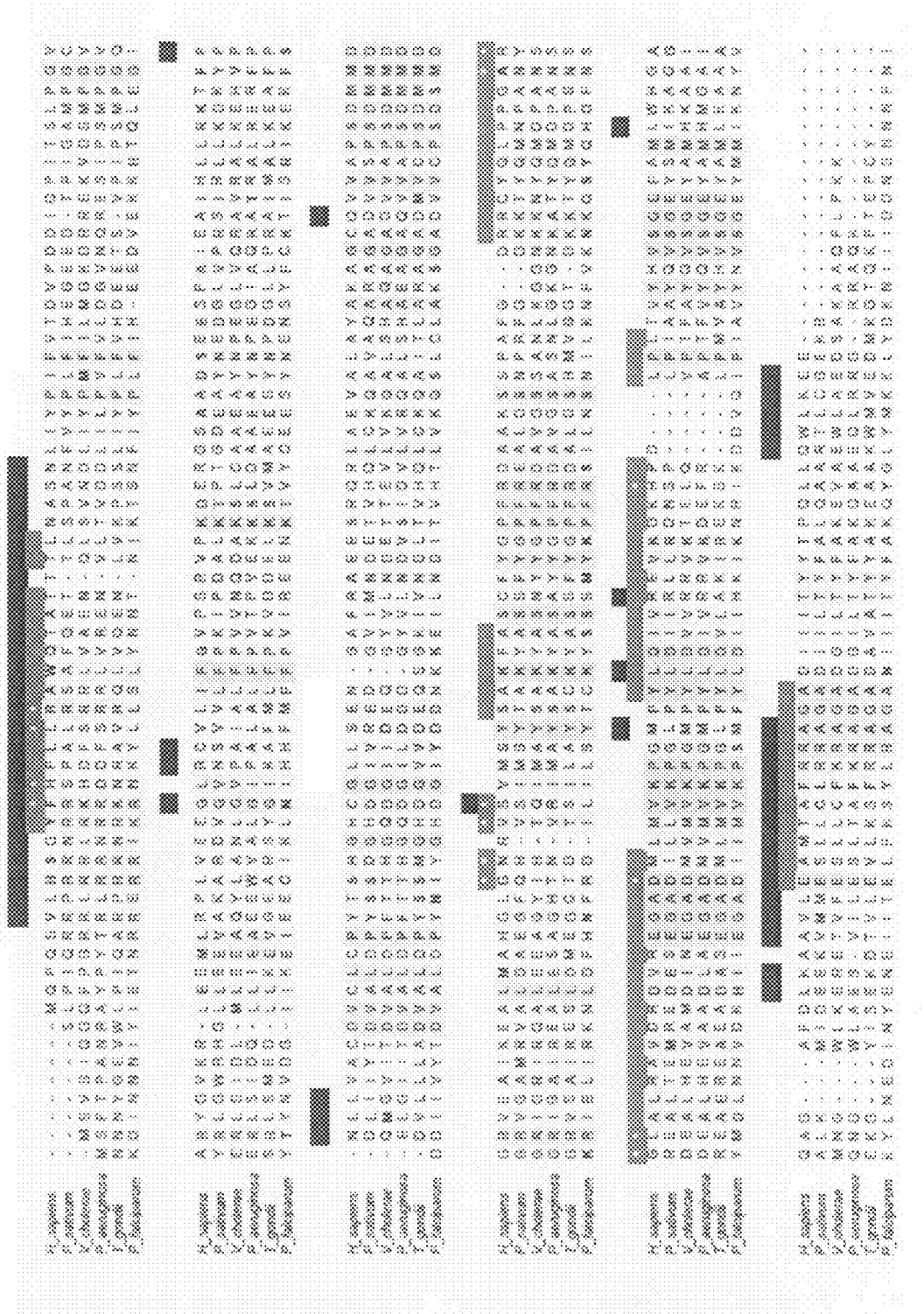
FIG. 42 illustrates sequence alignment for PBGS from human, pea, and the four target organisms—showing homology, and similarity. The bars above the sequence denote the residues located within the putative morphlock docking boxes for the pro-octamer dimer and the hexamer respectively. The asterisk denotes the residues that interact with morphlock-1 in its docked location (SEQ ID NOs: 148-153).

The distribution of PBGS into hexamers and octamers can be monitored by native polyacrylamide gel electrophoresis (PAGE) [Breinig, 2003], and this property was utilized to screen the compounds identified by Glide. Of the 76 purchased compounds, only morphlock-1 (FIGS. 32a and 32b) was found to dramatically shift the oligomeric equilibrium to the hexamer under the screening conditions (FIG. 41). Most significantly, the ratio of octamer to hexamer is dependent on the concentration of morphlock-1 (FIG. 32c). In these native PAGE analyses, which are at non-equilibrium conditions and use high protein concentrations (1 mg/ml, ~28 µM subunits), the observed $IC_{50}$ is ~500 µM. Kinetic analysis and additional native PAGE analysis using more sensitive staining techniques show an $IC_{50}$ of ~1 µM (see below).

Confirmation of the Chemical Identity of Morphlock-1

$^1$H-NMR, mass and UV/Vis spectroscopic analyses of morphlock-1 were consistent with 2-oxo-1,2-dihydro-benzo(cd)indole-6-sulfonic acid[2-hydroxy-2-(4-nitro-phenyl)-ethyl]-amide. 1H-NMR (300 MHz, D2O): δ 8.89 (brs, 1H), 8.45 (d, J=8.4 Hz, 1H), 8.01 (d, J=2.7 Hz, 1H), 7.98 (d, J=3.3 Hz, 1H), 7.83 (d, J=8.4 Hz, 1H), 7.76 (d, J=8.7 Hz, 1H), 7.24 (d, J=9.0 Hz, 1H), 6.95 (d, J=7.8 Hz, 1H), 5.93 (brs, 1H), 4.71 (q, J=9.9, 1H), 3.77 (d, J=4.2, 1H), 3.25-3.19 (m, 2H); MS (m/z): [MH]+ calculated for C19H15N3O6S, 414.07; found, 414; [MNa]+ calculated for C19H15N3O6S, 436.06; found, 436; UV/Vis: λmax 267 nm.

Characterization of the Effect of Morphlocks on the Target PBGS

Pea PBGS exhibits a protein concentration dependent specific activity that represents a dynamic equilibrium between high activity octamers and low activity hexamers, only the latter of which contain the putative binding site for morphlock-1 (FIG. 38). The protein concentration dependent specific activity data for pea PBGS in the absence of morphlock-1 fit well to a simple hyperbolic equation with a $K_{(0.5)}$ of 0.064 µM PBGS (FIG. 32d), suggesting that the protein is 50% hexamer at this concentration. At the lowest protein concentration assayed, the specific activity of pea PBGS was less than 1% of the maximal activity, suggesting that the hexamer is virtually inactive under these conditions. The dose response curve for morphlock-1 inhibition of pea PBGS (FIG. 37a) was initially carried out at 0.03 µM pea PBGS, where the hexamer is a significant component of the equilibrium mixture; the morphlock-1 concentration was varied from 0.1 µM to 0.1 mM. These inhibition data fit to a hyperbolic equation, and yield an apparent $IC_{50}$ of 1.2 µM morphlock-1. The protein concentration dependent specific activity of pea PBGS predicts that the apparent $IC_{50}$ of morphlock-1 will vary with protein concentration, showing less inhibition at higher protein concentration in the range of the $K_{(0.5)}$. Corroborating evidence that morphlock-1 inhibits through stabilization of the hexameric assembly is the increased $K_{(0.5)}$ of the protein concentration dependent activity in the presence of morphlock-1 (FIG. 32d). For this determination, the morphlock-1 concentration was set at 5 µM, which more than doubles the $K_{(0.5)}$ to 0.134 µM pea PBGS relative to the $K_{(0.5)}$ without morphlock-1 (0.064 µM).

Figure 33:
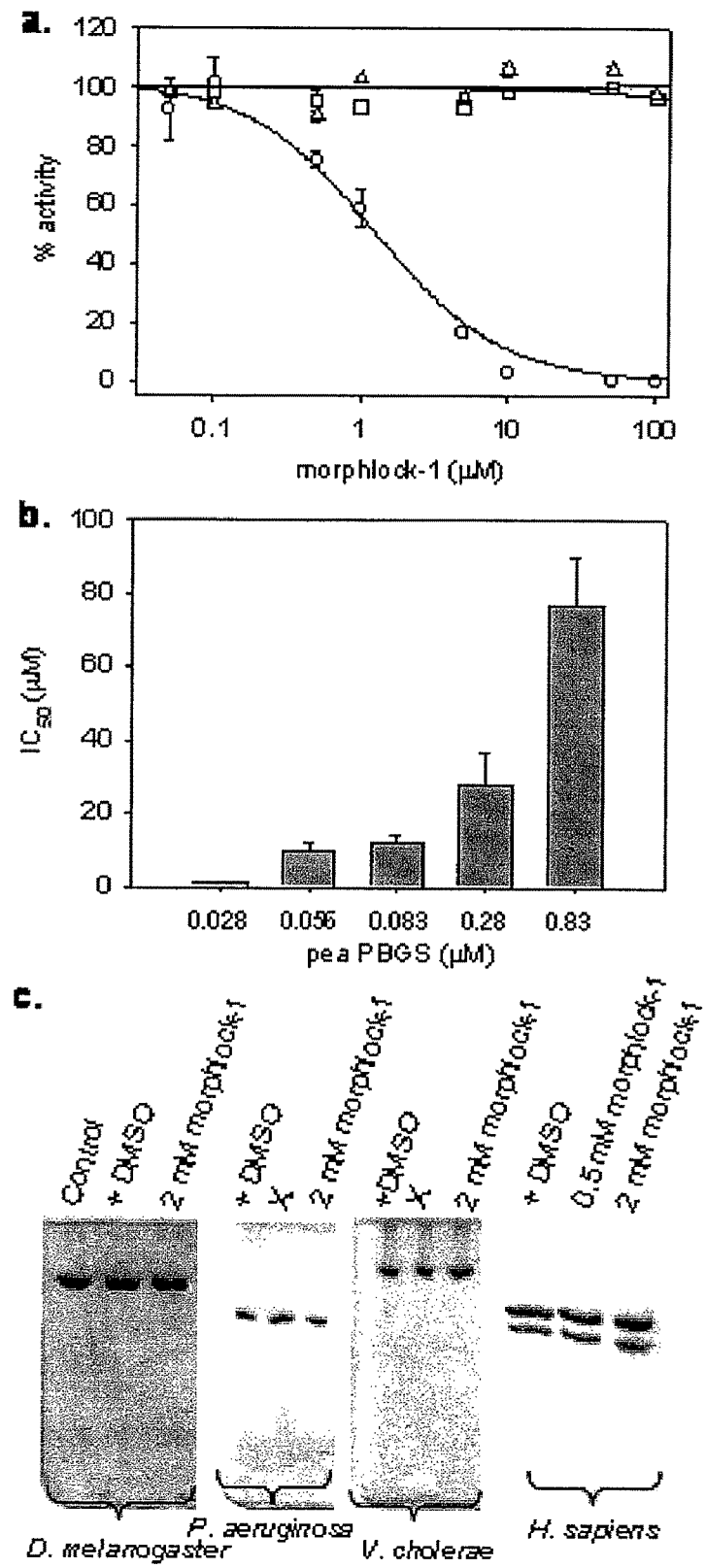
FIG. 33 illustrates the species-specific effects of morphlock-1 on PBGS—FIG. 33(a) Dose-response curves showing morphlock-1 inhibition of pea PBGS at 1 µg/ml (○) and human PBGS at 0.6 µg/ml (Δ) and 10 µg/ml (□). The proteins were incubated in the presence of 10× inhibitor for 30 minutes at 37° C. prior to assay. The concentrations on the X-axis represent the final concentration of morphlock-1 in the assay.

Pea PBGS exhibits a protein concentration-dependent specific activity that represents a dynamic equilibrium between high activity octamers and low activity hexamers, only the latter of which contains the putative binding site for morphlock-1. The protein concentration-dependent specific activity data for pea PBGS in the absence of morphlock-1 fit to a $K_{(0.5)}$ of 0.064 µM PBGS (FIG. 32(d)), suggesting that the protein is 50% hexamer at this concentration. At the lowest protein concentration assayed, the specific activity of pea PBGS was ~2, suggesting that the hexamer is virtually inactive under these conditions. Further evidence that morphlock-1 inhibits through stabilization of the hexameric assembly is the increased $K_{(0.5)}$ of the protein concentration-dependent specific activity in the presence of morphlock-1 (FIG. 32(d)). For this determination, morphlock-1 was set at 5 μM, which more than doubled the $K_{(0.5)}$ to 0.134 μM pea PBGS relative to the $K_{(0.5)}$ without morphlock-1. The dose response curve for morphlock-1 inhibition of pea PBGS (FIG. 33(a)) was initially carried out at 0.03 μM pea PBGS, where the hexamer is a significant component of the equilibrium, in order to optimize the observed inhibition; the morphlock-1 concentration was varied from 0.1 μM to 0.1 mM. These inhibition data fit to an apparent $IC_{50}$ of 1.2 μM morphlock-1. The protein concentration-dependent specific activity of pea PBGS predicts that the apparent $IC_{50}$ of morphlock-1 will vary with protein concentration, showing less inhibition at higher protein concentration in the range of the $K_{(0.5)}$.

The characterization of morphlock-1 with pea PBGS is illustrated in FIG. 32. Gel shift assays, enzyme inhibition studies, protein concentration-dependent specific activity studies and species selectivity studies may be applied to the PBGS from target pathogens.

High Throughput Screening

A complementary approach to our computational docking is high throughput screening (HTS) [61]. This approach has the potential to identify morphlocks that bind to sites other than those we have defined for in silico docking. "High throughput screening" (HTS) refers to a plurality of assays that test a plurality of compounds, performed robotically, the results of which are generally measured electronically by changes in magnitude or wavelength maxima of absorption or emission of light for the purpose of finding a drug candidate ("hit") among the compounds. In general, the assay measures an enzyme activity; and cleavage of a labeled substrate to a product causes a change in color, or wavelength of emission, or extent of emission, of such that multiple parallel samples can be read automatically. In general, multiwell plastic plates having at least 96 wells per plate, or 384 wells/plate, or 1536 wells/plate, are used in HTS. Because HTS is highly automated, it is generally performed on at least a plurality of compounds, for example, at least 1,000 compounds, for example, at least 2,000 compounds, at least 5,000 compounds, or at least 10,000 compounds. Libraries of compounds can be obtained, for example, from commercial sources such as ChemBridge (San Diego, Calif.), or Life Chemicals, Inc.

Species Selectivity of Morphlock-1 Inhibition

The putative morphlock-1 binding site is phylogenetically variable (see below). As such, morphlock-1 would not be expected to inhibit human PBGS. The effect of morphlock-1 on the activity of human PBGS was also determined at the midpoint of the protein concentration-dependent specific activity. FIG. 32(d) shows that morphlock-1 does not inhibit human PBGS at this protein concentration. As expected, 5 μM morphlock-1 has no affect on the protein concentration-dependent specific activity for human PBGS (FIG. 33(a)), nor does it effect the mobility of human PBGS on a native PAGE gel. To further establish the species-selectivity of morphlock-1, the gel shift assay was also carried out for PBGS from *P. aeruginosa*, and *V. cholerae*. As predicted from our strategy to target a phylogenetically variable drug-binding site, morphlock-1 did not cause any perturbation of the quaternary structure equilibrium for either *P. aeruginosa*, or *V. cholerae* PBGS.

Morphlock-1 Specifically Binds to the Pea PBGS Hexamer

Figure 40:
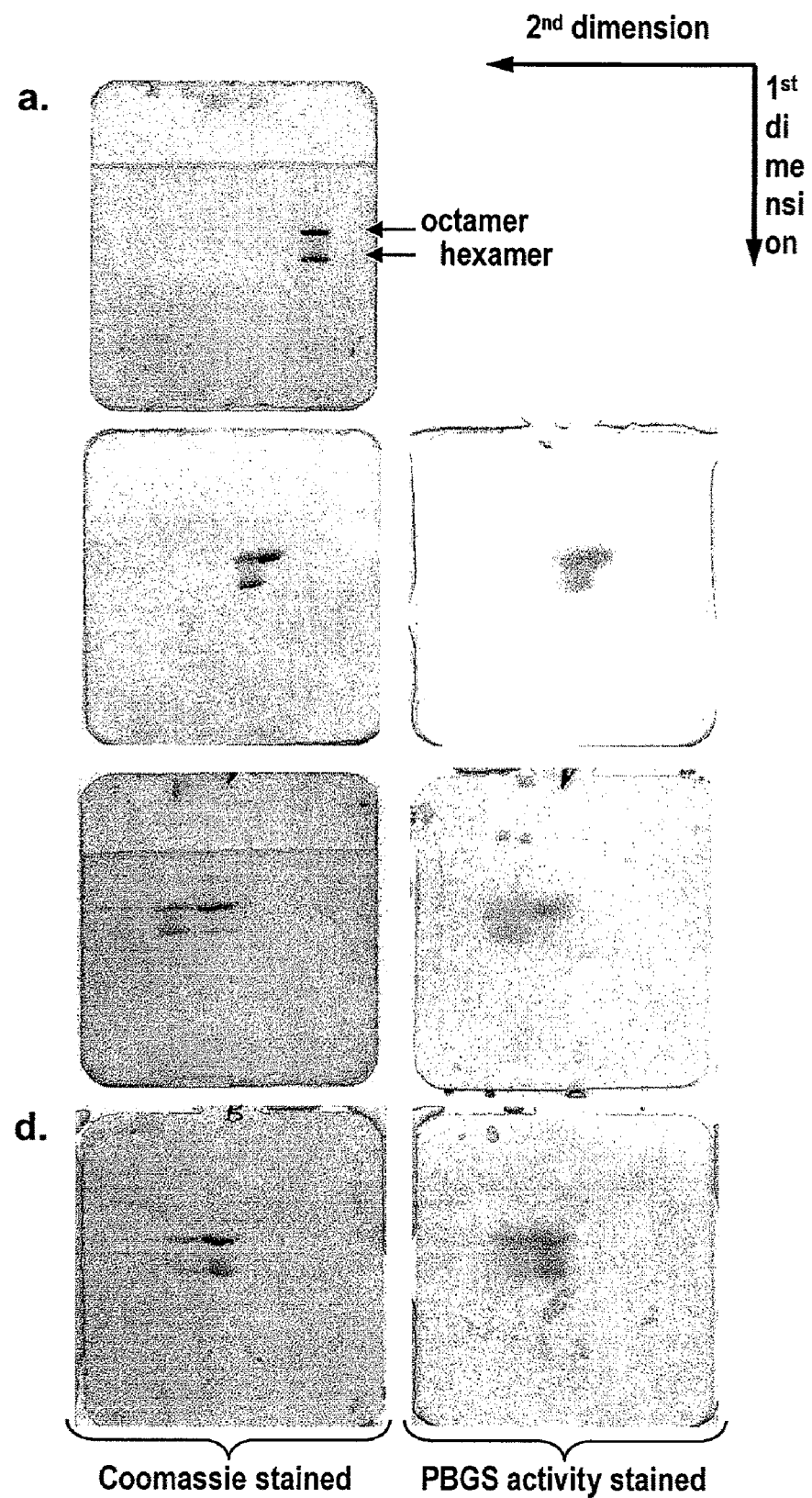
FIG. 40 illustrates two dimensional native PAGE that illustrates substrate mediated in-gel hexamer to octamer transition for pea PBGS—For all gels, a single 1 ml sample of 1 mg/ml pea PBGS was applied in the next to the right-most sample well of a 12.5% PhastGel.

The specificity of morphlock-1 for the pea PBGS hexamer was demonstrated using native PAGE that has been stained both for protein and for PBGS activity. Using two dimensional native PAGE, it was previously established that the substrate induced stabilization of the PBGS octameric assembly can occur within the native gel matrix [Jaffe, 1995]. The substrate-mediated in-gel transition of pea PBGS hexamer to octamer is shown in FIG. 40. Thus, even though pea PBGS separates into octamer and hexamer under native PAGE conditions, incubation of the resolved gel with substrate under assay conditions causes the transition of the inactive hexamer to the active octamer; consequently both bands stain for PBGS activity. FIG. 34 illustrates this phenomenon and how it is affected by morphlock-1. Pea PBGS resolves to octamer and hexamer on a native gel in the absence or presence of DMSO, and when activity stained, both bands show the complex formed between the product porphobilinogen and Ehrlich's reagent. However, under conditions where morphlock-1 stabilizes the hexamer, no activity is observed. The Coomassie and activity stained gels presented in FIG. 34a illustrate that morphlock-1 specifically binds to the hexameric assembly of pea PBGS, remains bound during the electrophoresis, and prevents the substrate mediated conversion of hexamer to octamer that allows unbound hexamer to stain for PBGS activity.

Morphlock-1 Inhibits the Substrate-Induced Stabilization of the PBGS Octamer

Substrate binding to a hexameric assembly of human PBGS has been shown to shift the equilibrium toward the active octamer because it stabilizes octamer-specific quaternary structure interactions [Tang, 2006; Tang, 2005]. Here we demonstrate the same phenomenon for pea PBGS and show that morphlock-1 competes with this process through stabilization of the hexamer (FIG. 34b). In the absence of morphlock-1, 5 mM ALA is sufficient to support nearly total conversion to the octamer. In the presence of 2 mM morphlock-1, this same concentration of ALA only converts ~50% of the hexamer to octamer.

Correlation of Inhibition Studies with Native Gel Shift Studies

The interconversion of pea PBGS hexamer and octamer is a dynamic equilibrium that responds to protein concentration, substrate concentration, magnesium concentration, inhibitor concentration, and ionic strength. Under the conditions illustrated in FIG. 32c, where the sample protein concentration is ~1 mg/ml (28 μM subunit), the gel shows ~90% octamer in the absence of morphlock-1 and it is easy to show that addition of morphlock-1 stabilizes the hexamer. However, 1 mg/ml is three orders of magnitude above that used for the activity assays shown in FIG. 4a where the apparent $IC_{50}$ is ~1 μM. A conundrum is that native PAGE at lower protein concentration (e.g. like those used for the activity assay) shows predominantly hexamer in the absence of additives. Consequently, when a dilute protein sample starts as predominantly hexamer in the gel matrix environment, it is not possible to illustrate the hexamer-stabilizing effect of morphlock-1 upon addition to the protein. To provide such a demonstration, we take advantage of the fact that both substrate and magnesium favor formation of the octameric assembly. As shown above (FIG. 34b), there is a competition between the hexamer-stabilizing effect of morphlock-1 and the octamer-stabilizing effects of substrate and/or magnesium. Hexamer stabilization by morphlock-1 is demonstrated at lower protein concentrations (50 μg/ml using silver stain detection or 5 μg/ml using Krypton IR detection) in the presence of either substrate or magnesium (FIG. 34c). At 50 μg/ml (1.4 μM subunit) and 1 mM ALA, native PAGE shows an apparent $IC_{50}$ of ~100 μM; at 5 μg/ml and 10 mM magnesium, the apparent $IC_{50}$ is ~1-3 μM. The gel run at 50 μg/ml is also shown activity stained and again the activity is only observed in the octameric assembly (FIG. 34c). The fact that no activity is associated with the hexamer in FIG. 34c, while activity is seen in the octamer, further supports the specific binding of morphlock-1 to the pea PBGS hexamer.

A preferred application of the inventive composition is for inhibiting or preventing development or growth of bacteria, archaea, and/or eucarya in a human or an animal host. Other applications of the composition of the invention include prevention or inhibition of biofilms on various surfaces including teeth, pipes, tubing, ships, or generally any surfaces immersed in water/air mixtures wherein bacteria causing damage can be found. Thus, for example, the compositions of the invention can be effective to prevent or inhibit growth of barnacles on a surface of a ship.

Depending on the targeted organism, a composition of the invention can be used to prevent or inhibit damage caused by certain species. All plants are in QSE (see FIG. 4), as well as many protists. Examples of bacteria in QSE are in the Table 2, so these organisms are primary targets for applying the composition of the invention. Using Table 2 as a guide, various applications of the composition of the invention can be envisioned such as, for example, a drug, a toothpaste, a soap, a disinfectant, an anti-biofilm composition and, with application to plants, a herbicide.

TABLE 2

Bacteria with PBGS in the SE quadrant

| Species name | Potential Damage |
| --- | --- |
| Yersinia enterocolitica | Food borne gastroenteritis |
| Yersinia pestis | Plague |
| Pseudomonas syringae | Plant pathogen (tomatoes) |
| Pseudomonas aeruginosa | Opportunistic human pathogen of compromised tissues. Notorious for antibiotic resistance |
| Actinobacillus actinomycetemcomitans | Periodontal disease |
| Pasturella multocida | Infective agent in animal bite wounds |
| Shewenella putrefasciens | Oil pipeline corrosion, fish spoilage |
| Methylococcus capsulatus | Uses methane as carbon source |
| Vibrio cholerae | Cholera - severe diarrhea |
| Xylella fastidiosa | Pierces disease in plants (e.g. grapes) |
| Caulobacter crescentus | Asymmetric cell division |
| Agrobacterium tumefaciens | Crown gall on rose and others like apple, pear, peach, cherry, etc. |
| Sinorhizobium meliloti | Nitrogen fixing bacteria for alfalfa |
| Brucella melitensis | Bacterial disease of domestic animals (sheep, goats). Malta fever in humans. |
| Rhodopseudomonas palustris | Purple non-sulfur phototropic bacterium. |
| Mesorhizobium loti | Biotech subject |
| Bradyrhizobium japonicum | Nitrogen fixation soybeans. |
| Brucella melitensis biovarsvis | Brucellosis - zoonotic disease |
| Magnetospirillum magnetotacticum | Forms magnetite |
| Rickettsia conorii | Mediterranean spotted fever |
| Rickettsia prowazekii | Epidemic typhus |
| Novosphingobium aromaticivorans | Food industry |
| Bordetella bromchseptica | Common in cats |
| Bordetella pertussis | Whooping cough |
| Nitrosomonas europaea | Auxotropic nitrifying bacteria |
| Burkholderia mallei | Glanders (horses); potential bioterrorism agent |
| Burkholderia pseudomallei | Melioidosis, Whitmore's disease, endemic in tropical climates |
| Burkholderia fungorum | "Group", human and plant pathogens and environmentally important bacteria |
| Neisseria meningitides | Bacterial meningitis |
| Neisseria gonorrhoeae | Gonorrhea |

TABLE 2-continued

Bacteria with PBGS in the SE quadrant

| Species name | Potential Damage |
| --- | --- |
| Ralstonia solanaccarum | Plant disease, "Southern wilt" |
| Ralstonia metallidurans | Heavy metal resistant |
| Chlamydia muridarum | Chlamydia - STD |
| Chlamydia trachomatis | Chlamydia - STD |
| Chlamydophila pneumoniae | 10% of pneumonia |
| Chlamydophila psittaci | Psittacosis (parrot fever) |
| Chlorobium vibrioforme | Green sulfur bacterium |
| Clorobium tepidum | Green sulfur bacterium |
| Rhodothermus marinus | Hermophillic halophillic bacterium |
| Cytophaga hutchinsonii | Digests crystalline cellulose |
| Shewanella oneidensis | Can turn soluble metals insoluble. Bioremediation |
| Vibrio vulnificus | Warm seawater infects open wounds |
| Vibrio parahaemolyticus | Warm seawater infects open wounds; diarrhea |
| Xanthomonas campestris | Plant pathogen |
| Xanthomonas axonopodis | Plant pathogen |
| Pirellula | Plant pathogen |
| Brown algae Fucus vesiculosus | Bladder wrack |

Advantageously, the composition of the present invention is effective to cure or prevent a disease caused by bacteria, archaea, and/or eucarya. The composition is effective to prevent formation of the multimeric PBGS (e.g., octameric PBGS or another active form having a lesser number of monomers) and thereby inhibit or prevent development or growth of bacteria, archaea, and/or eucarya. In certain embodiments, the multimeric PBGS contains an allosteric magnesium binding site. In one variant of this embodiment, the composition is effective to cure or prevent a disease caused by contacting bacteria, archaea, and/or eucarya. In yet another variant of this embodiment, the composition is at least one of a drug, a toothpaste, a soap, a disinfectant, an anti-biofilm composition, and a herbicide.

In certain embodiments, the composition does not contain the allosteric magnesium binding site and the catalytic zinc binding site. In one variant of this embodiment, the composition is effective to cure or prevent a disease caused by contacting bacteria, archaea, and/or eucarya. In yet another variant of this embodiment, the composition is at least one of a drug, a toothpaste, a soap, and a disinfectant.

Test Agents

Test agents that can be screened with methods of the present invention include polypeptides, β-turn mimetics, polysaccharides, phospholipids, hormones, prostaglandins, steroids, aromatic compounds, heterocyclic compounds, benzodiazepines, oligomeric N-substituted glycines, oligocarbamates, polypeptides, saccharides, fatty acids, steroids, purines, pyrimidines, derivatives, small molecules, siNA, siRNA, dsRNA, dsDNA, anti-senseDNA, nucleic acids, antibodies, polyclonal antibodies, monoclonal antibodies, structural analogs or combinations thereof. Some test agents are synthetic molecules, and others natural molecules.

Test agents are obtained from a wide variety of sources including libraries of synthetic or natural compounds. Combinatorial libraries can be produced for many types of compound that can be synthesized in a step-by-step fashion. Large combinatorial libraries of compounds can be constructed by the encoded synthetic libraries (ESL) method described in WO 95/12608, WO 93/06121, WO 94/08051, WO 95/35503 and WO 95/30642. Peptide libraries can also be generated by phage display methods (see, e.g., Devlin, WO 91/18980). Libraries of natural compounds in the form of bacterial, fungal, plant and animal extracts can be obtained from commercial sources or collected in the field. Known pharmacological agents can be subject to directed or random chemical modifications, such as acylation, alkylation, esterification, amidification to produce structural analogs.

Combinatorial libraries of peptides or other compounds can be fully randomized, with no sequence preferences or constants at any position. Alternatively, the library can be biased, i.e., some positions within the sequence are either held constant, or are selected from a limited number of possibilities. For example, in some cases, the nucleotides or amino acid residues are randomized within a defined class, for example, of hydrophobic amino acids, hydrophilic residues, sterically biased (either small or large) residues, towards the creation of cysteines, for cross-linking, prolines for SH-3 domains, serines, threonines, tyrosines or histidines for phosphorylation sites, or to purines.

The test agents can be natural occurring proteins or their fragments. Such test agents can be obtained from a natural source, e.g., a cell or tissue lysate. Libraries of polypeptide agents can also be prepared, e.g., from a cDNA library commercially available or generated with routine methods. The test agents can also be peptides, e.g., peptides of from about 5 to about 30 amino acids, with from about 5 to about 20 amino acids being preferred, and from about 7 to about 15 being particularly preferred. The peptides can be digests of naturally occurring proteins, random peptides, or "biased" random peptides. In some methods, the test agents are polypeptides or proteins.

The test agents can also be nucleic acids. Nucleic acid test agents can be naturally occurring nucleic acids, random nucleic acids, or "biased" random nucleic acids. For example, digests of prokaryotic or eukaryotic genomes can be similarly used as described above for proteins.

In some preferred methods, the test agents are small molecules (e.g., molecules with a molecular weight of not more than about 1,000). Preferably, high throughput assays are adapted and used to screen for such small molecules. In some methods, combinatorial libraries of small molecule test agents as described above can be readily employed to screen for small molecule modulators of morpheeins forms, including, for example, PBGS. A number of assays are available for such screening.

Libraries of test agents to be screened with the claimed methods can also be generated based on structural studies of morpheein proteins. Such structural studies allow the identification of test agents that are more likely to bind to morpheein proteins. The three-dimensional structure of morpheein proteins (e.g., its catalytic domain) can be studied in a number of ways, e.g., crystal structure and molecular modeling. Methods of studying protein structures using x-ray crystallography are well known in the literature. See Physical Bio-chemistry, (85-86). Computer modeling of a target protein (e.g., morpheein proteins) provides another means for designing test agents for screening modulators of the target protein. Methods of molecular modeling have been described in the literature, e.g., U.S. Pat. No. 5,612,894 entitled "System and method for molecular modeling utilizing a sensitivity factor", and U.S. Pat. No. 5,583,973 entitled "Molecular modeling method and system". In addition, protein structures can also be determined by neutron diffraction and nuclear magnetic resonance (NMR).

Modulators of the present invention also include antibodies that specifically bind to morpheein proteins. Such antibodies can be monoclonal or polyclonal. Such antibodies can be generated using methods well known in the art. For example, the production of non-human monoclonal antibodies, e.g., murine or rat, can be accomplished by, for example, immunizing the animal with morpheein proteins or its fragment. Such an immunogen can be obtained from a natural source, by peptides synthesis or by recombinant expression.

Humanized forms of mouse antibodies can be generated by linking the CDR regions of non-human antibodies to human constant regions by recombinant DNA techniques. e(90) and WO 90/07861. Human antibodies can be obtained using phage-display methods. See, e.g., Dower et al., WO 91/17271; McCafferty et al., WO 92/01047. In these methods, libraries of phage are produced in which members display different antibodies on their outer surfaces. Antibodies are usually displayed as Fv or Fab fragments. Phage displaying antibodies with a desired specificity are selected by affinity enrichment to morpheein proteins.

Human antibodies against morpheein proteins can also be produced from non-human transgenic mammals having transgenes encoding at least a segment of the human immunoglobulin locus and an inactivated endogenous immunoglobulin locus. See, e.g., Lonberg et al., WO93/12227; Kucherlapati, WO 91/10741. Human antibodies can be selected by competitive binding experiments, or otherwise, to have the same epitope specificity as a particular mouse antibody. Such antibodies are particularly likely to share the useful functional properties of the mouse antibodies. Human polyclonal antibodies can also be provided in the form of serum from humans immunized with an immunogenic agent. Optionally, such polyclonal antibodies can be concentrated by affinity purification using morpheein proteins.

Pharmaceutical Compositions and Administration

Administration of therapeutically effective amounts is by any of the routes normally used for introducing protein or encoding nucleic acids into ultimate contact with the tissue to be treated. The protein or encoding nucleic acids are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions that are available (see, e.g., Remington's Pharmaceutical Sciences, 17.sup.th ed. 1985)).

The protein or encoding nucleic acids, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intravenous, intramuscular, intradermal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. The disclosed compositions can be administered, for example, by intravenous infusion, orally, topically, intraperitoneally, intravesically or intrathecally. The formulations of compounds can be presented in unit-dose or multi-dose sealed containers, such as ampules and vials. Injection solutions and suspensions can be prepared from sterile powders, granules, and tablets of the kind previously described.

In certain cases, alteration of a genomic sequence in a pluripotent cell (e.g., a hematopoietic stem cell) is desired. Methods for mobilization, enrichment and culture of hematopoietic stem cells are known in the art. See for example, U.S. Pat. Nos. 5,061,620; 5,681,559; 6,335,195; 6,645,489 and 6,667,064.

Antibiotics, herbicides, and fungicides are often based on the inhibition of an essential pathway that is specific to the bacteria, plant, or fungus and that is not present in humans/animals. For example, 1) the penicillin class of antibiotics is directed against bacterial cell wall biosynthesis, and animal cells do not have cell walls, or 2) the herbicide glyphosate is directed against aromatic amino acid biosynthesis, and humans do not have this pathway, we must eat aromatic amino acids.

In certain embodiments, the composition comprises a pharmaceutically-acceptable medium in addition to the agent. The expression "pharmaceutically-acceptable medium" denotes a medium, such as, for example, a solvent, that is able to deliver the inhibitor, as well as any other active agents in the composition, to the target organism in a relatively safe and effective manner. The medium itself need not have any pharmaceutical activity.

As used herein, "pharmaceutically-acceptable medium" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the inhibitor of the present invention, its use in therapeutic compositions is contemplated. Supplementary or additional active ingredients also can be incorporated into the compositions.

Solutions of the active ingredients as free base or pharmacologically acceptable salts can be prepared in water suitably mixed with a surfactant, such as, for example, hydroxypropylcellulose. Dispersions also can be prepared in glycerol, liquid polyethylene glycols, mixtures thereof and in oils. Under ordinary conditions of storage and use, these preparations contain a preservative to prevent growth of all microorganisms.

The compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The composition of the present invention is advantageously administered in the form of injectable compositions either as liquid solutions or suspensions; solid forms suitable for solution in, or suspension in liquid prior to injection also may be prepared. These preparations also may be emulsified. A typical composition for such purposes comprises a 50 mg or up to about 100 mg of human serum albumin per milliliter of phosphate buffered saline. Other pharmaceutically acceptable carriers include aqueous solutions, non-toxic excipients, including salts, preservatives, buffers and the like. Examples of non-aqueous solvents are propylene glycol, polyethylene glycol, vegetable oil and injectable organic esters, such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, anti-oxidants, chelating agents and inert gases. The pH and exact concentration of the various components in the pharmaceutical are adjusted according to well know parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders. When the route is topical, the form may be a cream, ointment, salve or spray.

An effective amount of the therapeutic agent is determined based on the intended goal. The term "unit dose" refers to a physically discrete unit suitable for use in a subject, each unit containing a predetermined quantity of the therapeutic composition calculated to produce the desired response in association with its administration, i.e., the appropriate route and treatment regimen. The quantity to be administered, both according to number of treatments and unit dose, depends on the subject to be treated, the state of the subject and the protection desired. Precise amounts of the therapeutic composition also depend on the judgment of the practitioner and are peculiar to each individual.

Another application of the inventive composition is a herbicide, wherein the composition additionally comprises a herbicidally-effective medium. The expression "herbicidally-effective medium" denotes a medium, such as a solvent, that is able to deliver the inhibitor, as well as any other active agents in the composition, to the target organism. The medium itself need not have any herbicidal activity.

Guidance for applying antibacterial compositions on crops is provided as follows: since all photosynthetic eukaryots fall in the QSE quadrant of FIG. 4, they are themselves targets for the inhibitors proposed in this invention. However, the armpit inhibitor binding site shown in FIG. 13 has significant phylogenetic variation between plants and bacteria. Hence, agents that would act as an antibacterial spray on crops would be those capable of binding to this site in the bacterial PBGS, but not in the plant PBGS.

Compositions of the present invention include both dilute compositions, which are ready for immediate use, and concentrated compositions, which require to be diluted before use, usually with water.

The solid compositions may be in the form of granules, or dusting powders wherein the active ingredient is mixed with a finely divided solid diluent, e.g. kaolin, bentonite, kieselguhr, dolomite, calcium carbonate, talc, powdered magnesia, Fuller's earth or gypsum or a combination thereof. They may also be in the form of dispersible powders or grains, comprising a wetting agent to facilitate the dispersion of the powder or grains in liquid. Solid compositions in the form of a powder may be applied as dusts.

Liquid compositions may comprise a solution, suspension, or dispersion of the active ingredients in water optionally containing a surface-active agent, or may comprise a solution or dispersion of the active ingredient in a water-immiscible organic solvent, which is dispersed as droplets in water. The herbicidal composition is suitable either for tank mixing to produce a dilute composition ready for immediate use or for the formation of a concentrate.

The solutions or dispersions may be prepared by dissolving the active ingredients in water or an organic solvent optionally containing wetting or dispersing agent(s) and then, when organic solvents are used, adding the mixture so obtained to water optionally containing wetting or dispersing agent(s). Suitable organic solvents include, for example, ethylene dichloride, isopropyl alcohol, propylene glycol, diacetone alcohol, toluene, kerosene, methylnaphthalene, xylene or trichloroethylene, or a combination thereof.

Other additives and adjuvants may also be present in compositions of the present invention. Examples include antifreeze agents such as ethylene glycol and propylene glycol; dyes; dispersants; theological agents; anti-foam agents such as silicone based agents; and humectants such as ethylene glycol.

Development of herbicide on this basis allows developing herbicide resistant crops by making these resistant crops transgenic (i.e., containing genetic material artificially transferred from another species) for a PBGS that is the top half of the four quadrants of FIG. 4, e.g., human PBGS.

Herbicide Resistant Plant

Further provided is a herbicide resistant plant adapted to be transgenic for a multimeric porphobilinogen synthase that substantially exist in a multimeric form of a hugging dimer. In certain embodiments, the multimeric porphobilinogen synthase is derived from a human. In certain embodiments, the multimeric porphobilinogen synthase contains no allosteric magnesium binding site. The following provides guidance to making the herbicide resistant plant adapted to be transgenic for a multimeric porphobilinogen synthase.

The expression in a plant of a gene that exists in double-stranded DNA form involves transcription of messenger RNA (mRNA) from one strand of the DNA by RNA polymerase enzyme, and the subsequent processing of the mRNA primary transcript inside the nucleus. This processing involves a 3' non-translated region, which adds polyadenylate nucleotides to the 3' end of the RNA. Transcription of DNA into mRNA is regulated by a region of DNA usually referred to as the promoter. The promoter region contains a sequence of bases that signals RNA polymerase to associate with the DNA and to initiate the transcription of mRNA using one of the DNA strands as a template to make a corresponding complimentary strand of mRNA. This mRNA is then used as a template for the production of the protein encoded therein by the cells protein biosynthetic machinery.

In the instant invention, the promoter chosen will have the desired tissue and developmental specificity. Therefore, promoter function should be optimized by selecting a promoter with the desired tissue expression capabilities and approximate promoter strength and selecting a transformant that produces the desired PBGS activity. This selection approach from the pool of transformants is routinely employed in expression of heterologous structural genes in plants because there is variation between transformants containing the same heterologous gene due to the site of gene insertion within the plant genome (commonly referred to as "positional effect"). In addition to promoters that are known to cause transcription (constitutively or tissue-specific) of DNA in plant cells, other promoters may be identified for use in the current invention by screening a plant cDNA library for genes that are selectively or preferably expressed during the time of interest and then isolating the promoter regions by methods known in the art.

In a preferred embodiment of the invention, the PBGS transgene is to be expressed in the chloroplast in response to light. More specifically, the PBGS transgene is transcribed into mRNA in the nucleus and the mRNA is translated into a precursor polypeptide (Chloroplast Transport Peptide (CTP)/PBGS) in the cytoplasm. The precursor polypeptide is then transported (imported) into the chloroplast. Several chloroplast light inducible promoters that are active in plant cells have been described in the literature. Examples of such promoters include the light-inducible promoter from the small subunit of ribulose-1,5-bisphosphate carboxylase (ss-RUBISCO), a very abundant plant polypeptide, the chlorophyll a/b binding protein gene promoters and the phytochrome promoter which has been utilized recently in a light-switchable promoter system. Some of these promoters have been used to create various types of DNA constructs that have been expressed in plants; see, e.g., PCT publication WO 84/02913.

Other promoters that are known to or are found to cause transcription of DNA in plant cells in response to light can be used in the present invention. Such promoters may be obtained from a variety of sources such as plants and plant viruses and include, but are not limited to, the enhanced CaMV35S promoter and promoters isolated from plant genes such as small subunit of ribulose-1,5-biphosphate carboxylase (ssRUBISCO) genes. As described below, it is preferred that the particular promoter selected should be capable of causing sufficient expression to result in the production of an effective amount of PBGS enzyme to produce sufficient tetrapyrroles to sustain growth. In one embodiment, said promoter is leaky in order to provide tetrapyrroles necessary for the non-photosynthetic functions of the plant.

Nucleic Acids

One aspect of the present invention is the polynucleotide sequences set forth in, for example, SEQ ID NOs: 1-2, 4, the complement of these sequences, the RNA versions of both DNA strands and the information otherwise contained within the linear sequence of these polynucleotide sequences, and fragments thereof. The polynucleotide encoding PBGS is exemplified by SEQ ID NOs: 1-2, 4. In the case of nucleic acid segments, sequences for use with the present invention are those that have greater than about 50 to 60% homology with any portion of the polynucleotide sequences described herein, sequences that have between about 61% and about 70%; sequences that have between about 71 and about 80%; or between about 81% and about 90%; or between 91% and about 99%; or which contain nucleotides that are identical, functionality equivalent, or functionally irrelevant, with respect to the nucleotides present in SEQ ID NOs: 1-2, 4 are considered to be essentially similar. Also encompassed within the present invention are nucleic acids that encode polypeptides that are at least 40% identical or similar to the amino acid sequences shown in SEQ ID NOs: 3, 5-135.

The invention also encompasses other nucleic acids or nucleic acid like molecules that are sufficient in any regard to mimic, substitute for, or interfere with the PBGS polynucleotide sequences, as exemplified by SEQ ID NOs: 1-2, 4, or fragments thereof. It will also be understood that the nucleic acid and amino acid sequences may include additional residues, such as additional 5'- or 3'-sequences, and yet still be essentially as set forth in one of the sequences disclosed herein, so long as the sequence meets the criteria set forth, including the maintenance of functionality, or for the purpose of engineering altered functionality with respect to SEQ ID NOs: 1-2, 4.

Included within the invention are DNA or RNA segments including oligonucleotides, polynucleotides and fragments thereof, including DNA or RNA or nucleic acid-like sequences of genomic or synthetic origin, single or double stranded. The invention includes nucleic acid molecules, or nucleic acid-like molecules that are able to hybridize to the sequences in SEQ ID NOs: 1-2,4, under stringent or under permissive hybridization conditions, or to the complement of said sequences.

The invention also includes oligonucleotide, or oligonucleotide-like sequences such as phosphorthioate, or peptide nucleic acid sequences, which possess sufficient similarity with the sequences disclosed herein such that they are able to stably hybridize to the disclosed sequences, or their complements. Such sequences may be intended as antisense regulators of gene expression, or for the selective amplification or extension of adjoining sequences, for instance by PCR using a given annealing temperature, as would be determined by someone skilled in the art. In addition to the sequences disclosed here, related sequences in other organisms, or homologs, will be readily identified by hybridization using the present sequences. Similar techniques will also apply to the identification of mutant alleles, polymorphisms, deletions, insertions, and so forth, in genomic and cDNA sequences. Whole or partial sequences referred to above may also be identified and isolated using techniques that involve annealing of short oligonucleotides to complementary sequences, such as those as might be present in the genomic DNA of a particular organism, or in genomic or cDNA, including expression cDNA, libraries. Thus, PCR is used to obtain DNA sequences homologous to, and which lie between, two primers, usually between 15 to 30 nucleotides which have annealing temperatures typically between 60-80 degrees Celsius may be substantially purified.

It will be understood that this invention is not limited to the particular nucleic acid sequences presented herein. Recombinant vectors, including for example plasmids, phage, viruses, and other sequences, and isolated DNA or RNA segments may therefore variously include the PBGS gene sequences or their complements, and coding regions, as well as those that may bear selected alterations or modifications that nevertheless include PBGS segments or may encode biologically or experimentally relevant amino acid sequences. Such sequences may be created by the application of recombinant DNA technology, where changes are engineered based on the consideration of the nucleotides or amino acids being exchanged, deleted, inserted, fused, or otherwise modified.

Proteins and Polypeptides

One aspect of the invention is, for example, the protein, polypeptide, oligopeptide, or amino acid sequences or fragments thereof, of PBGS as set forth in SEQ ID NOs: 3, 5-135. The PBGS polypeptide is exemplified by SEQ ID NOs: 3, 5-135. Sequences that have greater than about 40-50% homology with any portion of the amino acid sequences described herein, sequences that have between about 51% and about 60%; sequences that have between about 61% and about 70% sequences that have between about 70 and about 80%; or between about 81% and about 90%; or between 91% and about 99%; or those that contain amino acids that are identical, functionally equivalent, or functionally irrelevant, for instance those specified by conservative, evolutionarily conserved, and degenerate substitutions, with respect to the amino acid sequences presented in SEQ ID NOs: 3, 5-135 are included. The invention thus applies to PBGS polypeptide sequences, or fragments thereof, and nucleic acids which encode such polypeptides, such as those of other species. Reference is particularly, but not exclusively, made to the conserved regions of PBGS, in contrast to similarity throughout the entire length. The invention thus encompasses amino acid sequences, or amino acid-like molecules, that are sufficient in any regard to mimic, substitute for, or interfere with the PBGS amino acid sequences, or fragments thereof.

The invention encompasses PBGS amino acid sequences that have been altered in any form, either through the use of recombinant engineering, or through post-translational or chemical modifications, including those that may be produced by natural, biological, artificial, or chemical methods. Naturally, it will be understood that this invention is not limited to the particular amino acid sequences presented herein. Altered amino acid sequences include those which have been created by the application of recombinant technology such that specific residues, regions, or domains have been altered, and which may be functionally identical, or which may possess unique biological or experimental properties with regards to function or interactions with natural and artificial ligands.

For instance such modifications may confer longer or shorter half-life, reduced or increased sensitivity to ligands that modify function, ability to detect or purify polypeptides, solubility, and so forth. Alternatively, such sequences may be shorter oligopeptides that possess an antigenic determinant, or property that interferes, or competes, with the function of a larger polypeptide, and those that affect interactions between PBGS other proteins, other nucleic acid regions, and other proteins. Such sequences may be created by the application of the nucleotides or amino acids being exchanged, deleted, inserted, fused, or otherwise modified. Likewise, the current invention within, the sequences that may be naturally present as extensions of, or insertions within, the sequences disclosed herein, including alternative or longer N- and C-terminal sequences, or alternatively spliced protein isoforms.

Production and purification of polypeptides may be achieved in any of a variety of expression systems known to those skilled in the art, including recombinant DNA techniques, genetic recombination, and chemical synthesis. For instance, expression in prokaryotic cells may be achieved by placing protein coding nucleic sequences downstream of a promoter, such as T7, T3, lacI, lacZ, trp, or other cellular, viral, or artificially modified promoters including those that may be inducible by IPTG, tetracycline, maltose, and so forth. Such promoters are often provided for in commercially available recombinant DNA vectors such as pRSET ABC, pBluescript, pKK223-3, and others, or are easily constructed to achieve such a purpose, and often include the presence of multiple cloning sites (MCS) to facilitate typically contain efficient ribosome binding sites, and in some cases transcription termination signals.

Peptides, oligopeptides and polypeptides may also be produced by chemical synthesis, for instance solid phase techniques, either manually or under automated control such as Applied Biosystems 431 peptide synthesizer (Perkin Elmer). After synthesis, such molecules are often further purified by preparative high performance liquid chromatography. Thus, the invention provides methods for the production of epitopes for antibody production, or the production of small molecules that enhance or interfere with a specific function or interaction of the PBGS polypeptides.

Methods to produce and purify said polypeptides in eukaryotic systems are widely available and understood by those proficient in the art. Cells for such production are known to include yeast and other fungi, Drosophila and Sf9 cells, cells of other higher eukaryotic organisms such as HeLa, COS, CHO and others, as well as plant cells. Similarly, expression could be achieved in prokaryotic or eukaryotic extracts that are able to translate RNAs into proteins, such as rabbit reticulocyte lysates.

Vectors

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC®. 2.0 from INVITROGEN® and BACPACK® BACULOVIRUS EXPRESSION SYSTEM FROM CLONTECH.

Vectors may be of bacterial origin, which may comprise a promoter of a bacteriophage such as phage or T7 which is capable of functioning in the bacteria. In one of the most widely used expression systems, the nucleic acid encoding the PBGS may be transcribed from the vector by T7 RNA polymerase (Studier et al, Methods in Enzymol. 185: 60-89, 1990). In the *E. coli* BL21 (DE3) host strain, used in conjunction with pET vectors, the T7 RNA polymerase is produced from the 1-lysogen DE3 in the host bacterium, and its expression is under the control of the IPTG inducible lac UV5 promoter. This system has been employed successfully for over-production of many proteins. Alternatively, the polymerase gene may be introduced on a lambda phage by infection with an int-phage such as the CE6 phage, which is commercially available (Novagen, Madison, USA). Other vectors include vectors containing the lambda PL promoter such as PLEX® (Invitrogen, NL), vectors containing the trc promoters such as PTrcHisXpress® (Invitrogen), or pTrc99 (Pharmacia Biotech, SE), or vectors containing the tac promoter such as pKK223-3 (Pharmacia Biotech), or PMAL (New England Biolabs, MA, USA).

One of skill in the art will understand that cloning also requires the step of transforming a host cell with a recombinant nucleic acid molecule. A host cell is "transformed" by a nucleic acid when the nucleic acid is translocated into the cell from the extracellular environment. Any method of transferring a nucleic acid into the cell may be used; the term, unless otherwise indicated herein, does not imply any particular method of delivering a nucleic acid into a cell, nor that any particular cell type is the subject of transfer. For example, bacterial host cells, such as *E. coli* HB101, can be transformed by electroporation using any commercially-available electroporation apparatus known in the art, such as a GenePulser apparatus (Bio-Rad, Hercules, Calif.). In one embodiment, mammalian cells, such as BHK-21 cells or Vero cells (ATCC CCL-81), are transformed with a recombinant plasmid containing a cloned cDNA by the method of "transfection." The term "transfection" refers to the transfer of genetic material into a eukaryotic cell, such as a mammalian cell, from the external environment of the cell.

One of skill in the art will appreciate the variety of methods of transfection that are available in the art. Such methods include the nucleic acid/CaPO4 co-precipitation method, the diethylaminoethyl (DEAE)-dextran method, the polybrene method, the cationic liposome method ("lipofection"), the electroporation method, the microinjection method, and the microparticle bombardment method. A description of transfection methods can be found in M. A. Aitken et al., Molecular Biomethods Handbook, Chapter 20, p. 235-250.

According to another embodiment of the instant invention, in vitro transcription is carried out on a recombinant plasmid carrying a cloned cDNA of the invention, under the control of an expressible promoter (i.e., a promoter which is effectively enabled or activated in vitro in the presence of corresponding transcription factors and RNA polymerase). The transcription process generates a fully-infectious mRNA transcript that can be used to transfect (i.e., infect) a cell host, such as BHK-21 (hamster kidney cells) or Vero cells. In one embodiment, the cDNA is operably linked with the bacteriophage transcriptional promoter, T7; to enable the in vitro transcription of the cDNA using bacteriophage T7 DNA-dependent RNA polymerase. One of ordinary skill in the art will appreciate that any suitable promoter, such as, for example, SP6, T3, any bacterial, viral, phage, or eukaryotic promoter, for controlling the transcription of, for example, the PBGS gene, or fragment thereof, and for controlling the expression of a nucleotide sequence encoding a reporter is contemplated by the present invention. It will be appreciated that the promoter is typically selected from promoters which are functional in mammalian cells susceptible to infection by the PBGS gene, or fragment thereof, encoding sequences of the invention, although prokaryotic or phage promoters and promoters functional in other eukaryotic cells may be used. The promoter is typically derived from promoter sequences of viral or eukaryotic genes. For example, it may be a promoter derived from the genome of a cell in which expression or transcription of, for example, the PBGS gene, or fragment thereof, encoding sequence or construct is to occur.

With respect to eukaryotic promoters, they may be promoters that function in a ubiquitous manner (such as promoters of α-actin, β-actin, tubulin) or, alternatively, a tissue-specific manner (such as promoters of the genes for pyruvate kinase). Tissue-specific or cell-specific promoters specific for lymphocytes, dendritic cells, skin, brain cells and epithelial cells, for example the CD2, CD11c, keratin 14, Wnt-1 and Rhodopsin promoters, respectively. Preferably the epithelial cell promoter SPC is used. They may also be promoters that respond to specific stimuli, for example promoters that bind steroid hormone receptors. Viral promoters may also be used, for example the Moloney murine leukaemia virus long terminal repeat (MMLV LTR) promoter, the rous sarcoma virus (RSV) LTR promoter, the human cytomegalovirus (CMV) IE promoter, or SV40 promoter.

It may also be advantageous for the promoters to be inducible so that the levels of expression of, for example, the PBGS gene, or fragment thereof encoding sequence can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above. It will be appreciated that the sources of promoter sequences, which typically can be retrieved using recombinant techniques from different cloning vectors and plasmids, etc., can be obtained from commercial sources, such as, NEW ENGLAND BIOLABS, INC. (MA), PROMEGA CORPORATION (WI), or BD BIOSCIENCES (CA), or from the laboratories of academic research groups upon request.

The invention also relates to cells which contain such recombinant constructs, where the host cell refers to mammalian, plant, yeast, insect, or other eukaryotic cells, or to prokaryotic, or archae, and vectors that are designed for a given host. Promoter-vector combinations could be chosen by a person skilled in these arts. In some cases, the desired outcome may not be protein, but RNA, and recombinant vectors would include those with inserts present in either forward or reverse orientations.

Many of the vectors and hosts have specific features that facilitate expression or subsequent purification. For instance DNA sequences to be expressed as proteins often appear as fusion with unrelated sequences that encode polyhistidine tags, or HA, FLAG, myc and other epitope tags for immunochemical purification and detection, or phosphorylation sites, or protease recognition sites, or additional protein domains such as glutathione S-transferase (GST), maltose binding protein (MBP), and so forth which facilitate purification. Vectors may also be designed which contain elements for polyadenylation, splicing and termination, such that incorporation of naturally occurring genomic DNA sequences that contain introns and exons can be produced and processed, or such that unrelated introns and other regulatory signals require RNA processing prior to production of mature, translatable RNAs. Proteins produced in the systems described above could be subject to a variety of post-translational modifications, such as glycosylation, phosphorylation, nonspecific or specific proteolysis or processing.

Purification of PBGS, or variants produced as described above can be achieved by any of several widely available methods. Cells may be subject to freeze-thaw cycles or sonication to achieve disruption, or may be fractionated into subcellular components prior to further purification. Purification may be achieved by one or more techniques such as precipitation with salts or organic solvents, ion exchange, hydrophobic interaction, HPLC and FPLC chromatograpic techniques. Affinity chromatographic techniques could include the use of polyclonal or monoclonal antibodies raised against the expressed polypeptide, or antibodies raised against or available for an epitopic tag such as HA or FLAG. Similarly, purification can be aided by affinity chromatography using fusions to the desired proteins such as GSH-affinity resin, maltose affinity resin, carbohydrate (lectin) affinity resin or, in a one embodiment, Ni-affinity resin, and so forth. In some instances purification is achieved in the presence of denaturing agents such as urea or guanidine, and subsequent dialysis techniques may be required to restore functionality, if desired.

Any method of in vitro transcription known to one of ordinary skill in the art is contemplated by the instant invention. It will be understood that the method of in vitro transcription of a DNA sequence relies on the operable linkage to an appropriate promoter and that the cognate RNA polymerase is used to direct transcription of the DNA starting at the promoter sequence. It will be further appreciated that the RNA polymerase and promoter can be of bacterial, eukaryotic, or viral (including bacteriophage) origin. Bacteriophage-RNA polymerases are very robust, and the availability of purified recombinant proteins facilitates the generation of large quantities of RNA from cloned cDNA sequences. In contrast, eukaryotic in vitro transcription systems yield relatively small quantities of RNA. Bacteriophage-RNA polymerases, such as from bacteriophages SP6, T7, and T3, are especially suitable for the generation of RNA from DNA sequences cloned downstream of their specific promoters because, first, their promoters are small and easily incorporated into plasmid vectors and second, the polymerases are quite specific for their cognate promoters, which results in very little incorrect transcriptional initiation from DNA templates. Any suitable promoter, however, is contemplated by the instant invention, including, for example, bacterial, phage, viral, and eukaryotic promoters. Strong termination sequences are not available for these polymerases so that DNA templates can be linearized with a restriction enzyme 3' to the desired end of the RNA transcript and the polymerase is forced to stop at this point-a process referred to as "run-off" transcription. A full description of in vitro transcription can be found in M. A. Aitken et al., Molecular Biomethods Handbook, Chapter 26, p. 327-334 and Sambrook, J. and D. W. Russell, Molecular Cloning: A Laboratory Manual, Third Edition (2001).

Morpheeins May be Isolated Using Tagged Protein Purification Strategies

Prior to the introduction of purification tags, the standard approach for purification of an enzyme from a cellular lysate typically involved a multi-stage fractionation scheme that eliminates other proteins from the sample while retaining the protein of interest [17]. This approach is still in use and a reasonable hypothetical purification scheme is as follows: a centrifugation step is used to eliminate insoluble components from a tissue homogenate or cell lysate, a salt cut is used to fractionate proteins with different solubility properties, and a series of column chromatography steps are used to separate the proteins into discreet fractions based on their surface charge, hydrophobicity, or size. Examples of isolation schemes include use an ammonium sulfate fractionation, a hydrophobic column, an anion exchange column, and a final size exclusion column into a buffer where the protein is known to be stable (e.g. containing required metal ions).

The invention provides for the isolation of morpheein proteins of the invention using purification tags, non-limiting examples of which are GST-tag and His-tag. In this approach, the DNA sequence coding for the protein of interest is modified so that the resulting protein is produced with a "tag" of amino acids attached. Depending on the system used, the tag can be a small number of residues, or larger than the protein of interest itself. These tagged proteins are then purified using a resin that specifically binds the tag, which can be either cleaved after purification (in the case of large tags) or left in place with the assumption that a few extra residues at the N or C terminus will not impact the function of the protein of interest. In certain embodiments of the invention provides for the removal of tags post-purification.

Host Cells

As used herein, the terms "cell," "cell line," and "cell culture" may be used interchangeably. All of these term also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5a, JM109, and KC8, as well as a number of commercially available bacterial hosts such as SURE®. Competent Cells and SOLOPACK® Gold Cells (STRATAGENE®, La Jolla). Alternatively, bacterial cells such as E. coli LE392 could be used as host cells for phage viruses.

Examples of eukaryotic host cells for replication and/or expression of a vector include HeLa, NIH3T3, Jurkat, 293, Cos, CHO, Saos, and PC12, etc. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Plastid-Directed Expression of PBGS Activity

In a preferred embodiment of the invention, the PBGS gene is fused to a CTP, in order to target the PBGS protein to the plastid. As used hereinafter, chloroplast and plastid are intended to include the various forms of plastids including amyloplasts. Many plastid-localized proteins are expressed from nuclear genes as precursors and are targeted to the plastid by a CTP, which is removed during the import steps. Examples of such chloroplast proteins include the small subunit of ribulose-1,5-biphosphate carboxylase (ssRUBISCO, SSU), 5-enolpyruvateshikimate-3-phosphate synthase (EPSPS), ferredoxin, ferredoxin oxidoreductase, the light-harvesting-complex protein I and protein II, and thioredoxin F. The glyphosate-tolerant EPSP synthase plant gene also encodes a polypeptide which contains a CTP, which enables the EPSP synthase polypeptide to be transported into a chloroplast inside the plant cell [48]. It has been demonstrated that non-plastid proteins may be targeted to the chloroplast by use of protein fusions with a CTP and that a CTP sequence is sufficient to target a protein to the plastid. Those skilled in the art will also recognize that various other chimeric constructs can be made that utilize the functionality of a particular plastid transit peptide to import the PBGS enzyme into the plant cell plastid. The PBGS gene could also be targeted to the plastid by transformation of the gene into the chloroplast genome [49]. Generally chloroplast uptake signals such as the CTP are rich in Ser, Thr and small hydrophobic amino acid residues.

The RNA produced by a DNA construct of the present invention may also contain a 5' non-translated leader sequence. This sequence can be derived from the promoter selected to express the gene and can be specifically modified so as to increase translation of the mRNA. The 5' non-translated regions can also be obtained from viral RNAs, from suitable eukaryotic genes, or from a synthetic gene sequence. The present invention is not limited to constructs wherein the non-translated region is derived from the 5' non-translated sequence that accompanies the promoter sequence. Rather, the non-translated leader sequence can be derived from an unrelated promoter or coding sequence.

In monocots, an intron is preferably included in the gene construct to facilitate or enhance expression of the coding sequence. Examples of suitable introns include the HSP70 intron and the rice actin intron, both of which are known in the art. Another suitable intron is the castor bean catalase intron [50].

The 3' non-translated region of the chimeric plant gene contains a polyadenylation signal that functions in plants to cause the addition of polyadenylate nucleotides to the 3' end of the RNA. Examples of suitable 3' regions are (1) the 3' transcribed, non-translated regions containing the polyadenylation signal of *Agrobacterium* tumor-inducing (Ti) plasmid genes, such as the nopaline synthase (NOS) gene, and (2) plant genes like the soybean storage protein genes and the small subunit of the ribulose-1,5-bisphosphate carboxylase (ssRUBISCO) gene.

In developing the nucleic acid constructs of this invention, the various components of the construct or fragments thereof will normally be inserted into a convenient cloning vector, e.g., a plasmid that is capable of replication in a bacterial host, e.g., *E. coli*. Numerous vectors exist that have been described in the literature, many of which are commercially available. After each cloning, the cloning vector with the desired insert may be isolated and subjected to further manipulation, such as restriction digestion, insertion of new fragments or nucleotides, ligation, deletion, mutation, resection, etc. so as to tailor the components of the desired sequence. Once the construct has been completed, it may then be transferred to an appropriate vector for further manipulation in accordance with the manner of transformation of the host cell.

A recombinant DNA molecule of the invention typically includes a selectable marker so that transformed cells can be easily identified and selected from non-transformed cells. Examples of such include, but are not limited to, a neomycin phosphotransferase (nptII) gene [51], which confers kanamycin resistance. Cells expressing the nptII gene can be selected using an appropriate antibiotic such as kanamycin or G418. Other commonly used selectable markers include the bar gene, which confers bialaphos resistance; a mutant EPSP synthase gene [52], which confers glyphosate resistance; a nitrilase gene, which confers resistance to bromoxynil [53]; a mutant acetolactate synthase gene (ALS), which confers imidazolinone or sulphonylurea resistance [54]; and a methotrexate resistant DHFR gene [55].

Plants that can be made to express the PBGS transgene include, but are not limited to, acacia, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, cauliflower, celery, cherry, cilantro, citrus, clementines, coffee, corn, cotton, cucumber, Douglas fir, eggplant, escarole, eucalyptus, fennel, figs, gourd, grape, grapefruit, honey dew, jicama, kiwifruit, lettuce, leeks, lemon, lime, Loblolly pine, mango, melon, mushroom, nut, oat, oil seed rape, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, esunflower, sweet potato, sweetgum, tangerine, tea, tobacco, tomato, triticale, turf, a vine, watermelon, wheat, yams, and zucchini.

A PBGS gene can be inserted into the genome of a plant by any suitable method. Suitable plant transformation vectors include those derived from a Ti plasmid of *Agrobacterium tumefaciens*, as well as those disclosed, e.g., by [56-58] and EPO publication 120,516. In addition to plant transformation vectors derived from the Ti or root-inducing (Ri) plasmids of *Agrobacterium*, alternative methods can be used to insert the DNA constructs of this invention into plant cells. Such methods may involve, for example, the use of liposomes, electroporation, chemicals that increase free DNA uptake, free DNA delivery via microprojectile bombardment, and transformation using viruses or pollen. DNA may also be inserted into the chloroplast genome [49].

A plasmid expression vector suitable for the introduction of a PBGS gene in monocots using microprojectile bombardment is composed of the following: a CTP; a light inducible promoter; the PBGS gene; an intron that provides a splice site to facilitate expression of the gene, such as the Hsp70 intron [59]; and a 3' polyadenylation sequence such as the nopaline synthase 3' sequence (NOS 3'; [60]). This expression cassette may be assembled on high copy replicons suitable for the production of large quantities of DNA to be injected into the plant.

A particularly useful *Agrobacterium*-based plant transformation vector for use in transformation of dicotyledonous plants is plasmid vector pMON530 [61]. Plasmid pMON530 is a derivative of pMON505 prepared by transferring the 2.3 kb StuI-HindIII fragment of pMON316 [61] into pMON526. Plasmid pMON526 is a simple derivative of pMON505 in which the SmaI site is removed by digestion with XmaI, treatment with Klenow polymerase and ligation. Plasmid pMON530 retains all the properties of pMON505 and the CaMV35S-NOS expression cassette and now contains a unique cleavage site for SmaI between the promoter and polyadenylation signal.

Binary vector pMON505 is a derivative of pMON200 [61] in which the Ti plasmid homology region, LIH, has been replaced with a 3.8 kb HindIII to SmaI segment of the mini RK2 plasmid, pTJS75 [62]. This segment contains the RK2 origin of replication, oriV, and the origin of transfer, oriT, for conjugation into *Agrobacterium* using the tri-parental mating procedure [63]. Plasmid pMON505 retains all the important features of pMON200 including the synthetic multi-linker for insertion of desired DNA fragments, the chimeric NOS/NP-TII'/NOS gene for kanamycin resistance in plant cells, the spectinomycin/streptomycin resistance determinant for selection in *E. coli* and *A. tumefaciens*, an intact nopaline synthase gene for facile scoring of transformants and inheritance in progeny, and a pBR322 origin of replication for ease in making large amounts of the vector in *E. coli*. Plasmid pMON505 contains a single T-DNA border derived from the right end of the pTiT37 nopaline-type T-DNA. Southern blot analyses have shown that plasmid pMON505 and any DNA that it carries are integrated into the plant genome, that is, the entire plasmid is the T-DNA that is inserted into the plant genome. One end of the integrated DNA is located between the right border sequence and the nopaline synthase gene and the other end is between the border sequence and the pBR322 sequences.

Another particularly useful Ti plasmid cassette vector is pMON17227. This vector is described in PCT Publication WO 92/04449 and contains a gene encoding an enzyme conferring glyphosate resistance (denominated CP4), which is an excellent selection marker gene for many plants, including potato and tomato. The gene is fused to the *Arabidopsis* EPSPS chloroplast transit peptide (CTP2) and expressed from the FMV promoter as described therein.

When adequate numbers of cells (or protoplasts) containing the PBGS gene are obtained, the cells (or protoplasts) are regenerated into whole plants. Choice of methodology for the regeneration step is not critical, with suitable protocols being available for hosts from Leguminosae (alfalfa, soybean, clover, etc.), Umbelliferae (carrot, celery, parsnip), Cruciferae (cabbage, radish, canola/rapeseed, etc.), Cucurbitaceae (melons and cucumber), Gramineae (wheat, barley, rice, maize, etc.), Solanaceae (potato, tobacco, tomato, peppers), various floral crops, such as sunflower, and nut-bearing trees, such as almonds, cashews, walnuts, and pecans. See, e.g., [64-68].

In one embodiment, the PBGS gene is derived from a species in which the PBGS enzyme does not comprise $Mg^{2+}$ but comprises $Zn^{2+}$. In a preferred embodiment, the species is yeast or human. In another preferred embodiment, a mutant PBGS gene is used to generate a transgenic plant. In a further embodiment, the PBGS gene is introduced into the plant genome by homologous recombination. The wild type human PBGS genomic DNA and full length cDNA which may be used to generate a transgenic plant are shown below:

```
Human PBGS gene (SEQ ID NO: 1):[69]
cttacgcggtctgtgggagaccggagcgggagacagcggtgacaggagca gcggccgggagcccttaggaggcagacagagcctgcagccaatgcccca ggagccctcggttccaaccaactgatgcccctgtgcccactggcccacgc catgcagccccagtccgttctgcacagcggctacttccacccactacttc gggcctggcagacagccaccaccaccctcaatgcctccaacctcatctac -continued
cccatctttgtcacggatgttcctgatgacatacagcctatcaccagcct cccaggagtggccaggtatggtgtgaagcggctggaagagatgctgaggc ccttggtggaagagggcctacgctgtgtcttgatctttggcgtccccagc agagttcccaaggacgagcggggttccgcagctgactccgaggagtcccc agctattgaggcaatccatctgttgaggaagaccttccccaacctcctgg tggcctgtgatgtctgcctgtgtccctacacctcccatggtcactgcggg ctcctgagtgaaaacggagcattccgggctgaggagagccgccagcggct ggctgaggtggcattggcgtatgccaaggcaggatgtcaggtggtagccc cgtcggacatgatggatggacgcgtggaagccatcaaagaggccctgatg gcacatggacttggcaacagggtatcggtgatgagctacagtgccaaatt tgcttcctgtttctatggcccttccgggatgcagctaagtcaagcccag cttttggggaccgccgctgctaccagctgcccctggagcacgaggcctg gctctccgagctgtggaccgggatgtacgggaaggagctgacatgctcat ggtgaagccgggaatgccctacctggacatcgtgcgggaggtaaaggaca agcaccctgacctccctctcgccgtgtaccacgtctctggagagtttgcc atgctgtggcatggagcccaggccggggcatttgatctcaaggctgccgt actggaggccatgactgccttccgcagagcaggtgctgacatcatca cctactacacaccgcagctgctgcagtggctgaaggaggaatgatggaga cagtgccaggcccaagaactagaactttaaaacgttcccggggcctcaga caagtgaaaaccaaagtaaatgctgcttttagaactgtgccctcatgccc tcttcctgctcacatgctagcggggcccagcagccctgggtggttttgcc agcatgctaactcttgtaactcgcagctgcatcctatgagctctcccaag cttccccgcccctcccctgggtcagccgtgaggcccacctttgccaccct cagctcttcctctggtgtggcttcagcttgaaagcaacctggagtcggg ggcacagcctttggggcctggctgggagagggtcttggagcattagggga agaagagagcagtgggatcttggggcctgagaagccttggaacgcttctg gcagcagagctgggtgtgggaatgaggcctagatcgatatccctgggtta gagttgaaatttgccgcaattccactggaaggcatttcccacgaggccag aggttgccaggctgcctgaggtctcctattctactctgaaccataaaccc agagaagaattactcattaaccagcataaatactgcctgaggatcaaaac tcagaggcaaagagggagttcctgactgctagaggtgccaccaccacaaa cacttttattcaggagatacttttttgagaatctctgctctgttcctagg ttcagtgctgggtcctgggaatacagcaggacagacctcagcttatctct tcatagaaattatacaaagagaattggggagacagctaagaagaaaacaa agaaataaagcagttacaaattgtgataagtgctttgaaggaaagaaggg gtctgagacaacaacagggaagggcctctcttgaaacagtagttgggaa ggaggcagacatgcaccagtgatgtggtgacaggtgctctgaaggaggtc accaggacctgacctctttgaaggatcagaaaatacttccctgaaggact gacatttgagcctagacctgaagggtgagccatcaagctaagacaattgg ggaagagcattccaggagagggaggagttgtgcaaaggccctggggctc cttctagctggaggaatgcaaggctagcttgtctggagcactgagaggat
```

-continued

```
ggcctgaactgagtggagagagacagaccaggaccaaaccatgcagaggt caagggccacattcacctttcagagtgactcaatcaatttgtagtttg taaaagtattttaacagctctgcggcaaagtgcaatgaaaagtcttgat ggcatggactggagcggggacagtggggatggagaaaggggaatggattg tggatgtgtttagaaggtagattcgatgtgaaggatgaatctggcttgac cttctgggtggctgatgggccatttactgagatggggcagcctggaagag gaacagaagcagggtcggggtggagggagaatactaaacttagcttgaga catttgcaataaggaagctatatctagagtgcttatgtgactcacctaa ggccactcaacaagtttgtggcagaactggattagaactgcacagaaaac agccaagctgggatttgaaccatgtagtccaactccaaggcctctgccc ctaaccactgtgccataccacctcccaataatcaacagcaaaattatagg tctaacaatgttttatagacacccctccatttatgtgatgggtttgcatc ctgataaaccatcataagttgaaaatatgatcataagttgaaaatatga tcataagtcaaaaatgtatttaatatacctaacctaccaaacatcatagc ttagcctagcctgccttaaacatgctcagaacacttacattagcctacag tgggcaaaactatccaacacaaaatctatattgtaataaagttgtaaaga atttgaataaaaattcaatatttgaaaaaaaaaaaaaaaa
```

Human PBGS cDNA (SEQ ID NO: 2):[69]
```
gcagccaaagccccaggagccctaggttccaaccaactgatgccctgtg cccactggccacgccatgcagcccagtccgttctgcacagcggctact tccacccactacttcgggcctggcagacagccaccaccaccctcaatgcc tccaacctcatctacccatctttgtcacggatgttcctgatgacataca gcctatcaccagcctcccaggagtggccaggtatggtgtgaagcggctgg aagagatgctgaggcccttggtggaagagggcctacgctgtgtcttgatc tttggcgtcccagcagagttcccaaggacgagcggggttccgcagctga ctccgaggagtcccagctattgaggcaatccatctgttgaggaagacct tccccaacctcctggtggcctgtgatgtctgcctgtgtccctacacctcc catggtcactgcgggctcctgagtgaaaacggagcattccgggctgagga gagccgccagcggctggctgaggtggcattggcgtatgccaaggcaggat gtcaggtggtagccccgtcggacatgatggatggacgcgtggaagccatc aaagaggccctgatggcacatggacttggcaacagggtatcggtgatgag ctacagtgccaaatttgcttcctgtttctatggcccttcgggatgcag ctaagtcaagcccagcttttggggaccgccgctgctaccagctgcccct ggagcacgaggcctggctctccgagctgtggacgggatgtacgggaagg agctgacatgctcatggtgaagccgggaatgccctacctggacatcgtgc gggaggtaaaggacaagcaccctgacctccctctcgccgtgtaccacgtc tctggagagtttgccatgctgtggcatggagcccaggccggggcatttga tctcaaggctgccgtactggaggccatgactgccttccgcagagcaggtg ctgacatcatcatcacctactacacaccgcagctgctgcagtggctgaag gaggaatgatggaggacagtgccaggcccaagaactagaactttcaaacg ttcccggggcctcagacaagtgacaaccaaagtaaatgctgcttttagaa
``` ctgt

Human PBGS amino acid sequence (SEQ ID NO: 3):[69]
MQPQSVLHSGYFHPLLRAWQTATTTLNASNLIYPIFVTDVPDDIQPITSL

PGVARYGVKRLEEMLRPLVEEGLRCVLIFGVPSRVPKDERGSAADSEESP

AIEAIHLLRKTFPNLLVACDVCLCPYTSHGHCGLLSENGAFRAEESRQRL

AEVALAYAKAGCQVVAPSDMMDGRVEAIKEALMAHGLGNRVSVMSYSAKF

ASCFYGPFRDAAKSSPAFGDRRCYQLPPGARGLALRAVDRDVREGADMLM

VKPGMPYLDIVREVKDKHPDLPLAVYHVSGEFAMLWHGAQAGAFDLKAAV

LEAMTAFRRAGADIIITYYTPQLLQWLKEE

The compositions of the invention is suitable as antimicrobial active ingredients in personal care preparations, for example shampoos, bath additives, hair-care products, liquid and solid soaps (based on synthetic surfactants and salts of saturated and/or unsaturated fatty acids), lotions and creams, deodorants, other aqueous or alcoholic solutions, e.g. cleansing solutions for the skin, moist cleansing cloths, oils or powders. The invention therefore relates also to a personal care preparation comprising the composition of the invention and optionally cosmetically tolerable carriers or adjuvants as described in U.S. Pat. No. 6,689,372 to Holzl et al. The composition should be used in amounts effective to have the antimicrobial effect, i.e. inhibit or prevent microbial activity. Other constituents can be used, for example sequestering agents, colorings, perfume oils, thickening or solidifying (consistency regulator) agents, emollients, UV absorbers, skin-protective agents, antioxidants, additives that improve mechanical properties, such as dicarboxylic acids and/or Al, Zn, Ca and Mg salts of fatty acids, and optionally preservatives. Further, the invention provides a method of antimicrobial treatment of skin, mucosa or hair which comprises, contacting the surface of the skin, mucosa or hair of a person in need of said antimicrobial treatment with an antimicrobially effective amount of the compound of the invention.

The personal care preparation according to the invention may be formulated as a water-in-oil or oil-in-water emulsion, as an alcoholic or alcohol-containing formulation, as a vesicular dispersion of an ionic or non-ionic amphiphilic lipid, as a gel, a solid stick or as an aerosol formulation.

As a water-in-oil or oil-in-water emulsion, the cosmetically tolerable adjuvant contains, for example, from 5 to 50% of an oily phase, from 5 to 20% of an emulsifier and from 30 to 90% water. The oily phase may contain any oil suitable for cosmetic formulations, e.g. one or more hydrocarbon oils, a wax, a natural oil, a silicone oil, a fatty acid ester or a fatty alcohol. Preferred mono- or poly-ols are ethanol, isopropanol, propylene glycol, hexylene glycol, glycerol and sorbitol.

Cosmetic formulations according to the invention may be contained in a wide variety of cosmetic preparations as described in U.S. Pat. No. 6,689,372 to Holzl et al. Especially the following preparations, for example, come into consideration: skin-care preparations, e.g. skin-washing and cleansing preparations in the form of tablet-form or liquid soaps, soapless detergents or washing pastes; bath preparations, e.g. liquid (foam baths, milks, shower preparations) or solid bath preparations, e.g. bath cubes and bath salts; skin-care preparations, e.g. skin emulsions, multi-emulsions or skin oils; cosmetic personal care preparations, e.g. facial make-up in the form of day creams or powder creams, face powder (loose or pressed), rouge or cream make-up, eye-care preparations, e.g., eyeshadow preparations, mascara, eyeliner, eye creams or eye-fix creams; lip-care preparations, e.g., lipsticks, lip gloss, lip contour pencils, nail-care preparations, such as nail varnish, nail varnish removers, nail hardeners or cuticle removers; intimate hygiene preparations, e.g., intimate washing lotions or intimate sprays; foot-care preparations, e.g., foot baths, foot powders, foot creams or foot balsams, special deodorants and antiperspirants or callous-removing preparations; light-protective preparations, such as sun milks, lotions, creams and oils, sun blocks or tropicals, pre-tanning preparations or after-sun preparations; skin-tanning preparations, e.g., self-tanning creams; depigmenting preparations, e.g., preparations for bleaching the skin or skin-lightening preparations; insect-repellents, e.g., insect-repellent oils, lotions, sprays or sticks; deodorants, such as deodorant sprays, pump-action sprays, deodorant gels, sticks or roll-ons; antiperspirants, e.g., antiperspirant sticks, creams or roll-ons; preparations for cleansing and caring for blemished skin, e.g., soapless detergents (solid or liquid), peeling or scrub preparations or peeling masks; hair-removal preparations in chemical form (depilation), e.g., hair-removing powders, liquid hair-removing preparations, cream- or paste-form hair-removing preparations, hair-removing preparations in gel form or aerosol foams; shaving preparations, e.g., shaving soap, foaming shaving creams, non-foaming shaving creams, foams and gels, pre-shave preparations for dry shaving, after-shaves or after-shave lotions; fragrance preparations, e.g., fragrances (eau de cologne, eau de toilette, eau de parfum, parfum de toilette, perfume), perfume oils or cream perfumes; dental-care, denture-care and mouth-care preparations, e.g., toothpastes, gel tooth-pastes, tooth powders, mouthwash concentrates, anti-plaque mouthwashes, denture cleaners or denture fixatives; cosmetic hair-treatment preparations, e.g., hair-washing preparations in the form of shampoos and conditioners, hair-care preparations, e.g., pretreatment preparations, hair tonics, styling creams, styling gels, pomades, hair rinses, treatment packs, intensive hair treatments, hair-structuring preparations, e.g., hair-waving preparations for permanent waves (hot wave, mild wave, cold wave), hair-straightening preparations, liquid hair-setting preparations, foams, hairsprays, bleaching preparations; e.g., hydrogen peroxide solutions, lightening shampoos, bleaching creams, bleaching powders, bleaching pastes or oils, temporary, semi-permanent or permanent hair colourants, preparations containing self-oxidizing dyes, or natural hair colourants, such as henna or camomile.

The oral composition according to the invention may be, for example, in the form of a gel, a paste, a cream or an aqueous preparation (mouthwash).

The oral composition according to the invention may also comprise compounds that release fluoride ions which are effective against the formation of caries, for example inorganic fluoride salts, e.g. sodium, potassium, ammonium or calcium fluoride, or organic fluoride salts, e.g. amine fluorides, which are known under the trade name Olafluor.

The compositions of the invention are also suitable for the treatment of textile fibre materials. Such materials are undyed and dyed or printed fibre materials, e.g. of silk, wool, polyamide or polyurethanes, and especially cellulosic fibre materials of all kinds. Such fibre materials are, for example, natural cellulose fibres, such as cotton, linen, jute and hemp, as well as cellulose and regenerated cellulose. Preferred suitable textile fibre materials are made of cotton. The compositions of the invention can also be used in washing and cleaning formulations, e.g. in liquid or powder washing agents or softeners.

The compositions of the invention are also suitable for imparting anti-microbial properties to plastics, e.g., polyethylene, polypropylene, polyurethane, polyester, polyamide, polycarbonate, latex etc. Fields of use of compositions of the invention are, for example, floor coverings, plastics coatings, plastics container and packaging materials, kitchen and bathroom utensils (e.g., brushes, shower curtains, sponges, bathmats), latex filter materials (air and water filters), plastics articles used in the field of medicine, e.g. dressing materials, syringes, catheters etc., so-called "medical devices", gloves and mattresses.

Paper, for example, paper used for hygiene purposes, may also be provided with anti-microbial properties using the compositions according to the invention.

It is also possible for non-wovens, e.g. nappies/diapers, sanitary towels, panty liners, and cloths for hygiene and household uses, to be provided with antimicrobial properties in accordance with the invention.

The compositions can be used also in household and all-purpose cleaners for cleaning and disinfecting hard surfaces.

In addition to preserving cosmetic and household products, technical products, such as paper treatment liquors, printing thickeners of starch or of cellulose derivatives, surface-coatings and paints, can be preserved and provided with antimicrobial properties.

The compositions of the invention are also suitable for the antimicrobial treatment of wood and for the antimicrobial treatment of leather and the provision of leather with antimicrobial properties.

The compounds according to the invention are also suitable for the protection of cosmetic products and household products from microbial damage.

Further, the composition of the present invention can be used as an oral composition such as a dentifrice composition in association with an orally-acceptable carrier as described in U.S. Pat. No. 6,740,311 to White, Jr., et al. Non-limiting examples of such oral composition are toothpastes, tooth powders, prophylaxis pastes, lozenges, gums and the like suitable for humans and animals.

Further, the compositions of the invention can be used to prepare antimicrobial surfaces. Further provided is a method of making an antibacterial surface, the method comprising: (1) providing the composition of the invention wherein the composition is effective to inhibit or prevent formation of the active form of the multimeric porphobilinogen synthase and thereby inhibiting or preventing development or growth of bacteria, archaea, and/or eucarya, provided that the active form of the multimeric porphobilinogen synthase contains an allosteric magnesium binding site and the composition is at least one of a drug, a toothpaste, a soap, a disinfectant, an anti-biofilm composition, and a herbicide; (2) providing a surface-forming matrix; and (3) combining the composition with the surface-forming matrix and thereby making the antibacterial surface. In one variant of the method, the antibacterial surface is adapted to prevent or inhibit a formation of a biofilm.

The term "a surface-forming matrix" as used herein includes polymers, biodegradable and non-biodegradabe, silicas, ceramics and combinations thereof for mixing, layering or otherwise associating the composition with the matrix. The composition can also be put on the top or a bottom surface of the matrix.

Further, this invention provides a method for manipulating growth or development of a plant comprising applying the composition of the invention in a form of a herbicide to the plant, wherein the plant is herbicide resistant and is adapted to be transgenic for a multimeric porphobilinogen synthase that substantially exist in a multimeric form of a hugging dimer. In one variant of the method, the multimeric porphobilinogen synthase contains no allosteric magnesium binding site.

The invention will be illustrated in more detail with reference to the following Examples, but it should be understood that the present invention is not deemed to be limited thereto.

EXAMPLES

Example 1

Figure 17A:
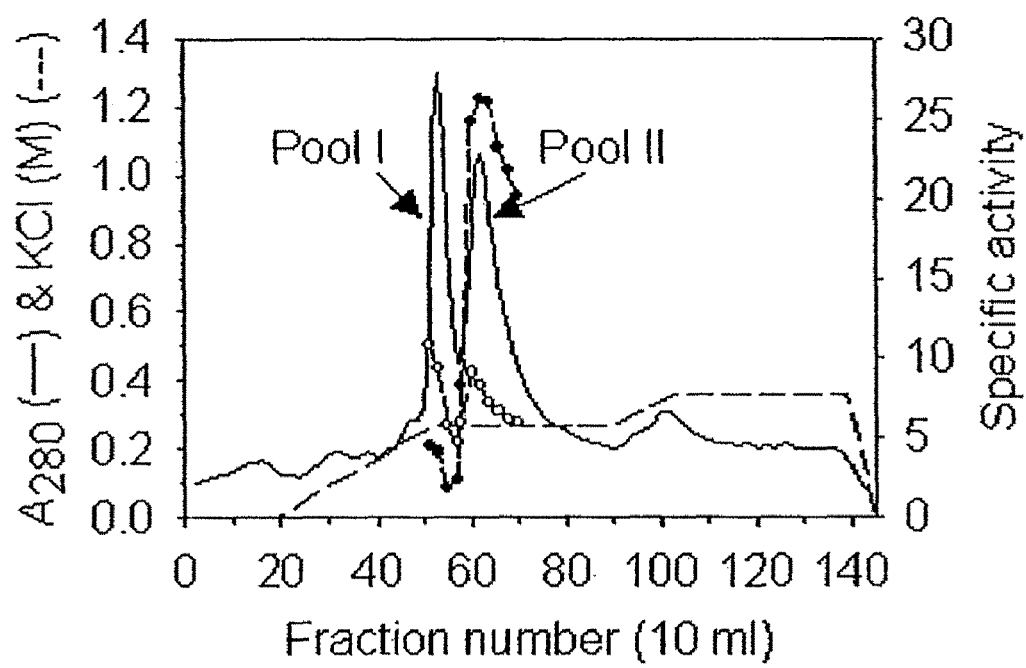
FIG. 17A shows the chromatographic separation of two peaks of heterologously expressed WT+F12L (both genes on the same mRNA) in on Q-Sepharose (KCl gradient (---), A280 (-)). Pool I contains hetero-hexamers and Pool II contains hetero-octamers.

Discovery of the hexameric assembly of human PBGS variant F12L.
Protein Expression The parent human PBGS is the well-characterized N59/C162A [70]. N59 corresponds to the more soluble of two co-dominant alleles encoding the PBGS protein. C162A is a benign mutation that removes the possibility of a slowly forming aberrant disulfide bond. The artificial gene for N59/C162A is called Wt below. The sense strand primer used for the QuikChange mutagenesis of Wt to the F12L variant was GGCTACCTCCACCCACTGCTTCGGGCC (SEQ ID NO: 4). Several constructs were prepared for the coexpression of Wt and F12L in *E. coli*. Both the order of the genes and the number of promoters were varied, but these variations did not affect the outcome. The construct containing Wt and F12L under the control of one promoter is described. Plasmid DNA containing Wt (pET3aWt) was digested with BamHI and NdeI to cut out Wt. The pET17b vector DNA was linearized by digestion with BamHI and NdeI and ligated with Wt such that the ATG start codon of Wt was 6 basepairs downstream of the ribosomal binding site encoded by the vector. The resultant plasmid was transformed into *E. coli* XL1blue. Plasmid DNA (pET17bWt) was prepared and linearized with SpeI and Bpu1102I. Plasmid DNA containing the gene F12L (pET3aF12L) was digested with XbaI and Bpu1102I to produce a fragment containing the ribosomal binding site and the gene for F12L. The gene for F12L and the linearized pET 17Wt vector were ligated such that the ribosomal binding site of the F12L gene was 35 base pairs downstream of the stop codon of Wt, and the terminator was 52 base pairs downstream of the stop codon for the F12L gene. Plasmid pET17bWtF12L was transformed into *E. coli* XL1blue, plasmid DNA was prepared and transformed into *E. coli* BLR (DE3) for protein expression as previously described [70].
Protein Purification The bulk of the protein purification procedure (cell disruption, ammonium sulfate fractionation, hydrophobic chromatography on Phenyl-Sepharose, anion exchange chromatography, and gel filtration chromatography on Sephacryl S-300) followed the procedures previously described [70] with the exception that a 70 ml Q-Sepharose column was used in place of the DEAE agarose column for the anion exchange step. The Q-Sepharose was run at room temperature using 30 mM potassium phosphate, pH 7.0, 10 mM 2-mercaptoethanol, 10 µM Zn(II), and employed a KCl gradient as shown in FIG. 17A. The gradient was controlled by a Rainin HPLC system run at a flow rate of 3 ml min$^{-1}$ and 10 ml fractions were collected.
Kinetic Characterization of the PBGS Variants was Used to Show that WT and F12L have Different Functional Characteristic:

All kinetic determinations were carried out in 0.1 M bis-tris propane, 10 mM 2-mercaptoethanol, 10 µM Zn. For the pH rate profiles, the reported pH reflects the assay pH after the addition of 10 mM ALA-HCl. For $K_m$ and $V_{max}$ determinations, concentrations of ALA were 10 µM, 30 µM, 100 µM, 300 µM, 1 mM, 3 mM, and 10 mM and were each done in duplicate. Variations in the concentration of ALA-HCl did not lead to variations in final pH because the stock 0.1 M ALA-HCl was diluted into 0.1 M HCl prior to addition of a constant volume to the assay mixture. All assays were at 37° C. for a fixed time using Ehrlich's reagent to determine porphobilinogen formed.
Analytical Ultracentrifugation:

Protein samples were dialyzed into 30 mM potassium phosphate, pH 7.5, 0.1 mM DTT, and 10 µM ZnCl$_2$ just prior to loading into the ultracentrifuge. Loading concentrations were 10.6 µM and 12.8 µM for wild type and F12L mutant enzyme, respectively. All sedimentation equilibrium experiments were carried out at 4° C. using a Beckman Optima XL-A analytical ultracentrifuge equipped with an An60 Ti rotor and using six-channel, 12-mm path length, charcoal-filled Epon centerpieces using quartz windows. Data were collected at three rotor speeds (8,000, 11,000, and 14,000 rpm) and represent the average of 20 scans using a scan step size of 0.001 cm. Temperature-corrected partial specific volumes and solution density were calculated using the Sednterp program [71]; the solution density was 1.00191 gm/mL and the partial specific volumes were 0.7394 and 0.7397 mL/gm for the wild type and mutant proteins respectively. Data were analyzed using the HID program from the Analytical Ultracentrifugation Facility at the University of Connecticut (Storrs, Conn.). Model analysis of the data ruled out a single species as the residuals from the fits were clearly nonrandom.
A Crystal Structure was Determined for F12L F12L was dialyzed against 50 mM bis-tris propane, 10 mM βME, and 10 µM ZnCl$_2$. Crystals were formed using the sitting drop method, equal volume of F12L (4.0 mg ml-1) was mixed with the precipitant (0.4 M monoammonium hydrogen phosphate). ALA was added equimolar to the protein subunit concentration and crystals formed in 3-5 days. Diffraction data were collected at 100K on MAR345 image plate detector coupled with RU-200 rotating anode generator equipped with OSMIC optics and operated at 50 kV and 100 ma. Crystals were cryoprotected before freezing by transferring them at reservoir solutions containing 12%, 17%, 23% and 30% glycerol for 3 min in each solution. A few data sets were collected showing high degree of disorder and lack of any ligand in the active site area. Because of that, a crystal of F12L was soaked in 2 mM ALA, which was added to the first two cryoprotectant solutions and 0.2 mM ZnCl$_2$, which was added to the last two solutions in addition to ALA. The final data set consisted of 525 frames corresponding to 0.5° oscillation with exposure time 3.5 min per frame. Crystals belong to a hexagonal system, space group P6$_3$, unit cell parameters a=b=89.6 Å, c=153.2 Å. There are two molecules in the asymmetric unit. Diffraction data were reduced with the program package HKL2000, R$_{merge}$(I)=5.0% for 33,615 reflections for the 45-2.2 Å resolution range.

The structure was solved by molecular replacement with the AmoRe program package by using molecule A of human PBGS structure (pdb code 1E51) as an initial model. Refinement was carried out with program CNS. The final model included one dimer of F12L—molecule A (residues 11-82, 97-124, 140-169, 172-212, 222-330) and B (residues 3-82, 97-122, 140-169, 172-212, 226-328), one molecule of an intermediate product of the catalytic reaction bound in the active site of molecule A, 241 water molecules and two atoms of Zn which appear to have low occupancies. The crystallographic R-factor is 19.9%, R(free) is 28.6% for 2.2 Å resolution data, and the RMS deviations for bond lengths and bond angles are 0.18 Å and 2.0°, respectively. All residues belong to allowed conformation regions on the Ramachandran plot.

The Properties of Human PBGS Variant F12L

Human PBGS variant F12L is remarkably different from the wild type protein. Characterization of purified F12L confirmed that the catalytic activity is very low under conditions where wild type human PBGS is most active. However, F12L exhibits a remarkably altered pH rate profile and shows considerable activity at basic pH values (FIG. 12). The $K_m$ and $V_{max}$ values of F12L and wild type human PBGS were determined at pH 7, which is optimal for the wild type protein, and at pH 9, which is optimal for F12L; the results are presented in Table 1. F12L exhibits normal Michaelis-Menten kinetics with extraordinarily high $K_m$ values, well above physiological concentrations of the substrate 5-aminolevulinic acid (ALA). However, at pH 9 the $V_{max}$ of F12L is significantly higher than that of the wild type protein. Under conditions of optimal pH and in the presence of an optimal configuration of metal ions, wild type PBGS from all species characterized are reported to have $K_m$ values in the range of 100 μM [14,31,70, 72], as is seen here for wild type human PBGS at pH 7. The kinetic behavior of wild type human PBGS at pH 9 did not exhibit standard Michaelis-Menten kinetics, the basis of which was not at first apparent. On cursory examination, the wild type protein appeared to exhibit an extreme negative cooperativity with a Hill coefficient on the order of 0.35. In fact, the best fit for the data was to a double hyperbolic equation, which was later appreciated to derive from catalysis by a mixture of quaternary isoforms (morpheein forms, octamer and hexamer) where the two forms have very different Km values. This phenomenon is described in more detail below.

Further evidence for extraordinary differences between the F12L variant and the wild type protein came from variations in mobility during anion exchange chromatography (FIG. 16A) and during native gel electrophoresis (FIG. 16B), both of which suggest a difference in oligomeric structure. Separation on an anion exchange column generally reflects a different surface charge, which cannot be due to the replacement of neutral leucine for neutral phenylalanine. Separation of two species with identical charge/mass ratio by electrophoresis indicates either a different size or a different shape. Together, these differences suggested that F12L and wild type human PBGS exist in different oligomeric states.

When the wild type and mutant proteins were subjected to sedimentation equilibrium analysis using an analytical ultracentrifuge, the molecular weight for the wild type protein and F12L were found to be 244,000±8,900 and 197,900±6,500 Daltons, respectively. The former is midway between that expected for an octamer and a hexamer, while the latter is midway between that expected for a hexamer and a tetramer. In model analysis of the data, the wild type protein fit best to a three-state model of dimer, hexamer, and octamer at 7.6%, 51%, and 42% respectively, while F12L fit best to a two-state model of tetramer and hexamer at a ratio of 70% to 30%, with octamer absent. Hence the inventor undertook the determination of the crystal structure of human PBGS variant F12L. The Crystal Structure of Human PBGS and the F12L Variant Show Remarkable Differences in the Structure of the Monomer, which Dictates a New Quaternary Isoform and Reveals the First Example of a Morpheein:

Seventeen previously determined crystal structures of PBGS [29,30,40,73-79] from fungi, metazoa, and bacteria reveal a common homo-octameric structure in which four dimers are related by a 90° rotation around a central axis (FIG. 2). PBGS is a member of the aldolase superfamily of TIM α/β barrel proteins [80]. In each subunit the catalytic core resides completely within the barrel and a 20+ amino acid N-terminal arm is involved in extensive subunit interactions. The sequence of the catalytic core is phylogenetically conserved, but that of the N-terminal arm is not. The PBGS dimer seen in the octamer (FIG. 2, left) involves highly conserved barrel-to-barrel contacts and the N-terminal arm of one subunit is hugging the barrel of the sister subunit. Hence, this has been referred to as the hugging dimer [9]. The side chain of amino acid 12 does not participate in the hugging interaction. Assembly of the tetramer, which is by addition of a second hugging dimer rotated 90° around the central axis (FIG. 2, middle), adds an additional reciprocal interaction between the arm of one subunit and the base of an α/β barrel from a neighboring dimer. The side chain of amino acid 12 participates in this subunit interaction. Addition of two more dimers, each rotated 90° around the central axis results in the octamer (FIG. 2, right). The octamer, rotated 90° toward the reader relative to the view of the dimer and tetramer, and gives a pinwheel representation. Prior to the determination of the crystal structure of F12L, it was presumed that all PBGS proteins shared the same homo-octameric structure [9]. However, for PBGS from green plants and some bacteria, there is kinetic evidence suggesting that the maximally active octamer can dissociate into smaller, less active, structural units [13,14]. This kinetic evidence is a protein concentration to the specific activity as illustrated in FIGS. 5 and 20B for pea PBGS.

Strikingly, the newly determined crystal structure of the F12L human PBGS allele (PDB Code 1PV8) reveals a quaternary structure that involves significant rearrangement of the N-terminal arm relative to the α/β barrel (FIG. 9). In this case, the dimer retains the aforementioned barrel-to-barrel contacts but the N-terminal arms are detached rather than hugging (FIG. 9, left). Assembly of the tetramer retains the aforementioned reciprocal interaction between the arm of one subunit and the base of an α/β barrel from a neighboring dimer. However, because the arm is jutting out, this association dictates a 120° rotation around the central axis. Hence, in the oligomeric structure there are three detached-dimers, each rotated 120° around a central axis to form a hexamer (FIG. 9, right, viewed in the pinwheel representation). The unprecedented structural transition from the octamer observed for wild type human PBGS to the hexamer observed for F12L is an outstanding example of how a small mutational change can have a profound effect on the structure and function of a protein and indicates how close in energy these two quaternary forms are. It is also clear from viewing these structures that any equilibration between octamer and hexamer must proceed through the interconversion of the hugging dimer and the detached dimer. This interconversion process is illustrated in FIG. 24.

The new structure of F12L (2.2 Å resolution) contains significant regions of disorder that impede a structural comparison of the active site relative to the previously deposited wild type human PBGS structure (PDB code 1E51, 2.83 Å resolution). Amino acid 12 does not interact directly with active site residues in either structure. Furthermore, for those amino acids observed in both structures, most are superimposable. Thus, to further probe the basis for the unusual kinetic properties of F12L (e.g., FIG. 12, Table 1), the inventor undertook coexpression of F12L and wild type human PBGS.

Example 2

This example describes experiments demonstrating that the quaternary structure, rather than the specific mutation is responsible for the unusual properties of F12L.

Figure 17B:
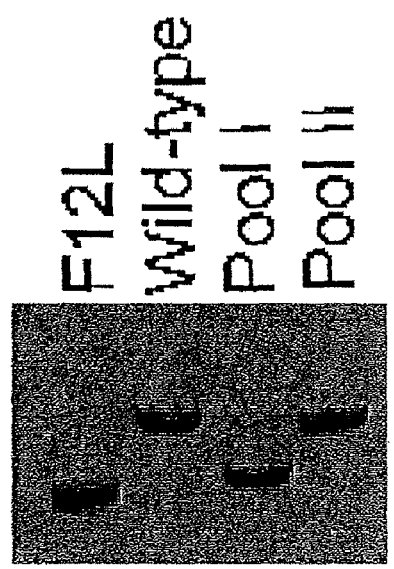
FIG. 17B shows the differential mobility of two pools of WT+F12L relative to wild type (WT) human PBGS and F12L on native gel electrophoresis.
Figure 17C:
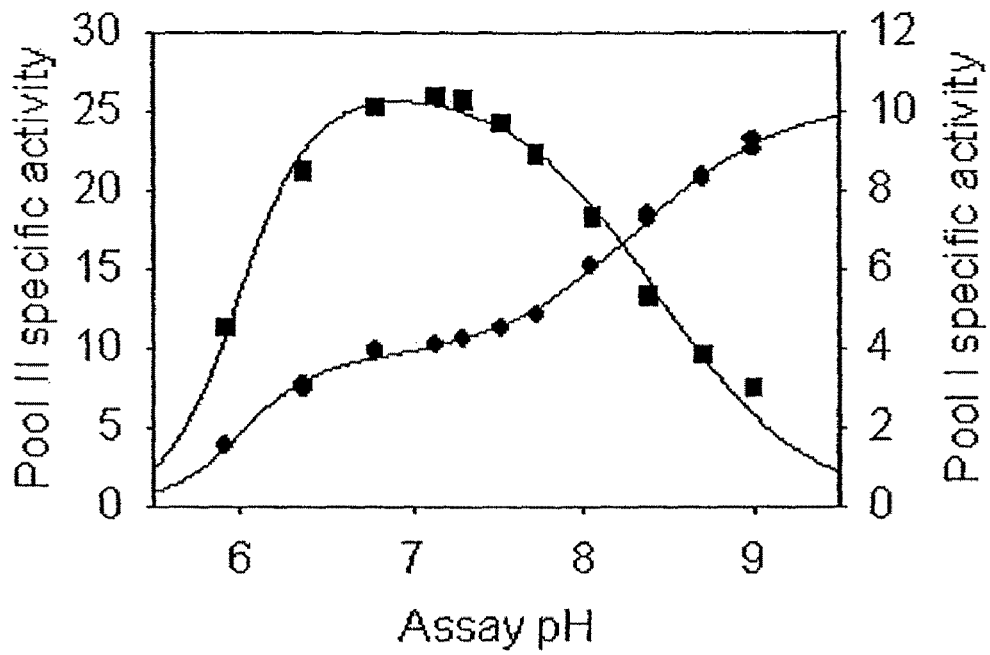
FIG. 17C shows the pH rate profiles for Pool I (●) and Pool II (■) of WT+F12L (as per FIG. 17A) following further purification on Sephacryl S300.

Coexpression of Wild Type Human PBGS and F12L Revealed that the Quaternary Structure is the Basis for the Kinetic Differences:

A coexpression system was prepared to produce both wild type human PBGS and the F12L variant in a 1:1 ratio from the same RNA message. Purification of the co-expressed protein, called WT+F12L, was found to yield two distinct peaks of PBGS protein on anion exchange chromatography (FIG. 17A). The peak to elute first (Pool I) runs comparably to F12L on a native gel, while the second peak (Pool II) runs comparably to wild type human PBGS (FIG. 17B). Pool I showed enhanced activity at pH 9 and Pool II showed enhanced activity at pH 7 (FIG. 17C). Both pools were individually subjected to analysis by mass spectroscopy following a tryptic digest and each was found to contain significant amounts of both the N-terminal 2010.2 Dalton Phe-containing peptide and the 1976.2 Dalton Leu-containing peptide, confirming that both pools contain heteromeric species. The percentage of each chain in the heteromeric pools was quantified by N-terminal sequencing to show that the Pool I contains 48.5% Phe and 51.5% Leu while Pool II contains 71.1% Phe and 28.3% Leu. These ratios were later found to vary with each purification, which was revealed to be through the disproportionation reaction illustrated in Example 3. These ratios do not obviously reveal what governs the quaternary structure of the heteromeric species. Pools I and II were further purified by gel filtration on Sephacryl S300, which reduced cross contamination of the heteromers. The pH rate profiles of the S300 purified Pools I and II are remarkably like F12L and wild type human PBGS, respectively (FIG. 17C). Based on the chromatographic, mass spectroscopy, and quantitative N-terminal sequencing data, it is concluded that Pool I is comprised of heterohexamers and that Pool II is comprised of heterooctamers. The pH rate profiles are found to be dominated more by the quaternary structure than by the amino acid composition at position 12.

Figure 17D:
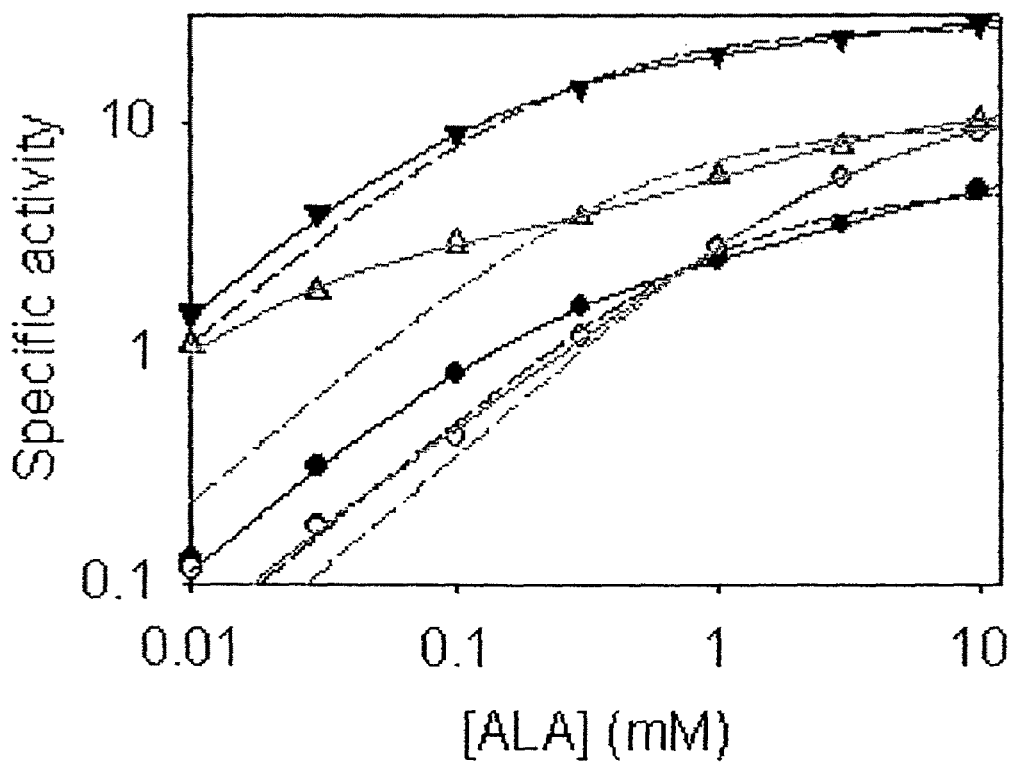
FIG. 17D shows a plot of activity versus concentration of ALA (10 µM-10 mM) for determining the $K_m$ and $V_{max}$ values for the S300 purified Pool I (circles) and Pool II (triangles) at pH 7 (filled) and pH 9 (open). The solid lines represent best fits of the data to the double hyperbolic equation (indicative of catalysis by a mixture of morpheein forms). The dashed lines, each poor fits, show the results of fitting the data to a single hyperbolic equation.

The kinetic parameters $K_m$ and $V_{max}$ of the S300 purified pools were determined at pH 7 and at pH 9 (Table 3 contains data for hetero-hexamers (Pool I) initially at 70% Leu and 30% Phe and for hetero-octamers (Pool II) initially at 30% Leu and 70% Phe). The kinetic data do not follow a simple Michaelis-Menten relationship (hyperbolic fit), but can be attributed to catalysis by two different forms of the enzyme that have different $K_m$ and $V_{max}$ values (double hyperbolic fit) [81]. FIG. 17D shows activity as a function of substrate concentration; the kinetic data uniformly fit a model where hexameric and octameric forms of the enzyme exhibited high and low $K_m$ values, respectively. This double hyperbolic fit (solid lines) is far superior to the single hyperbolic fit (dashed lines). With the exception of the trace amount of octamer present for Pool I that is detected at pH 9, all the kinetic values are well determined (see Table 3). The data for wild type human PBGS at pH 9 also provided a superior fit to the octamer-hexamer model and this solution is included in Tables 1 and 3. The factors that govern equilibration of human PBGS heteromers under assay conditions remain to be elucidated.

Pool I and Pool II are the two pools of PBGS activity eluted from the Q-Sepharose column, as illustrated in FIG. 17A, and following further purification on a Sephacryl S-300 column. $K_{m1}$ and $K_{m2}$ (both mM) are interpreted as the $K_m$ for the octamer and hexamer, respectively.

TABLE 3

Kinetic parameters of homomeric and heteromeric human PBGS.[a]

|  |  | F12L[b] | WT[b] | WT + F12L Pool I | WT + F12L Pool II |
|---|---|---|---|---|---|
| $K_{m1}$ | pH 7 |  | 0.25 ± 0.01 | 0.47 ± 0.07 | 0.19 ± 0.01 |
| $V_{max1}$ | pH 7 |  | 55.5 ± 0.2 | 2.98 ± 0.38 | 13.06 ± 0.40 |
| $K_{m2}$ | pH 7 | 17.7 ± 1.1 |  | 7.34 ± 1.53 | 5.05 ± 0.96 |
| $V_{max2}$ | pH 7 | 1.14 ± 0.05 |  | 6.60 ± 0.23 | 9.05 ± 0.37 |
| $K_{m1}$ | pH 9 |  | 0.015 ± 0.001[c] | 0.69 ± 0.15 | 0.05 ± 0.01 |
| $V_{max1}$ | pH 9 |  | 8.16 ± 0.13 | 2.99 ± 0.80 | 1.89 ± 0.25 |
| $K_{m2}$ | pH 9 | 4.6 ± 0.1 | 4.46 ± 0.80 | 4.17 ± 1.80 | 1.50 ± 0.24 |
| $V_{max2}$ | pH 9 | 18.2 ± 0.2 | 6.67 ± 0.36 | 2.74 ± 0.66 | 4.78 ± 0.19 |

[a]The $K_m$ and $V_{max}$ values were obtained by varying [ALA] from 3 μM-10 μM and were calculated by fitting the kinetic data to equation 1. $K_{m1}$ and $K_{m2}$ (both mM) are interpreted as the Km values for the octamer and hexamer, respectively. The reported Vmax values (μmol h$^{-1}$ mg$^{-1}$) reflect the mole fraction of quaternary species under assay condition.
[b]Data were taken from Table 1 and reference [39].
[c]A previous reported [39] $K_{m1}$ at pH 9 for WT was 0.35 ± 0.09; this was a misprint that represented the alternative fit of the kinetic data to the Hill equation.

The reported $V_{max}$ values (in units of μmoles h$^{-1}$ mg$^{-1}$) reflect the mole fraction of quaternary species under assay conditions, which remains to be determined. Fitted $K_m$ values are independent of the distribution of quaternary species.

Example 3

This example describes experiments demonstrating that the octameric and hexameric morpheein forms of human PBGS can exist in a dynamic equilibrium, thus proving that morpheein equilibria, such as are illustrated in FIG. 24, can exist.

The kinetic behavior of oligomers described above led to the hypothesis that turnover facilitates the interconversion of the oligomeric structures. The experiments below demonstrate that the interactions of ligands at the enzyme active site promote the structural interconversion between human PBGS quaternary structure isoforms, favoring formation of the octamer. This observation illustrates that the assembly and disassembly of oligomeric proteins can be facilitated by the protein motions that accompany enzymatic catalysis.

Although the thermodynamic foundation for the preference of wild-type human PBGS and F12L to assemble into octamer and hexamer respectively remains unclear, the current study capitalizes on this differential preference to evaluate factors that effect the interconversion of quaternary structure isoforms of WT+F12L. The experiments below substantiate the hypothesis that the hetero-oligomers of human PBGS can interconvert, as shown in FIG. 24, upon addition of substrate. This is the first time such a dynamic structural rearrangement has been demonstrated. The current work exploits the different kinetic, chromatographic, and electrophoretic properties of the hexamers and octamers, and utilizes dynamic light scattering to determine the factors that catalyze the interconversion of PBGS quaternary structure isoforms.

PBGS from any organism has not been observed in a form smaller than the dimer. Thus heteromeric WT+F12L proteins are believed to be made up of stable dimers of three compositions, which are at position 12, Phe+Phe, Phe+Leu, and Leu+Leu. As some heterologously expressed human PBGS partitions to inclusion bodies, one cannot assume that the ratio of these dimers is 1:2:1 in the soluble isolated protein. However, because the homomeric Phe12 containing protein folds and assembles preferentially as the octamer and the homomeric Leu12 containing protein folds and assembles exclusively as the hexamer, one can propose that Phe+Phe dimers will preferentially assemble to the octamer and that Leu+Leu dimers will preferentially assemble to the hexamer. This is qualitatively consistent with the observed Phe:Leu ratio of the hetero-oligomers reported previously [39] and confirmed herein. Following this rationale, one can also propose that a dynamic re-equilibration of heteromeric oligomers (FIG. 24) would result in a disproportionation reaction that favors accumulation of Phe12 in the octamer and Leu12 in the hexamer.

Equilibrium Dialysis Experiments

The dialysis buffer was 0.1 M BTP-HCl at desired pH values, 10 mM βME and 10 μM $ZnCl_2$. The reported pH values reflect the dialysis buffer pH after the addition of ALA (where included). Protein solutions (~200 μl at 3-7 mg/mL) were dialyzed in the presence or absence of ALA against 300 mL of buffer at 37° C. for 24 hours or longer under gentle agitation (50-60 PRM) in an air shaker. Samples of the buffer were periodically withdrawn for determination of porphobilinogen concentration using Ehrlich's reagent (see above). Samples were also taken from the dialysis cassette at desired time points for native gel electrophoresis. Gels were then scanned and the fractional intensity of the protein bands at each time point was analyzed using SigmaGel™ Gel Analysis Software (Jandel Corporation).

Native Gel Electrophoresis

Native gel electrophoresis was done on a PhastGel system (Amersham Bioscience). Samples were prepared by mixing the protein solution with native gel running buffer (0.1 M Tris/HCl pH 8.8, 20% glycerol, 0.0025% Bromophenol Blue) to reach a final protein concentration of ~1 mg/mL. Four μl of each sample solution was loaded on homogeneous 12.5 polyacrylamide gel (Amersham Bioscience, 12.5% total acrylamide in separation zone, buffer 0.112 M acetate, 0.112 M Tris, pH 6.5). The gels were run with PhastGel native buffer strips (Amersham Bioscience, 0.88 M L-alanine, 0.25 M Tris, pH 8.8, made of 3% Agarose IEF). After separation, gels were developed on PhastGel system using Coomassie staining.

Light Scattering Measurements

The molecular weight change during substrate induced dynamic interconversion was monitored using a temperature-controlled DynoPro Dynamic Light Scattering Instrument (Protein Solutions Inc.) at 37° C. Protein (~1 mg/mL) was preincubated in assay buffer at 37° C. for 10 min. Immediately after the addition of ALA to a final concentration of 10 mM, the solution mixture was filtered through a 0.2 μm membrane into a 37° C. pre-warmed light scattering cuvette. The cuvette was kept at 37° C. in an incubator during the experiment except the times at which the light scattering measurements were taken. The average molecular weight calculated was based on the measurement of $KC/R_{90}$ [82]. The calculated molecular weights are lower than that expected for octamer and hexamer presumably due to the presence of a small concentration of the dimers.

Mass Spectral Analysis of the Disproportionation of Heteromeric Oligomers

WT+F12L Pool I and Pool II protein solutions underwent 24 hours of equilibrium dialysis in the presence of 10 mM ALA. The hexameric and octameric forms of the protein were separated after the dialysis using a 1 ml Mono-Q column. The Mono-Q buffer was 30 mM potassium phosphate, pH 7.0, 10 mM βME and 10 μl $ZnCl_2$. The hexameric and octameric forms were separated using a 0.02-1.0 M KCl gradient in 27 column volumes. Fractions containing hexameric and octameric forms were pooled and concentrated to a final concentration of ~1 mg/mL. The concentrated pools were dialyzed against 300 mL of 2 mM BTP-HCl buffer at pH 7.0 for 3 hours to remove the phosphate from the Mono-Q buffer. Samples were subject to overnight trypsin (Promega, sequencing grade modified) digestion using 1:20 (w/w) trypsin:protein ratio. The tryptic peptide mixtures were spotted on a gold plate with cyano-4-hydroxycinnamic acid matrix on top of that. The mass spectral data was collected using Reflex IV Matrix Assisted Laser Desorption/Ionization Time-of-Flight mass spectrometer (Bruker Inc.)

Figure 25A:
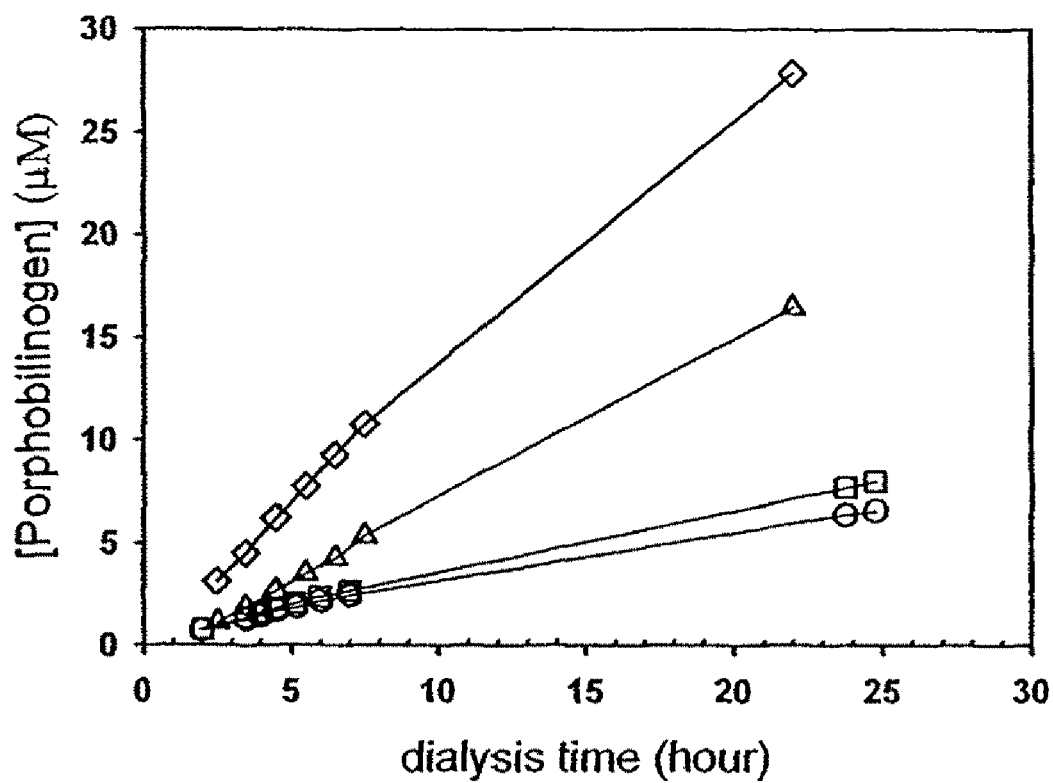
FIGS. 25A-C demonstrate dynamic interconversion of heteromeric WT+F12L human PBGS during equilibrium dialysis.
Figure 25B:
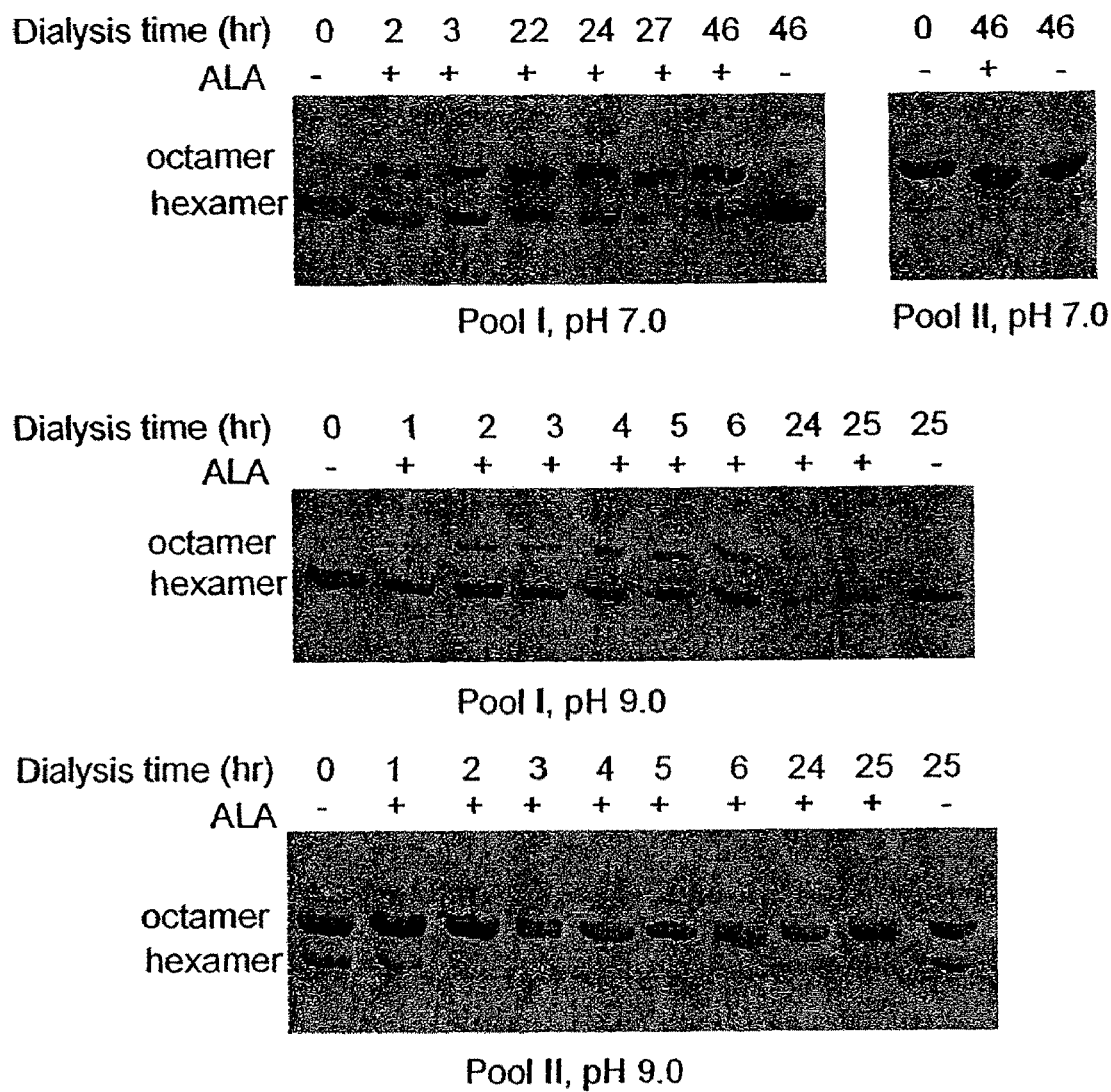
Figure 25C:
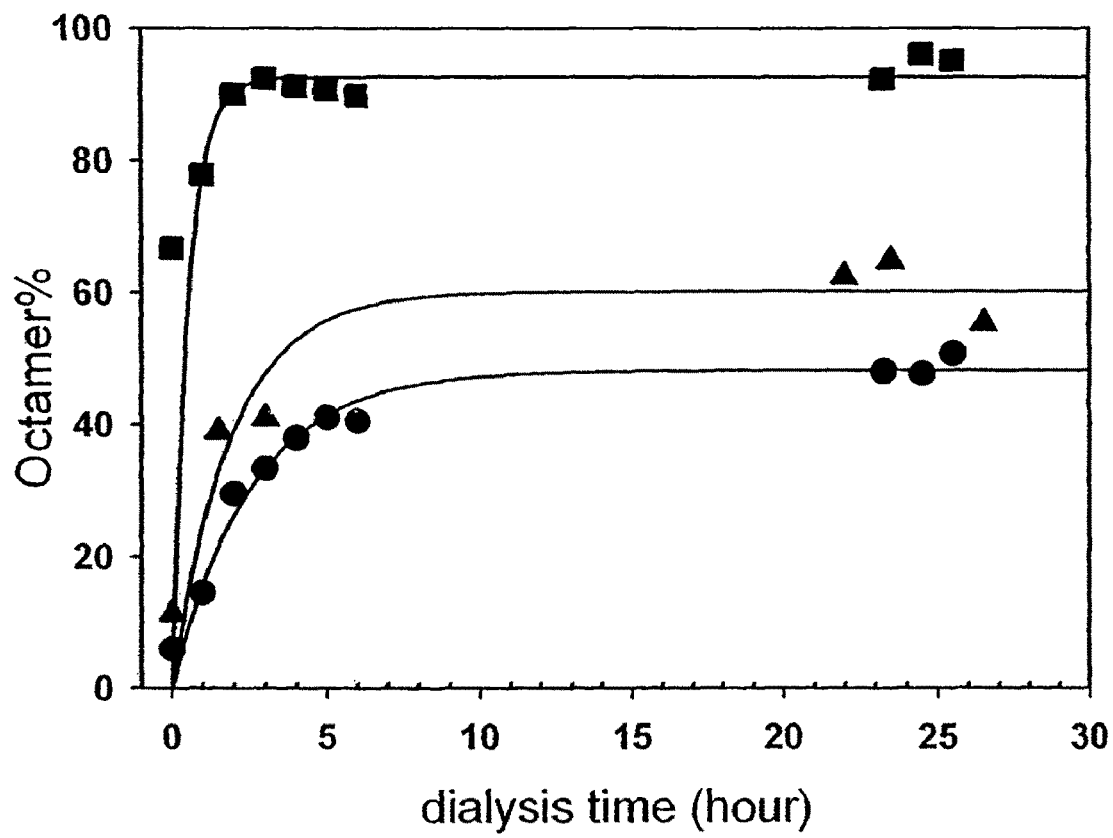

Interconversion and reequilibration of (WT+F12L) heteromeric oligomers were monitored by equilibrium dialysis. Using heteromeric Pool I and Pool II, equilibrium dialysis was used to provide a physical demonstration that substrate can promote the reequilibration between octamer and hexamer as per the reaction illustrated in FIG. 24. The proteins comprised of Pool I and Pool II were separately dialyzed at 37° C. in the presence and absence of the substrate, ALA, and the quaternary structure was probed by native gel electrophoresis as a function of dialysis time. Product formation was monitored in the dialysate and indicated that catalysis was ongoing throughout the dialysis procedure (FIG. 25A). The electrophoretic results (FIG. 25B) show that the oligomeric structures are stable for at least 46 hours when dialysis is carried out in the absence of substrate. However, the presence of the substrate causes a dramatic reequilibration of quaternary structure isoforms, favoring accumulation of the octamer in all cases (Pool I and Pool II at pH 7.0 and pH 9.0). These pH values correspond to the optimal pH for the activity of the octamer and the hexamer respectively[39]. Densitometry was used to estimate the rate and extent of the re-equilibration reaction for Pool I at pH 7 and pH 9 and for Pool II at pH 9 (FIG. 25C), where the data was fitted to a exponential function and fit to rate constants of $0.54 \, h^{-1}$ (Pool I, pH 7), $0.4 \, h^{-1}$ (Pool I, pH 9), and $1.8 \, h^{-1}$ (Pool II, pH 7) respectively. The rate and extent of conversion of Pool I to octamer was greater at pH 7 than at pH 9, suggesting that there is a pH dependence to the equilibrium between the PBGS quaternary structure isoforms. This is consistent with data on wild type human PBGS (octamer) where kinetic evidence indicates catalysis by both octamer and hexamer at pH 9 but catalysis only by octamer at pH 7 [39].

Analysis of Pool I and Pool II Oligomers Following the Substrate Induced Interconversion of Quaternary Isoforms.

Figure 26A:
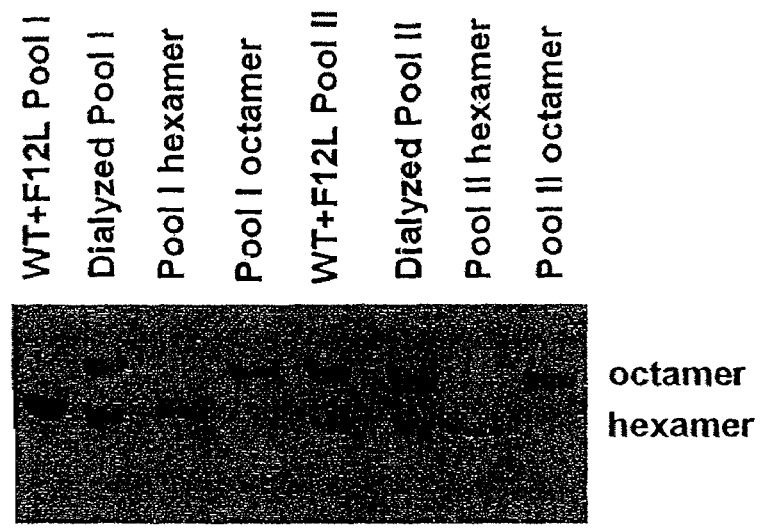
FIGS. 26A and B demonstrate analysis of the disproportionation products of human Wt+F12L Pool I and Pool II, first introduced in FIG. 17A.

Using freshly prepared hetero-oligomers of WT+F12L, the Pool I and Pool II proteins were separated chromatographically and then dialyzed for 24 hours at pH 7 in the presence of 10 mM ALA. Following dialysis, the re-equilibrated hetero-oligomers were again separated into their hexameric and octameric components by chromatography on a Mono-Q column. The separated proteins were characterized for their specific activity and for their Phe12 and Leu12 content. The specific activity of hexamer and octamer are dramatically different with hexamer showing optimal activity at pH 9 and the activity of octamer is maximal at pH 7 (Table 4) [39]. A native gel of these proteins shows the relative distribution of octamer and hexamer in samples before dialysis and after Mono-Q chromatography (FIG. 26A). Following chromatographic separation, the proteins were called Pool I hexamer, Pool I octamer, Pool II hexamer, and Pool II octamer and are described below. The peak to elute first on the Mono-Q column runs comparably to the F12L mutant, which is the hexamer. The hexameric structure is substantiated by native gel electrophoresis and by specific activity at pH 7 and pH 9 (FIG. 26A and Table 4). The second peak to elute runs comparably to the WT human PBGS, which is the octamer. The octameric structure is substantiated by native gel electrophoresis and specific activity at pH 7 and pH 9 (FIG. 26A and Table 4). Consistent with the documented characteristics of human PBGS hexamers and octamers [39], Pool I hexamer and Pool II hexamer have very low activity at pH 7 and considerable activity at pH 9. Pool I octamer and Pool II octamer both show substantially higher activity at pH 7 than at pH 9.

Figure 26B:
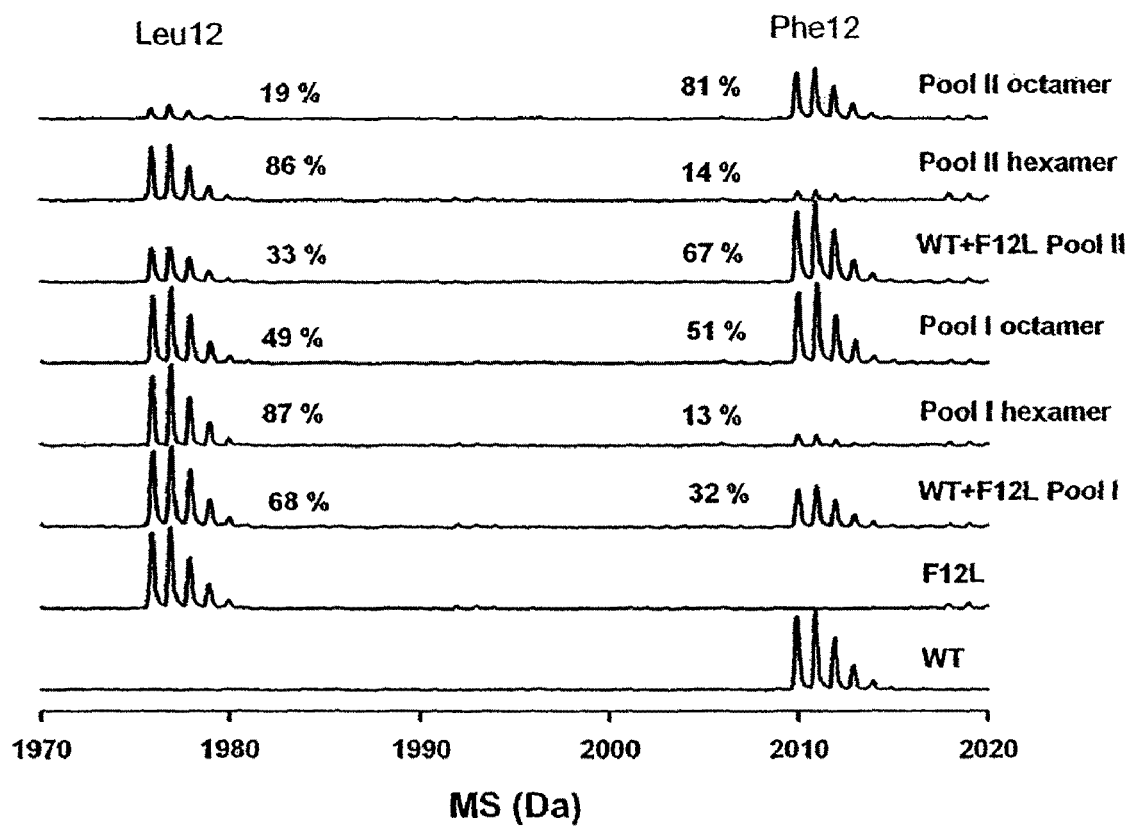
FIG. 26B shows mass spectral data for the N-terminal tryptic peptide of WT+F12L Pool I and WT+F12L Pool II before and after the disproportionation reaction and Mono-Q chromatography. WT and F12L are included as standards.

To address the hypothesis that hetero-oligomeric WT+F12L pools will disproportionate, resulting in accumulation of Phe12 in the octamer and Leu12 in the hexamer, the Phe12 and Leu12 content of the heteromeric PBGS oligomers was determined before dialysis and after Mono-Q chromatography. The proteins were subjected to tryptic digestion and the N-terminal peptide was analyzed by laser desorption mass spectroscopy. Prior work had established that this technique gives quantitative results that are comparable to those obtained by quantitative N-terminal sequencing for these two very similar peptides [39]. The mass of the N-terminal tryptic peptides are 2010.2 Da for the Phe12-containing peptide and 1976.2 Da for the Leu12-containing peptide (FIG. 26B). The data confirm that both Pool I and Pool II contain heteromeric species. The Pool I protein, initially a hetero-hexamer at a Phe:Leu ratio of 32:68, when dialyzed against ALA, yields the Pool I hexamer and a Pool I octamer of respective ratios 13:86 and 51:49. This demonstrates a dramatic disproportionation of the Leu-containing species to the hexamer and the Phe-containing species to the octamer. The dramatic change in the Phe:Leu ratio was also observed when the Pool II protein, initially at 67:32, was dialyzed against ALA. On native gel, Pool II shows a major octamer band and a light hexamer band (FIG. 26A). After 24 hours of dialysis in the presence of ALA, the Pool II octamer was enriched in Phe (Phe:Leu ratio of 81:19) and the small amount of remaining hexamer was enriched in Leu (Phe:Leu ratio of 14:86). The mass spectral data unequivocally establishes the disproportionation of heteromeric PBGS isoforms under turnover conditions. The mass spectral data also confirm that human PBGS with phenylalanine at position 12 prefers the octamer, which assembles from the hugging dimer, and protein with leucine at position 12 prefers the hexamer, which assembles from the detached dimer. It remains unclear whether the dynamic structural interconversion illustrated in FIG. 24 is further complicated by the dissociation of dimers into their component monomers. Such a re-equilibration of dimers could result in the disproportionation of a population of Phe+Leu dimers into Phe+Phe and Leu+Leu dimers.

Figure 27A:
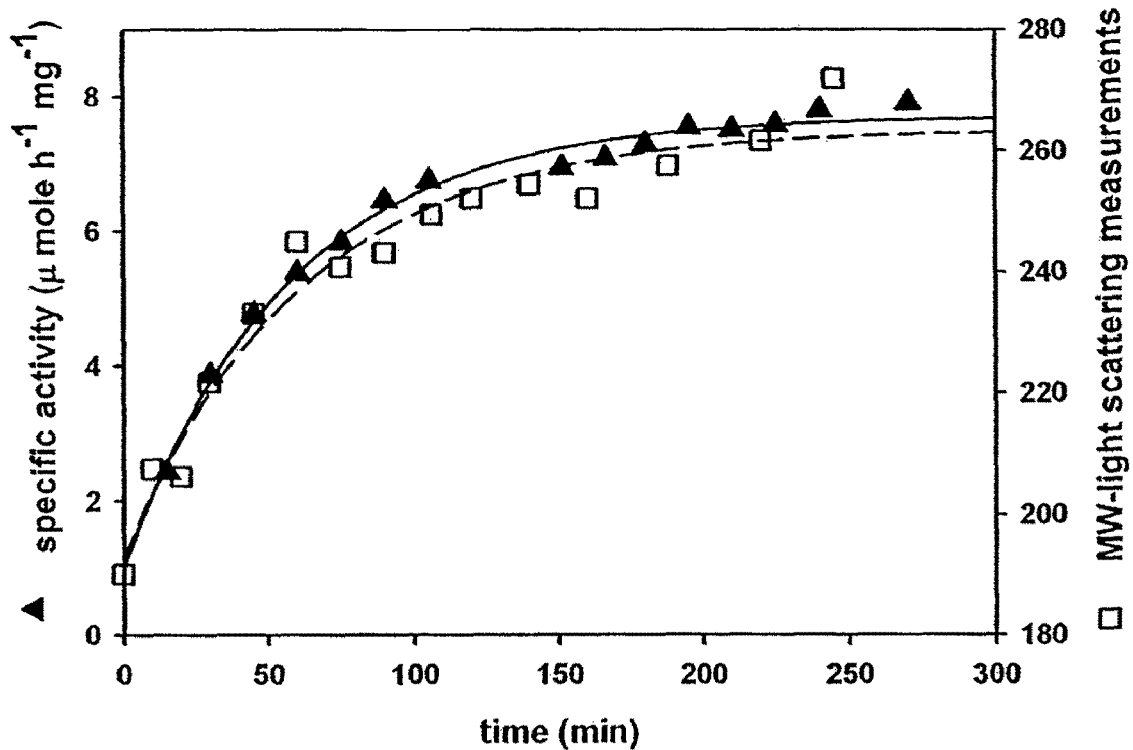
FIG. 27A illustrates the substrate induced dynamic interconversion (disproportionation) of WT+F12L hetero-hexamers (Pool I) to WT+F12L hetero-octamers at pH 7 by monitoring the increase in specific activity with time (▲) and the increase in molecular size by dynamic light scattering. Pools I is introduced in FIG. 17A.
Figure 27B:
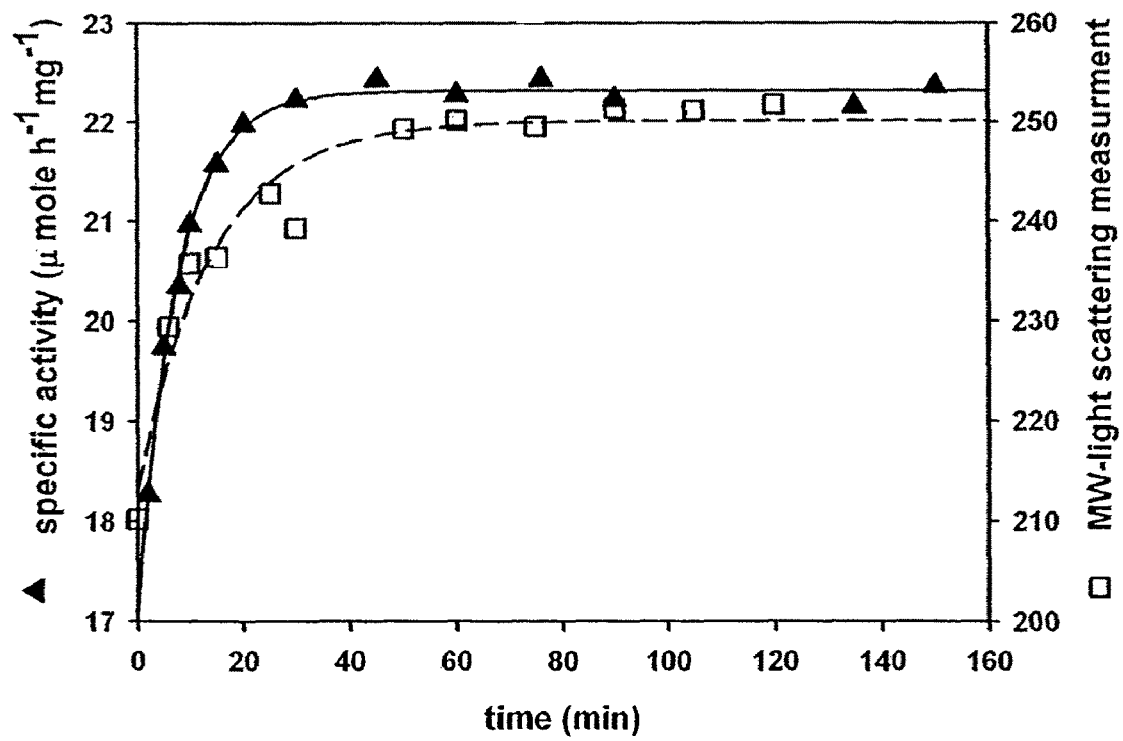
FIG. 27B is like FIG. 27A but starts with Pool II. Pool II is introduced in FIG. 17A.

It has been observed that dynamic interconversion of WT+F12L hetero-oligomeric PBGS quaternary structure isoforms is accompanied by an increase in activity at pH 7. Prior kinetic studies of PBGS showed that the dependence of activity on substrate concentration does not follow a simple hyperbolic Michaelis-Menten relationship (Tables 1 and 3). The kinetic data are best fit using a double hyperbolic equation, which is applicable to a model in which two enzymes of different kinetic parameters are catalyzing the same reaction [81]. The substrate induced structural interconversion (FIGS. 25A-C and 26A-C) and the resulting specific activity changes (Table 4) suggest that the heteromeric WT+F12L pools undergo structural rearrangement under assay conditions. Since substrate induced interconversion favors the octamer, which has increased activity at pH 7 relative to the hexamer, then the time course of product formation should show an increase in rate with time. This change is proposed to be most dramatic for Pool I (the heterologously expressed heterohexamer of WT+F12L) at pH 7, where the difference between the activities of octamer and hexamer is the greatest. As predicted, the specific activity of WT+F12L Pool I protein increases with time (FIG. 27A). The rate constant ($1.05\ h^{-1}$) is based on fitting the data to an exponential rate equation and is about twice as fast as that determined from the equilibrium dialysis experiment ($0.54\ h^{-1}$), qualitatively consistent with an expected delay caused by the time required for substrate and product to cross the dialysis membrane. Similar behavior was observed for WT+F12L pool II where the rate constant is $7.9\ h^{-1}$ (FIG. 27B).

Structural interconversion between hexamer and octamer not only has an effect on the protein's activity; it also alters the average molecular weight of protein. Using dynamic light scattering, the molecular weight change during the structural rearrangement of Pools I and II in the presence of substrate was monitored (FIGS. 27A-B). The light scattering data yield rate constants that are comparable to the rate constants from the time course activity assay ($1.0\ h^{-1}$ for Pool I at pH 7, $5.0\ h^{-1}$ for Pool II), thus supporting the conclusion that the increase in activity is due to the interconversion of hexamer to octamer in the presence of substrate.

Light scattering was used as a method for monitoring the equilibration of quaternary structure isoforms. Light scattering has been used as a powerful tool for protein characterization, including purification monitoring [83], aggregation [84], assembly [85], structural stability [86], and crystal growth [87]. The current work is the first use of light scattering to monitor the molecular weight change due to the dynamic interconversion of quaternary structure isoforms of a homomeric protein. This demonstration opens possibilities for investigation of the kinetics of protein structure changes that in some cases could be very difficult to monitor by other spectroscopy techniques.

The dynamic interconversion of PBGS quaternary isoforms and the resulting disproportionation introduces the morpheein concept of quaternary structure equilibrium. The morpheein concept describes alternate quaternary structures of a protein with different functional characteristics, such as the octameric and hexameric forms of PBGS. The differences in oligomeric multiplicity, structure, and function result from a dramatic conformational change in the monomer. The interconversion and disporprotionation between heteromeric human PBGS morpheein forms, as demonstrated herein, substantiates the reaction illustrated in FIG. 25.

TABLE 4

Specific activities ($\mu mol\ h^{-1}\ mg^{-1}$) of hexameric and octameric forms of human PBGS before and after substrate induced disproportionation.

|      | F12L | WT   | WT + F12L Pool I | WT + F12L Pool I | Pool I hexamer | Pool I octamer | Pool II hexamer | Pool II octamer |
|------|------|------|------------------|------------------|----------------|----------------|-----------------|-----------------|
| pH 7 | 0.3  | 56.9 | 7.9              | 21.8             | 0.5            | 11.5           | 0.2             | 17.6            |
| pH 9 | 14.5 | 13.1 | 6.6              | 5.4              | 5.8            | 6.8            | 1.6             | 5.7             |

Example 4

This example describes building the models for the hexameric morpheein forms of *P. aeruginosa* PBGS and *R. capsulatus* PBGS.

The only existing crystal structure on which one can base a model of hexameric *R. capsulatus* (or any other) PBGS is that of hexameric human PBGS clinical variant F12L, PDB code 1PV8 [39]. Unfortunately, the crystal structure of F12L shows significant disorder, which limits its use as the sole foundation for homology model building. However, comparison of human PBGS octameric and hexameric structures (PDB codes 1E51 and 1PV8) show near identity for the amino acids that comprise a TIM-like αβ-barrel domain. The differences between the octamer and the hexamer are in the 24 N-terminal amino acids and in the disordered regions [39]. Hence, one can use a higher quality crystal structure of a PBGS octamer for homology model building the αβ-barrel domain of *R. capsulatus* PBGS. The chosen structure is PDB code 1GZG [40], which is a highly ordered, high resolution crystal structure of *Pseudomonas aeruginosa* PBGS, and 56% sequence identical to *R. capsulatus* PBGS. The model building procedure was a two step process. The first step was construction of a model of a hexameric form of *P. aeruginosa* PBGS; the second step was to use that hexamer to build the *R. capsulatus* PBGS hexamer.

*P. aeruginosa* PBGS hexamer preparation used various capacities of the program Swiss-PDB Viewer [88] and some in-house programs. First, the N-terminal arms (amino acid numbers<32) were removed from the structure file for the 1GZG dimer. The resulting αβ-barrel domains were successively overlaid upon the three dimers of hexameric 1PV8 to create a hexameric assembly of *P. aeruginosa* PBGS αβ-barrels. There is no significant sequence identity between the N-terminal arms of human and *P. aeruginosa* PBGS, hence there is an alignment ambiguity when trying to build the outstretched arms of the *P. aeruginosa* PBGS hexamer. However, there is a region of the arm that is α-helical in both the human octamer and the human hexamer. Hence, a structure alignment of octameric forms of human PBGS and *P. aeruginosa* PBGS was used to determine the proper sequence alignment for this α-helical segment. This information was used to spatially position the amino acids 22-29 of *P. aeruginosa* PBGS in the hexamer according to the position of this helix in the hexamer of human PBGS. Loop and side-chain prediction was performed in a graphical user environment [89], developed in the FCCC Molecular Modeling Facility, that integrates the functions of the programs Loopy [90], and SCWRL [91]. Within this environment, the program Loopy [90] was used to model the backbone of amino acids 29-32, so as to connect the N-terminal α-helix to the αβ-barrel domain of each subunit. The most N-terminal amino acids were built onto the structure within the Swiss-PDB viewer software using phi, psi, and omega angle information for the corresponding amino acids of hexameric human PBGS. Finally, the program SCWRL [91] was used to position the side chains for the N-terminal arm segments resulting in a model for hexameric *P. aeruginosa* PBGS, which could then be used for preparing hexameric models of other PBGS as has been done before for the octameric forms of pea and *D. melanogaster* PBGS [13,16]. The model for hexameric *R. capsulatus* PBGS was build using the same integrated graphical environment developed in house. This software integrates sequence alignment, threading, loop model building to accommodate insertions and deletions; and side chain optimization similar to that used for previously published models [13,16].

Example 5

Experimental Data with Rosmarinic Acid

Figure 22A:
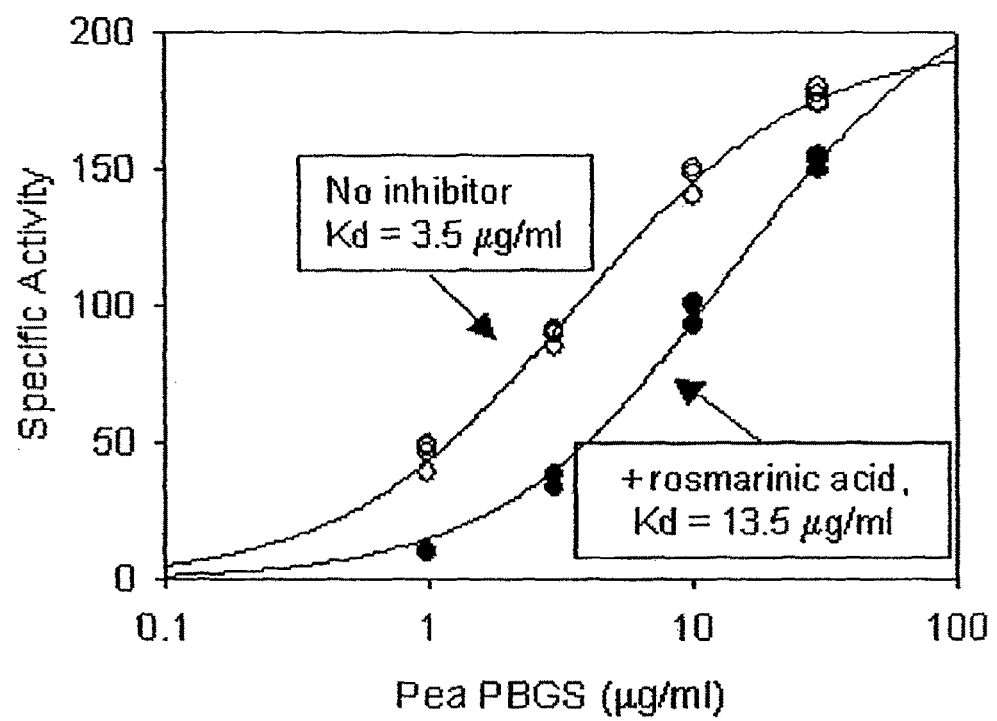
FIG. 22A shows the effect of rosmarinic acid on the protein concentration dependence of pea PBGS.
Figure 22B:
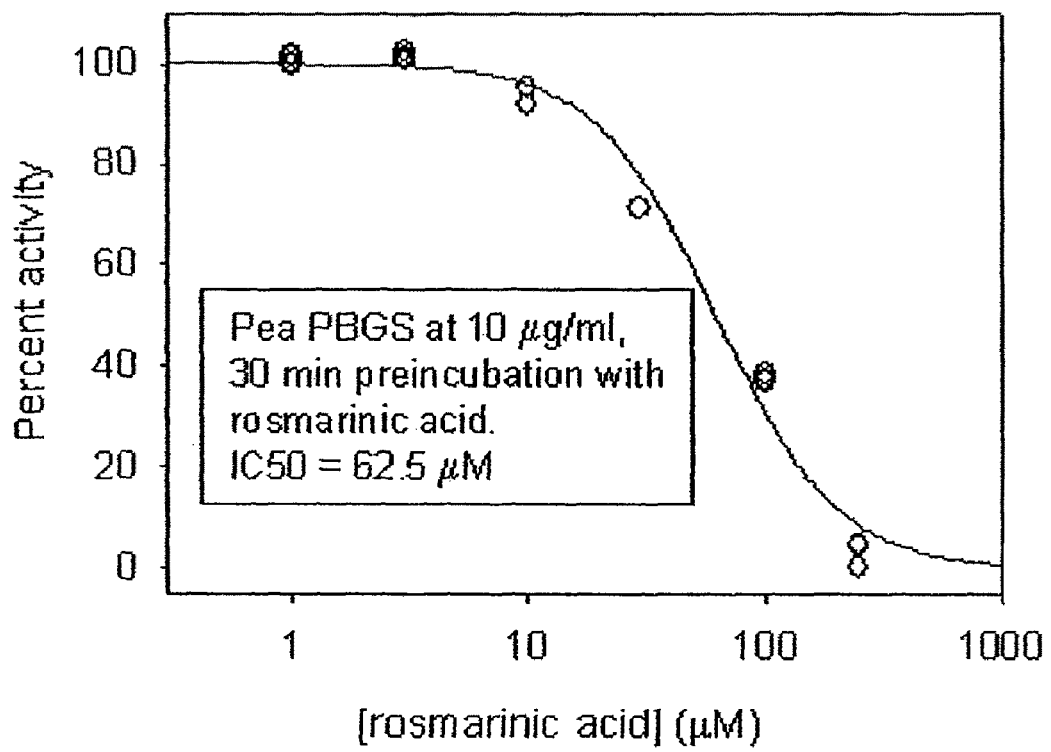
FIG. 22B shows a dose response curve for rosmarinic acid acting on pea PBGS.
Figure 22C:
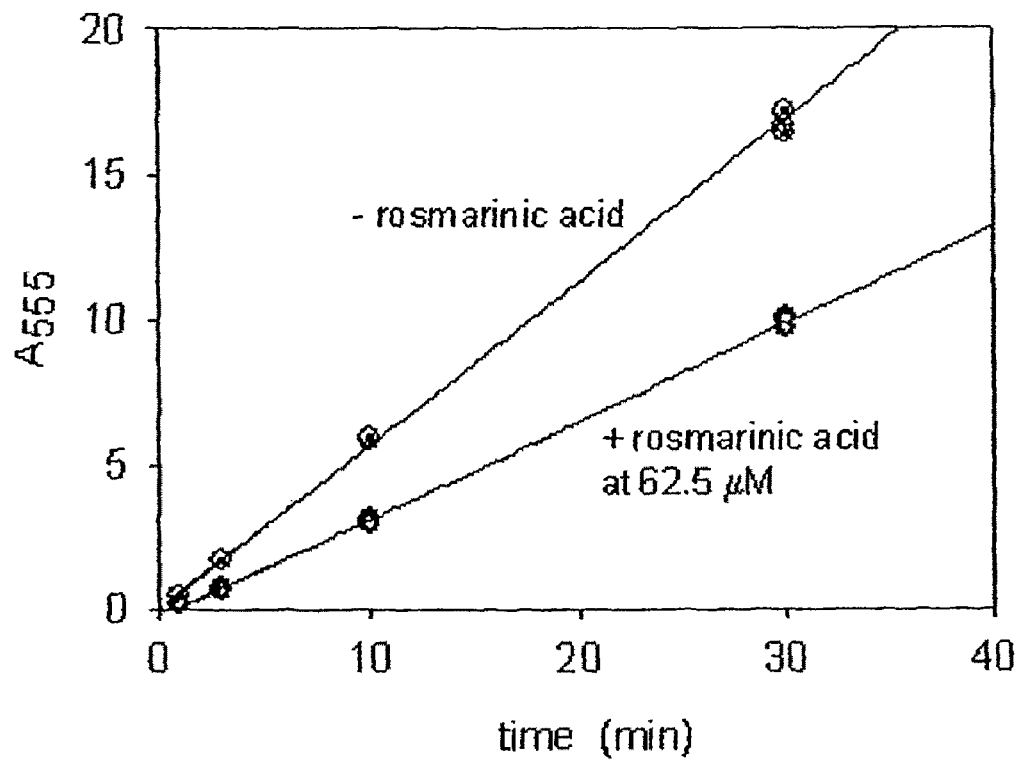
FIG. 22C shows that the enzyme catalyzed reaction rate is linear following treatment with rosmarinic acid.
Figure 23A:
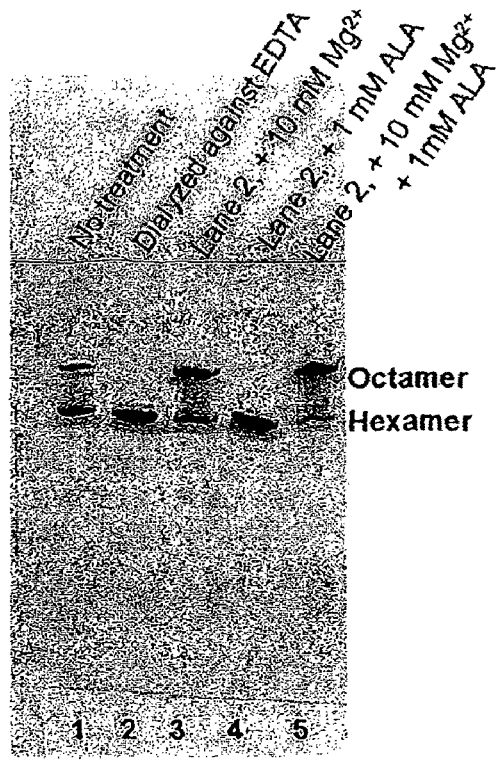
FIG. 23A shows the differential effects of various treatments on the morpheein equilibrium of pea PBGS, as analyzed by 12.5% acrylamide native gel electrophoresis. The protein is pea PBGS variant C326A, which has all the characteristics of the wild type protein. Lane 1—as purified; Lane 2—dialyzed against EDTA at low salt (10 mM BTP) to make the hexamer; Lane 3—hexameric pea PBGS (same as lane 2) treated with 10 mM magnesium, which helps to form the octamer from the hexamer; Lane 4—hexameric pea PBGS treated with ALA alone, which does not reform the octamer from the hexamer; Lane 5—hexameric pea PBGS treated with 10 mM magnesium and 1 mM ALA, which is more effective than magnesium alone at shifting the equilibrium toward the octamer.
Figure 23B:
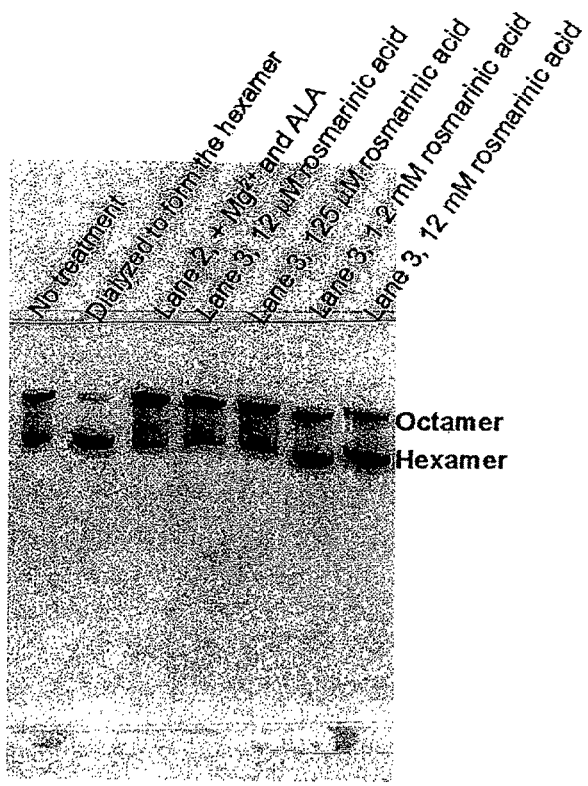
FIG. 23B shows that rosmarinic acid stabilizes the hexamer of pea PBGS C326A against conversion from hexamer to octamer. Lane 1—as purified; Lane 2—dialyzed against EDTA at low salt (10 mM BTP) to make the hexamer; Lane 3—hexameric pea PBGS (same as lane 2) preincubated at 37 C for 30 min followed by 5 min with 1 mM ALA and 1 mM $MgCl_2$, which shifts the equilibrium away from the hexamer and toward the octamer. Lane 4-7 like lane 3, but with the addition of rosmarinic acid in the preincubation mixture at 12.5 µM, 125 µM, 1.25 mM, and 12.5 mM rosmarinic acid. Increasing concentrations of rosmarinic acid are shown to prevent conversion of the hexamer to the octamer by magnesium and ALA.

Inhibition data with rosmarinic acid (benzenepropanoic acid, α-[[(2E)-3-(3,4-dihydroxyphenyl)-1-oxo-2-propenyl]oxy]-3,4-dihydroxy-, (αR)-(9CI)) is consistent with a slow-tight binding inhibition model wherein rosmarinic acid binds preferentially to the quaternary forms of pea PBGS that are smaller than the octamer. FIG. 22A, open symbols, illustrates the protein concentration dependence of the specific activity of pea PBGS, which shows half maximal activity at 3.5 μg/ml PBGS. This means that at 3.5 μg/ml (under assay conditions), the equilibrium of quaternary isoforms (morpheein forms) contains about 50% octamer and about 50% smaller less active isoforms (e.g. hexamers). If an inhibitor acted through preferential binding to these smaller forms, one would expect a more profound inhibition under conditions where the morpheein equilibrium contains these smaller forms. In other words, the inhibitor would be expected to shift the protein concentration dependence to a higher protein concentration, which is shown for rosmarinic acid in FIG. 22A (see below). FIGS. 22B and 22C show experiments that were done to determine how best to demonstrate this shift in protein concentration dependence. FIG. 22B shows a dose response curve for pea PBGS, which indicates that the $IC_{50}$ for rosmarinic acid is ~63 μM, when the inhibitor is given 30 minutes to act on the protein prior to the addition of substrate. Not shown is the dependence of the inhibition on the preincubation time, where inhibition by any one concentration of rosmarinic acid increases with increasing preincubation time, showing that rosmarinic acid acts as a slow-binding inhibitor. FIG. 22C shows that once inhibition has taken place, the protein does not recover within a 30 minute assay time. The data obtained in FIGS. 22A, 22B, and 22C, were used to choose the appropriate conditions necessary to demonstrate the effect of rosmarinic acid on the protein concentration dependence of pea PBGS, as follows. The closed circles of FIG. 22A show the protein concentration dependence of the specific activity of pea PBGS following a 30 minute treatment with 30 μM rosmarinic acid, which results in half maximal activity at 13.5 μg/ml PBGS. Thus, following this treatment with rosmarinic acid, the equilibrium of quaternary forms has shifted from 3.5 μM to 13.5 μM; under these conditions it takes 13.5 μg/ml PBGS to obtain an equilibrium with 50% octamer. This is consistent with the interpretation that rosmarinic acid stabilizes the smaller, less active forms of PBGS, as illustrated schematically in by the balls in FIG. 13. FIG. 23A-B (described in detail below) support this conclusion with native gel electrophoresis data.

FIG. 23A shows the effects of magnesium and ALA on the hexamer-octamer equilibrium of pea PBGS (variant C326A) [13]. Lane 1—Pea PBGS as purified runs as an octamer/hexamer mixture. Lane 2—hexameric pea PBGS can be prepared (from lane 1) by dialysis against 1 mM EDTA, 10 mM BTP. This suggests that magnesium stabilizes the octameric. Lane 3—hexameric pea PBGS, from lane 2, incubated with 10 mM $MgCl_2$. Magnesium, which is proposed to be the specific allosteric activator that stabilizes the octamer, indeed fills this role. Lane 4—hexameric pea PBGS, from lane 2, incubated with 1 mM ALA, does not run differently from lane 2. This is consistent with the data on the human protein which shows that the hexameric form does not bind ALA very well. Lane 5—hexameric incubated with both 10 mM $MgCl_2$ and 1 mM ALA. One can observe a dramatic conversion of the hexamer to the octamer under conditions where the protein is active and the equilibrium can be drawn toward the octamer. This, like all other incubations, was for 5 min at 37° C.

FIG. 23B shows that rosmarinic acid stabilizes the hexameric pea PBGS against conversion to the octamer in the presence of ALA and magnesium. FIG. 23B is obtained using pea PBGS (C326A) under the following conditions: Lane 1—as purified; Lane 2—dialyzed to make the hexamer; Lane 3—hexameric pea PBGS (from lane 2) preincubated at 37 C for 30 min followed by 5 min with 1 mM ALA and 1 mM $MgCl_2$. Again this demonstrates how substrate plus magnesium causes conversion of the hexamer to the octamer; Lane 4-7 Like lane 3, but with the addition of rosmarinic acid in the preincubation mixture at 12.5 µM, 125 µM, 1.25 mM, and 12.5 mM rosmarinic acid.

Based on the inventor's modeling results, the interactions of this biphenyl compound (rosmarinic acid) with the "arm pit" of the pea PBGS hexamer are predominantly through hydrogen bonds between the protein subunits A, B, and E and the polar moieties of the rosmarinic acid. The protein contains additional hydrogen bonding potential within 4.0 angstroms of the rosmarinic acid. Hence, a derivative of the rosmarinic acid can be made to have an improved binding by adding additional hydrogen bonding potential to the rosmarinic acid molecule. For instance, one could add a hydroxyl group at the 5 position of either phenyl moiety and improve hydrogen bonding to the protein. Additional hydrophobic interactions with the protein could be obtained by substituting a phenyl or benzyl group at the 2 position of the propanoic acid portion of the molecule.

Example 6

A Prophetic Example

Inhibition of GDP-Mannose Dehydrogenase

Figure 29A:
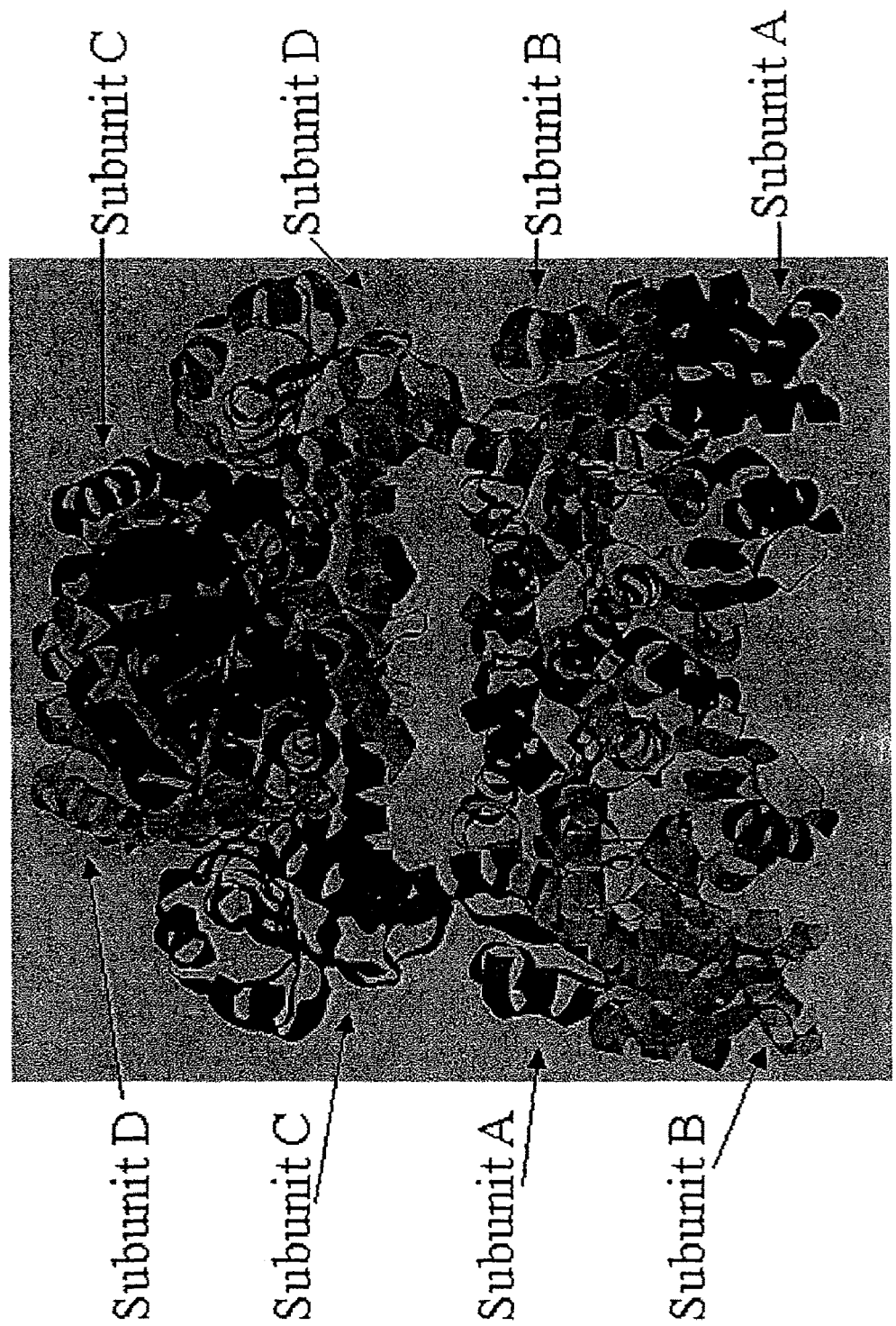
FIG. 29A is an illustration of the crystallographic asymmetric unit for *Pseudomonas aeruginosa* GDP-Mannose dehydrogenase, which is a tetramer [18]. The protein subunits are represented with ribbons, subunits A and C are in black, subunits B and D are in gray.

The alginates are a family of polysaccharides that exist in the cell walls of brown algae and in the capsular material (biofilm) that is laid down by some pathogenic *Pseudomonas* and *Azotobacter*. In the service of mankind alginate has been used as a wound dressing, but to the scourge of mankind the alginate laid down by pathogens provides a barrier against the host immune response and against antibiotics. Thus, inhibition of alginate biosynthesis is an attractive target for antibiotic development, particularly toward the antibiotic resistant *Pseudomonas aeruginosa* that have become ubiquitous hospital pathogens. *Pseudomonas aeruginosa* GDP-mannose dehydrogenase (GMD, EC 1.1.1.132) is a key regulatory enzyme in the biosynthesis of alginate [92]. The inventor proposes the existence of GMD morpheein forms based published kinetic phenomena [19]. The specific activity is dependent upon the concentration of the enzyme and is dependent upon the order of addition of reaction components. Activity assays initiated by addition of enzyme show marked hysteresis, whereas assays of the same composition started by the addition of the NAD cofactor show a constant activity, suggesting that substrate initiates a re-equilibration of GMD morpheein forms from a less active form to a more active form. Measurements of GMD size and cooperativity suggest that the catalytically active form is a hexamer, perhaps in equilibrium with a trimer [19]. However the published crystal structure (FIG. 29A) shows a tetramer made up of two loosely associated dimers [18]. In support of an active and an inactive form, it has been reported that GMD "interconverts readily" between two forms, which are a "cooperative" form with a low affinity for NAD but a higher $V_{max}$ and a "noncooperative" form with a high affinity for NAD but a lower $V_{max}$ [19,93]. The inventor proposes that the available crystal structure represents the low $V_{max}$ morpheein.

Figure 29B:
FIG. 29B is side view of the AB dimer, including enzyme-bound ligands in space filling representation, white. The illustration on the left uses ribbons to represent subunits A and B, while the illustration on the right uses a space filling representation. In the right hand illustration one can see how the active site ligand are buried.
Figure 29C:
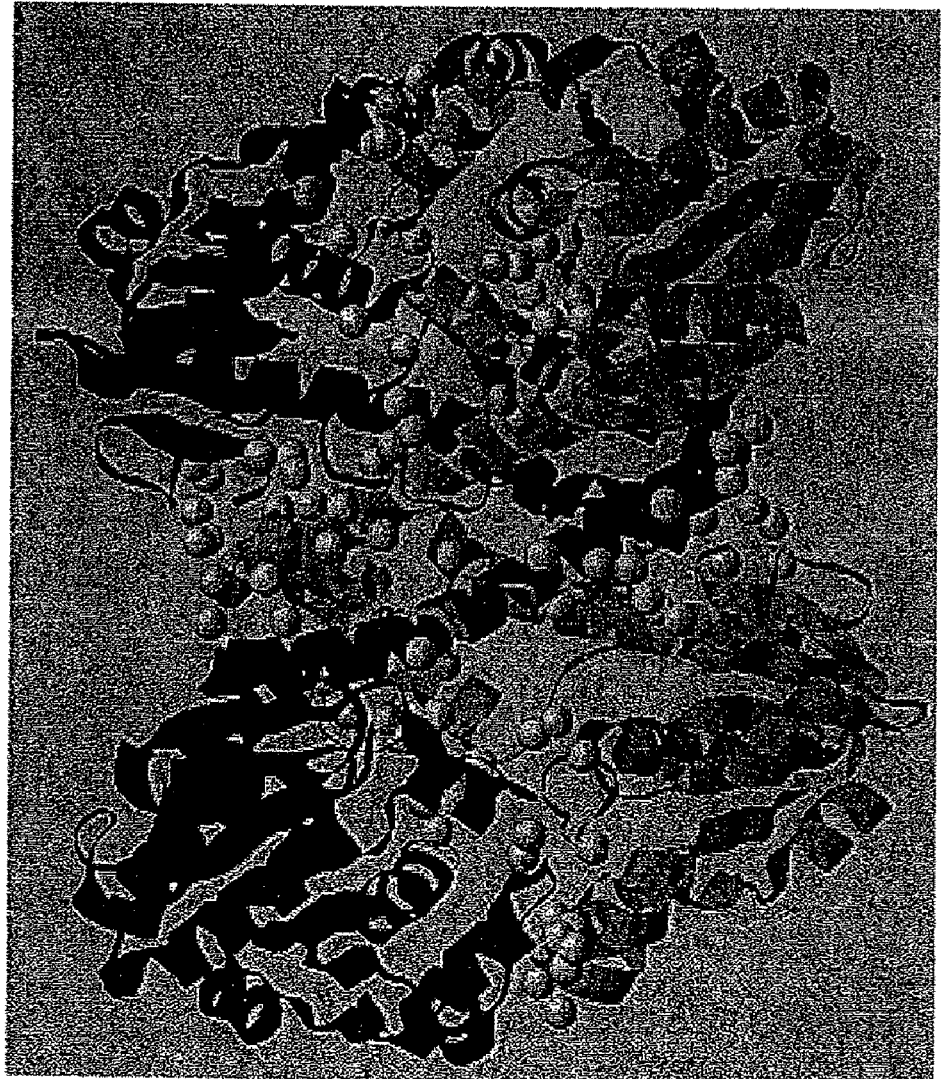
FIG. 29C is a similar side view of the AB dimer, illustrating the large number of ordered water molecules that solvate the dimer interface.

The crystallographic tetramer of *Pseudomonas aeruginosa* GDP-Mannose dehydrogenase (FIG. 29A, PDB code 1MV8) shows the intimate, almost pretzel-like relationship between subunits A and B or C and D, but the weak interaction between the AB and CD dimers. FIG. 29B shows a side view of the AB dimer, the left half uses a ribbon representation for the protein and a white space filling representation for the enzyme bound ligands. The right half uses a space filling representation for the protein as well. A comparison of the left and right halves shows how the active site ligands are located between subunits, and in fact are nearly buried between them. One can imagine that the protein might need to substantially reorient these subunits in order to release the ligands, which in the crystal structure are NAD and an analog of GDP-mannose. The inventor proposes that this dimer or tetramer is the low activity form that binds NAD very tightly and also proposes that it may be possible to trap this form to prevent formation of the active hexamer, whose structure remains unknown. In support of the notion that this structure can readily unravel are the large number of water molecules that lie at the subunit interfaces. FIG. 29C shows the water molecules (as white spheres) that are within 4.0 A of both subunits A and B.

Figure 29D:
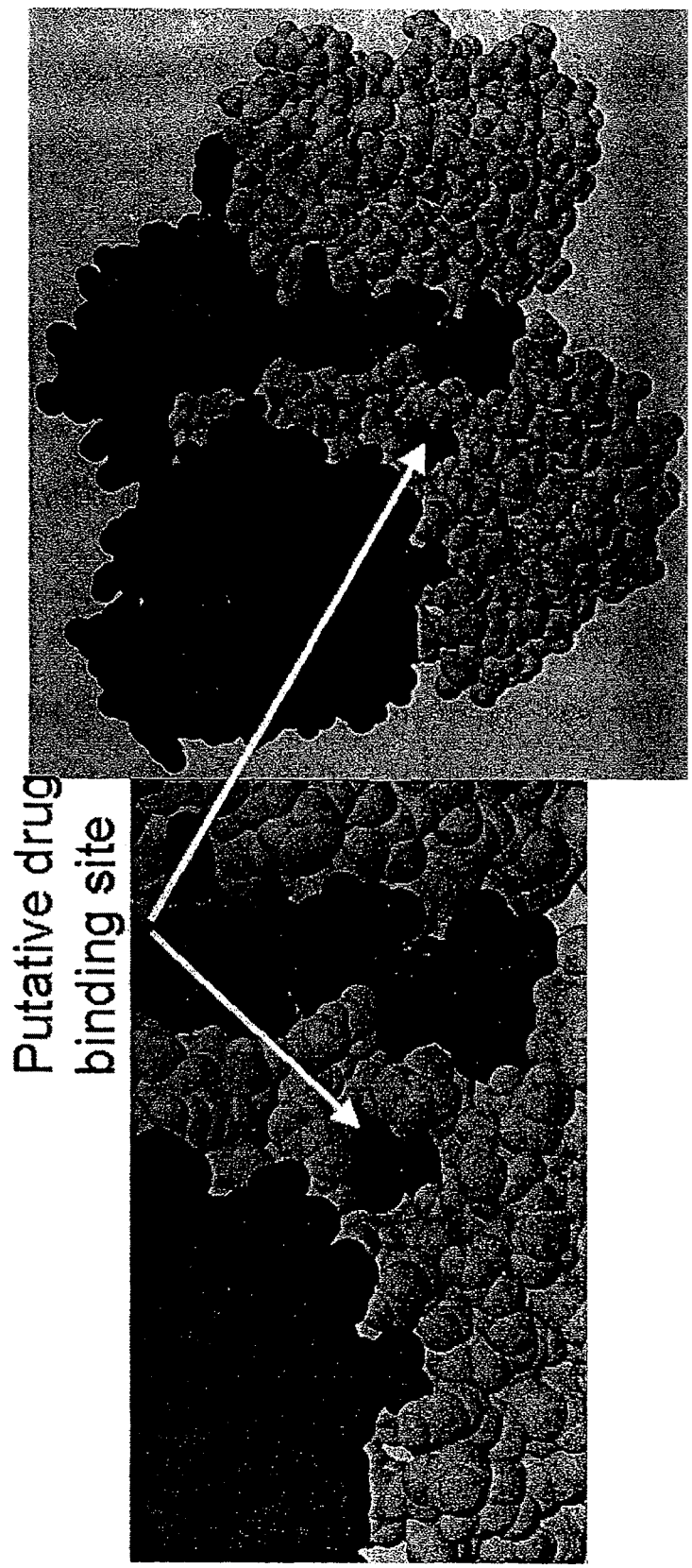
FIG. 29D uses a space filling representation of the side view of the AB dimer to show the surface cleft that is predicted as a putative drug binding site. This site is enlarged on the left.

The surface of the AB dimer of GMD has at least one deep pocket which can be targeted for drug discovery (FIG. 29D). This binding pocket is comprised of residues from both subunits and a ligand bound at this site would be expected to draw the morpheein equilibrium toward this putatively less active form. This example relies on the presumption that the intimately intertwined dimer must come apart and re-associate in order to form the more active hexameric morpheein. To test this hypothesis, the 1.6 A crystal structure of *Pseudomonas aeruginosa* GMD will be used, this pocket will be selected as the drug binding site, and the cited in silico methods will be used to dock compounds into this site. Hit molecules would then be tested for their ability to inhibit GMD in a way that effects the protein concentration dependence to the specific activity.

Example 7

A Prophetic Example

Locking the Bacterial Histidine Containing Phosphocarrier Protein Kinase/Phosphatase as the Phosphatase Active Oligomer The bifunctional HPr kinase/phosphatase (HPrK/P, EC 2.7.1.–/3.1.3.) of most gram-positive (and some gram negative) bacteria is involved in the regulation of carbon catabolite repression or activation. This complex regulatory pathway allows bacteria to adapt rapidly to environmental changes in carbon sources [20], thus ensuring their survival. The inventor proposes that HPrK/P exists as morpheein forms for the following reasons. The complex kinetics of HPrK/P shows varying degrees of cooperativity dependent upon the reaction conditions. The crystal structures of HPrK/P from *Lactobacillis casei* [94], *Staphylococcus xylosis* [95] and *Mycoplasma pneunoniae* [96] all show a hexameric assembly composed of two trimers. Based on these crystal structures, it has been suggested that nucleotide binding would either involve an unusual configuration of the nucleotide, or that the protein would have to change its quaternary structure to accommodate the nucleotide [20]. Hence, this hexameric morpheein form is proposed to be the one with phosphatase activity; this morpheein form cannot be a kinase if it cannot bind the nucleotide. A detailed analysis of *B. subtilis* HPrK/P suggests a pH dependent structural equilibrium of monomers, dimers, and hexamers [97]; the lower oligomeric states, whose structures are unknown, are proposed to be the kinase active forms. The oligomeric structure equilibrium is affected by allosteric activators and substrates, which suggests that the oligomerization state is an important factor in the switch between kinase and phosphatase activity [97]. A tryptophan fluorescence study, which predated the crystal structure determinations, concluded that the enzyme exists as a heterogeneous population of oligomers, approximately a 50/50 mixture of two forms. One form contained the single tryptophan residue in a solvent exposed position and the other form contained the tryptophan in a position that was buried from solvent [98]. The inventor has mapped the unique tryptophan of *B. subtilis* HPrK/P onto the crystal structure of *Lactobacillus casei* HPrK/P (PDB code 1KKJ) and finds this tryptophan to be completely solvent exposed, (illustrated in FIG. 30) which is interpreted to reflect the population of oligomers (~50%) where tryptophan fluorescence was readily quenched by the addition of iodide. Because this tryptophan is on the surface of the hexamer, a simple dissociation of hexamer to trimers, dimers, or monomers would not change the solvent exposed character of the unique tryptophan. Hence, the kinase active form is proposed to involve an alternate morpheein configuration wherein this tryptophan is buried.

Figure 31:
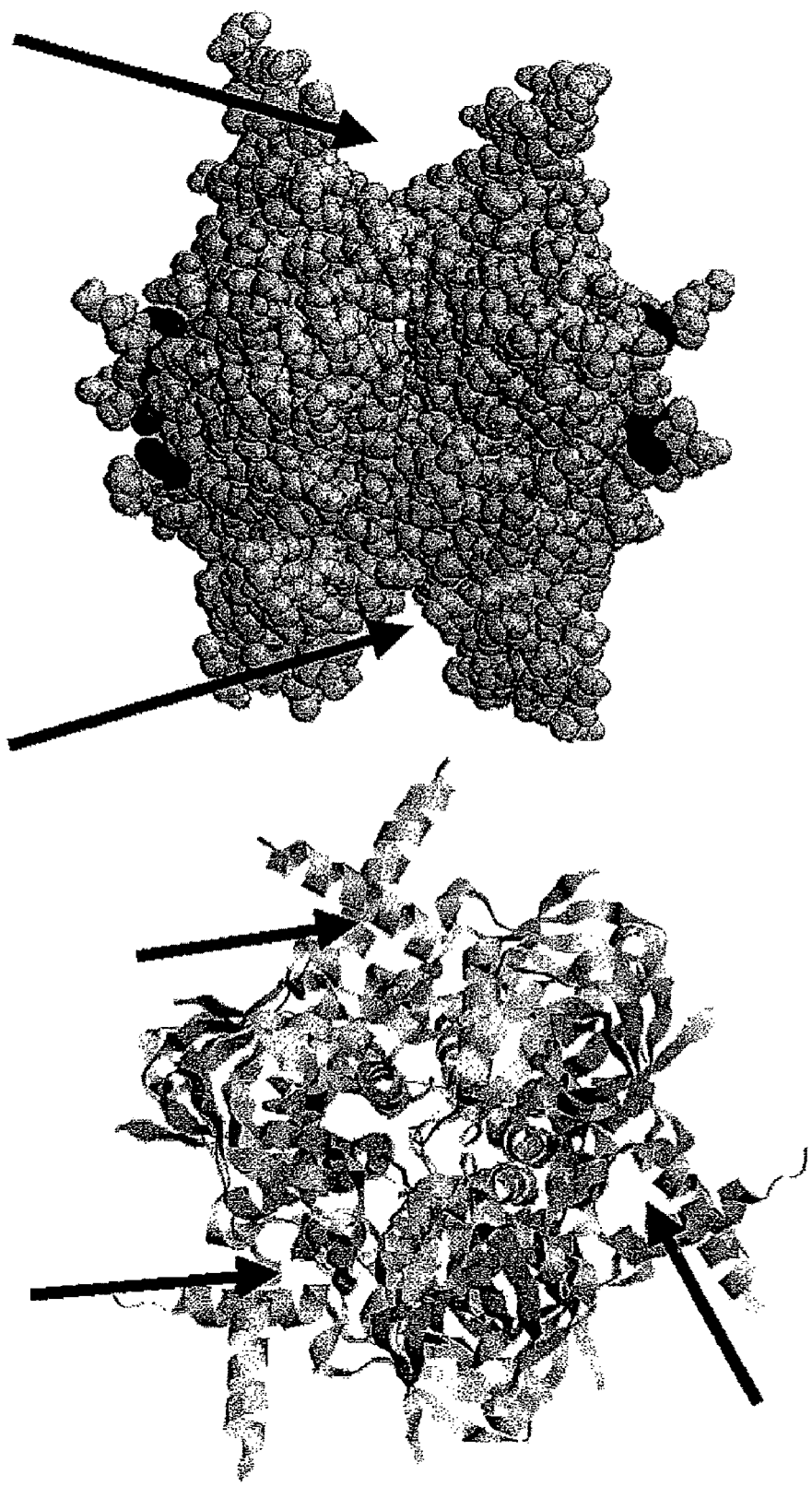
FIG. 31 illustrates the same two orientations of the crystal structure of *Lactobacillus casei* HPrK/P, in the hexameric assembly, without the HPr protein. The arrows depict an alternative drug binding site. The top illustration uses a space filling representation and the bottom uses a ribbon diagram.

Since there is no available crystal structure for the kinase active form of HPrK/P, the inventor suggests a rationale for trapping the phosphatase active hexameric form. When HPr is phosphorylated at Ser-46, it is capable of interacting with a carbon catabolite control protein. In the absence of this interaction, one could predict that the bacteria would not be capable of turning on the genes necessary for metabolizing the available carbon sources. Hence, one could argue that trapping HPrK/P in the hexameric assembly might act to inhibit bacterial cell growth, or to encourage the bacteria to enter a sporulation state. The *L. casei* structure, illustrated in FIG. 30 shows the three surface tryptophans forming the base of a unique surface binding site for a putative drug molecule that will trap this hexameric, putatively kinase inactive form of the protein. Surface tryptophan residues clustered such as these should form an excellent binding site, however the cleft is a shallow one. Furthermore, this tryptophan is not conserved in all HPrK/P from pathogenic organisms. FIG. 31 illustrates an alternative cleft in the hexameric assembly of HPrK/P, which is a deep surface cleft and is expected to be a common structure (if not a common sequence) for all the HPrK/P proteins.

Example 8

Figure 35:
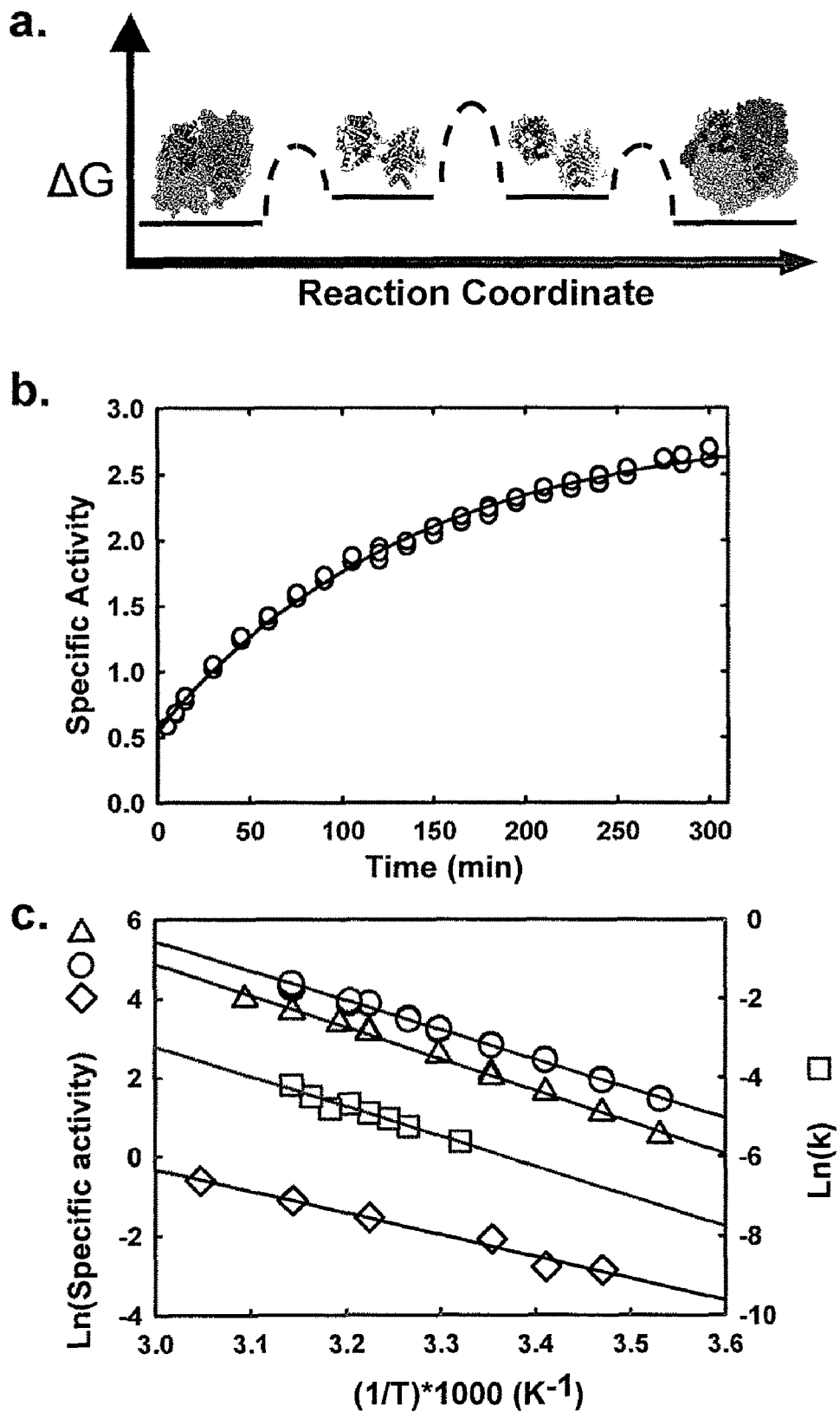
FIG. 35 illustrates thermodynamic analysis of the conversion of WT+F12L hetero-hexamers to hetero-octamers and substrate turnover by WT, F12L, and WT+F12L hetero-octameric human PBGS.

Temperature Dependence of the Rate of Approach to the WT+F12L Morpheein Equilibrium The inter-conversion of the WT+F12L hetero-hexamers and hetero-octamers requires at least three steps, which are oligomer dissociation, conformational change at the level of dimer, and oligomer association; each step has specific thermodynamic properties (e.g. Keq and Ea), as illustrated schematically in FIG. 35a. The equilibrium position of the first and third steps, each a dissociation constant, must be protein concentration dependent (i.e. to the third power of the pro-hexamer dimer concentration and to the fourth power of the pro-octamer dimer concentration). The association rates must also be protein concentration dependent, but the association/dissociation events do not require protein backbone conformational changes. In contrast, the middle step is a protein concentration independent event that minimally requires changes in backbone and side chain conformation at several positions along the N-terminal 24 amino acids of each chain. In the absence of turnover, the WT+F12L PBGS hetero-oligomers appear stable; that is, interconversion is not observed. Re-equilibration appears to require some process that is part of catalytic turnover (e.g. some active site based covalent inhibitors also promote hetero-oligomer equilibration (5)). There are no independent data addressing the rates of the first and third steps in the absence of turnover, but we can conclude that the middle step, the conformational change in the human PBGS dimer, is of low probability in the absence of active site ligands. The presence of active site ligands lowers the activation energy for the dimer interconversion step. With this in mind, the free energy of activation for the conversion of hetero-hexamers to hetero-octamers was determined and compared that with the free energy of activation for substrate turnover.

To determine the free energy of activation for the conversion of hetero-hexamers to hetero-octamers, we took advantage of the dramatic differences in the activity of octameric (high activity) and hexameric (low activity) human PBGS at pH 7.0 (3, 5). Because of this difference, the transition from purified hetero-hexamers to a mixture of hetero-hexamers and hetero-octamers under turnover conditions is accompanied by a progressive increase in the specific activity; this process was monitored at several temperatures. Starting with purified hetero-hexamers, (FIG. 34a) the specific activity increased, which is fit to a first-order exponential as exemplified in FIG. 35b (5). At all temperatures, the assay included a 10 min pre-incubation of 10 μg/mL hetero-hexamer in 0.1 M BTP, pH 7.3, 10 μM ZnCl2, 10 mM BME, and the reaction was initiated by the addition of a temperature equilibrated aliquot of 0.1 M ALA-HCl to a final concentration of 10 mM (which brought the final pH to 7.0). The time-courses for conversion of hetero-hexamer to hetero-octamer were monitored by periodically removing aliquots from the incubations and immediately quantifying porphobilinogen using Ehrlich's reagent and calculating specific activities based on the total incubation time. Rate constants, obtained over the range of 28-45° C., are presented as an Arrhenius plot (FIG. 35c). The Arrhenius plot is linear over the range of temperatures employed, which suggests that the rate limiting step is the same at all temperatures. An activation energy for hetero-hexamer to hetero-octamer conversion (Ea=63±5 kJ/mol) was determined from the slope of the plot. The contributions of the individual processes to the energy barrier for conversion of hexamer to octamer are unknown. However, we previously monitored this process at 5 μg/ml and 0.9 mg/ml, two widely different enzyme concentrations, by specific activity increase and dynamic light scattering respectively. The observed identical rates of approach to equilibrium (5), indicate that the rate of hetero-hexamer to hetero-octamer conversion is independent of protein concentration. In the direction from heterohexamers to heterooctamers, the hexamer dissociation process and the internal dimer conformational change process are expected to be independent of protein concentration, suggesting that one of these is the rate determining process.

Example 9

Activation Energy for Catalysis by WT, F12L and WT+F12L Hetero-Octameric Human PBGS As some aspect of substrate turnover is a prerequisite for the conversion of metastable hetero-hexamers to hetero-octamers, the free energies of activation for substrate turnover by WT, F12L and WT+F12L hetero-octameric human PBGS were determined. Assay conditions were the same as those used to determine the activation energy for conversion of hetero-hexamers to hetero-octamers (pH 7.0, 10 mM ALA-HCl). The Arrhenius plots from whose slope the activation energies were derived, are shown in FIG. 35c. The activation energies for substrate turnover by WT octamer and WT+F12L hetero-octamer were determined to be 62±1 kJ/mol and 67±1 kJ/mol respectively, values that are remarkably similar to that for the conversion of hetero-hexamers to hetero-octamers. However, for the F12L variant, a lower activation energy of 45±3 kJ/mol for substrate turnover was obtained, indicating that the rate limiting step in catalysis by the PBGS hexamer is different from that for catalysis by the PBGS octamer, and different from the rate limiting step for hetero-hexamer to hetero-octamer conversion.

Example 10

The Synthesis of 6-{N-[1-(4-NITROPHENYL)-1-HYDROXYETHYL]SULFAMOYL}BENZ(CD)INDOL-2(1H)-ONE (Morphlock 1)

The synthesis route leading to 6-{N-[1-(4-Nitrophenyl)-1-hydroxyethyl]sulfamoyl}benz(cd)indol-2(1H)-one is shown in Scheme 1.

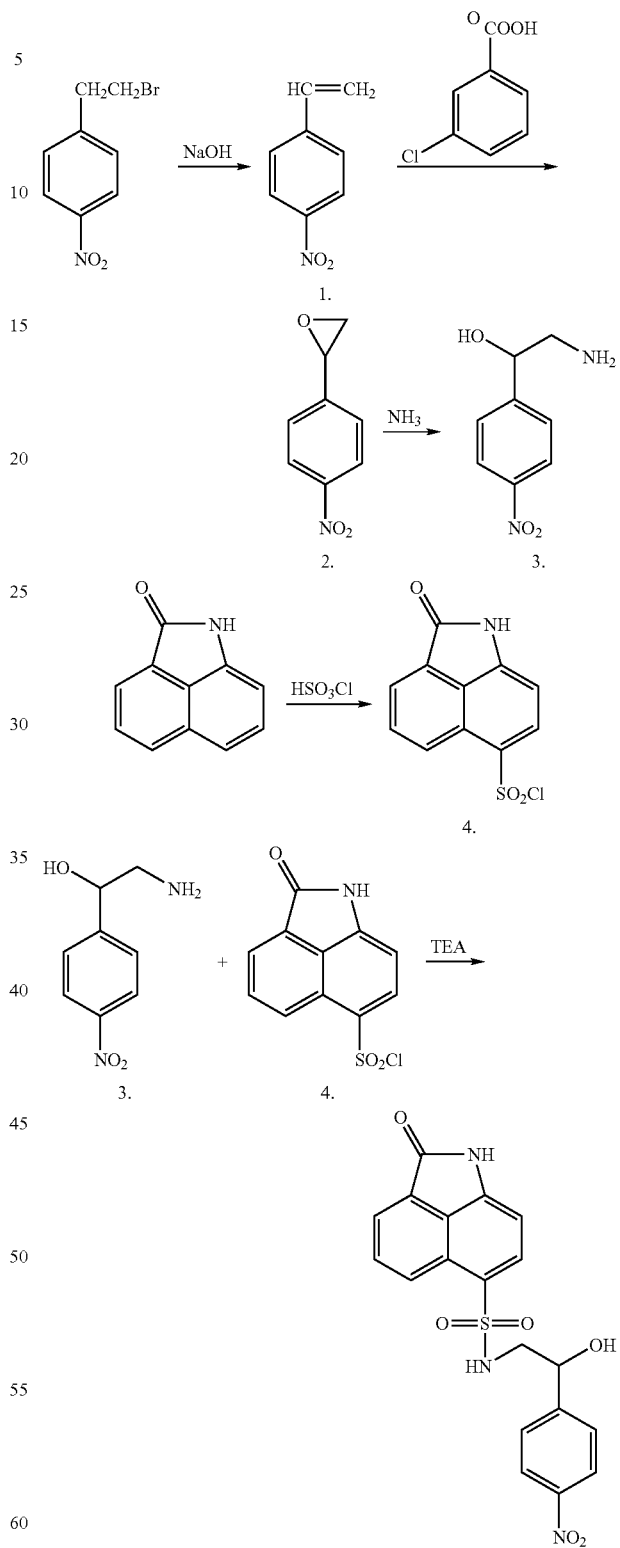

MATERIALS AND METHODS: All solvents were obtained from Fisher unless otherwise noted. 4-Nitrophenylbromide, 3-chlorobenzoylperoxide, benz[cd]indol-2(1H)-one, and chlorosulfonic acid were obtained from Aldrich. Petroleum ether and DMF were obtained from Acros, while triethylamine was obtained from Sigma. TLC analysis was performed on EMD Silica Gel 60 $F_{254}$ coated plates. Melting points were determined using a Fisher-Johns melting point apparatus and are uncorrected. $^1$H-NMR analysis was recorded on a Bruker Advance WB 300 MHz instrument with TMS as an internal standard. Mass Spectroscopy was carried out at HT Laboratories (San Diego, Calif.) using electrospray. SYNTHESIS: 4-Nitrostyrene (1). Exactly 13.71 g (0.34 moles) of sodium hydroxide was dissolved in 200 ml anhydrous ethanol. The temperature was raised to 40° C. and 10.0 g (0.043 moles) of 4-nitrophenylbromide was added with stirring. The reaction mixture was heated 40° C. for 30 minutes and then poured into a solution of 40 g of sodium chloride in 200 ml water. The resulting mixture was extracted with 3×25 ml of diethyl ether. The combined organic extracts were dried over magnesium sulfate and the solvent was removed in vacuo. The residue was extracted twice with hot petroleum ether and the combined extracts were placed in the freezer for 72 hours. The crystalline product was filtered and dried under high vacuum. Evaporation of the filtrate gave a second crop of crystals. Total weight of styrene was 5.465 g (84% yield). TLC analysis (1:1 ether/hexane) Rf=0.84. $^1$H-NMR ($d_6$DMSO): δ6.12 (d, 1H, $CH_2$), 6.54 (d, 1H, $CH_2$). 6.89 (dd, 1H, CH), 7.61 (d, 2H, Ar), 8.21 (d, 2H, Ar ortho to $NO_2$).

4-Nitrophenyloxirane (2). A solution consisting of (1) 3.396 g (22.5 mmoles) and 3-chlorobenzoylperoxide 3.881 g (22.5 mmoles) in 40 ml chloroform was stirred at 0-4° C. for 92 hours, then at ambient temperature for 24 hours. Any precipitate that formed during this period was dissolved by the addition of extra chloroform. TLC (1:1 ether/hexane) indicated the complete disappearance of the starting olefin. The solution was washed with 2×15 ml of 10% sodium hydroxide, 20 ml of water, followed by 20 ml of saturated brine. The organic phase was dried with sodium sulfate. Evaporation of the chloroform gave a white residue. This was slurried in 60 ml hexane, filtered and dried under vacuum which yielded 2.383 g (64%). TLC (1:1 ether/hexane) Rf=0.70. Melting point was 80-81° C. $^1$H-NMR ($CDCl_3$) δ2.78 (dd, 1H, $CH_2$), 3.2 (dd, 1H, $CH_2$), 3.97 (t, 1H, CH), 7.46 (d, 2H, Ar), 8.22 (d, 2H, Ar ortho to $NO_2$).

2-Hydroxy-4-nitrophenethylamine hydrochloride (3). Oxirane (2) 0.500 g (3.03 mmoles), 12 ml of 5.05 M methanolic ammonia (60.6 mmoles), and 25 ml anhydrous methanol were sealed in a 130 ml stainless steel bomb. The bomb was stirred at 60° C. for 14 hours and 90 hours at ambient temperature The solvent was removed under reduced pressure and the residue treated with two portions of methanol followed by evaporation in order to remove any remaining ammonia. The residue was dissolved in methanol and acidified with hydrochloric acid, then treated with carbon. The carbon was filtered and the solvent was removed under reduced pressure to yield 0.662 g (60%) of the amine hydrochloride salt. $^1$H-NMR ($d_6$DMSO) δ2.90 (m, 1H, $CH_2$), 3.13 (m, 1H, $CH_2$), 4.99 (t, 1H, CH), 6.42 (d, 1H, OH), 7.62 (d, 2H, Ar), 8.20 (s, 2H, $NH_2$), 8.29 (d, 2H, Ar ortho to $NO_2$). ESIMS calculated for $C_8H_{10}N_2O_3$ 182, found 183 $(M+H)^+$.

6-Chlorosulfonylbenz[cd]indol-2(1H)-one (4). Benz[cd]indol-2(1H)-one (2.523 g; 14.9 mmoles) was added slowly to 5.1 ml of chlorosulfonic acid while keeping the temperature below 15° C. The reaction mixture was heated to 60° C. and held there until no more HCL gas evolved. Then, the reaction mixture was poured into 125 ml of cold water. The resulting solid suspension was extracted twice with ethyl acetate. The combined ethyl acetate extracts were washed with water, saturated sodium bicarbonate, saturated brine, then dried with sodium sulfate. The solvent was removed and the residue was recrystallized from chloroform/ethyl acetate. The yield of the title compound was 1.620 g (41%). A Beilstein test confirmed the presence of the chlorine atom. Melting point was 194-197° C. (dec) $^1$H-NMR ($d_6$DMSO) δ6.86 (d, 1H, Ar), 7.79 (m, 2H, Ar), 7.98 (d, 1H, Ar), 8.72 (d, 1H, Ar), 10.83 (s, 1H, NH).

6-{N-[1-(4-Nitrophenyl)-1-hydroxyethyl]sulfamoyl}benz (cd)indol-2(1H)-one (5). 2-Hydroxy-4-nitrophenethylamine hydrochloride (3) 0.820 g (3.75 mmoles), 4-chlorosulfonyl-benz[cd]indol-2(1H)-one (4) 1.004 g (3.75 mmoles) and triethylamine (1.04 ml; 7.5 mmoles) were dissolved in 20 ml anhydrous dimethylformamide with stirring. The reaction was heated at 100° C. for 20 hours. The solvent was removed under reduced pressure. The residue was dissolved in ethyl acetate washed with 0.5 N HCl, water, followed by saturated brine. The ethyl acetate layer was dried with sodium sulfate, the solvent was removed and the residue recrystallized from acetonitrile to yield 1.55 g (21%) of the title compound. TLC (ethyl acetate) Rf=0.68. $^1$H-NMR, ($CD_3CN$) δ3.13-3.29 (m, 2H, $CH_2$), 3.74 (d, 1H, J=3.9 Hz, OH), 4.71 (d, 1H, J=4.5 Hz, NH), 5.91 (t, 1H, CH), 6.94 (d, 1H, J=7.5 Hz), 7.23 (d, 2H, J=8.4 Hz), 7.74-7.93 (m, 3H), 7.98 (dd, 2H, J=2.7 & 6.9 Hz), 8.44 (d, 1H, J=8.4 Hz), 8.86 (s, 1H, NH).

Example 11

MODIFICATIONS: Various modification of 6-{N-[1-(4-Nitrophenyl)-1-hydroxyethyl]sulfamoyl}benz(cd)indol-2 (1H)-one will be apparent to a person skilled in the art In Scheme 2, non-limiting examples of analogs of 6-{N-[1-(4-Nitrophenyl)-1-hydroxyethyl]sulfamoyl}benz(cd)indol-2(1H)-one (labeled as "A" in Scheme 2) are shown.

Scheme 2

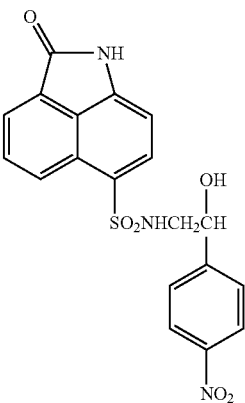

"B"
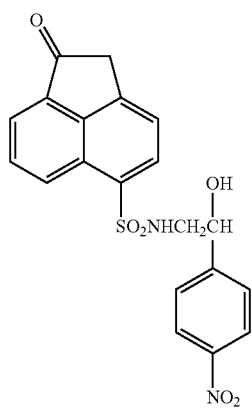
"C"
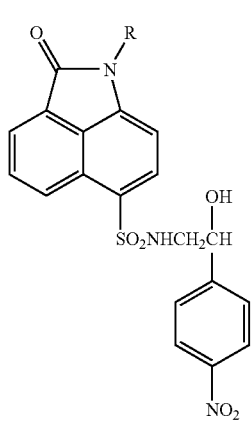
"D"
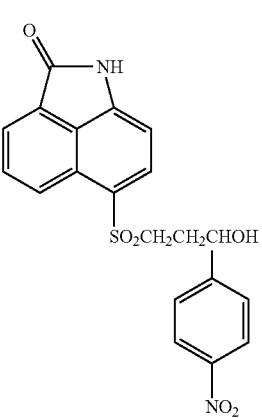
"E"
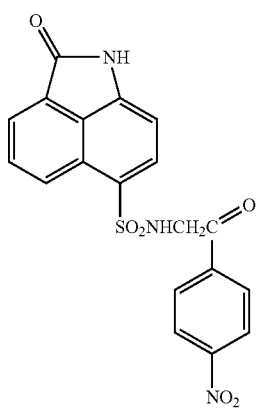
"F"
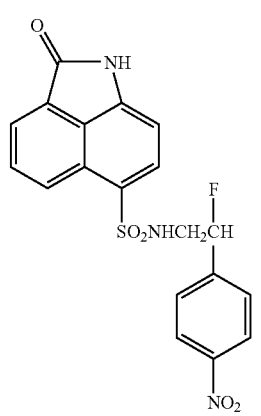
"G"
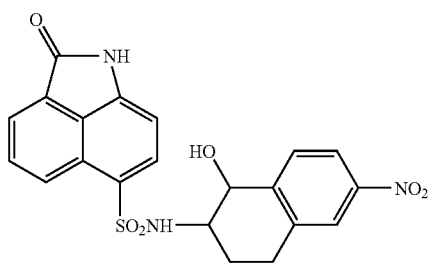
"H"
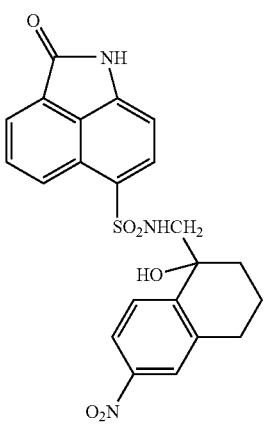
"I"

95
-continued
"J"
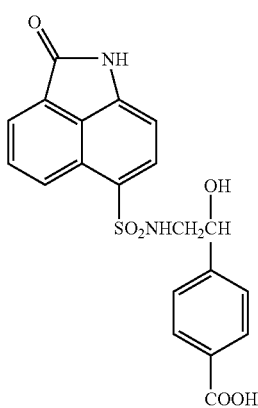
"K"
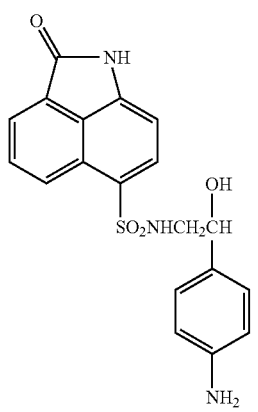
"L"
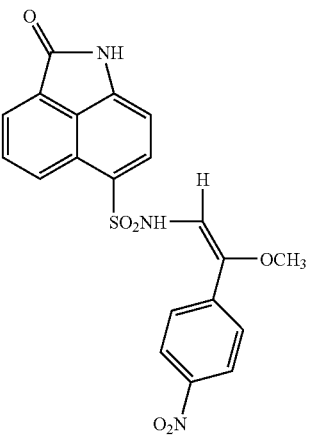
Methods of making compounds B-L presented in Scheme 2 will now be described.
96
Example 12
Synthesis of
DL-5-{N-[1-(4-NITROPBENYL)-1-HYDROXYE-THYL]SULFAMOYL}-1-OXOACENAPTHALENE
(6) (Compound "B")
The synthesis route leading to (6) is shown in Scheme 3.
Scheme 3
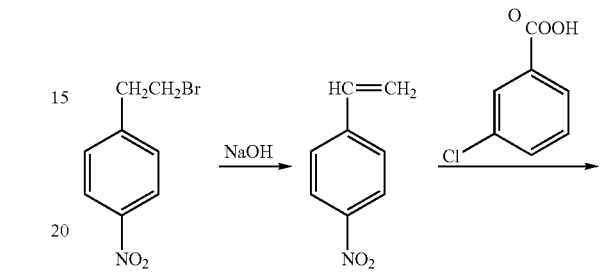

MATERIALS AND METHODS: All solvents were obtained from Fisher unless otherwise noted. 4-Nitrophenylbromide, 3-chlorobenzoylperoxide, 1-Hydroxyacenapthalene, and chlorosulfonic acid were obtained from Aldrich. Petroleum ether and DMF were obtained from Acros, while triethylamine was obtained from Sigma. TLC analysis was performed on EMD Silica Gel 60 $F_{254}$ coated plates. Melting points were determined using a Fisher-Johns melting point apparatus and are uncorrected. $^1$H-NMR analysis was recorded on a Bruker Advance WB 300 MHz instrument with TMS as an internal standard. Mass Spectroscopy was carried out at HT Laboratories (San Diego, Calif.) using electrospray. SYNTHESIS: 4-Nitrostyrene (1). Exactly 13.71 g (0.34 moles) of sodium hydroxide was dissolved in 200 ml anhydrous ethanol. The temperature was raised to 40° C. and 10.0 g (0.043 moles) of 4-nitrophenylbromide was added with stirring. The reaction mixture was heated 40° C. for 30 minutes and then poured into a solution of 40 g of sodium chloride in 200 ml water. The resulting mixture was extracted with 3×25 ml of diethyl ether. The combined organic extracts were dried over magnesium sulfate and the solvent was removed in vacuo. The residue was extracted twice with hot petroleum ether and the combined extracts were placed in the freezer for 72 hours. The crystalline product was filtered and dried under high vacuum. Evaporation of the filtrate gave a second crop of crystals. Total weight of styrene was 5.465 g (84% yield). TLC analysis (1:1 ether/hexane) Rf=0.84. $^1$H-NMR ($d_6$DMSO): δ6.12 (d, 1H, $CH_2$), 6.54 (d, 1H, $CH_2$). 6.89 (dd, 1H, CH), 7.61 (d, 2H, Ar), 8.21 (d, 2H, Ar ortho to $NO_2$).
4-Nitrophenyloxirane (2). A solution consisting of (1) 3.396 g (22.5 mmoles) and 3-chlorobenzoylperoxide 3.881 g (22.5 mmoles) in 40 ml chloroform was stirred at 0-4° C. for 92 hours, then at ambient temperature for 24 hours. Any precipitate that formed during this period was dissolved by the addition of extra chloroform. TLC (1:1 ether/hexane) indicated the complete disappearance of the starting olefin. The solution was washed with 2×15 ml of 10% sodium hydroxide, 20 ml of water, followed by 20 ml of saturated brine. The organic phase was dried with sodium sulfate. Evaporation of the chloroform gave a white residue. This was slurried in 60 ml hexane, filtered and dried under vacuum which yielded 2.383 g (64%). TLC (1:1 ether/hexane) Rf=0.70. Melting point was 80-81° C. $^1$H-NMR ($CDCl_3$) δ2.78 (dd, 1H, $CH_2$), 3.2 (dd, 1H, $CH_2$), 3.97 (t, 1H, CH), 7.46 (d, 2H, Ar), 8.22 (d, 2H, Ar ortho to $NO_2$).
2-Hydroxy-4-nitrophenethylamine hydrochloride (3). Oxirane (2) 0.500 g (3.03 mmoles), 12 ml of 5.05 M methanolic ammonia (60.6 mmoles), and 25 ml anhydrous methanol were sealed in a 130 ml stainless steel bomb. The bomb was stirred at 60° C. for 14 hours and 90 hours at ambient temperature The solvent was removed under reduced pressure and the residue treated with two portions of methanol followed by evaporation in order to remove any remaining ammonia. The residue was dissolved in methanol and acidified with hydrochloric acid, then treated with carbon. The carbon was filtered and the solvent was removed under reduced pressure to yield 0.662 g (60%) of the amine hydrochloride salt. $^1$H-NMR ($d_6$DMSO) δ2.90 (m, 1H, $CH_2$), 3.13 (m, 1H, $CH_2$), 4.99 (t, 1H, CH), 6.42 (d, 1H, OH), 7.62 (d, 2H, Ar), 8.20 (s, 2H, $NH_2$), 8.29 (d, 2H, Ar ortho to $NO_2$). ESIMS calculated for $C_8H_{10}N_2O_3$ 182, found 183 $(M+H)^+$.
1-Oxoacenapthalene (4). 1-Hydroxyacenapthalene was oxidized to 1-oxoacenapthalene (4) with potassium dichromate.
1-Oxoacenapthalene-5-sulfonylchloride (5).
1-Oxoacenapthalene (4) was added slowly to chlorosulfonic acid while keeping the temperature below 15° C. The reaction mixture was heated to 60° C. and held there until no more HCL gas evolved. Then, the reaction mixture was poured into cold water. The resulting solid suspension was extracted twice with ethyl acetate. The combined ethyl acetate extracts were washed with water, saturated sodium bicarbonate, saturated brine, then dried with sodium sulfate. The solvent was removed and the residue was recrystallized. A Beilstein test confirmed the presence of the chlorine atom. Analysis was performed using NMR and MS.
5-{N-[1-(4-nitrophenyl)-1-hydroxyethyl]sulfamoyl}-1-oxoacenapthalene (6). 2-Hydroxy-4-nitrophenethylamine hydrochloride (3), 1-Oxoacenapthalene-5-sulfonylchloride (5), and triethylamine were dissolved in anhydrous dimethylformamide with stirring. The reaction was heated at 100° C. for 20 hours. The solvent was removed under reduced pressure. The residue was dissolved in ethyl acetate washed with 0.5 N HCl, water, followed by saturated brine. The ethyl acetate layer was dried with sodium sulfate, the solvent was removed and the residue recrystallized. Analysis was performed using NMR and MS.

Example 13

Synthesis of: DL-4-{N-[1-(4-NITROPHENYL)-1-HYDROXYETHYL] SULFAMOYL}ACENAPTHALENE (5) (Compound "C")

The synthesis scheme leading to dl-4-{N-[1-(4-nitrophenyl)-1-hydroxyethyl]sulfamoyl}acenapthalene is shown in Scheme 4.

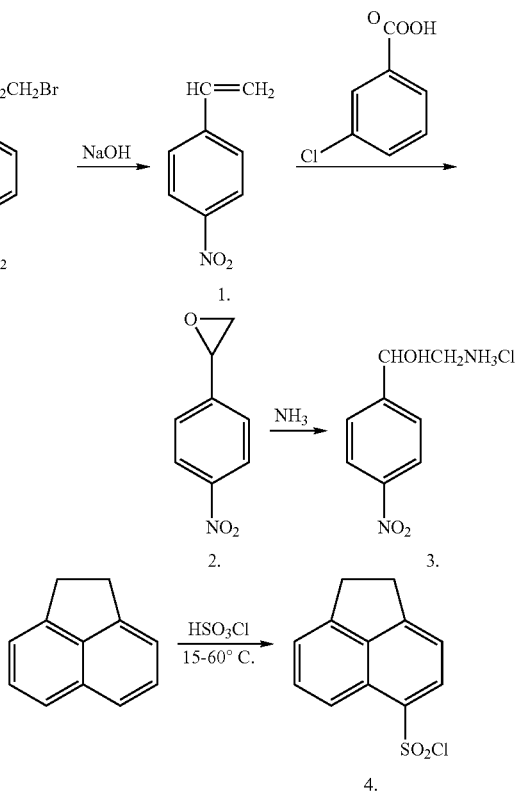

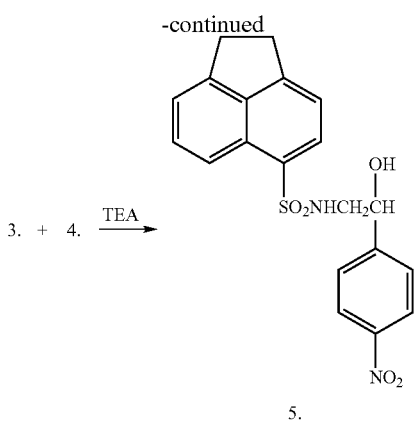

3. + 4. $\xrightarrow{\text{TEA}}$

5.

MATERIALS AND METHODS: All chemicals and reagents were used as received from the supplier. All solvents were obtained from Fisher unless otherwise noted. 4-Nitrophenylbromide, 3-chlorobenzoylperoxide, acenapthalene, and chlorosulfonic acid were obtained from Aldrich. Petroleum ether and DMF were obtained from Acros, while triethylamine was obtained from Sigma. TLC analysis was performed on EMD Silica Gel 60 $F_{254}$ coated plates. Melting points were determined using a Fisher-Johns melting point apparatus and are uncorrected. $^1$H-NMR analysis was recorded on a Bruker Advance WB 300 MHz instrument with TMS as an internal standard. Mass Spectroscopy was carried out at HT Laboratories (San Diego, Calif.) using electrospray.

SYNTHESIS: 4-Nitrostyrene (1). Exactly 13.71 g (0.34 moles) of sodium hydroxide was dissolved in 200 ml anhydrous ethanol. The temperature was raised to 40° C. and 10.0 g (0.043 moles) of 4-nitrophenylbromide was added with stirring. The reaction mixture was heated 40° C. for 30 minutes and then poured into a solution of 40 g of sodium chloride in 200 ml water. The resulting mixture was extracted with 3×25 ml of diethyl ether. The combined organic extracts were dried over magnesium sulfate and the solvent was removed in vacuo. The residue was extracted twice with hot petroleum ether and the combined extracts were placed in the freezer for 72 hours. The crystalline product was filtered and dried under high vacuum. Evaporation of the filtrate gave a second crop of crystals. Total weight of styrene was 5.465 g (84% yield). TLC analysis (1:1 ether/hexane) Rf=0.84. $^1$H-NMR ($d_6$DMSO): δ 6.12 (d, 1H, $CH_2$), 6.54 (d, 1H, $CH_2$). 6.89 (dd, 1H, CH), 7.61 (d, 2H, Ar), 8.21 (d, 2H, Ar ortho to $NO_2$).

4-Nitrophenyloxirane (2). A solution consisting of (1) 3.396 g (22.5 mmoles) and 3-chlorobenzoylperoxide 3.881 g (22.5 mmoles) in 40 ml chloroform was stirred at 0-4° C. for 92 hours, then at ambient temperature for 24 hours. Any precipitate that formed during this period was dissolved by the addition of extra chloroform. TLC (1:1 ether/hexane) indicated the complete disappearance of the starting olefin. The solution was washed with 2×15 ml of 10% sodium hydroxide, 20 ml of water, followed by 20 ml of saturated brine. The organic phase was dried with sodium sulfate. Evaporation of the chloroform gave a white residue. This was slurried in 60 ml hexane, filtered and dried under vacuum which yielded 2.383 g (64%). TLC (1:1 ether/hexane) Rf=0.70. Melting point was 80-81° C. $^1$H-NMR ($CDCl_3$) δ 2.78 (dd, 1H, $CH_2$), 3.2 (dd, 1H, $CH_2$), 3.97 (t, 1H, CH), 7.46 (d, 2H, Ar), 8.22 (d, 2H, Ar ortho to $NO_2$).

2-Hydroxy-4-nitrophenethylamine hydrochloride (3). Oxirane (2) 0.500 g (3.03 mmoles), 12 ml of 5.05 M methanolic ammonia (60.6 mmoles), and 25 ml anhydrous methanol were sealed in a 130 ml stainless steel bomb. The bomb was stirred at 60° C. for 14 hours and 90 hours at ambient temperature The solvent was removed under reduced pressure and the residue treated with two portions of methanol followed by evaporation in order to remove any remaining ammonia. The residue was dissolved in methanol and acidified with hydrochloric acid, then treated with carbon. The carbon was filtered and the solvent was removed under reduced pressure to yield 0.662 g (60%) of the amine hydrochloride salt. $^1$H-NMR ($d_6$DMSO) δ 2.90 (m, 1H, $CH_2$), 3.13 (m, 1H, $CH_2$), 4.99 (t, 1H, CH), 6.42 (d, 1H, OH), 7.62 (d, 2H, Ar), 8.20 (s, 2H, $NH_2$), 8.29 (d, 2H, Ar ortho to $NO_2$). ESIMS calculated for $C_8H_{10}N_2O_3$ 182, found 183 $(M+H)^+$.

Acenapthalene-5-sulfonylchloride (4). Acenapthalene was added slowly to chlorosulfonic acid while keeping the temperature below 15° C. The reaction mixture was heated to 60° C. and held there until no more HCL gas evolved. Then, the reaction mixture was poured into cold water. The resulting solid suspension was extracted twice with ethyl acetate. The combined ethyl acetate extracts were washed with water, saturated sodium bicarbonate, saturated brine, then dried with sodium sulfate. The solvent was removed and the residue was recrystallized. A Beilstein test confirmed the presence of the chlorine atom. Analysis was performed using NMR and MS.

5-{N-[1-(4-nitrophenyl)-1-hydroxyethyl] sulfamoyl}acenapthalene (5). 2-Hydroxy-4-nitrophenethylamine hydrochloride (3), acenapthalene-5-sulfonylchloride (4) and triethylamine were dissolved in 20 ml anhydrous dimethylformamide with stirring. The reaction was heated at 100° C. for 20 hours. The solvent was removed under reduced pressure. The residue was dissolved in ethyl acetate washed with 0.5 N HCl, water, followed by saturated brine. The ethyl acetate layer was dried with sodium sulfate, the solvent was removed and the residue recrystallized. Analysis was performed using NMR and MS.

Example 14

Synthesis of:
dl-6-{N-[1-(4-nitrophenyl)-1-hydroxyethyl]sulfamoyl} benz(cd)indol-2(1-alkyl)-one (6) (Compound "D")

The synthesis route leading to (6) is shown in Scheme 5.

Scheme 5

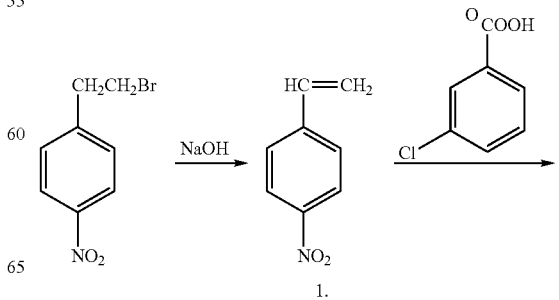

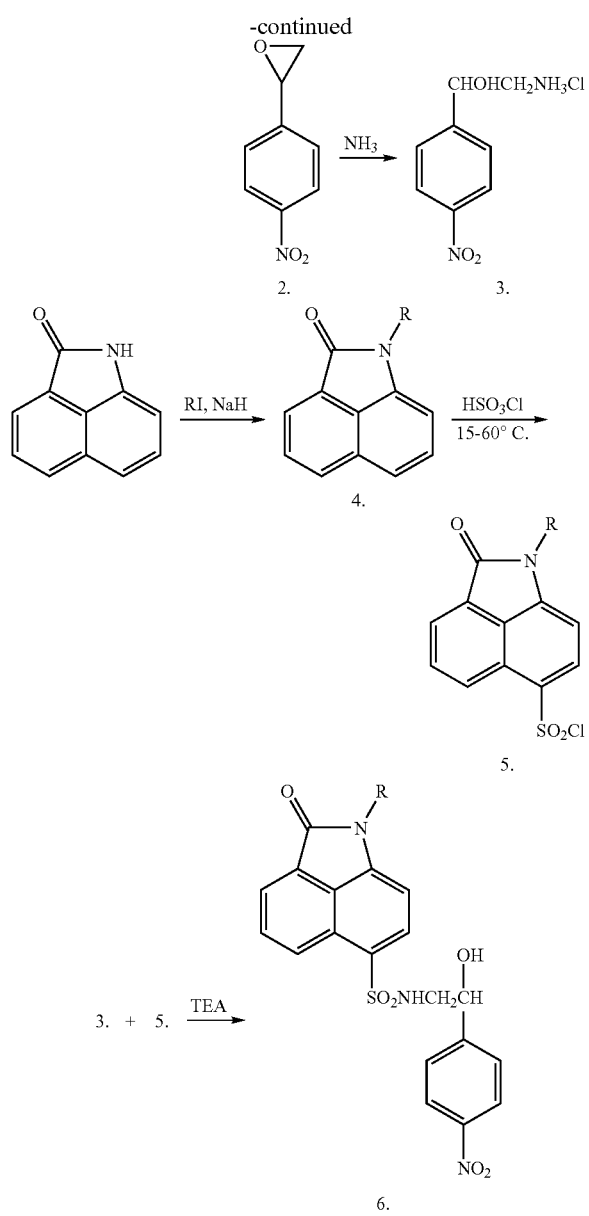

MATERIALS AND METHODS: All chemicals and reagents were used as received from the supplier. All solvents were obtained from Fisher unless otherwise noted. 4-Nitrophenylbromide, 3-chlorobenzoylperoxide, benz[cd]indol-2(1H)-one, and chlorosulfonic acid were obtained from Aldrich. Petroleum ether and DMF were obtained from Acros, while triethylamine was obtained from Sigma. TLC analysis was performed on EMD Silica Gel 60 $F_{254}$ coated plates. Melting points were determined using a Fisher-Johns melting point apparatus and are uncorrected. $^1$H-NMR analysis was recorded on a Bruker Advance WB 300 MHz instrument with TMS as an internal standard. Mass Spectroscopy was carried out at HT Laboratories (San Diego, Calif.) using electrospray. SYNTHESIS: 4-Nitrostyrene (1). Exactly 13.71 g (0.34 moles) of sodium hydroxide was dissolved in 200 ml anhydrous ethanol. The temperature was raised to 40° C. and 10.0 g (0.043 moles) of 4-nitrophenylbromide was added with stirring. The reaction mixture was heated 40° C. for 30 minutes and then poured into a solution of 40 g of sodium chloride in 200 ml water. The resulting mixture was extracted with 3×25 ml of diethyl ether. The combined organic extracts were dried over magnesium sulfate and the solvent was removed in vacuo. The residue was extracted twice with hot petroleum ether and the combined extracts were placed in the freezer for 72 hours. The crystalline product was filtered and dried under high vacuum. Evaporation of the filtrate gave a second crop of crystals. Total weight of styrene was 5.465 g (84% yield). TLC analysis (1:1 ether/hexane) Rf=0.84. $^1$H-NMR ($d_6$DMSO): δ6.12 (d, 1H, $CH_2$), 6.54 (d, 1H, $CH_2$). 6.89 (dd, 1H, CH), 7.61 (d, 2H, Ar), 8.21 (d, 2H, Ar ortho to $NO_2$).

4-Nitrophenyloxirane (2). A solution consisting of (1) 3.396 g (22.5 mmoles) and 3-chlorobenzoylperoxide 3.881 g (22.5 mmoles) in 40 ml chloroform was stirred at 0-4° C. for 92 hours, then at ambient temperature for 24 hours. Any precipitate that formed during this period was dissolved by the addition of extra chloroform. TLC (1:1 ether/hexane) indicated the complete disappearance of the starting olefin. The solution was washed with 2×15 ml of 10% sodium hydroxide, 20 ml of water, followed by 20 ml of saturated brine. The organic phase was dried with sodium sulfate. Evaporation of the chloroform gave a white residue. This was slurried in 60 ml hexane, filtered and dried under vacuum which yielded 2.383 g (64%). TLC (1:1 ether/hexane) Rf=0.70. Melting point was 80-81° C. $^1$H-NMR ($CDCl_3$) δ2.78 (dd, 1H, $CH_2$), 3.2 (dd, 1H, $CH_2$), 3.97 (t, 1H, CH), 7.46 (d, 2H, Ar), 8.22 (d, 2H, Ar ortho to $NO_2$).

2-Hydroxy-4-nitrophenethylamine hydrochloride (3). Oxirane (2) 0.500 g (3.03 mmoles), 12 ml of 5.05 M methanolic ammonia (60.6 mmoles), and 25 ml anhydrous methanol were sealed in a 130 ml stainless steel bomb. The bomb was stirred at 60° C. for 14 hours and 90 hours at ambient temperature The solvent was removed under reduced pressure and the residue treated with two portions of methanol followed by evaporation in order to remove any remaining ammonia. The residue was dissolved in methanol and acidified with hydrochloric acid, then treated with carbon. The carbon was filtered and the solvent was removed under reduced pressure to yield 0.662 g (60%) of the amine hydrochloride salt. $^1$H-NMR ($d_6$DMSO) δ2.90 (m, 1H, $CH_2$), 3.13 (m, 1H, $CH_2$), 4.99 (t, 1H, CH), 6.42 (d, 1H, OH), 7.62 (d, 2H, Ar), 8.20 (s, 2H, $NH_2$), 8.29 (d, 2H, Ar ortho to $NO_2$). ESIMS calculated for $C_8H_{10}N_2O_3$ 182, found 183 (M+H)$^+$.

Benz[cd]indol-2(1-alkyl)-one (4). Benz[cd]indol-2(1H)-one was treated with an alkyl iodide or alkyl mesylate in the presence of a suitable base to yield (4).

6-Chlorosulfonylbenz[cd]indol-2(1-alkyl)-one (5) Benz[cd]indol-2(1-alkyl)-one (4) was added slowly to chlorosulfonic acid while keeping the temperature below 15° C. The reaction mixture was heated to 60° C. and held there until no more HCL gas evolved. Then, the reaction mixture was poured into cold water. The resulting solid suspension was extracted twice with ethyl acetate. The combined ethyl acetate extracts were washed with water, saturated sodium bicarbonate, saturated brine, then dried with sodium sulfate. The solvent was removed and the residue was recrystallized. A Beilstein test confirmed the presence of the chlorine atom. Analysis was performed using NMR and MS.

6-{N-[1-(4-nitrophenyl)-1-hydroxyethyl]sulfamoyl}benz[cd]indol-2(1-alkyl)-one (6). 2-Hydroxy-4-nitrophenethylamine hydrochloride (3), 6-Chlorosulfonylbenz[cd]indol-2(1-alkyl)-one (5), and triethylamine were dissolved in anhydrous dimethylformamide with stirring. The reaction was heated at 100° C. for 20 hours. The solvent was removed under reduced pressure. The residue was dissolved in ethyl acetate washed with 0.5 N HCl, water, followed by saturated brine. The ethyl acetate layer was dried with sodium sulfate, the solvent was removed and the residue recrystallized. Analysis was performed using NMR and MS.

Example 15

Syntheses of: DL-6-(3-[4-NITROPHENYL]-3-HYDROXY) PROPYLSULFONYLBENZ[CD]INDOL-2(1H)-ONE (6). Compound "E").

The synthesis scheme leading to (6) is shown in Scheme 6.

coated plates. Melting points were determined using a Fisher-Johns melting point apparatus and are uncorrected. $^1$H-NMR analysis was recorded on a Bruker Advance WB 300 MHz instrument with TMS as an internal standard. Mass Spectroscopy was carried out at HT Laboratories (San Diego, Calif.) using electrospray.

6-Chlorosulfonylbenz[cd]indol-2(1H)-one, (1). Benz[cd]indol-2(1H)-one (2.523 g; 14.9 mmoles) was added slowly to 5.1 ml of chlorosulfonic acid while keeping the temperature below 15° C. The reaction mixture was heated to 60° C. and

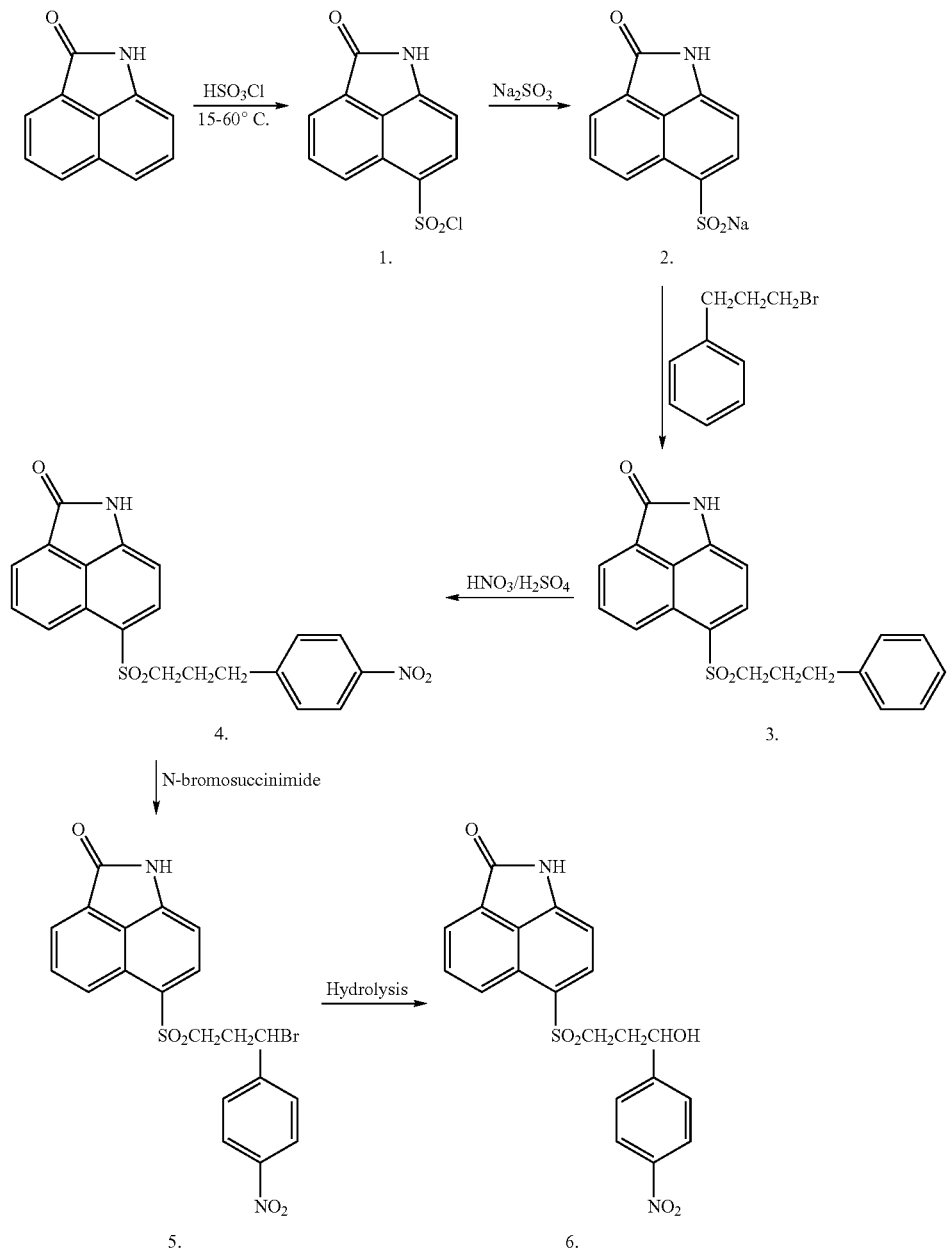

Scheme 6

MATERIALS AND METHODS: All chemicals and reagents were used as received from the supplier. All solvents were obtained from Fisher unless otherwise noted. Benz[cd]indol-2(1H)-one, and chlorosulfonic acid were obtained from Aldrich. TLC analysis was performed on END Silica Gel 60 $F_{254}$ held there until no more HCL gas evolved. Then, the reaction mixture was poured into 125 ml of cold water. The resulting solid suspension was extracted twice with ethyl acetate. The combined ethyl acetate extracts were washed with water, saturated sodium bicarbonate, saturated brine, then dried with sodium sulfate. The solvent was removed and the residue was recrystallized from chloroform/ethyl acetate. The yield of the title compound was 1.620 g (41%). A Beilstein test confirmed the presence of the chlorine atom. Melting point was 194-197° C. (dec) $^1$H-NMR (d$_6$DMSO) ⌂6.86 (d, 1H, Ar), 7.79 (m, 2H, Ar), 7.98 (d, 1H, Ar), 8.72 (d, 1H, Ar), 10.83 (s, 1H, NH).

Benz[cd]indol-2(1H)-one-6-sulfonic acid sodium salt (2). Treatment of indole (1) with sodium sulfite converted it to the sodium sulfonate derivative, (2)

6-(3-phenylpropyl)sulfonylbenz[cd]indol-2(1H)-one (3). Reaction of benz[cd]indol-2(1H)-one-6-sulfonic acid sodium salt (2) with 3-phenylpropyl bromide produced compound (3).

6-(3-[4-Nitrophenyl]propyl)sulfonylbenz[cd]indol-2(1H)-one (4). 6-(3-phenylpropyl)sulfonylbenz[cd]indol-2(1H)-one (3) was nitrated with a mixture of nitric and sulfuric acids while cooled in an ice bath to give nitro compound (4).

6-(3-[4-Nitrophenyl]-3-bromo)propylsulfonylbenz[cd]indol-2(1H)-one (5). Bromination of 6-(3-[4-nitrophenyl]propyl)sulfonylbenz[cd]indol-2(1H)-one (4) with N-bromosuccinimide produced bromo compound (5).

6-(3-[4-Nitrophenyl]-3-hydroxy)propylsulfonylbenz[cd]indol-2(1H)-one (6). Hydrolysis of 6-(3-[4-nitrophenyl]-3-bromo)propylsulfonylbenz[cd]indol-2(1H)-one (5) produced the final product (6).

Example 16

Synthesis of 6-{N-[1-(4-NITROPHENYL)-1-OXO-ETHYL]SULFAMOYL}BENZ[CD]INDOL-(1H)-ONE (6) from Morphlock 1

(compound "F"). The synthesis scheme leading to (6) is shown in Scheme 7. 6-{N-[1-(4-nitrophenyl)-1-oxoethyl]sulfamoyl}benz[cd]indol-2(1H)-one (6). 6-{N-[1-(4-Nitrophenyl)-1-hydroxyethyl]sulfamoyl}benz(cd)indol-2(1H)-one (5) was converted into (1) by oxidation with potassium dichromate.

Scheme 7

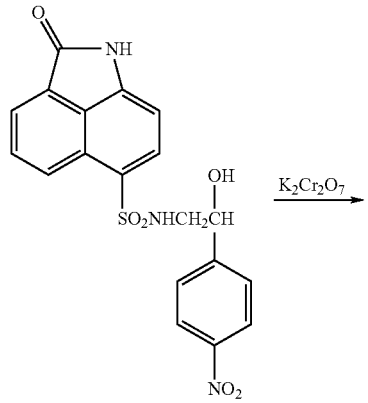

Morphlock 1

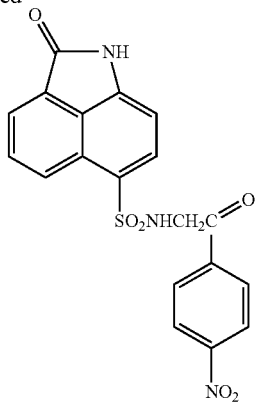

1.

Example 17

Synthesis of DL-6-{N-[1-(4-NITROPHENYL)-1-FLUOROETHYL] SULFAMOYL}BENZ[CD]INDOL-2(1H)-ONE (2) from Morphlock 1 (Compound "G")

The synthesis scheme leading to (2) is shown in Scheme 8.

Scheme 8

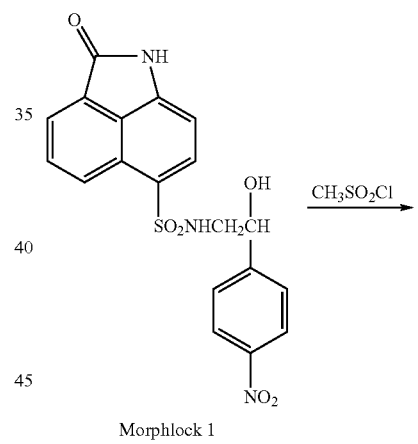

Morphlock 1

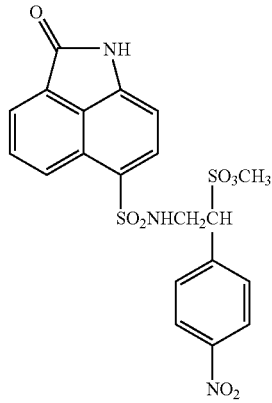

1.

6-{N-[1-(4-nitrophenyl)-1-mesylethyl]sulfamoyl}benz[cd]indol-2(1H)-one (1) Morphlock 1 was treated with mesyl chloride (methanesulfonyl chloride) to yield methylsulfonate (1).

6-{N-[1-(4-nitrophenyl)-1-fluoroethyl]sulfamoyl}benz[cd]indol-2(1H)-one (2).

6-{N-[1-(4-nitrophenyl)-1-mesylethyl]sulfamoyl}benz[cd]indol-2(1H)-one (1) was reacted with sodium fluoride to produce fluoro compound (2).

Example 18

Synthesis of 6-(1-HYDROXY-6-NITRO-1,2,3,4-TETRAHYDRONAPTHYL-2H-SULFAMOYL)BENZ[CD]INDOL-2-(1H)-ONE (7) (Compound "H")

The synthesis scheme leading to (7) is shown in Scheme 9.

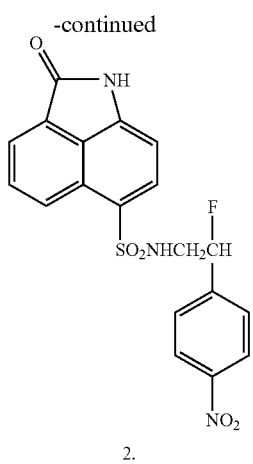

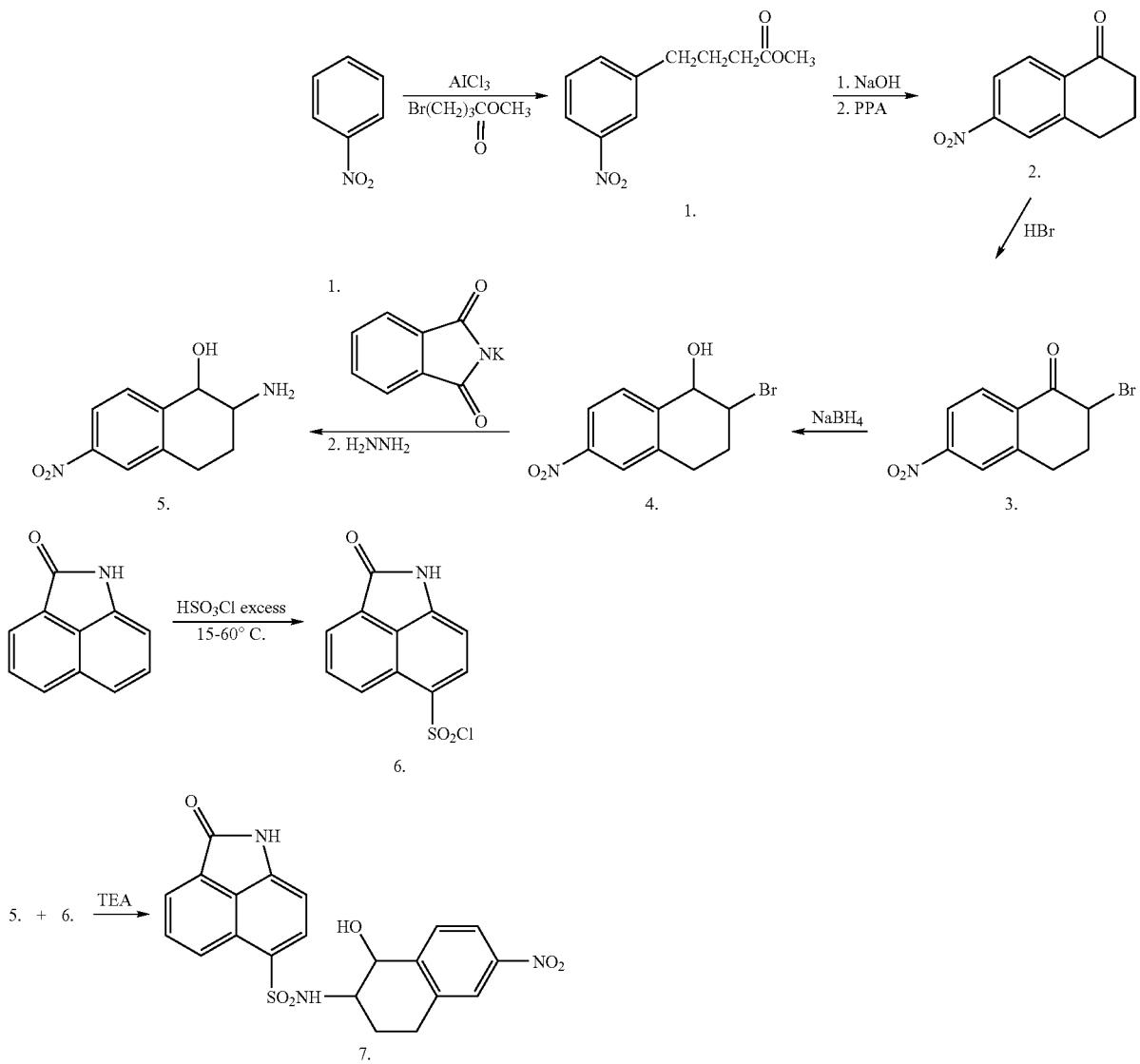

MATERIALS AND METHODS: All chemicals and reagents were used as received from the supplier. TLC's were run on EMD Silica Gel 60 $F_{254}$ coated plates. Melting points were determined using a Fisher-Johns melting point apparatus and are uncorrected. $^1$H-NMR spectra were run on a Bruker Advance WB 300MHz instrument, using TMS as an internal standard.

3-(3-Nitrophenyl)lbutyric acid methylester (1). Nitrobenzene was treated with 4-bromobutyric acid methylester in the presence of aluminum chloride to produce ketone (1).

6-Nitro-1-tetralone (2). 3-(3-Nitrophenyl)lbutyric acid methylester (1) was hydrolysed to the free acid which crystallized with the addition of polyphosphoric acid to yield tetralone (2).

2-Bromo-6-nitro-1-tetralone (3). Bromination of 6-nitro-1-tetralone (2) with hydrogen bromide produced bromo compound (3).

1-Hydroxy-2-bromo-6-nitrotetralin (4). 2-Bromo-6-nitro-1-tetralone (3) was reduced with sodium borohydride to yield hydroxy compound (4).

1-Hydroxy-2-amino-6-nitrotetralin (5). Treatment of 1-hydroxy-2-bromo-6-nitrotetralin (4) with potassium phthalimide followed by treatment with hydrazine formed amino compound (5).

6-Chlorosulfonylbenz[cd]indol-2(1H)-one (6). Benz[cd]indol-2(1H)-one (2.523 g; 14.9 mmoles) was added slowly to 5.1 ml of chlorosulfonic acid while keeping the temperature below 15° C. The reaction mixture was heated to 60° C. and held there until no more HCL gas evolved. Then, the reaction mixture was poured into 125 ml of cold water. The resulting solid suspension was extracted twice with ethyl acetate. The combined ethyl acetate extracts were washed with water, saturated sodium bicarbonate, saturated brine, then dried with sodium sulfate. The solvent was removed and the residue was recrystallized from chloroform/ethyl acetate. The yield of the title compound (6) was 1.620 g (41%). A Beilstein test confirmed the presence of the chlorine atom. Melting point was 194-197° C. (dec) $^1$H-NMR ($d_6$DMSO) δ 6.86 (d, 1H, Ar), 7.79 (m, 2H, Ar), 7.98 (d, 1H, Ar), 8.72 (d, 1H, Ar), 10.83 (s, 1H, NH).

6-(1-Hydroxy-6-nitro-1,2,3,4-tetrahydronapthyl-2H-sulfamyl)benz[cd]indol-2-(1H)-one (7). 1-Hydroxy-2-amino-6-nitrotetralin (5), 4-chlorosulfonylbenz[cd]indol-2(1H)-one (6), and triethylamine (1.04 ml; 7.5 mmoles) were dissolved in anhydrous dimethylformamide with stirring. The reaction was heated at 100° C. for 20 hours. The solvent was removed under reduced pressure. The residue was dissolved in ethyl acetate washed with 0.5 NHCl, water, followed by saturated brine. The ethyl acetate layer was dried with sodium sulfate, the solvent was removed and the residue recrystallized to give the title compound (7).

Example 19

Synthesis of N-(1-HYDROXY-6-NITRO-1,2,3,4-TETRAHYDRONAPTHYL) BENZ[CD]INDOL-2(1H)-ONE-5-SULFONAMIDE (6) (Compound "I")

The synthesis scheme leading to (6) is shown in Scheme 10

Scheme 10

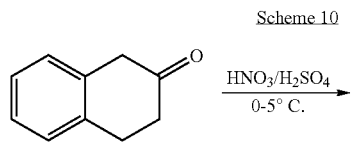

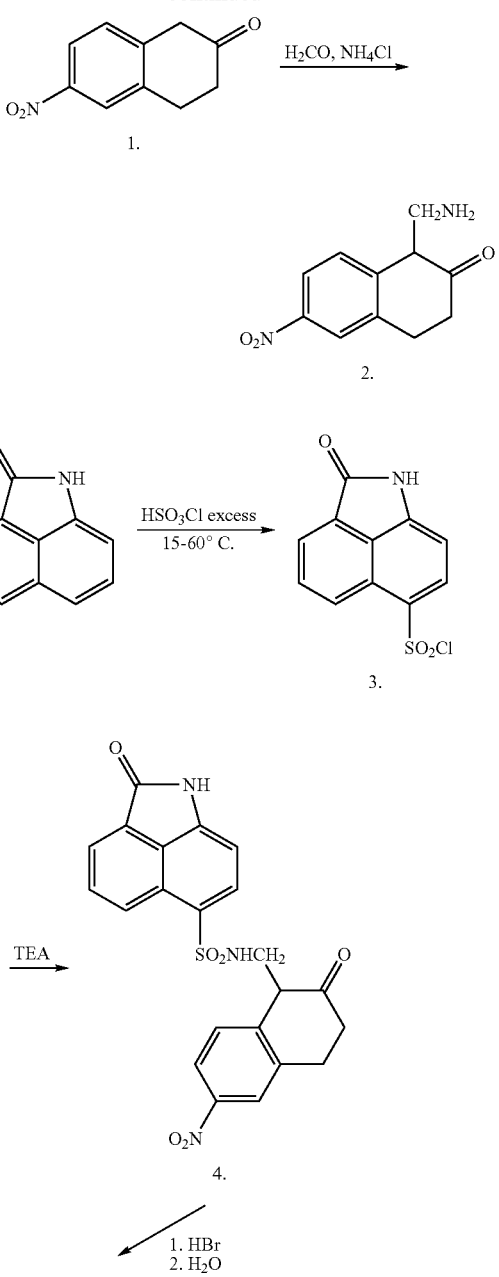

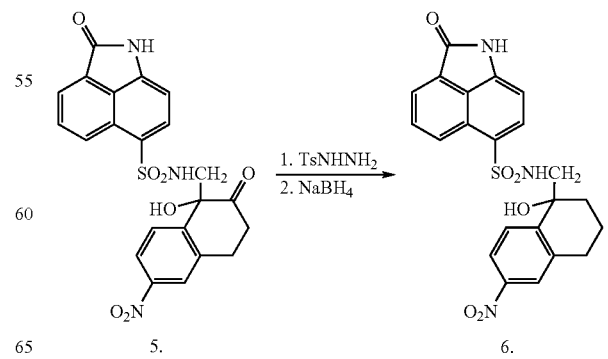

MATERIALS AND METHODS: All chemicals and reagents were used as received from the supplier. TLC's were run on EMD Silica Gel 60 $F_{254}$ coated plates. Melting points were determined using a Fisher-Johns melting point apparatus and are uncorrected. $^1$H-NMR spectra were run on a Bruker Advance WB 300 MHz instrument, using TMS as an internal standard.

6-Nitro-2-tetralone (1). Treatment of 2-tetralone with a mixture of nitric and sulfuric acid while cooling in an ice bath yielded nitro compound (1).

1-Aminomethyl-6-nitro-2-tetralone (2). Reaction of 6-nitro-2-tetralone (1) with ammonium chloride and formaldehyde gave amino compound (2).

6-Chlorosulfonylbenz[cd]indol-2(1H)-one (3). Benz[cd]indol-2(1H)-one (2.523 g; 14.9 mmoles) was added slowly to 5.1 ml of chlorosulfonic acid while keeping the temperature below 15° C. The reaction mixture was heated to 60° C. and held there until no more HCL gas evolved. Then, the reaction mixture was poured into 125 ml of cold water. The resulting solid suspension was extracted twice with ethyl acetate. The combined ethyl acetate extracts were washed with water, saturated sodium bicarbonate, saturated brine, then dried with sodium sulfate. The solvent was removed and the residue was recrystallized from chloroform/ethyl acetate. The yield of the title compound was 1.620 g (41%). A Beilstein test confirmed the presence of the chlorine atom. Melting point was 194-197° C. (dec) $^1$H-NMR ($d_6$DMSO) ▯6.86 (d, 1H, Ar), 7.79 (m, 2H, Ar), 7.98 (d, 1H, Ar), 8.72 (d, 1H, Ar), 10.83 (s, 1H, NH).

N-(1-methylene-2-oxo-6-nitro-1,2,3,4-tetrahydronapthyl)benz[cd]indol-2(1H)-one-5-sulfonamide (4). 1-Aminomethyl-6-nitro-2-tetralone (2), 4-chlorosulfonylbenz[cd]indol-2(1H)-one (4), and triethylamine were dissolved in anhydrous dimethylformamide with stirring. The reaction was heated at 100° C. for 20 hours. The solvent was removed under reduced pressure. The residue was dissolved in ethyl acetate washed with 0.5 N HCl, water, followed by saturated brine. The ethyl acetate layer was dried with sodium sulfate, the solvent was removed and the residue recrystallized to give compound (4).

N-(1-hydroxy-1-methylene-2-oxo-6-nitro-1,2,3,4-tetrahydronapthyl)benz[cd]indol-2(1H)-one-5-sulfonamide (5). Treatment of N-(1-methylene-2-oxo-6-nitro-1,2,3,4-tetrahydronapthyl)benz[cd]indol-2(1H)-one-5-sulfonamide (4) with hydrobromic acid followed by hydrolysis produced hydroxy compound (5).

N-(1-hydroxy-1-methylene-6-nitro-1,2,3,4-tetrahydronapthyl)benz[cd]indol-2(1H)-one-5 sulfonamide (6). Reaction of N-(1-hydroxy-1-methylene-2-oxo-6-nitro-1,2,3,4-tetrahydronapthyl)benz[cd]indol-2(1H)-one-5-sulfonamide (5) with tosylhydrazine followed by reductive cleavage of the formed tosylhydrozone with sodium borohydride produced the title compound (6).

Example 20

Synthesis of
DL-6-{N-[1-(4-CARBOXYPHENYL)-1-HYDROXYETHYL]SULFAMOYL}BENZ[CD]INDOL-2(1H)-ONE (4) (Compound "J")

The synthesis scheme leading to (4) is shown in Scheme 11.

Scheme 11

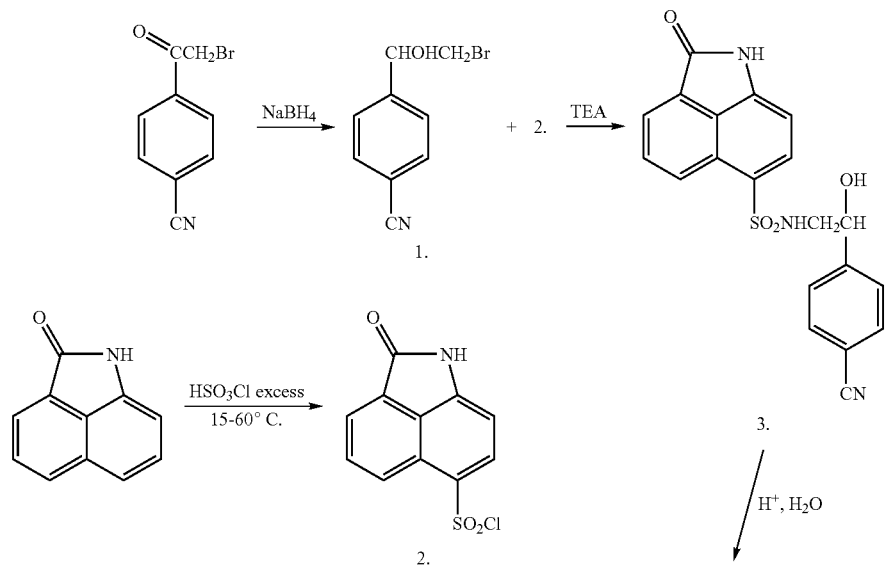

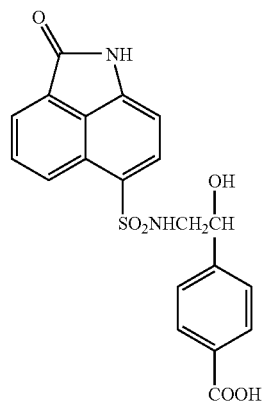

4.

MATERIALS AND METHODS: All chemicals and reagents were used as received from the supplier. TLC's were run on EMD Silica Gel 60 $F_{254}$ coated plates. Melting points were determined using a Fisher-Johns melting point apparatus and are uncorrected. $^1$H-NMR spectra were run on a Bruker Advance WB 300 MHz instrument, using TMS as an internal standard.

1-Hydroxy-1-(4-cyanophenyl)bromoethane (1). Sodium borohydride reduction of 4-cyano-α-bromoacetophenone produced hydroxy compound (1).

6-Chlorosulfonylbenz[cd]indol-2(1H)-one (2). Benz[cd]indol-2(1H)-one (2.523 g; 14.9 mmoles) was added slowly to 5.1 ml of chlorosulfonic acid while keeping the temperature below 15° C. The reaction mixture was heated to 60° C. and held there until no more HCL gas evolved. Then, the reaction mixture was poured into 125 ml of cold water. The resulting solid suspension was extracted twice with ethyl acetate. The combined ethyl acetate extracts were washed with water, saturated sodium bicarbonate, saturated brine, then dried with sodium sulfate. The solvent was removed and the residue was recrystallized from chloroform/ethyl acetate. The yield of the sulfonamide compound was 1.620 g (41%). A Beilstein test confirmed the presence of the chlorine atom. Melting point was 194-197° C. (dec) $^1$H-NMR (d$_6$DMSO) δ 6.86 (d, 1H, Ar), 7.79 (m, 2H, Ar), 7.98 (d, 1H, Ar), 8.72 (d, 1H, Ar), 10.83 (s, 1H, NH).

6-{N-[1-(4-cyanophenyl)-1-hydroxyethyl]sulfamoyl}benz[cd]indol-2-(1H)-one (3). 1-Hydroxy-1-(4-cyanophenyl)bromoethane (1), 4-chlorosulfonylbenz [cd]indol-2(1H)-one (4), and triethylamine were dissolved in anhydrous dimethylformamide with stirring. The reaction was heated at 100° C. for 20 hours. The solvent was removed under reduced pressure. The residue was dissolved in ethyl acetate washed with 0.5 N HCl, water, followed by saturated brine. The ethyl acetate layer was dried with sodium sulfate, the solvent was removed and the residue recrystallized to give compound (3).

6-{N-[1-(4-carboxyphenyl)-1-hydroxyethyl]sulfamoyl}benz[cd]indol-2(1H)-one (4). Hydrolysis of 6-{N-[1-(4-cyanophenyl)-1-hydroxyethyl]sulfamoyl}benz[cd]indol-2-(1H)-one (3) gave the carboxylic derivative (4).

Example 21

Synthesis of DL-6-{N-[1-(4-AMINOPHENYL)-1-HYDROXYETHYL [SULFAMOYL}BENZ[CD]INDOL-2(1H)-ONE HYDROCHLORIDE (1) (Compound "K")

The synthesis scheme leading to (1) is shown in Scheme 12.

Scheme 12

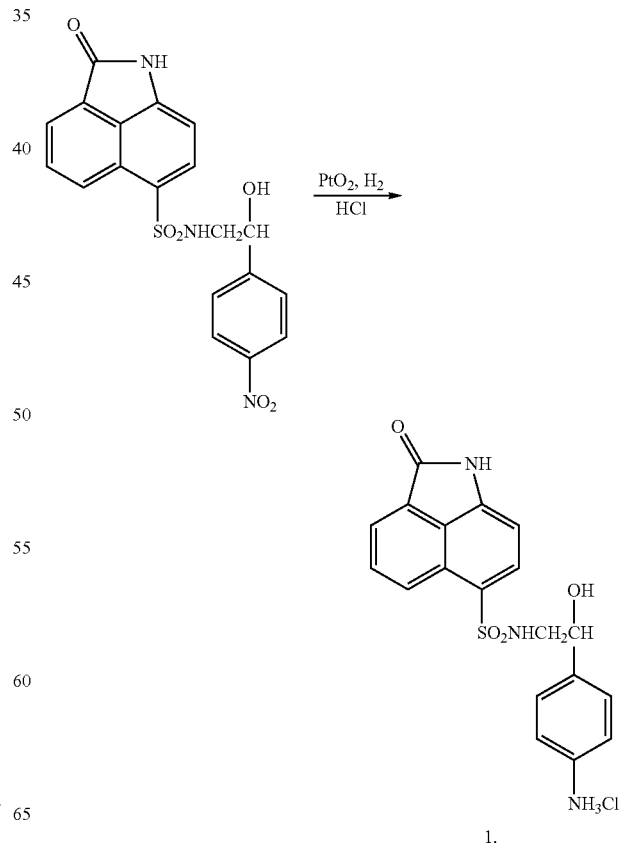

1.

MATERIALS AND METHODS: All chemicals and reagents were used as received from the supplier. TLC's were run on EMD Silica Gel 60 $F_{254}$ coated plates. Melting points were determined using a Fisher-Johns melting point apparatus and are uncorrected. $^1$H-NMR spectra were run on a Bruker Advance WB 300 MHz instrument, using TMS as an internal standard.

6-{N-[1-(4-aminophenyl)-1-hydroxyethyl]sulfamoyl}benz[cd]indol-2(11H)-one hydrochloride (1). Morphlock 1 was catalytically reduced with hydrogen using a $PtO_2$ catalyst to give amine (1).

Example 22

Synthesis of 6-{N-[1-(4-NITROPHENYL)-1-METHOXYVINYL]SULFAMOYL}BENZ[CD]INDOL-2(1H)-ONE (3) (Compound "L")

The synthesis scheme leading to (3) is shown in Scheme 13.

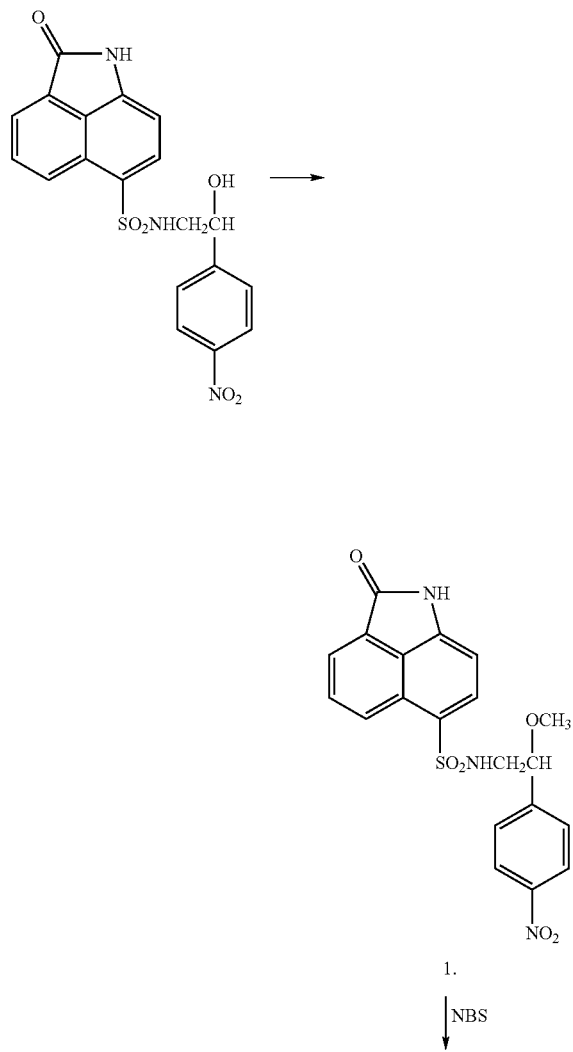

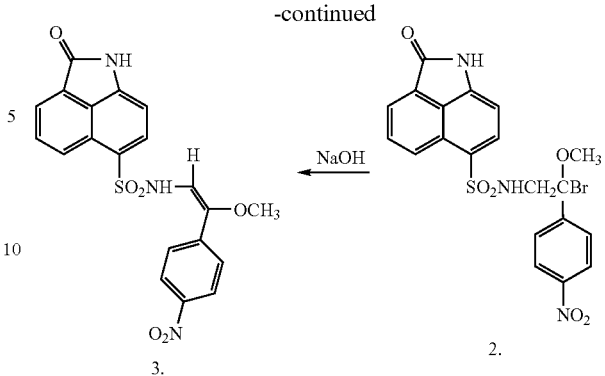

MATERIALS AND METHODS: All chemicals and reagents were used as received from the supplier. TLC's were run on EMD Silica Gel 60 $F_{254}$ coated plates. Melting points were determined using a Fisher-Johns melting point apparatus and are uncorrected. $^1$H-NMR spectra were run on a Bruker Advance WB 300 MHz instrument, using TMS as an internal standard.

6-{N-[1-(4-nitrophenyl)-1-methoxyethyl]sulfamoyl}benz[cd]indol-2(1H)-one (1). Reaction of Morphlock 1 with methyl iodide produced (1).

6-{N-[1-(4-nitrophenyl)-1-methoxy-1-bromoethyl]sulfamoyl}benz[cd]indol-2(1H)-one (2). Reaction of 6-{N-[1-(4-nitrophenyl)-1-methoxyethyl]sulfamoyl}benz[cd]indol-2(1H)-one (1) with N-bromosuccinimide produced bromo compound (2).

6-{N-[1-(4-nitrophenyl)-1-methoxyvinyl]sulfamoyl}benz[cd]indol-2(1H)-one (3). Dehydrohalogenation of 6-{N-[1-(4-nitrophenyl)-1-methoxy-1-bromoethyl]sulfamoyl}benz[cd]indol-2(1H)-one (2) with sodium hydroxide gave compound (3).

While the invention has been described in detail and with reference to specific examples thereof, it will be apparent to one skilled in the art that various changes and modifications can be made therein without departing from the spirit and scope thereof.

REFERENCES

[1] Anfinsen, C. B. (1973) Principles that govern the folding of protein chains. *Science* 181 (96), 223-230
[2] Caspar, D. L. and Klug, A. (1962) Physical principles in the construction of regular viruses. *Cold Spring Harb Symp Quant Biol* 27, 1-24
[3] Morgan, G. J. (2003) Historical review: viruses, crystals and geodesic domes. *Trends Biochem Sci* 28 (2), 86-90
[4] Koshland, D. E., Jr. et al. (1966) Comparison of experimental binding data and theoretical models in proteins containing subunits. *Biochemistry* 5 (1), 365-385
[5] Monod, J. et al. (1965) On the Nature of Allosteric Transitions: A Plausible Model. *J Mol Biol* 12, 88-118
[6] Jordan, P. M. (1994) Highlights in haem biosynthesis. *Curr Opin Struct Biol* 4 (6), 902-911
[7] Battersby, A. R. and Leeper, F. J. (1997) Biosynthesis of vitamin B12. *Topics in Current Chemistry* 195(Biosynthesis: Polyketides and Vitamins), 143-193
[8] Battersby, A. R. (2000) Tetrapyrroles: the pigments of life. *Nat Prod Rep* 17 (6), 507-526
[9] Jaffe, E. K. (2000) The porphobilinogen synthase family of metalloenzymes. *Acta Crystallogr D Biol Crystallogr* 56 (Pt 2), 115-128

[10] Berman, H. M. et al. (2000) The Protein Data Bank. *Nucleic Acids Res* 28 (1), 235-242

[11] Jaffe, E. K. (2003) An unusual phylogenetic variation in the metal ion binding sites of porphobilinogen synthase. *Chem Biol* 10 (1), 25-34

[12] Jaffe, E. K. and Hanes, D. (1986) Dissection of the early steps in the porphobilinogen synthase catalyzed reaction. Requirements for Schiff's base formation. *J Biol Chem* 261 (20), 9348-9353

[13] Kervinen, J. et al. (2000) Porphobilinogen synthase from pea: expression from an artificial gene, kinetic characterization, and novel implications for subunit interactions. *Biochemistry* 39 (30), 9018-9029

[14] Petrovich, R. M. et al. (1996) *Bradyrhizobium japonicum* porphobilinogen synthase uses two Mg(II) and monovalent cations. *J Biol Chem* 271 (15), 8692-8699

[15] Bollivar, D. W. et al. (2004) *Rhodobacter capsulatus* porphobilinogen synthase, a high activity metal ion independent hexamer. *BMC Biochem* 5 (1), 17

[16] Kundrat, L. et al. (2003) A structural basis for half-of-the-sites metal binding revealed in *Drosophila melanogaster* porphobilinogen synthase. *J. Biol. Chem.* 278 (33), 31325-31330

[17] Bevan, D. R. et al. (1980) Mechanism of porphobilinogen synthase. Requirement of Zn2+ for enzyme activity. *J Biol Chem* 255 (5), 2030-2035

[18] Snook, C. F. et al. (2003) Crystal structure of GDP-mannose dehydrogenase: a key enzyme of alginate biosynthesis in *P. aeruginosa*. *Biochemistry* 42 (16), 4658-4668

[19] Naught, L. E. et al. (2002) Allosterism and cooperativity in *Pseudomonas aeruginosa* GDP-mannose dehydrogenase. *Biochemistry* 41 (30), 9637-9645

[20] Poncet, S. et al. (2004) HPr kinase/phosphorylase, a Walker motif A-containing bifunctional sensor enzyme controlling catabolite repression in Gram-positive bacteria. *Biochim Biophys Acta* 1697 (1-2), 123-135

[21] Rochet, J. C. et al. (2000) Pig heart CoA transferase exists as two oligomeric forms separated by a large kinetic barrier. *Biochemistry* 39 (37), 11291-11302

[22] Bzowska, A. et al. (1995) Calf spleen purine nucleoside phosphorylase: purification, sequence and crystal structure of its complex with an N(7)-acycloguanosine inhibitor. *FEBS Lett* 367 (3), 214-218

[23] Koellner, G. et al. (1998) Crystal structure of the ternary complex of *E. coli* purine nucleoside phosphorylase with formycin B, a structural analogue of the substrate inosine, and phosphate (Sulphate) at 2.1 A resolution. *J Mol Biol* 280 (1), 153-166

[24] Poole, L. B. (2005) Bacterial defenses against oxidants: mechanistic features of cysteine-based peroxidases and their flavoprotein reductases. *Arch Biochem Biophys* 433 (1), 240-254

[25] Wood, Z. A. et al. (2002) Dimers to doughnuts: redox-sensitive oligomerization of 2-cysteine peroxiredoxins. *Biochemistry* 41 (17), 5493-5504

[26] Akagi, R. et al. (1999) A novel mutation of delta-aminolaevulinate dehydratase in a healthy child with 12% erythrocyte enzyme activity. *Br J Haematol* 106 (4), 931-937

[27] Maruno, M. et al. (2001) Highly heterogeneous nature of delta-aminolevulinate dehydratase (ALAD) deficiencies in ALAD porphyria. *Blood* 97 (10), 2972-2978

[28] Jaffe, E. K. (2004) The porphobilinogen synthase catalyzed reaction mechanism. *Bioorg Chem* 32 (5), 316-325

[29] Frankenberg, N. et al. (1999) High resolution crystal structure of a Mg2+-dependent porphobilinogen synthase. *J Mol Biol* 289 (3), 591-602

[30] Kervinen, J. et al. (2001) Mechanistic basis for suicide inactivation of porphobilinogen synthase by 4,7-dioxosebacic acid, an inhibitor that shows dramatic species selectivity. *Biochemistry* 40 (28), 8227-8236

[31] Jaffe, E. K. et al. (1995) Characterization of the role of the stimulatory magnesium of *Escherichia coli* porphobilinogen synthase. *Biochemistry* 34 (1), 244-251

[32] Frankenberg, N. et al. (1999) Production, purification, and characterization of a Mg2+-responsive porphobilinogen synthase from *Pseudomonas aeruginosa*. *Biochemistry* 38 (42), 13968-13975

[33] Schneider, H. A. (1976) Enzymic capacities for chlorophyll biosynthesis. Activation and de novo synthesis of enzymes. *Z Naturforsch [C]* 31 (1-2), 55-63

[34] Papenbrock, J. et al. (2000) Role of magnesium chelatase activity in the early steps of the tetrapyrrole biosynthetic pathway. *Plant Physiol* 122 (4), 1161-1169

[35] Papenbrock, J. and Grimm, B. (2001) Regulatory network of tetrapyrrole biosynthesis—studies of intracellular signalling involved in metabolic and developmental control of plastids. *Planta* 213 (5), 667-681

[36] Walker, D. A. (1976) Regulatory mechanisms in photosynthetic carbon metabolism. *Curr Top Cell Regul* 11, 203-241

[37] Stolz, M. and Dornemann, D. (1996) Purification, metal cofactor, N-terminal sequence and subunit composition of a 5-aminolevulinic acid dehydratase from the unicellular green alga Scenedesmus obliquus, mutant C-2A'. *Eur J Biochem* 236 (2), 600-608

[38] Tamai, H. et al. (1979) *Plant Cell Physiol.* 20, 435-444

[39] Breinig, S. et al. (2003) Control of tetrapyrrole biosynthesis by alternate quaternary forms of porphobilinogen synthase. *Nat. Struct. Biol.* 10, 757-763

[40] Frere, F. et al. (2002) Structure of porphobilinogen synthase from *Pseudomonas aeruginosa* in complex with 5-fluorolevulinic acid suggests a double Schiff base mechanism. *J Mol Biol* 320 (2), 237-247

[41] Xiang, Z. et al. (2002) Evaluating conformational free energies: the colony energy and its application to the problem of loop prediction. *Proc. Natl. Acad. Sci. US* 99, 7432-7437

[42] Friesner, R. A. et al. (2004) Glide: a new approach for rapid, accurate docking and scoring. 1. Method and assessment of docking accuracy. *J Med Chem* 47 (7), 1739-1749

[43] Halgren, T. A. et al. (2004) Glide: a new approach for rapid, accurate docking and scoring. 2. Enrichment factors in database screening. *J Med Chem* 47 (7), 1750-1759

[44] Cooperman, B. S, and Kashlan, O. B. (2003) A comprehensive model for the allosteric regulation of Class Ia ribonucleotide reductases. *Adv Enzyme Regul* 43, 167-182

[45] Dhanasekaran, S. et al. (2004) Delta-aminolevulinic acid dehydratase from *Plasmodium falciparum*: indigenous versus imported. *J Biol Chem* 279 (8), 6934-6942

[46] Irwin, J. J. and Shoichet, B. K. (2005) ZINC—a free database of commercially available compounds for virtual screening. *J Chem Inf Model* 45 (1), 177-182

[47] Shimizu-Sato, S. et al. (2002) A light-switchable gene promoter system. *Nat Biotechnol* 20 (10), 1041-1044

[48] Eichholtz, D. A. et al. (1994) Glyphosate-tolerant 5-enolpyruvyl-3-phosphoshikimate synthases. Monsanto Company (St. Louis, Mo.)

[49] Daniell, H. et al. (1998) Containment of herbicide resistance through genetic engineering of the chloroplast genome. *Nat. Biotechnol.* 16 (4), 345-348

[50] Suzuki, M. et al. (1994) Isolation and characterization of two tightly linked catalase genes from castor bean that are differentially regulated. *Plant Mol. Biol.* 25 (3), 507-516

[51] Potrykus, I. et al. (1985) Molecular and general genetics of a hybrid foreign gene introduced into tobacco by direct gene transfer. *Mol. Gen. Genet.* 199 (2), 169-177

[52] Hinchee, M. A. et al. (1988) Production of transgenic soybean plants using *Agrobacterium*-mediated DNA transfer. *Bio/Technology* 6, 915-922

[53] Stalker, D. M. et al. (1988) Purification and properties of a nitrilase specific for the herbicide bromoxynil and corresponding nucleotide sequence analysis of the bxn gene. *J. Biol. Chem.* 263 (13), 6310-6314

[54] (1985)

[55] Thillet, J. et al. (1988) Site-directed mutagenesis of mouse dihydrofolate reductase. Mutants with increased resistance to methotrexate and trimethoprim. *J. Biol. Chem.* 263 (25), 12500-12508

[56] Herrera-Estrella, L. et al. (1983) Expression of chimaeric genes transferred into plant cells using a Ti-plasmid-derived vector. *Nature* 303, 209-213

[57] Bevan, M. (1984) Binary Arobacterium vectors for plant transformation. *Nucleic Acids Res.* 12 (22), 8711-8721

[58] Klee, H. J. et al. (1985) Vectors for transformation of higher plants. *Bio/Technology* 3, 637-642

[59] PCT Publication WO 93/19189.

[60] Fraley, R. T. et al. (1983) Expression of bacterial genes in plant cells. *Proc. Natl. Acad. Sci. USA* 80 (15), 4803-4807

[61] Rogers, S. G. et al. (1987) *Improved vectors for plant transformation: expression cassette vectors and new slectable markers*, San Diego: Academic Press

[62] Schmidhauser, T. J. and Helinski, D. R. (1985) Regions of broad-host-range plasmid RK2 involved in replication and stable maintenance in nine species of Gram-negative bacteria. *J. Bacteriol.* 164, 446-455

[63] Horsch, R. B. and Klee, H. J. (1986) Rapid assay of foreign gene expression in leaf discs transformed by *agrobacterium tumefaciens*: Role of T-DNA borders in the transfer process. *Proc. Natl. Acad. Sci. USA* 83 (12), 4428-4432

[64] Hayashimoto, A. et al. (1990) A polyethylene glycol-mediated protoplast transformation system for production of fertile transgenic rice plants. *Plant Physiol.* 93, 857-863

[65] Datta, S. K. et al. (1990) Genetically engineered fertile indica rice recovered from protoplasts. *Bio/Technology* 8, 736-740

[66] Vasil, V. et al. (1992) Herbicide resistant fertile transgenic wheat plants obtained by microprojectile bombardment of regenerable embryogenic callus. *Bio/Technology* 10, 667-674

[67] Vasil, V. et al. (1990) Regeneration of plants from embryogenic suspension culture protoplasts of wheats (*Triticum aestivum* L.). *Bio/Technology* 8, 429-434

[68] Fromm, M. (1990) In *UCLA Symposium on Molecular Strategies for Crop Improvement*

[69] Wetmur, J. G. et al. (1986) Human delta-aminolevulinate dehydratase: nucleotide sequence of a full-length cDNA clone. *Proc Natl Acad Sci USA* 83 (20), 7703-7707

[70] Jaffe, E. K. et al. (2001) The molecular mechanism of lead inhibition of human porphobilinogen synthase. *J Biol Chem* 276 (2), 1531-1537

[71] Laue, T. et al. (1992) In *Analytical Ultracentrifugation in Biochemistry and Polymer Science* (Harding, S. et al., eds.), pp. 90-125, The Royal Society

[72] Frankenberg, N. et al. (1999) *Pseudomonas aeruginosa* contains a novel type V porphobilinogen synthase with no required catalytic metal ions. *Biochemistry* 38 (42), 13976-13982

[73] Erskine, P. T. et al. (1997) X-ray structure of 5-aminolaevulinate dehydratase, a hybrid aldolase. *Nat Struct Biol* 4 (12), 1025-1031

[74] Erskine, P. T. et al. (1999) X-ray structure of 5-aminolevulinic acid dehydratase from *Escherichia coli* complexed with the inhibitor levulinic acid at 2.0 A resolution. *Biochemistry* 38 (14), 4266-4276

[75] Erskine, P. T. et al. (1999) The Schiff base complex of yeast 5-aminolaevulinic acid dehydratase with laevulinic acid. *Protein Sci* 8 (6), 1250-1256

[76] Erskine, P. T. et al. (2000) MAD analyses of yeast 5-aminolaevulinate dehydratase: their use in structure determination and in defining the metal-binding sites. *Acta Crystallogr D Biol Crystallogr* 56 (Pt 4), 421-430

[77] Erskine, P. T. et al. (2001) The X-ray structure of yeast 5-aminolaevulinic acid dehydratase complexed with two diacid inhibitors. *FEBS Lett* 503 (2-3), 196-200

[78] Erskine, P. T. et al. (2001) The x-ray structure of yeast 5-aminolaevulinic acid dehydratase complexed with substrate and three inhibitors. *J Mol Biol* 312 (1), 133-141

[79] Jaffe, E. K. et al. (2002) Species-specific inhibition of porphobilinogen synthase by 4-oxosebacic acid. *J Biol Chem* 277 (22), 19792-19799

[80] Murzin, A. G. et al. (1995) SCOP: a structural classification of proteins database for the investigation of sequences and structures. *J Mol Biol* 247 (4), 536-540

[81] Segel, I. (1975) *Enzyme Kinetics*, John Wiley and Sons, Inc

[82] van Holde, K. E. et al. (1998) *Principles of Physical Biochemistry*, Prentice-Hall, Englewood Cliffs, N.J.

[83] Schonfeld, H. J. et al. (1998) Quasi-elastic light scattering and analytical ultracentrifugation are indispensable tools for the purification and characterization of recombinant proteins. *Biochem. Soc. Trans.* 26 (4), 753-758

[84] Wu, H. et al. (1997) Dimeric association and segmental variability in the structure of human CD4. *Nature* 387 (6632), 527-530

[85] Moradian-Oldak, J. et al. (1998) Temperature and pH-dependent supramolecular self-assembly of amelogenin molecules: a dynamic light-scattering analysis. *J. Struct. Biol.* 122 (3), 320-327

[86] Gast, K. et al. (1997) Ribonuclease T1 has different dimensions in the thermally and chemically denatured states: a dynamic light scattering study. *FEBS Lett.* 403 (3), 245-248

[87] Ferre-D'Amare, A. R. and Burley, S. K. (1997) Dynamic light scattering in evaluation crystallizability of macromolecules. *Methods Enzymol.* 276, 157-166

[88] Kaplan, W. and Littlejohn, T. G. (2001) Swiss-PDB Viewer (Deep View). *Brief Bioinform* 2 (2), 195-197

[89] Canutescu, A. A. and Dunbrack, R. L., Jr. (2005) MolIDE (Molecular Integrated Development Environment): a homology modeling framework you can click with. *Bioinformatics*

[90] Xiang, Z. et al. (2002) Evaluating conformational free energies: the colony energy and its application to the problem of loop prediction. *Proc Natl Acad Sci USA* 99 (11), 7432-7437

[91] Canutescu, A. A. et al. (2003) A graph-theory algorithm for rapid protein side-chain prediction. *Protein Sci* 12 (9), 2001-2014

[92] Shankar, S. et al. (1995) Exopolysaccharide alginate synthesis in *Pseudomonas aeruginosa*: enzymology and regulation of gene expression. *Adv Enzymol Relat Areas Mol Biol* 70, 221-255

[93] Roychoudhury, S. et al. (1989) Purification and characterization of guanosine diphospho-D-mannose dehydrogenase. A key enzyme in the biosynthesis of alginate by *Pseudomonas aeruginosa. J Biol Chem* 264 (16), 9380-9385

[94] Fieulaine, S. et al. (2001) X-ray structure of HPr kinase: a bacterial protein kinase with a P-loop nucleotide-binding domain. *Embo J* 20 (15), 3917-3927

[95] Marquez, J. A. et al. (2002) Structure of the full-length HPr kinase/phosphatase from *Staphylococcus xylosus* at 1.95 A resolution: Mimicking the product/substrate of the phospho transfer reactions. *Proc Natl Acad Sci USA* 99 (6), 3458-3463

[96] Allen, G. S. et al. (2003) Crystal structure of HPr kinase/phosphatase from *Mycoplasma pneumoniae. J Mol Biol* 326 (4), 1203-1217

[97] Ramstrom, H. et al. (2003) Properties and regulation of the bifunctional enzyme HPr kinase/phosphatase in *Bacillus subtilis. J Biol Chem* 278 (2), 1174-1185

[98] Jault, J. M. et al. (2000) The HPr kinase from *Bacillus subtilis* is a homo-oligomeric enzyme which exhibits strong positive cooperativity for nucleotide and fructose 1,6-bisphosphate binding. *J Biol Chem* 275 (3), 1773-1780

What is claimed is:

1. A method of identifying a compound that inhibits formation of an active form of a multimeric protein from a less active form of the multimeric protein by binding at a site other than an active site and/or an allosteric metal ion binding site of the multimeric protein comprising an assembly having a plurality of units, wherein each of said units comprises a first complementary surface and a second complementary surface and wherein the first complementary surface of one unit is associated with the second complementary surface of another unit, provided that the assembly is at least one of different quaternary isoforms, the method comprising: a) providing a multimeric protein with a biochemical function; (b) identifying a compound that binds to the multimeric protein; and (c) testing for the ability of the compound to affect the biochemical function in at least one assembly of the multimeric protein, wherein when a compound inhibits formation of the active form of the multimeric protein from the less active form of the multimeric protein by binding at a site other than an active site and/or metal ion binding site of the multimeric protein, the compound is identified as an inhibitor, further wherein said multimeric protein is selected from the group consisting of porphobilinogen synthase, a Class Ia ribonucleotide reductase, *Pseudomonas aeruginosa* GDP-Mannose dehydrogenase, *Bacillus subtilis* HPr, mammalian CoA transferase, purine nucleoside phosphorylase, and peroxiredoxins.

2. The method of claim 1, said biochemical function of said multimeric protein correlates to a human disease or condition.

3. The method of claim 1, wherein the effect of the compound on the biochemical function is selected from the group consisting of inhibition, binding, and allosteric effect.

4. A method of identifying an agent adapted to affect a multimeric protein by binding to a binding site other than an active site and/or an allosteric metal ion binding site of said multimeric protein, wherein the multimeric protein comprises an equilibrium of assembly states, each assembly having a plurality of units, wherein each of said units comprises a first complementary surface and a second complementary surface and wherein the first complementary surface of one unit is associated with the second complementary surface of another unit, provided that the assembly is at least one of different quaternary isoforms on condition that:

(i) one conformation of said units determines a first quaternary isoform but does not allow formation of other quaternary isoforms;
(ii) a different conformation of said units determines one of a different quaternary isoforms, but does not allow formation of the first quaternary isoform;
(iii) different quaternary isoforms comprising the different conformations of said units are in an equilibrium; and
(iv) the conformation of said different quaternary isoforms influences a function of said multimeric protein,
the method comprising:
providing a test agent;
providing the multimeric protein;
contacting the multimeric protein with the test agent under assay conditions; and
measuring the equilibrium of quaternary isoforms of the multimeric protein,
wherein the agent adapted to affect the multimeric protein is identified when it affects the multimeric protein by binding to a binding site other than an active site and/or an allosteric metal ion binding site of the multimeric protein and thereby affects the equilibrium of quaternary isoforms of the multimeric protein, wherein said multimeric protein is selected from the group consisting of porphobilinogen synthase, a Class Ia ribonucleotide reductase, *Pseudomonas aeruginosa* GDP-Mannose dehydrogenase, *Bacillus subtilis* HPr, mammalian CoA transferase, purine nucleoside phosphorylase, and peroxiredoxins.

5. The method of claim 4, wherein the quaternary isoform is selected from the group consisting of a dimer, a trimer, a tetramer, a hexamer, and an octamer.

6. The method of claim 4, wherein the agent is adapted to affect a biological function of said multimeric protein.

7. The method of claim 4, wherein the agent is bound to a quaternary isoform having a lesser activity.

8. The method of claim 4, wherein the agent inactivates the enzymatic activity of the multimeric protein.

9. The method of claim 4, wherein the agent is an inhibitor which inhibits formation of an active form of the multimeric protein.

* * * * *